United States Patent
Maehata et al.

(10) Patent No.: US 11,779,018 B2
(45) Date of Patent: Oct. 10, 2023

(54) HETEROCYCLIC COMPOUND AND ARTHROPOD PEST CONTROL COMPOSITION CONTAINING SAME

(71) Applicant: SUMITOMO CHEMICAL COMPANY, LIMITED, Chuo-ku (JP)

(72) Inventors: Ryota Maehata, Takarazuka (JP); Kohei Orimoto, Takarazuka (JP); Takamasa Tanabe, Chuo-ku (JP); Yasumasa Saito, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 304 days.

(21) Appl. No.: 17/042,641

(22) PCT Filed: Mar. 29, 2019

(86) PCT No.: PCT/JP2019/013938
§ 371 (c)(1),
(2) Date: Sep. 28, 2020

(87) PCT Pub. No.: WO2019/189731
PCT Pub. Date: Oct. 3, 2019

(65) Prior Publication Data
US 2021/0030003 A1 Feb. 4, 2021

(30) Foreign Application Priority Data

Mar. 30, 2018 (JP) .................. 2018-066971

(51) Int. Cl.
*A01N 43/80* (2006.01)
*A01N 43/40* (2006.01)
(Continued)

(52) U.S. Cl.
CPC ............. *A01N 43/80* (2013.01); *A01N 43/40* (2013.01); *A01N 43/78* (2013.01); *C07D 277/22* (2013.01);
(Continued)

(58) Field of Classification Search
CPC .. C07D 277/22; C07D 401/04; C07D 409/04; C07D 413/04; C07D 417/04; A01N 43/80; A01N 43/40; A01N 43/78
See application file for complete search history.

(56) References Cited

U.S. PATENT DOCUMENTS 6,518,266 B1 2/2003 Dhanoa et al.
2015/0181880 A1 7/2015 Takahashi et al.
(Continued)

FOREIGN PATENT DOCUMENTS

CN 104379567 A 2/2015
EP 0 911 329 A1 4/1999
(Continued)

OTHER PUBLICATIONS

English translation of the International Search Report dated Jun. 18, 2019, PCT/JP2019/013938, 3 pages.
English translation of the International Preliminary Report on Patentability and Written Opinion of the International Searching Authority dated Oct. 6, 2020 in PCT/JP2019/013938, 7 pages.
Sanath K. Meegalla, et al., "Synthesis and GABA Receptor Potency of 3-thiomethyl-4-(hetero)aryl-5-amino-1-phenylpyrazoles" Bioorganic & Medicinal Chemistry Letters, vol. 14, Issue 19, 2004, pp. 4949-4953.
Office Action dated Apr. 4, 2022 in corresponding Indian Patent Application No. 202047045834 (with English Translation), 6 pages.
Extended European Search Report dated Dec. 8, 2021 in European Patent Application No. 19776019.2, 6 pages.
Japanese Office Action dated Feb. 7, 2023 in Japanese Patent Application No. 2020-511075 (with unedited computer-generated English Translation), 7 pages.
Combined Chinese Office Action and Search Report dated Sep. 29, 2022 in Chinese Patent Application No. 201980023330.3 (with unedited computer generated English Translation), 17 pages.
2nd official action dated Apr. 21, 2023 in the corresponding Chinese application No. 201980023330.3, with English translation—13 pages.

*Primary Examiner* — Amanda L. Aguirre
(74) *Attorney, Agent, or Firm* — Oblon, McClelland, Maier & Neustadt, L.L.P.

(57) ABSTRACT

The present invention provides a compound that has an excellent control effect on arthropod pests, and is represented by formula (I) [wherein Q represents a group represented by Q1, or the like, n is 0, 1, or 2, $R^2$ represents a C1-C6 alkyl group which may optionally have one or more halogen atoms, or the like, $Y^a$ represents an oxygen atom, a sulfur atom, or $NR^{3a}$, $G^1$ represents a nitrogen atom or $CR^{5a}$, $G^2$ represents a nitrogen atom or $CR^{5b}$, $A^2$ represents a nitrogen atom or $CR^{4a}$, $A^3$ represents a nitrogen atom or $CR^{4b}$, $A^4$ represents a nitrogen atom or $CR^{4c}$, and $R^{3a}$, $R^{4a}$, $R^{4b}$, $R^{4c}$, $R^{5a}$, and $R^{5b}$ represent a C1-C6 chain hydrocarbon group or the like, and T represents a C1-C10 chain hydrocarbon group which may optionally have one or more halogen atoms, or the like].

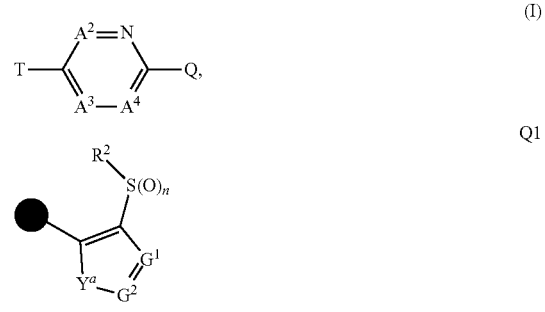

11 Claims, No Drawings

(51) Int. Cl.
*A01N 43/78* (2006.01)
*C07D 277/22* (2006.01)
*C07D 401/04* (2006.01)
*C07D 409/04* (2006.01)
*C07D 413/04* (2006.01)
*C07D 417/04* (2006.01)

(52) U.S. Cl.
CPC ......... *C07D 401/04* (2013.01); *C07D 409/04* (2013.01); *C07D 413/04* (2013.01); *C07D 417/04* (2013.01)

(56) References Cited

U.S. PATENT DOCUMENTS

| 2018/0243298 A1 | 8/2018 | Black et al. |
| 2018/0311218 A1 | 11/2018 | Siddiqui et al. |

FOREIGN PATENT DOCUMENTS

| WO | WO 99/52882 A1 | | 10/1999 | |
| WO | WO-0047578 A1 | * | 8/2000 | ................ A61P 1/18 |
| WO | WO 01/07413 A1 | | 2/2001 | |
| WO | WO 2009/137651 A2 | | 11/2009 | |
| WO | WO-2009137651 A2 | * | 11/2009 | ............ A01N 43/50 |
| WO | WO 2013/191113 A1 | | 12/2013 | |
| WO | WO 2016/113205 A1 | | 7/2016 | |
| WO | WO 2016/160938 A1 | | 10/2016 | |
| WO | WO-2016160938 A1 | * | 10/2016 | ........... A61K 31/506 |
| WO | WO 2016/196644 A1 | | 12/2016 | |

* cited by examiner

HETEROCYCLIC COMPOUND AND ARTHROPOD PEST CONTROL COMPOSITION CONTAINING SAME

TECHNICAL FIELD

This application claims priority to and the benefit of Japanese Patent Application Nos. 2018-066971 filed Mar. 30, 2018, the entire contents of which are incorporated herein by reference.

The present invention is related to a certain class of heterocyclic compound and a composition for controlling harmful arthropods comprising the same.

BACKGROUND ART

To date, in order to control harmful arthropods, some compounds have been studied. For example, it is described that a certain class of compound has an effect on controlling pests in the Patent Document 1.

CITATION LIST

Patent Document

Patent Document 1: WO 2013/191113

SUMMARY OF THE INVENTION

Problems to be Solved by Invention

An object of the present invention is to provide a compound having an excellent efficacy for controlling harmful arthropods.

Means to Solve Problems

The present invention includes the followings.
[1] A compound represented by formula (I):

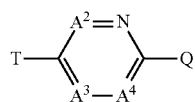

(I)

[wherein
Q represents a group represented by formula Q1, a group represented by formula Q2, or a group represented by formula Q3,

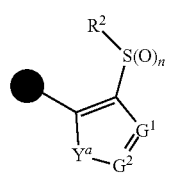

Q1

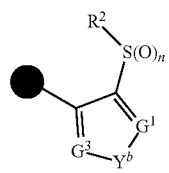

Q2

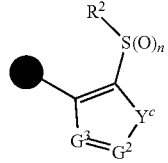

Q3 n is 0, 1 or 2,
$R^2$ represents a C1-C6 alkyl group which may optionally have one or more halogen atoms, a cyclopropyl group, or a cyclopropylmethyl group,
$Y^a$ represents an oxygen atom, a sulfur atom, or $NR^{3a}$,
$Y^b$ represents an oxygen atom, a sulfur atom, or $NR^{3b}$,
$Y^c$ represents an oxygen atom, a sulfur atom, or $NR^{3c}$,
$G^1$ represents a nitrogen atom, or $CR^{5a}$,
$G^2$ represents a nitrogen atom, or $CR^{5b}$,
$G^3$ represents a nitrogen atom, or $CR^{5c}$,
$R^{3a}$, $R^{3b}$, and $R^{3c}$ are identical to or different from each other, and each represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $C(O)R^{13}$, $C(O)OR^{17}$, $C(O)NR^{15a}R^{16a}$, $C(O)NR^{11}S(O)_2R^{23}$, or a hydrogen atom,
$R^{5a}$, $R^{5b}$, and $R^{5c}$ are identical to or different from each other, and each represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15a}R^{16a}$, $NR^{24}NR^{11}C(O)NR^{15a}R^{16a}$, $N=CHNR^{15a}R^{16a}$, $N=S(O)_xR^{15}R^{16}$, $C(O)R^{13}$, $C(O)OR^{17}$, $C(O)NR^{15a}R^{16a}$, $C(O)NR^{11}S(O)_2R^{23}$, $CR^{24}=NOR^{17}$, $NR^{11}CR^{24}=NOR^{17}$, a cyano group, a nitro group, a halogen atom, or a hydrogen atom,
x is 0 or 1,
$A^2$ represents a nitrogen atom or $CR^{4a}$,
$A^3$ represents a nitrogen atom or $CR^{4b}$,
$A^4$ represents a nitrogen atom or $CR^{4c}$,
$R^{4a}$, $R^{4b}$, and $R^{4c}$ are identical to or different from each other, and each represents a C1-C6 chain hydrocarbon group which may optionally have one or more halogen atoms, a nitro group, $OR^8$, $NR^{18}R^{19}$, a cyano group, a halogen atom, or a hydrogen atom,
$R^{18}$ represents a C1-C6 chain hydrocarbon group which may optionally have one or more halogen atoms,
$R^{19}$ represents a C1-C6 chain hydrocarbon group which may optionally have one or more halogen atoms, or a hydrogen atom,
T represents a C1-C10 chain hydrocarbon group which have one or more halogen atoms, a (C1-C5 alkoxy)C2-C5 alkyl group which have one or more halogen atoms, a (C1-C5 alkylsulfanyl)C2-C5 alkyl group which have one or more halogen atoms, a (C1-C5 alkylsulfinyl)C2-C5 alkyl group which have one or more halogen atoms, a (C1-C5 alkylsulfonyl group)C2-C5 alkyl group which have one or more halogen atoms, a (C3-C7 cycloalkyl)C1-C3 alkyl group which may optionally have one or more substituents selected from Group G, a C3-C7 cycloalkyl group which may optionally have one or more substituents selected from Group G, $OR^1$, $S(O)_mR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12,

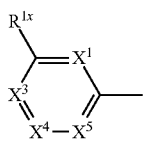

T-1

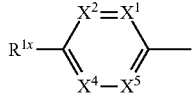

T-2

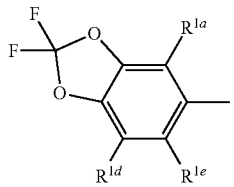

T-3

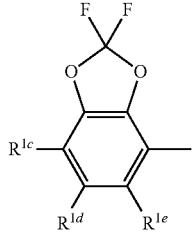

T-4

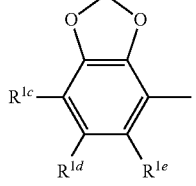

T-5

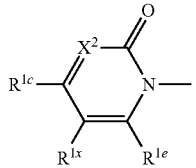

T-6

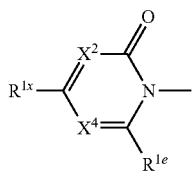

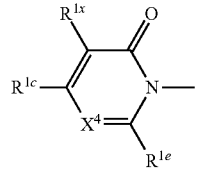

T-7

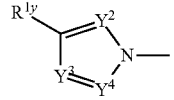

T-8

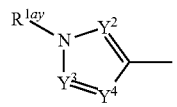

T-9

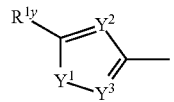

T-10

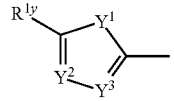

T-11

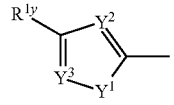

T-12

$X^1$ represents a nitrogen atom, or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{1e}$,
$R^{1a}$, $R^{1b}$, $R^{1c}$, $R^{1d}$, and $R^{1e}$ are identical to or different from each other, and each represents a C1-C6 chain hydrocarbon group which may optionally have one or more halogen atoms, a C3-C6 cycloalkyl group which may optionally have one or more halogen atoms, a halogen atom, or a hydrogen atom,
$Y^1$ represents $NR^{25}$, an oxygen atom, or a sulfur atom,
$Y^2$ represents a nitrogen atom, or $CR^{26}$,
$Y^3$ represents a nitrogen atom, or $CR^{27}$,
$Y^4$ represents a nitrogen atom, or $CR^{28}$,
$R^{25}$ represents a C1-C6 chain hydrocarbon group which may optionally have one or more halogen atoms, a C1-C6 alkoxy group which may optionally have one or more halogen atoms, a C3-C7 cycloalkyl group which may optionally have one or more halogen atoms, a (C3-C7 cycloalkyl)C1-C6 alkyl group which may optionally have one or more halogen atoms, or a hydrogen atom,
$R^{26}$, $R^{27}$, and $R^{28}$ are identical to or different from each other, and each represents a C1-C6 chain hydrocarbon group which may optionally have one or more halogen atoms, a C3-C6 cycloalkyl group which may optionally have one or more halogen atoms, a halogen atom, or a hydrogen atom,
$R^{1x}$ represents $OR^7$, $OS(O)_2R^7$, $S(O)_mR^7$, $NR^8S(O)_2R^7$, a C1-C5 chain hydrocarbon group which have one or more halogen atoms, a cyano group, or a halogen atom,
$R^{1y}$ represents $OR^7$, $OS(O)_2R^7$, $S(O)_mR^7$, $NR^8S(O)_2R^7$, a cyano group, a C1-C5 chain hydrocarbon group which have one or more halogen atoms, or a halogen atom, $R^{1ay}$ and $R^7$ are identical to or different from each other, and each represents a C1-C6 chain hydrocarbon group which have one or more halogen atoms, $R^8$ represents a C1-C6 chain hydrocarbon group which may optionally have one or more halogen atoms, or a hydrogen atom, m is 0, 1, or 2, $R^1$ represents a C1-C10 chain hydrocarbon group which have one or more halogen atoms, a (C1-C5 alkoxy)C2-C5 alkyl group which have one or more halogen atoms, a (C1-C5 alkylsulfanyl)C2-C5 alkyl group which have one or more halogen atoms, a (C1-C5 alkylsulfinyl group)C2-C5 alkyl group which have one or more halogen atoms, a (C1-C5 alkylsulfonyl)C2-C5 alkyl group which have one or more halogen atoms, a (C3-C7 cycloalkyl)C1-C3 alkyl group which have one or more substituents selected from Group G, or a C3-C7 cycloalkyl group which have one or more substituents selected from Group G, $R^{11}$, $R^{17}$, $R^{24}$, and $R^{29}$ are identical to or different from each other, and each represents a C1-C6 chain hydrocarbon group which may optionally have one or more halogen atoms, or a hydrogen atom, $R^{30}$ represents a C1-C6 chain hydrocarbon group which may optionally have one or more halogen atoms, or a hydrogen atom, $R^{12}$ represents a C1-C6 chain hydrocarbon group which may optionally have one or more halogen atoms, a C1-C6 alkyl group having one substituent selected from Group F, a phenyl group which may optionally have one or more substituents selected from Group H, a 5- or 6-membered aromatic heterocyclic group which may optionally have one or more substituents selected from Group H, $S(O)_2R^{23}$, or a hydrogen atom, $R^{23}$ represents a C1-C6 chain hydrocarbon group which may optionally have one or more halogen atoms, or a phenyl group which may optionally have one or more substituents selected from Group D, $R^{11a}$ and $R^{12a}$ combined together with a nitrogen atom to which they are attached to form a 3 to 7 membered nonaromatic heterocyclic group which may optionally have one or more substituents selected from Group E, $R^{13}$ represents a C1-C6 chain hydrocarbon group which may optionally have one or more halogen atoms, a C3-C7 cycloalkyl group which may optionally have one or more halogen atoms, a (C3-C6 cycloalkyl)C1-C3 alkyl group which may optionally have one or more halogen atoms, a phenyl group which may optionally have one or more substituents selected from Group D, a 5- or 6-membered aromatic heterocyclic group which may optionally have one or more substituents selected from Group D, or a hydrogen atom, $R^{14}$ represent a C1-C6 chain hydrocarbon group which may optionally have one or more halogen atoms, a C3-C7 cycloalkyl group which may optionally have one or more halogen atoms, a (C3-C6 cycloalkyl)C1-C3 alkyl group which may optionally have one or more halogen atom, or a (phenyl which may optionally have one or more substituents selected from Group D)C1-C3 alkyl group, $R^{15}$ and $R^{16}$ are identical to or different from each other, and each represents a C1-C6 alkyl group which may optionally have one or more halogen atoms, $R^{15a}$ represents a C1-C6 alkyl group which may optionally have one or more halogen atoms, or a hydrogen atom, and $R^{16a}$ represents a C1-C6 chain hydrocarbon group which may optionally have one or more substituents selected from Group F, a C3-C7 cycloalkyl group which may optionally have one or more substituents selected from Group J, or a hydrogen atom, Group B: a group consisting of a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, a C1-C6 alkylsulfanyl group which may optionally have one or more halogen atoms, a C1-C6 alkylsulfinyl group which may optionally have one or more halogen atoms, a C1-C6 alkylsulfonyl group which may optionally have one or more halogen atoms, a C3-C6 cycloalkyl group which may optionally have one or more halogen atoms, a cyano group, a hydroxy group, and a halogen atom, Group C: a group consisting of a C1-C6 chain hydrocarbon group which may optionally have one or more halogen atoms, a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, and a halogen atom, Group D: a group consisting of a C1-C6 chain hydrocarbon group which may optionally have one or more halogen atoms, a hydroxy group, a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, a sulfanyl group, a C1-C6 alkylsulfanyl group which may optionally have one or more halogen atoms, a C1-C6 alkylsulfinyl group which may optionally have one or more halogen atoms, a C1-C6 alkylsulfonyl group which may optionally have one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, $R^{21}$ and $R^{22}$ are identical to or different from each other, and each represents a C1-C6 alkyl group which may optionally have one or more halogen atoms, Group E: a group consisting of a C1-C6 chain hydrocarbon group which may optionally have one or more halogen atoms, a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, a halogen atom, an oxo group, a hydroxy group, a cyano group, and a nitro group, Group F: a group consisting of a C1-C6 alkoxy group which may optionally have one or more halogen atoms, a phenyl group which may optionally have one or more substituents selected from Group D, a 5- or 6-membered aromatic heterocyclic group which may optionally have one or more substituents selected from Group D, a C3-C7 cycloalkyl group which may optionally have one or more halogen atoms, a 3 to 7 membered nonaromatic heterocyclic group which may optionally have one or more substituents selected from Group C, an amino group, $NHR^{21}$, $NR^{21}R^{22}$, and a cyano group, Group G: a group consisting of a C1-C6 alkyl group which have one or more halogen atoms, and a halogen atom, Group H: a group consisting of a C1-C6 alkyl group which may optionally have one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, an amino group, and a 5- or 6-membered aromatic heterocyclic group, $R^9$ represents a C1-C6 alkyl group which may optionally have one or more halogen atoms, or a C3-C6 cycloalkyl group which may optionally have one or more halogen atoms, $R^{10}$ represents a C1-C6 alkyl group which may optionally have one or more halogen atoms, a C3-C6 cycloalkyl group which may optionally have one or more halogen atoms, or a hydrogen atom, Group J: a group consisting of a C1-C6 alkyl group which may optionally have one or more halogen atoms, a halogen atom, and a cyano group]
(hereinafter, referred to as "Present compound" or "Compound of the present invention").

[2] The compound according to [1] wherein
$R^2$ represents a C1-C6 alkyl group,
$R^{3a}$, $R^{3b}$ and $R^{3c}$ are identical to or different from each other, and each represents a C1-C6 alkyl group which may optionally have one or more halogen atoms, a phenyl group, a pyridyl group, a pyrimidinyl group, a pyrazolyl group, a triazolyl group (the phenyl group, the pyridyl group, the pyrimidinyl group, the pyrazolyl group, and the triazolyl group may optionally have one or more substituents selected from Group H), or a hydrogen atom,
$R^{4a}$, $R^{4b}$, and $R^{4c}$ are identical to or different from each other, and each presents a hydrogen atom, or a halogen atom,
T represents $OR^1$, and $R^1$ represents a C1-C5 chain hydrocarbon group which have one or more halogen atoms,
Q represents a group represented by formula Q1, or a group represented by formula Q3, and
$R^{5a}$, $R^{5b}$, and $R^{5c}$ are identical to or different from each other, and each represents a C1-C6 alkyl group which may optionally have one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group may optionally have one or more substituents selected from Group H}, $OR^{12}$, $NR^{11}R^{12}$, $NR^{11}C(O)OR^{14}$, a halogen atom, or a hydrogen atom.

[3] The compound according to [1] or [2] wherein
$R^1$ represents a C1-C5 alkyl group having three or more fluorine atoms,
$R^{3a}$, $R^{3b}$, and $R^{3c}$ are identical to or different from each other, and each represent a C1-C6 alkyl group which may optionally have one or more halogen atoms, or a hydrogen atom,
$R^{4a}$, $R^{4b}$, and $R^{4c}$ represent a hydrogen atom, and
$R^{5a}$, $R^{5b}$, and $R^{5c}$ are identical to or different from each other, and each represents a C1-C6 alkyl group which may optionally have one or more halogen atoms, $OR^{12a}$, a halogen atom, or a hydrogen atom.

[4] The compound according to any one of [1] to [3] wherein $R^2$ represents an ethyl group.

[5] The compound according to any one of [1] to [4] wherein Q represents a group represented by formula Q1.

[6] The compound according to any one of [1] to [4] wherein Q represents a group represented by formula Q3.

[7] The composition for controlling a harmful arthropod comprising the compound according to any one of [1] to [6] and an inert carrier.

[8] A method for controlling a harmful arthropod which comprises applying an effective amount of the compound according to any one of [1] to [6] to a harmful arthropod or a habitat where a harmful arthropod lives.

[9] A composition comprising one or more ingredients selected from Group (a) and Group (b), and the compound according to any one of [1] to [6]:

Group (a): a group consisting of insecticidal ingredients, miticide ingredients, and nematicidal ingredients; and
Group (b): fungicidal ingredient.

[10] A method for controlling a harmful arthropod which comprises an effective amount of the composition according to [9] to a harmful arthropod or a habitat where a harmful arthropod lives.

[11] A seed or vegetative reproductive organ carrying an effective amount of the compound according to any one of [1] to [6] or an effective amount of the composition according to [9].

Effect of Invention

The present invention can control harmful arthropod.

The substituent(s) as described herein is/are explained. The term "halogen atom" represents fluorine atom, chlorine atom, bromine atom, or iodine atom.

When the substituents have two or more halogen atoms, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group, hexyl group, heptyl group, octyl group, nonyl group, and decyl group. Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1-ethyl-2-propenyl group, 3-butenyl group, 4-pentenyl group, 5-hexenyl group, 6-heptenyl group, 7-octenyl group, nonenyl group, and decenyl group.

Example of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, 6-heptynyl group, 7-octynyl group, nonynyl group, and decynyl group.

Examples of the term of "cycloalkyl group" include cyclopropyl group, cyclobutyl group, cyclopentyl group, cyclohexyl group, and cycloheptyl group.

The term of "alkoxy group" represents a group wherein the alkyl group as defied above is attached to an oxygen atom, and examples thereof include methoxy group, ethoxy group, propoxy group, isopropoxy group, butoxy group, pentyloxy group, and hexyloxy group.

The term of "alkenyloxy group" represents a group wherein one hydrogen atom on the alkenyl group as defined above is replaced with an oxygen atom, and examples thereof include vinyloxy group, 1-propenyloxy group, 2-propenyloxy group, isopropenyloxy group, 1-butenyloxy group, 2-butenyloxy group, 3-butenyloxy group, 1-isobutenyloxy group, 2-isobutenyloxy group, 1-pentenyloxy group, 2-pentenyloxy group, 3-pentenyloxy group, and 4-pentenyloxy group.

The term of "alkynyloxy group" represents a group wherein one hydrogen atom on the alkynyl group as defined above is replaced with an oxygen atom, and examples thereof include ethynyloxy group, 1-propynyloxy group, 2-propynyloxy group, 1-butynyloxy group, 2-butynyloxy group, 3-butynyloxy group, 1-pentynyloxy group, 2-pentynyloxy group, 3-pentynyloxy group, 4-pentynyloxy group, 1-hexynyloxy group, 2-hexynyloxy group, and 3-hexynyloxy group.

Examples of "three(3)- to seven(7)-membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the 3- to 7-membered nonaromatic heterocyclic ring which may optionally have one or more substituents selected from Group E include the below-mentioned group.

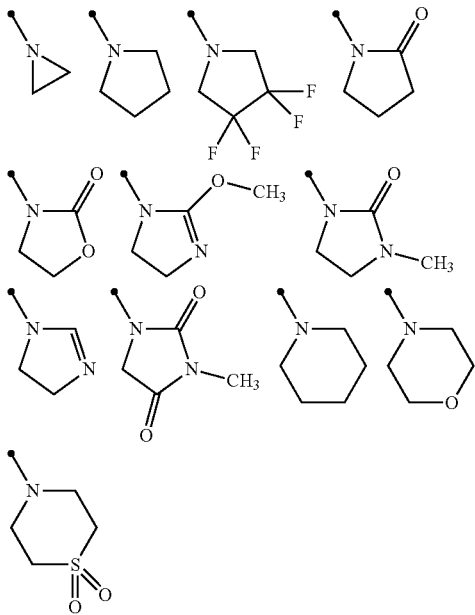

Examples of "C1-C10 chain hydrocarbon group which may optionally have one or more halogen atoms" include a C1-C10 chain hydrocarbon group which have one or more halogen atoms in addition to groups as exemplified above as "alkyl group", "alkenyl group" and "alkynyl group". Specific examples of "C1-C6 chain hydrocarbon group" and "C1-C5 chain hydrocarbon group" are encompassed by the "C1-C10 chain hydrocarbon group".

Examples of "C1-C5 alkyl group having three or more fluorine atoms" encompasses a perfluoroalkyl group, and examples thereof include trifluoromethyl group, 1,1,1-trifluoroethyl group, and trifluoroethyl group.

Examples of "C1-C6 alkoxy group which may optionally have one or more halogen atoms" include a C1-C6 alkoxy group which have one or more halogen atoms, in addition to the groups as exemplified above as "alkoxy group".

Examples of "C3-C7 cycloalkyl group which may optionally have one or more halogen atoms" include a C3-C7 cycloalkyl group which have one or more halogen atoms, in addition to the groups as exemplified above as "cycloalkyl group". Specific examples of "C3-C6 cycloalkyl group" is encompassed by the "C3-C7 cycloalkyl group".

The term of "(C1-C5 alkoxy)C2-C5 alkyl which have one or more halogen atoms" represents a group wherein the (C1-C5 alkoxy) and/or (C2-C5 alkyl) has/have one or more halogen atoms, and examples thereof 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group which have one or more halogen atoms" represents a group wherein (C1-C5 alkylsulfanyl group) and/or (C2-C5 alkyl) has/have one or more halogen atoms, and examples thereof include 2,2-difluoro-2-(trifluoromethylthio) ethyl group.

The term of "(C1-C5 alkylsulfinyl group)C2-C5 alkyl group which have one or more halogen atoms" represents a group wherein (C1-C5 alkylsulfinyl group) and/or (C2-C5 alkyl) has/have one or more halogen atoms, and examples thereof include 2,2-difluoro-2-(trifluoromethansulfinyl)ethyl group.

The term of "(C1-C5 alkylsulfonyl group)C2-C5 alkyl group which have one or more halogen atoms" represents a group wherein (C1-C5 alkylsulfonyl group) and/or (C2-C5 alkyl) has/have one or more halogen atoms, and examples of thereof include 2,2-difluoro-2-(trifluoromethansulfonyl) ethyl group.

The term of "(C3-C7 cycloalkyl)C1-C6 alkyl group which may optionally have one or more halogen atom" represents a group wherein (C3-C7 cycloalkyl) and/or (C1-C6 alkyl) may optionally have one or more halogen atoms, and examples thereof include (2,2-difluorocyclopropyl)methyl group, 2-cyclopropyl-1,1,2,2-tetrafluoroethyl group, 2-(2,2-difluorocyclopropyl)-1,1,2,2,-tetrafluoroethyl group, (2,2-difluorocyclopropyl)propyl group, (2,2-difluorocyclopropyl)butyl group, (2,2-difluorocyclopropyl)pentyl group, and (2,2-difluorocyclopropyl)pentyl group. Specific examples of "(C3-C6 cycloalkyl)C1-C3 alkyl group" are encompassed by the term of "(C3-C7 cycloalkyl)C1-C6 alkyl group".

The term of "(C3-C7 cycloalkyl)C1-C3 alkyl group which may optionally have one or more substituents selected from Group G" represents a group wherein (C3-C7 cycloalkyl) and/or (C1-C3 alkyl) may optionally have one or more substituents selected from Group G, and examples thereof include (2,2-difluorocyclopropyl)methyl group, [1-{trifluoromethyl)cyclopropyl)}methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl] ethyl group.

Examples of "phenyl which may optionally have one or more substituents selected from Group D)C1-C3 alkyl group" include benzyl group, 2-fluorobenzyl group, 4-chlorobenzyl group, 4-(trifluoromethyl)benzyl group, and 2-[4-(trifluromethyl)phenyl]ethyl group.

The term of "a five(5)- or six(6)-membered aromatic heterocyclic group" represents a five(5) membered aromatic heterocyclic group or a six(6) membered aromatic heterocyclic group, and examples of the five(5) membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. Examples of the six(6) membered aromatic heterocyclic group include pyridyl group, pyridazinyl group, pyrimidinyl group, pyrazinyl group, triazinyl group, and tetrazinyl group.

The terms of "alkylsulfanyl group", "alkylsulfinyl group", and "alkylsulfonyl group" represent an alkyl group containing a $S(O)_y$ moiety, which represents an alkylsulfanyl group, an alkylsulfinyl group, or an alkylsulfonyl group, when y is 0, 1 or 2 respectively.

The term of "alkylsulfanyl group" represents a sulfanyl group containing the above-mentioned alkyl group, and examples thereof include a methyl sulfanyl group, an ethyl sulfanyl group, a propyl sulfanyl group, and an isopropyl sulfanyl group.

The term of "alkylsulfinyl group" represents a sulfinyl group containing the above-mentioned alkyl group, and examples thereof include a methyl sulfinyl group, an ethyl sulfinyl group, a propyl sulfinyl group, and an isopropyl sulfinyl group.

The term of "alkylsulfonyl group" represents a sulfonyl group containing the above-mentioned alkyl group, and examples thereof include a methylsulfonyl group, an ethylsulfonyl group, a propylsulfonyl group, and an isopropylsulfonyl group.

The present compound may be existed as one or more stereoisomers. Examples of the stereoisomer include enantiomer, diastereoisomer, and geometric isomer. Each stereoisomer, and stereoisomer mixture(s) in an arbitrary ratio thereof are included in the present invention.

The present compound may form acid addition salts. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. The acid addition salt may be obtained by mixing the present compound with an acid.

Examples of the Embodiment of the present compound include the following compounds.

[Embodiment 1] The present compound wherein $R^{3a}$, $R^{3b}$ and $R^{3c}$ are identical to or different from each other, and each represents a C1-C6 alkyl group which may optionally have one or more halogen atoms, phenyl group, a pyridyl group, a pyrimidinyl group, a pyrazolyl group, a triazolyl group (the phenyl group, the pyridyl group, the pyrimidinyl group, the pyrazolyl group, and the triazolyl group may optionally have one or more substituents selected from Group H) or a hydrogen atom, $R^{5a}$, $R^{5b}$ and $R^{5c}$ are identical to or different from each other, and each represents a C1-C6 alkyl group which may optionally have one or more halogen atoms, phenyl group, a pyridyl group, a pyrimidinyl group, a pyrazolyl group, a triazolyl group {the phenyl group, the pyridyl group, the pyrimidinyl group, the pyrazolyl group, and the triazolyl group may optionally have one or more substituents selected from Group H}, $OR^{12}$, $NR^{11}R^{12}$, $NR^{11}C(O)OR^{14}$, a halogen atom, or a hydrogen atom.

[Embodiment 2] The present compound wherein $R^{3a}$, $R^{3b}$ and $R^{3c}$ are identical to or different from each other, and each represents a C1-C6 alkyl group which may optionally have one or more halogen atoms, or a hydrogen atom, $R^{5a}$, $R^{5b}$ and $R^{5c}$ are identical to or different from each other, and each represents a C1-C6 alkyl group which may optionally have one or more halogen atoms, $OR^{12a}$, a halogen atom, or a hydrogen atom.

[Embodiment 3] The compound according to Embodiment 1 wherein $R^2$ represents C1-C6 alkyl group.

[Embodiment 4] The present compound wherein $R^2$ represents an ethyl group.

[Embodiment 5] The compound according to Embodiment 1 wherein $R^2$ represents an ethyl group.

[Embodiment 6] The compound according to Embodiment 2 wherein $R^2$ represents an ethyl group.

[Embodiment 7] The compound according to Embodiment 3 wherein Q represents a group represented by formula Q1, or a group represented by formula Q3.

[Embodiment 8] The compound according to Embodiment 4 wherein Q represents a group represented by formula Q1, or a group represented by formula Q3.

[Embodiment 9] The compound according to Embodiment 5 wherein Q represents a group represented by formula Q1, or a group represented by formula Q3.

[Embodiment 10] The compound according to Embodiment 6 wherein Q represents a group represented by formula Q1, or a group represented by formula Q3.

[Embodiment 11] The compound according to Embodiment 8 wherein $Y^c$ represents an oxygen atom or sulfur atom.

[Embodiment 12] The compound according to Embodiment 7 wherein $Y^a$ represents an oxygen atom or a sulfur atom, $Y^c$ represents a sulfur atom, $G^2$ represents $CR^{5b}$, and $G^3$ represents a nitrogen atom.

[Embodiment 13] The compound according to Embodiment 8 wherein $Y^a$ represents an oxygen atom or a sulfur atom, $Y^c$ represents a sulfur atom, $G^2$ represents $CR^{5b}$, and $G^3$ represents a nitrogen atom.

[Embodiment 14] The compound according to Embodiment 9 wherein $Y^a$ represents an oxygen atom or a sulfur atom, $Y^c$ represents a sulfur atom, $G^2$ represents $CR^{5b}$, and $G^3$ represents a nitrogen atom.

[Embodiment 15] The compound according to Embodiment 10 wherein $Y^a$ represents an oxygen atom or a sulfur atom, $Y^c$ represents a sulfur atom, $G^2$ represents $CR^{5b}$, and $G^3$ represents a nitrogen atom.

[Embodiment 16] The compound according to Embodiment 7 wherein $Y^a$ and $Y^c$ represent a sulfur atom, $G^2$ represents $CR^{5b}$, and $G^3$ represents a nitrogen atom.

[Embodiment 17] The compound according to Embodiment 8 wherein $Y^a$ and $Y^c$ represent a sulfur atom, $G^2$ represents $CR^{5b}$, and $G^3$ represents a nitrogen atom.

[Embodiment 18] The compound according to Embodiment 9 wherein $Y^a$ and $Y^c$ represent a sulfur atom, $G^2$ represents $CR^{5b}$, and $G^3$ represents a nitrogen atom.

[Embodiment 19] The compound according to Embodiment 10 wherein $Y^a$ and $Y^c$ represent a sulfur atom, $G^2$ represents $CR^{5b}$, and $G^3$ represents a nitrogen atom.

[Embodiment 20] The compound according to Embodiment 4 wherein Q represents a group represented by formula Q1.

[Embodiment 21] The compound according to Embodiment 5 wherein Q represents a group represented by formula Q1.

[Embodiment 22] The compound according to Embodiment 6 wherein Q represents a group represented by formula Q1.

[Embodiment 23] The compound according to Embodiment 20 wherein $G^2$ represents $CR^{5b}$.

[Embodiment 24] The compound according to Embodiment 21 wherein $G^2$ represents $CR^{5b}$.

[Embodiment 25] The compound according to Embodiment 22 wherein $G^2$ represents $CR^{5b}$.

[Embodiment 26] The compound according to Embodiment 20 wherein $Y^a$ represents an oxygen atom or a sulfur atom, and $G^2$ represents $CR^{5b}$,

[Embodiment 27] The compound according to Embodiment 21 wherein $Y^a$ represents an oxygen atom or a sulfur atom, and $G^2$ represents $CR^{5b}$.

[Embodiment 28] The compound according to Embodiment 22 wherein $Y^a$ represents an oxygen atom or a sulfur atom, and $G^2$ represents $CR^{5b}$.

[Embodiment 29] The compound according to Embodiment 4 wherein Q represents a group represented by formula Q2.

[Embodiment 30] The compound according to Embodiment 5 wherein Q represents a group represented by formula Q2.

[Embodiment 31] The compound according to Embodiment 6 wherein Q represents a group represented by formula Q2.

[Embodiment 32] The compound according to Embodiment 29 wherein $Y^b$ represents $NR^{3b}$, $G^1$ represents $CR^{5a}$, and $G^3$ represents a nitrogen atom.
[Embodiment 33] The compound according to Embodiment 30 wherein $Y^b$ represents $NR^{3b}$, $G^1$ represents $CR^{5a}$, and $G^3$ represents a nitrogen atom.
[Embodiment 34] The compound according to Embodiment 31 wherein $Y^b$ represents $NR^{3b}$, $G^1$ represents $CR^{5a}$, and $G^3$ represents a nitrogen atom.
[Embodiment 35] The compound according to Embodiment 4 wherein Q represents a group represented by formula Q3.
[Embodiment 36] The compound according to Embodiment 5 wherein Q represents a group represented by formula Q3.
[Embodiment 37] The compound according to Embodiment 6 wherein Q represents a group represented by formula Q3.
[Embodiment 38] The compound according to Embodiment 35 wherein $Y^c$ represents an oxygen atom or a sulfur atom, and $G^2$ represents $CR^{5b}$.
[Embodiment 39] The compound according to Embodiment 36 wherein $Y^c$ represents an oxygen atom or a sulfur atom, and $G^2$ represents $CR^{5b}$.
[Embodiment 40] The compound according to Embodiment 37 wherein $Y^c$ represents an oxygen atom or a sulfur atom, and $G^2$ represents $CR^{5b}$.
[Embodiment 41] The compound according to Embodiment 35 wherein $Y^c$ represents a sulfur atom, $G^2$ represents $CR^{5b}$, and $G^3$ represents a nitrogen atom.
[Embodiment 42] The compound according to Embodiment 36 wherein $Y^c$ represents a sulfur atom, $G^2$ represents $CR^{5b}$, and G3 represents a nitrogen atom.
[Embodiment 43] The compound according to Embodiment 37 wherein $Y^c$ represents a sulfur atom, $G^2$ represents $CR^{5b}$, and $G^3$ represents a nitrogen atom.
[Embodiment 44] The compound according to Embodiment 3 wherein $A^2$ represents $CR^{4a}$, $A^4$ represents $CR^{4c}$, and $R^{4a}$, $R^{4b}$, and $R^{4c}$ are identical to or different from each other, and each represents a hydrogen atom or a halogen atom.
[Embodiment 45] The compound according to Embodiment 12 $A^2$ represents $CR^{4a}$, $A^4$ represents $CR^{4c}$, and $R^{4a}$, $R^{4b}$, and $R^{4c}$ are identical to or different from each other, and each represents a hydrogen atom or a halogen atom.
[Embodiment 46] The compound according to Embodiment 16 $A^2$ represents $CR^{4a}$, $A^4$ represents $CR^{4c}$, and $R^{4a}$, $R^{4b}$, and $R^{4c}$ are identical to or different from each other, and each represents a hydrogen atom or a halogen atom.
[Embodiment 47] The compound according to Embodiment 20 $A^2$ and $A^4$ represent CH, and $A^3$ represents a nitrogen atom or CH.
[Embodiment 48] The compound according to Embodiment 21 $A^2$ and $A^4$ represent CH, and $A^3$ represents a nitrogen atom or CH.
[Embodiment 49] The compound according to Embodiment 22 $A^2$ and $A^4$ represent CH, and $A^3$ represents a nitrogen atom or CH.
[Embodiment 50] The compound according to Embodiment 23 $A^2$ and $A^4$ represent CH, and $A^3$ represents a nitrogen atom or CH.
[Embodiment 51] The compound according to Embodiment 24 $A^2$ and $A^4$ represent CH, and $A^3$ represents a nitrogen atom or CH.
[Embodiment 52] The compound according to Embodiment 25 $A^2$ and $A^4$ represent CH, and $A^3$ represents a nitrogen atom or CH.
[Embodiment 53] The compound according to Embodiment 26 $A^2$ and $A^4$ represent CH, and $A^3$ represents a nitrogen atom or CH.
[Embodiment 54] The compound according to Embodiment 27 $A^2$ and $A^4$ represent CH, and $A^3$ represents a nitrogen atom or CH.
[Embodiment 55] The compound according to Embodiment 28 $A^2$ and $A^4$ represent CH, and $A^3$ represents a nitrogen atom or CH.
[Embodiment 56] The compound according to Embodiment 20 $A^2$, $A^3$, and $A^4$ represent CH.
[Embodiment 57] The compound according to Embodiment 21 $A^2$, $A^3$, and $A^4$ represent CH.
[Embodiment 58] The compound according to Embodiment 22 $A^2$, $A^3$, and $A^4$ represent CH.
[Embodiment 59] The compound according to Embodiment 23 $A^2$, $A^3$, and $A^4$ represent CH.
[Embodiment 60] The compound according to Embodiment 24 $A^2$, $A^3$, and $A^4$ represent CH.
[Embodiment 61] The compound according to Embodiment 25 $A^2$, $A^3$, and $A^4$ represent CH.
[Embodiment 62] The compound according to Embodiment 26 $A^2$, $A^3$, and $A^4$ represent CH.
[Embodiment 63] The compound according to Embodiment 27 $A^2$, $A^3$, and $A^4$ represent CH.
[Embodiment 64] The compound according to Embodiment 28 $A^2$, $A^3$, and $A^4$ represent CH.
[Embodiment 65] The compound according to any one of Embodiment 1 to Embodiment 64 wherein T represents a C1-C10 chain hydrocarbon group which have one or more halogen atoms, a (C1-C5 alkoxy)C2-C5 alkyl group which have one or more halogen atoms, a (C1-C5 alkylsulfanyl) C2-C5 alkyl group which have one or more halogen atoms, a (C1-C5 alkylsulfinyl group)C2-C5 alkyl group which have one or more halogen atoms, a (C1-C5 alkylsulfonyl group) C2-C5 alkyl group which have one or more halogen atoms, a (C3-C7 cycloalkyl)C1-C3 alkyl group which have one or more substituents selected from Group G, a C3-C7 cycloalkyl group which have one or more substituents selected from Group G, $OR^1$, $S(O)_mR^1$, $OS(O)_2R^1$, $NR^1R^{29}$, a group represented by formula T-1, a group represented by formula T-2, a group represented by formula T-3, a group represented by formula T-4, a group represented by formula T-5, a group represented by formula T-6, a group represented by formula T-7, or a group represented by formula T-8.
[Embodiment 66] The compound according to any one of Embodiment 1 to Embodiment 64 wherein T represents a C1-C10 chain hydrocarbon group which have one or more halogen atoms, a (C1-C5 alkoxy)C2-C5 alkyl group which have one or more halogen atoms, a (C1-C5 alkylsulfanyl) C2-C5 alkyl group which have one or more halogen atoms, a (C1-C5 alkylsulfinyl group)C2-C5 alkyl group which have one or more halogen atoms, a (C1-C5 alkylsulfonyl group) C2-C5 alkyl group which have one or more halogen atoms, a (C3-C7 cycloalkyl)C1-C3 alkyl group which have one or more substituents selected from Group G, a C3-C7 cycloalkyl group which have one or more substituents selected from Group G, $OR^1$, $S(O)_mR^1$, $OS(O)_2R^1$, or $NR^1R^{29}$.
[Embodiment 67] The compound according to any one of Embodiment 1 to Embodiment 64 wherein T represents $OR^1$.
[Embodiment 68] The compound according to any one of Embodiment 1 to Embodiment 64 wherein T represents OR, and $R^1$ represents a C1-C6 alkyl group which have one or more halogen atoms.

Next, a process for preparing the present compound is described.

Process 1

A compound represented by formula (A-1a) (hereinafter, referred to as "Compound (A-1a)", a compound represented by formula (A-1b) (hereinafter, referred to as "Compound (A-1b)", and a compound represented by formula (A-1c) "hereinafter, referred to as "Compound (A-1c)" can be prepared according to the below-mentioned scheme.

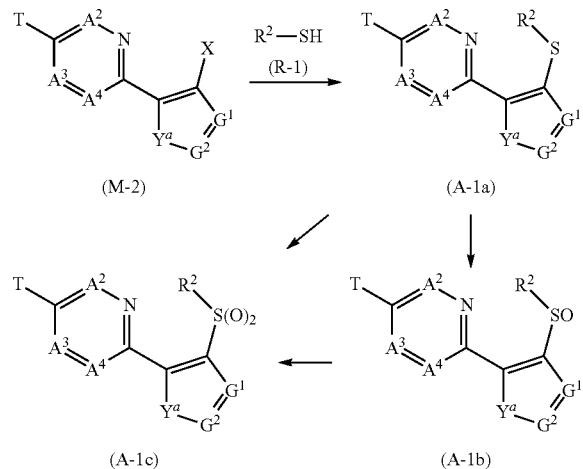

[wherein X represents a chlorine atom, a bromine atom, or an iodine atom, and the other symbols are the same as those defined above.]

The compound (A-1a) can be prepared by reacting a compound represented by formula (M-2) (hereinafter, referred to as "Compound (M-2)" with a compound represented by formula (R-1) "hereinafter, referred to as "Compound (R-1)" in the presence of a catalyst and a base.

The reaction is usually carried out in a solvent. Examples of the solvents to be used in the reaction include alcohols (such as methanol and ethanol) (hereinafter, collectively referred to as "alcohols"); nitriles (such as acetonitrile) (hereinafter, collectively referred to as "nitriles"); ethers (such as methyl tert-butyl ether (hereinafter, referred to as "MTBE"), tetrahydrofuran "hereinafter, referred to as "THF") and dimethoxyethane (hereinafter, collectively "ethers"); aromatic hydrocarbons (such as toluene and xylene) (hereinafter, collectively referred to as "aromatic hydrocarbons"); aprotic polar solvents (such as N,N-dimethylformamide (hereinafter, referred to as "DMF"), and N-methylpyrrolidone and dimethylsulfoxide (hereinafter, referred to as "DMSO") (hereinafter, collectively referred to as "aprotic polar solvents"); water; and mixed solvents of these two or more solvents.

Examples of the catalyst to be used in the reaction include palladium catalysts (such as tetrakis(triphenylphosphine) palladium (0), 1,1'-bis(diphenylphosphino)ferrocene palladium (II) dichloride, tris(dibenzylideneacetone) dipalladium (0), and palladium (II) acetate); nickel catalysts (such as bis(cyclooctadiene) nickel(0) and nickel(II) chloride); and copper catalysts (such as copper (I) iodide and copper (I) chloride).

Examples of the base to be used in the reaction include alkali metal hydrides (such as sodium hydride) (hereinafter, collectively referred to as "alkali metal hydrides"); alkali metal carbonates (such as potassium carbonate and sodium carbonate) (hereinafter, collectively referred to as "alkali metal carbonates"); and organic bases (such as pyridine and triethylamine) (hereinafter, collectively referred to as "organic bases").

In the reaction, the compound (R-1) is usually used within a range of 1 to 20 molar ratio(s), the metal catalyst is usually used within a range of 0.01 to 0.5 molar ratios, and the base is usually used within a range of 0.1 to 5 molar ratio(s), as opposed to 1 mole of the compound (M-2).

A ligand may be used in the reaction. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenlnyl, 1,2-bis (diphenylphosphino)ethane, 2,2'-bipyridine, 2-aminoethanol, 8-hydroxyqunoline, and 1,10-phenanthroline, and the others. When a ligand is used in the reaction, the ligand is usually used within a range of 0.01 to 1 molar ratio(s) as opposed to 1 mole of the compound (M-2).

The reaction temperature in the reaction is usually within a range of −20 to 200° C. The reaction period in the reaction is usually within a range of 0.1 to 72 hours.

When the reaction is completed, water is added to reaction mixtures, and the reaction mixtures are extracted with organic solvent(s), and the organic layers are worked up (for example, drying and concentration) to obtain the compound (A-1a).

The compound (R-1) is a commercially available compound, or can be prepared by using a known method.

The compound (A-b) can be prepared by reacting the compound (A-1a) with an oxidizing agent.

The reaction is usually carried out in a solvent. Examples of the solvents to be used in the reaction include halogenated hydrocarbons (such as dichloromethane and chloroform) (hereinafter, collectively referred to as "halogenated hydrocarbons"); nitriles; alcohols; acetic acid; water; and mixed solvents of two or more of these solvents.

Examples of the oxidizing agent to be used in the reaction include sodium periodate, m-chloroperoxybenzoic acid (hereinafter, referred to as "mCPBA") and hydrogen peroxide.

When hydrogen peroxide is used as an oxidizing agent, a base or a catalyst may be used as needed.

Examples of the base include sodium carbonate. When the base is used in the reaction, the base is usually used within a range of 0.01 to 1 molar ratio(s), as opposed to 1 mole of the compound (A-1a).

Examples of the catalyst include tungstic acid, and sodium tungstate. When the catalyst is used in the reaction, the catalyst is usually used within a range of 0.01 to 0.5 molar ratios as opposed to 1 mole of the compound (A-1a).

In the reaction, the oxidizing agent is usually used within a range of 1 to 1.2 molar ratio(s), as opposed to 1 mole of the compound (A-1a).

The reaction temperature in the reaction is usually within a range of −20 to 80° C. The reaction period in the reaction is usually within a range of 0.1 to 12 hours.

When the reaction is completed, water is added to reaction mixtures, and the mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (A-1b).

The compound (A-1c) can be prepared by reacting the compound (A-1b) with the oxidizing agent.

The reaction is usually carried out in a solvent. Examples of the solvents to be used in the reaction include halogenated hydrocarbons, nitriles, alcohols, acetic acid, water, and mixed solvents of two or more of these solvents.

Examples of the oxidizing agent to be used in the reaction include mCPBA and hydrogen peroxide.

When hydrogen peroxide is used as an oxidizing agent, a base or a catalyst may be used as needed.

Examples of the base include sodium carbonate. When a base is used in the reaction, the base is usually used within a range of 0.01 to 1 molar ratio(s) as opposed to 1 mole of the compound (A-1b).

Examples of the catalyst include sodium tungstate. When the catalyst is used in the reaction, the catalyst is usually used within a range of 0.01 to 0.5 molar ratios as opposed to 1 mole of the compound (A-1b).

In the reaction, the oxidizing agent is usually used within a range of 1 to 2 molar ratio(s) as opposed to 1 mole of the compound (A-1b).

The reaction temperature in the reaction is usually within a range of −20 to 120° C. The reaction period in the reaction is usually within a range of 0.1 to 12 hours.

When the reaction is completed, water is added to reaction mixtures, and the mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (A-1c).

Also the compound (A-1c) can be prepared by reacting the compound (A-1a) with an oxidizing agent in one step (one-spot)

The reaction can be carried out by using the oxidizing agent in 2 to 5 molar ratios as opposed to 1 mole of the compound (A-1a) according to a similar method to that described in the method for preparing the compound (A-1c) from the compound (A-1b).

Process 2

A compound represented by formula (A-2a) (hereinafter, referred to as "Compound (A-2a)") can be prepared by reacting a compound represented by formula (M-3) (hereinafter, referred to as "Compound (M-3)") with the compound (R-1) in the presence of a catalyst and a base. A compound represented by formula (A-2b) (hereinafter, referred to as "Compound (A-2b)") or a compound represented by formula (A-2c) (hereinafter, referred to as "Compound (A-2c)") can be prepared by reacting the compound (A-2a) with an oxidizing agent. The compound (A-2c) can be prepared by reacting the compound (A-2b) with an oxidizing agent.

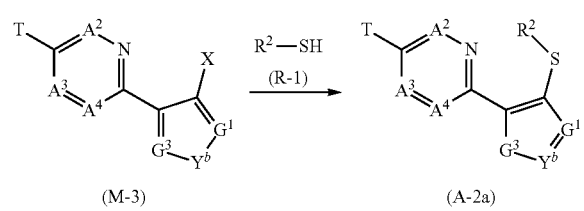

(M-3)   (A-2a)

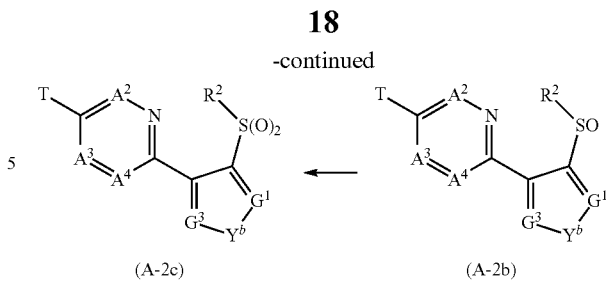

(A-2c)   (A-2b)

[wherein the symbols are the same as those defined above.]

These reactions can be carried out according to the Process 1.

Process 3

A compound represented by formula (A-3a) (hereinafter, referred to as "Compound (A-3a)") can be prepared by reacting a compound represented by formula (M-5) (hereinafter, referred to as "Compound (M-5)") with the compound (R-1) in the presence of a catalyst and a base. A compound represented by formula (A-3b) (hereinafter, referred to as "Compound (A-3b)") or a compound represented by formula (A-3c) (hereinafter, referred to as "Compound (A-3c)") can be prepared by reacting the compound (A-3a) with an oxidizing agent. The compound (A-3c) can be also prepared by reacting the compound (A-3b) with an oxidizing agent.

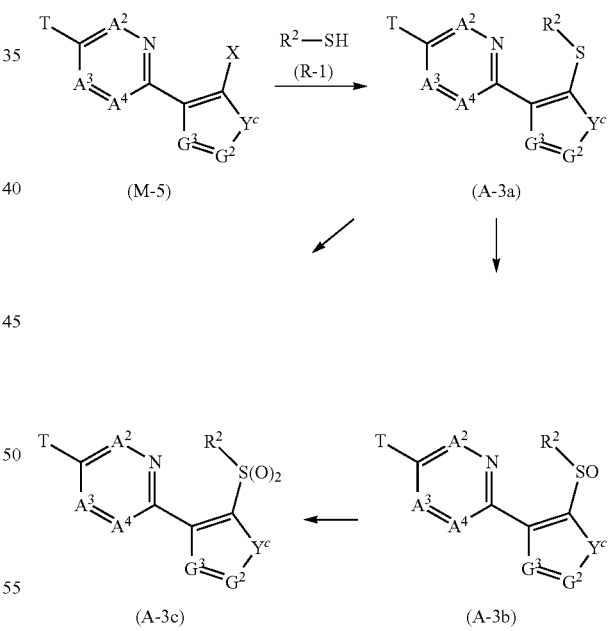

[wherein the symbols are the same as those defined above]

These reactions can be carried out according to the Process 1.

Process 4

A compound represented by formula (A-4) (hereinafter, referred to as "Compound (A-4)") can be prepared according to the below-mentioned scheme.

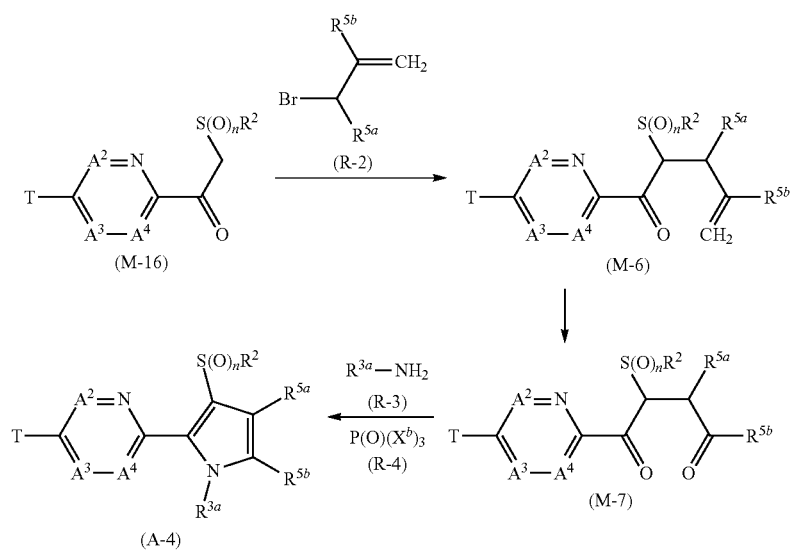

[wherein $X^b$ represents a chlorine atom or a bromine atom, and the other symbols are the same as those defined above.]

A compound represented by formula (M-6) (hereinafter, referred to as "Compound (M-6)") can be prepared by reacting a compound represented by formula (M-16) (hereinafter, referred to as "Compound (M-16)") with a compound represented by formula (R-2) (hereinafter, referred to as "Compound (R-2)") in the presence of a base.

The reaction is usually carried out in a solvent. Examples of the solvents to be used in the reaction include ethers, aromatic hydrocarbons, nitriles, aprotic polar solvents, and mixed solvents of two or more of these solvents.

Examples of the bases to be used in the reaction include alkali metal carbonates, and alkali metal hydrides.

In the reaction, the compound (R-2) is usually used within a range of 1 to 2 molar ratio(s), and the base is usually used within a range of 1 to 10 molar ratio(s), as opposed to 1 mole of the compound (M-16).

The reaction temperature in the reaction is usually within a range of −20 to 150° C. The reaction period in the reaction is usually within a range of 0.5 to 24 hours.

When the reaction is completed, water is added to reaction mixtures, and the reaction mixtures are extracted with organic solvent(s), and the organic layers re worked up (for example, drying and concentration) to obtain the compound (M-6).

The compound (M-16) is a known compound, or can be prepared according to a similar method to those described in WO 2016/121969 or WO 2017/065228 and so on.

The compound (R-2) is a commercially available compound, or can be prepared by using a known method.

A compound represented by formula (M-7) (hereinafter, referred to as "Compound (M-7)") can be prepared by reacting the compound (M-6) with an ozone, followed by reacting the resulting ozonide with a reducing agent.

The reaction between the compound (M-6) and an ozone is usually carried out in a solvent. Examples of the solvents to be used in the reaction include aromatic hydrocarbons, halogenated hydrocarbons, nitriles, aprotic polar solvents, alcohols, water, and mixed solvents of two or more of these solvents.

In the reaction between the compound (M-6) and an ozone, the ozone is usually used within a range of 1 to 100 molar ratio(s) as opposed to 1 mole of the compound (M-6).

The reaction temperature of the reaction between the compound (M-6) and an ozone is usually within a range of −78 to 30° C. The reaction period in the reaction is usually within a range of 0.1 to 24 hours.

When the reaction between the compound (M-6) and an ozone is completed, the reaction mixture containing an ozonide are reacted with a reducing agent, and water is added to reaction mixtures, and the mixtures are extracted with organic solvents, and the organic layers are worked up (for example, drying and concentration) to obtain the compound (M-7). Examples of the reducing agent include zinc and dimethyl sulfide.

The ozone can be prepared by using a known method.

A compound represented by formula (A-4) (hereinafter, referred to as "Compound (A-4)") can be prepared by reacting the compound (M-7), a compound represented by formula (R-3) (hereinafter, referred to as "Compound (R-3)") and a compound represented by formula (R-4) (hereinafter, referred to as "Compound (R-4)").

The reaction can be usually in a solvent. Examples of the solvents to be used in the reactions include aromatic hydrocarbons, nitriles, and mixed solvents of two or more of these solvents.

In the reaction, the compound (R-3) is usually used within a range of 1 to 10 molar ratio(s), and the compound (R-4) is usually used within a range of 1 to 10 molar ratio(s), as opposed to 1 mole of the compound (M-7).

The reaction temperature in the reaction is usually within a range of 0 to 120° C. The reaction period in the reaction is usually within a range of 0.1 to 48 hours.

When the reaction is completed, the reaction mixtures are worked up as usual to obtain the compound (A-4).

The compound (R-3) and the compound (R-4) are commercially available compounds or can be prepared by using the known method.

Process 5

A compound represented by formula (A-5) (hereinafter, referred to as "Compound (A-5)") can be prepared by reacting the compound (M-7) with an acid.

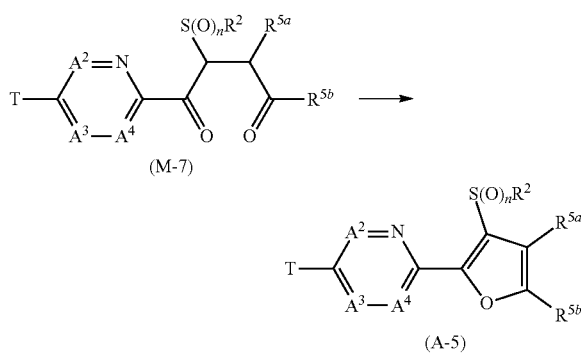

(M-7)

(A-5)

[wherein the symbols are the same as those defined above.]

The reaction is usually carried out in a solvent. Examples of the solvents to be used in the reaction include ethers, aromatic hydrocarbons, nitriles, aprotic polar solvents, and mixed solvents of two or more of these solvents.

Examples of the acid to be used in the reaction include polyphosphoric acid, 10-camphorsulfonic acid, and pyridinium p-toluene sulfonate, and the others.

In the reaction, the acid is usually within a range of 0.1 to 2 molar ratios, as opposed to 1 mole of the compound (M-7).

The reaction temperature in the reaction is usually within a range of −20 to 150° C. The reaction period in the reaction is usually within a range of 0.5 to 24 hours.

When the reaction is completed, water is added to reaction mixtures, and the reaction mixtures are extracted with organic solvent(s), and the organic layers re worked up (for example, drying and concentration) to obtain the compound (M-5).

Process 6

A compound represented by formula (A-6) (hereinafter, referred to as "Compound (A-6)") can be prepared by reacting the compound (M-7) with a sulfurizing agent.

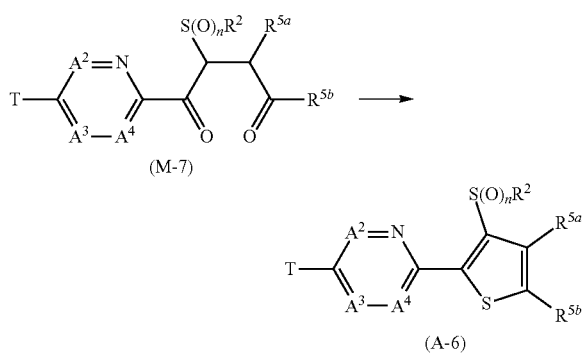

(M-7)

(A-6)

[wherein the symbols are the same as those defined above]

The reaction is usually carried out in a solvent. Examples of the solvents to be used in the reaction include ethers, aromatic hydrocarbons, nitriles, and mixed solvents of two or more of these solvents.

Examples of the sulfurizing agents to be used in the reaction include 2,4-bis(4-methoxyphenyl)-1,3-dithia-2,4-diphosphetan-2,4-disulfide (hereinafter, referred to as "Lawesson's reagent") and phosphorus pentasulfide.

In the reaction, the sulfurizing agent is usually used within a range of 1 to 2 molar ratio(s), as opposed to 1 mole of the compound (M-7).

The reaction temperature in the reaction is usually within a range of −20 to 150° C. The reaction period in the reaction is usually within a range of 0.5 to 24 hours.

When the reaction is completed, water is added to reaction mixtures, and the reaction mixtures are extracted with organic solvent(s), and the organic layers re worked up (for example, drying and concentration) to obtain the compound (A-6).

Process 7

A compound represented by formula (A-7) (hereinafter, referred to as "Compound (A-7)") can be prepared according to the below-mentioned scheme.

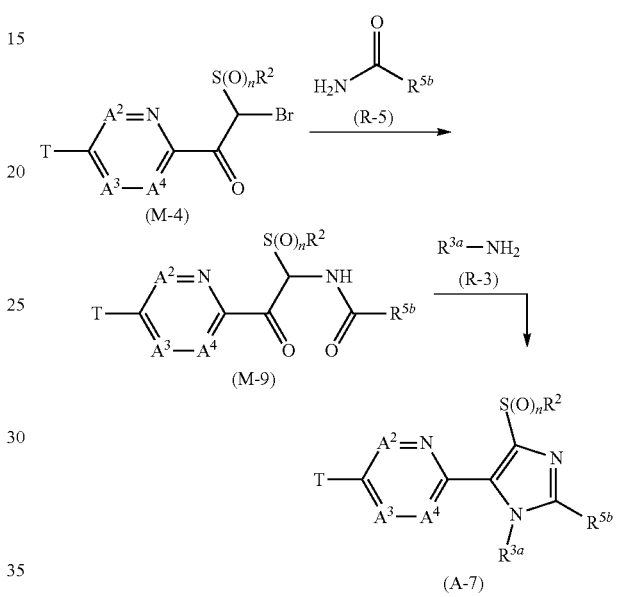

(M-4)

(M-9)

(A-7)

[wherein the symbols are the same as those defined above.]

A compound represented by formula (M-9) (hereinafter, referred to as "Compound (M-9)") can be prepared by reacting a compound represented by formula (M-4) (hereinafter, referred to as "Compound (M-4)") with a compound represented by formula (R-5) (hereinafter, referred to as "Compound (R-5)") in the presence of a base.

The reaction is usually carried out in a solvent. Examples of the solvent to be used in the reaction include ethers, aromatic hydrocarbons, nitriles, aprotic polar solvents, and mixed solvents of two or more of these solvents.

Examples of the base to be used in the reaction include alkali metal carbonates and alkali metal hydrides.

In the reaction, the Compound (R-5) is usually used within a range of 1 to 2 molar ratio(s), and the base is usually within a range of 1 to 10 molar ratio(s), as opposed to 1 mole of the compound (M-4).

The reaction temperature in the reaction is usually within a range of −20 to 150° C. The reaction period in the reaction is usually within a range of 0.5 to 24 hours.

When the reaction is completed, water is added to reaction mixtures, and the reaction mixtures are extracted with organic solvent(s), and the organic layers are worked up (for example, drying and concentration) to obtain the compound (M-9).

The compound (R-5) is a commercially available compound, or can be prepared according to a known method.

The compound (A-7) can be prepared by reacting the compound (M-9) with the compound (R-3) in the presence of an acid.

The reaction can be carried out by using the compound (M-9) in place of the compound (M-7) according to the Process 5.

Process 8

A compound represented by formula (A-8) (hereinafter, referred to as "Compound (A-8)") can be prepared by reacting the compound (M-9) with a halogenating agent.

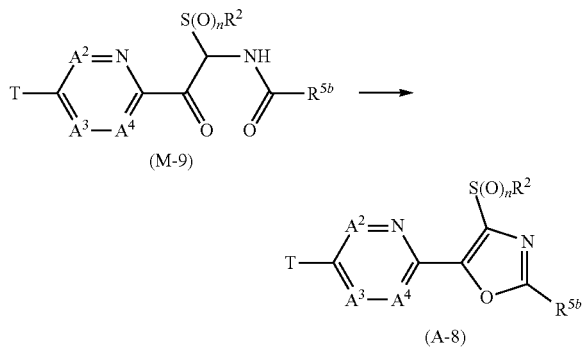

[Wherein the symbols are the same as those defined above]

The reaction is usually carried out in a solvent. Examples of the solvents to be used in the reaction include ethers, aromatic hydrocarbons, halogenated hydrocarbons, and mixed solvents of two or more of these solvents.

Examples of the halogenating agent to be used in the reaction include phosphoryl chloride and phosphoryl bromide, and the others.

In the reaction, the halogenating agent is usually within a range of 1 to 10 molar ratio(s) as opposed to 1 mole of the compound (M-9).

The reaction temperature in the reaction is usually within a range of 20 to 150° C. The reaction period in the reaction is usually within a range of 0.5 to 24 hours.

When the reaction is completed, water is added to reaction mixtures, and the reaction mixtures are extracted with organic solvent(s), and the organic layers re worked up (for example, drying and concentration) to obtain the compound (A-8).

Process 9

A compound represented by formula (A-9) (hereinafter, referred to as "Compound (A-9)") can be prepared by reacting the compound (M-9) with a sulfurizing agent.

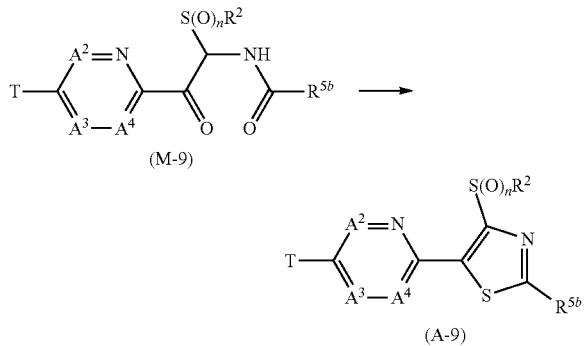

[Wherein the symbols are the same as those defined above]

The compound (A-9) can be prepared by using the compound (M-9) in place of the compound (M-7) according to a similar method to that for preparing the compound (A-6) from the compound (M-7), said method being described in the process 6.

Process 10

A compound represented by formula (A-10) (hereinafter, referred to as "Compound (A-10)") and a compound represented by formula (A-11) (hereinafter, referred to as "Compound (A-11)") can be prepared according to the below-mentioned scheme.

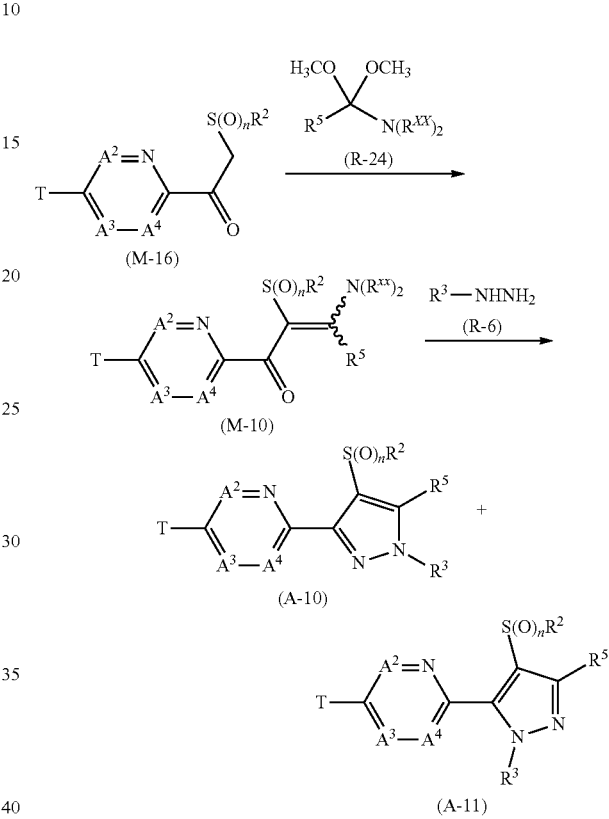

[wherein $T^x$ represents a C1-C3 alkyl group, $R^3$ represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $C(O)R^{13}$, $C(O)R^{17}$, $C(O)NR^{15a}R^{16a}$, $C(O)NR^{11}S(O)_2R^{23}$, or a hydrogen atom, $R^5$ represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15a}R^{16a}$, $NR^{24}NR^{11}C(O)NR^{15a}R^{16a}$, $N=CHNR^{15a}R^{16a}$, $N=S(O)_xR^{15}R^{16}$, $C(O)R^{13}$, $C(O)R^{17}$, $C(O)NR^{15a}R^{16a}$, $C(O)NR^{11}S(O)_2R^{23}$, $CR^{24}=NOR^{17}$, $NR^{11}CR^{24}=NOR^{17}$, a cyano group, a nitro group, a halogen atom, or a hydrogen atom, and the other symbols are the same as those defined above.]

A compound represented by formula (M-10) (hereinafter, referred to as "Compound (M-10)") can be prepared by reacting the compound (M-16) with a compound represented by formula (R24) (hereinafter, referred to as "Compound (R24)").

The reaction is usually carried out in a solvent. Examples of the solvents to be used in the reaction include ethers, aromatic hydrocarbons, nitriles, aprotic polar solvents, and mixed solvents of two or more of these solvents.

In the reaction, the compound (R24) is usually used within a range of 1 to 100 molar ratio(s) as opposed to 1 mole of the compound (M-16).

The reaction temperature in the reaction is usually within a range of 0 to 150° C. The reaction period in the reaction is usually within a range of 0.5 to 24 hours.

When the reaction is completed, water is added to reaction mixtures, and the reaction mixtures are extracted with organic solvent(s), and the organic layers re worked up (for example, drying and concentration) to obtain the compound (M-10).

The compound (R24) is a commercially available compound, or can be prepared according to a similar method to that described in WO 2013/185928.

The compound (A-10) and the compound (A-11) can be prepared by reacting the compound (M-10) with a compound represented by formula (R-6) (hereinafter, referred to as "Compound (R-6)").

The reaction is usually carried out in a solvent. Examples of the solvents to be used in the reaction include ethers, aromatic hydrocarbons, nitriles, aprotic polar solvents, alcohols, and mixed solvents of two or more of these solvents.

In the reaction, the compound (R-6) is usually used within a range of 1 to 5 molar ratio(s) as opposed to 1 mole of the compound (M-10).

The reaction temperature in the reaction is usually within a range of −20 to 150° C. The reaction period in the reaction is usually within a range of 0.1 to 24 hours.

When the reaction is completed, water is added to reaction mixtures, and the reaction mixtures are extracted with organic solvent(s), and the organic layers re worked up (for example, drying and concentration) to obtain the compound (M-10) and the compound (M-11).

The compound (R-6) is a commercially available compound, or can be prepared by using a known method.

Process 11

A compound represented by formula (A-12) (hereinafter, referred to as "Compound (A-12)") and a Compound represented by formula (A-13) (hereinafter, referred to as "Compound (A-13)") can be prepared by reacting the compound (M-10) with hydroxylamine.

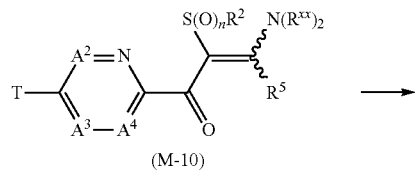

(M-10)

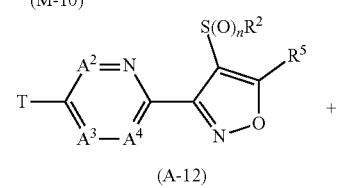

(A-12)

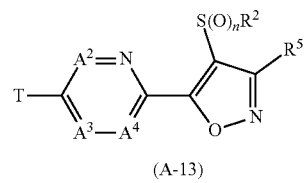

(A-13)

[wherein the symbols are the same as those defined above]

The reaction can be carried out by using hydroxylamine in place of the compound (R-6) according to the Process 10. Examples of hydroxylamine include anhydrous hydroxylamine, hydroxylamine hydrochloride salt, and hydroxylamine hydrate, and the others.

Process 12

A compound represented by formula (A-14) (hereinafter, referred to as "Compound (A-14)"), a compound represented by formula (A-15) (hereinafter, referred to as "Compound (A-15)"), a compound represented by formula (A-16) (hereinafter, referred to as "Compound (A-16)"), and a compound represented by formula (A-17) (hereinafter, referred to as "Compound (A-17)") can be prepared according the below-mentioned scheme.

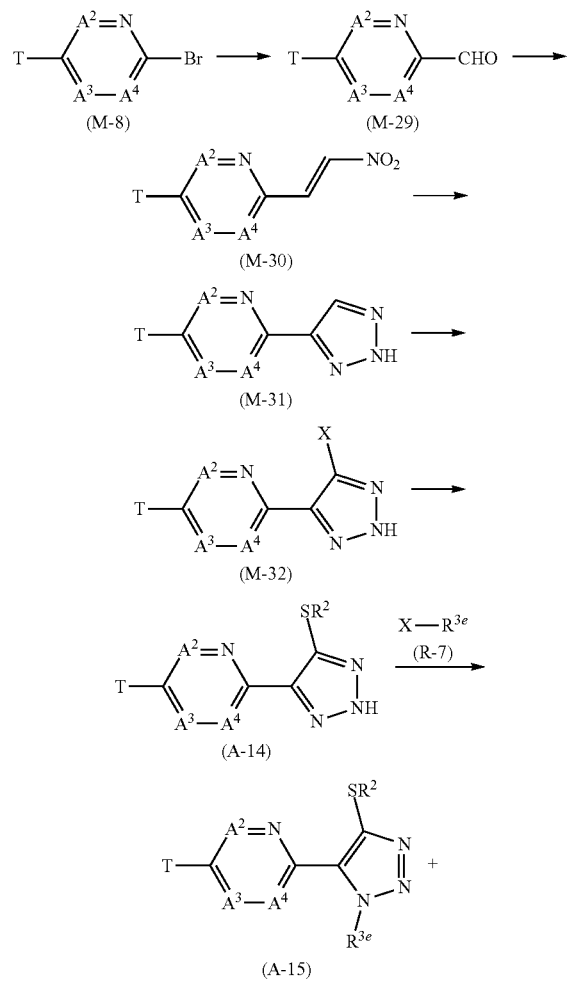

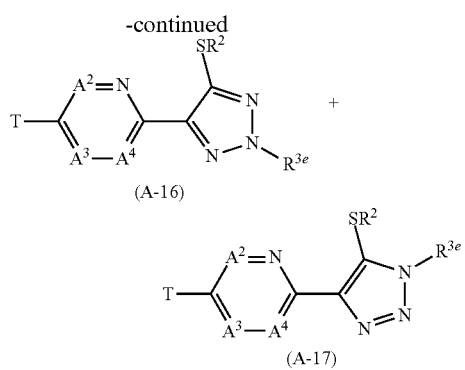

(A-16)

(A-17)

[wherein $R^{3a}$ represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $C(O)R^{13}$, $C(O)R^{17}$, $C(O)NR^{15a}R^{16a}$, or $C(O)NR^{11}S(O)_2R^{23}$, and the other symbols are the same as those defined above.]

A compound represented by formula (M-29) (hereinafter, referred to as "Compound (M-29)") can be prepared by reacting a compound represented by formula (M-8) (hereinafter, referred to as "Compound (M-8)"), a palladium catalyst (such as [1,1'-bis(diphenylphoshino)ferrocene] palladium (II) dichloride), carbon monooxide, and triethyl silane. The reaction can be conducted according to a similar method to that described in Organic Process Research & Development, 11 (1), 39-43, 2007.

A compound represented by formula (M-30) (hereinafter, referred to as "Compound (M-30)") can be prepared by reacting the compound (M-29), nitromethane and triethylamine. The reaction can be carried out according to a similar method to that described in Journal of Medicinal Chemistry (2014), 57, (10), 4382.

A compound represented by formula (M-31) (hereinafter, referred to as "Compound (M-31)") can be prepared by reacting the compound (M-30), sodium azide, and aluminium chloride. The reaction can be conducted according to a similar method to that described in Advanced Synthesis & Catalysis (2016), 358, (10), 1689.

A compound represented by formula (M-32) (hereinafter, referred to as "Compound (M-32)") can be prepared by reacting the compound (M-31) with N-chlorosuccinimide, N-bromosuccinimide, or N-iodosuccinimide. The reaction can be conducted according to a similar method to that described in Organic Letters (2009), 11, (23), 5490.

The compound (A-14) can be prepared by using the compound (M-32) in place of the compound (M-3) according to the method for preparing the compound (A-2a) from the compound (M-3) which is described in the process 2.

The compound (A-15), the compound (A-16), and the compound (A-17) can be prepared by reacting the compound (A-14) with a compound represented by formula (R-7) (hereinafter, referred to as "Compound (R-7)") in the presence of a base.

The reaction is usually carried out in a solvent. Examples of the solvent to be used in the reaction include ethers, aromatic hydrocarbons, aprotic polar solvents, and mixed solvents of two or more of these solvents.

Examples of the bases to be used in the reaction include organic bases, alkali metal hydrides, and alkali metal carbonates.

In the reaction, the compound (R-7) is usually used within a range of 1 to 10 molar ratio(s), and the base is usually used within a range of 0.1 to 5 molar ratios, as opposed to 1 mole of the compound (A-14).

The reaction temperature in the reaction is usually within a range of −20 to 120° C. The reaction period in the reaction is usually within a range of 0.1 to 24 hours.

When the reaction is completed, water is added to reaction mixtures, and the reaction mixtures are extracted with organic solvent(s), and the organic layers re worked up (for example, drying and concentration) to obtain the compound (A-15), the compound (A-16) and the compound (A-17).

The compound (R-7) is a commercially available Compound, or can be prepared by using a known method.

Process 13

A compound represented by formula (A-18) (hereinafter, referred to as "Compound (A-18)") can be prepared according to the below-mentioned scheme.

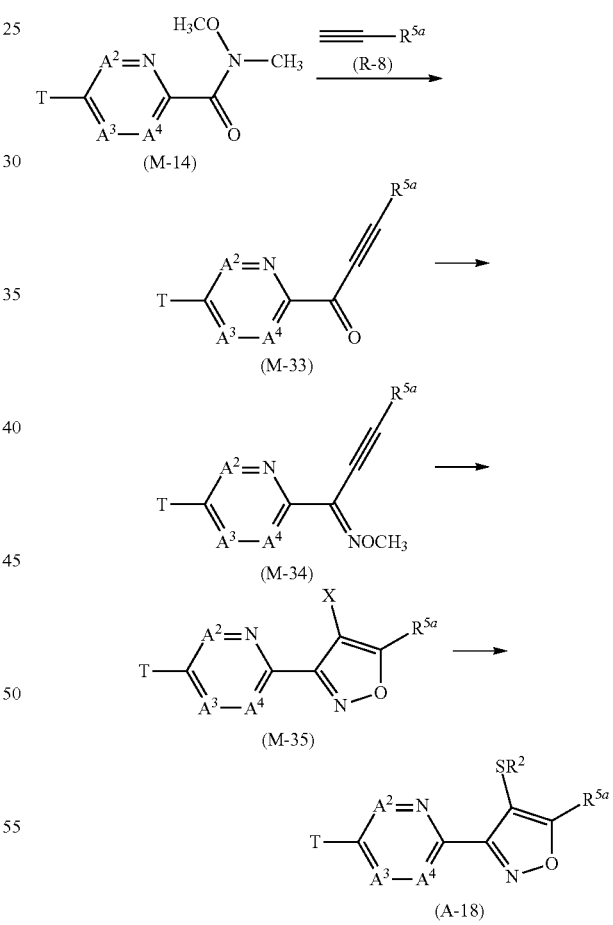

[wherein the symbols are the same as those defined above]

A compound represented by formula (M-33) (hereinafter, referred to as "Compound (M-33)") can be prepared by reacting a compound represented by formula (M-14) (hereinafter, referred to as "Compound (M-14)"), a compound represented by formula (R8) (hereinafter, referred to as "Compound (R8)"), and a base (such as butyl lithium). The reaction can be carried out according to a similar method to that described in Journal of the American Chemical Society (2008), 130, (30), 9942.

The compound (R) is a commercially available compound, or can be prepared by using the known method.

A compound represented by formula (M-34) (hereinafter, referred to as "Compound (M-34)") can be prepared by reacting the compound (M-33) with O-methyl hydroxylamine. The reaction can be carried out according to a similar method to that described in Journal of Organic Chemistry (2007), 72, (25), 9643.

A compound represented by formula (M-35) (hereinafter, referred to as "Compound (M-35)") can be prepared by reacting the compound (M-34) with N-chlorosuccinimide, N-bromosuccinimide, or N-iodosuccinimide. The reaction can be carried out according to a similar method to that described in Journal of Organic Chemistry (2007), 72, (25), 9643.

The compound (A-18) can be prepared by using the compound (M-35) in place of the compound (M-3) according to a similar method to that for preparing the Compound (A-2a) from the Compound (M-3), said method being described in the Process 2.

Process 14

A compound represented by formula (A-19) (hereinafter, referred to as "Compound (A-19)") and a compound represented by formula (A-20) (hereinafter, referred to as "Compound (A-20)") can be prepared according to the below-mentioned scheme.

ylenetetramine. The reaction is carried out according to a method described in Medicinal Chemistry (2014), 57, (5), 2058.

A compound represented by formula (M-37) (hereinafter, referred to as "Compound (M-37)") can be prepared by reacting the compound (M-36) with the compound (R-8). The reaction can be carried out according to a similar method to that described in Journal of Organic Chemistry (2016), 81, (9), 3688.

A compound represented by formula (M-38) (hereinafter, referred to as "Compound (M-38)") can be prepared by reacting the compound (M-37) with triisopropylsilylchloride. The reaction can be carried out according to a similar method to that described in RSC Advances (2016), 6, (41), 3, 4428.

A compound represented by formula (M-39) (hereinafter, referred to as "Compound (M-39)") can be prepared by reacting the compound (M-38) with N-bromosuccinimide. The reaction can be carried out according to a similar method to that described in WO 2010/135530.

A compound represented by formula (M-40) (hereinafter, referred to as "Compound (M-40)") can be prepared by using the compound (M-39) in place of the compound (M-3) according to a similar method that for preparing the compound (A-2a) from the compound (M-3).

The compound (A-19) can be prepared by reacting the compound (M-40) with tetrabutyl ammonium fluoride.

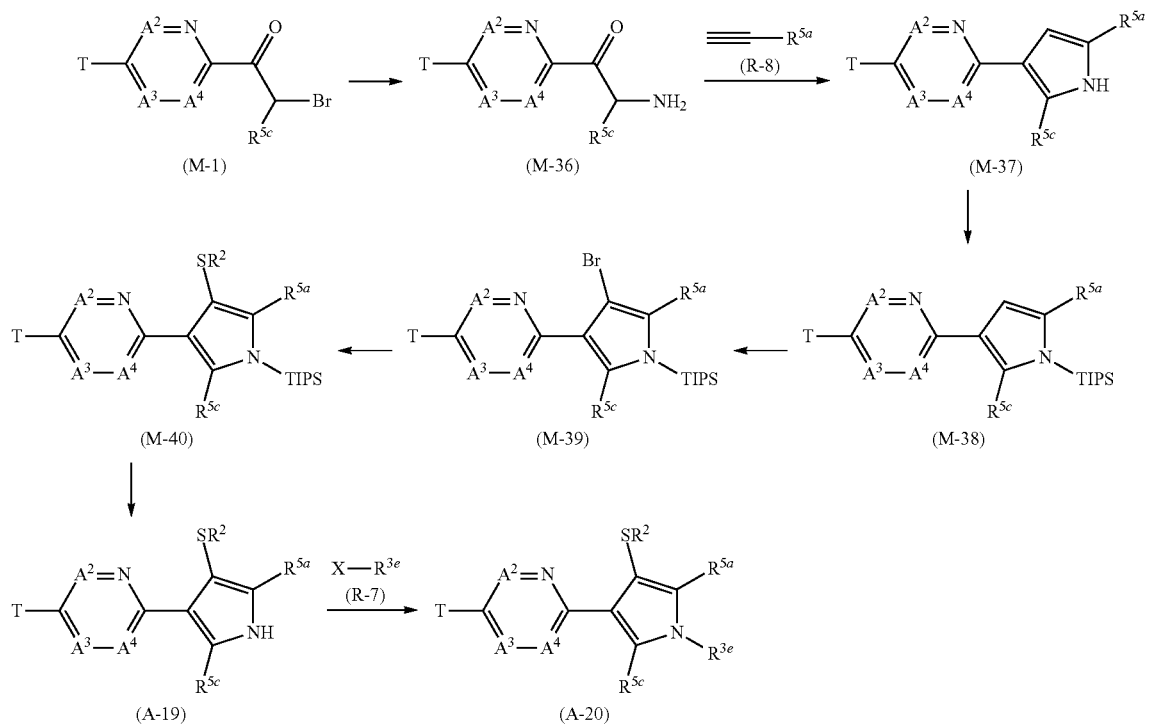

[wherein TIPS represents a triisopropylsilyl group, and the other symbols are the same as those defined above]

A compound represented by formula (M-36) (hereinafter, referred to as "Compound (M-36)") can be prepared by reacting a compound represented by formula (M-1) (hereinafter, referred to as "Compound (M-1)") with hexameth- The reaction is usually carried out in a solvent. Examples of the solvents to be used in the reaction include ethers, aromatic hydrocarbons, nitriles, aprotic polar solvents, and mixed solvents of two or more of these solvents.

In the reaction, tetrabutyl ammonium fluoride is usually used within a range of 1 to 2 molar ratio(s) as opposed to 1 mole of the compound (M-40).

The reaction temperature in the reaction is usually within a range of −20 to 100° C. The reaction period in the reaction is usually within a range of 0.1 to 24 hours.

When the reaction is completed, water is added to reaction mixtures, and the reaction mixtures are extracted with organic solvent(s), and the organic layers re worked up (for example, drying and concentration) to obtain the compound (A-19).

The compound (A-20) can be prepared by reacting the compound (A-19) with the compound (R-7). The reaction can be carried out by using the compound (A-19) in place of the compound (A-14) according to a similar method to that for preparing the compound (A-15) from the compound (A-14), said method being described in the Process 12.

Process 15

A compound represented by formula (A-21) (hereinafter, referred to as "Compound (A-21)") can be prepared according to the below-mentioned scheme.

A compound represented by formula (AM-42) (hereinafter, referred to as "Compound (M-42)") can be prepared by reacting a compound represented by formula (M-41) (hereinafter, referred to as "Compound (M-41)") with the compound (R-5). The reaction can be carried out according to a similar method to that described in WO 2008/051493.

A compound represented by formula (M-43) (hereinafter, referred to as "Compound (M-43)") can be prepared by reacting the compound (M-42) with lithium bis(trimethylsilyl)amide, and followed by reacting with bromine. The reaction can be carried out according to a similar method to that described in Journal of Organic Chemistry, (2008), 73(8), 3303.

The compound (A-21) can be prepared by using the compound (M-43) in place of the compound (M-2) according to a similar method to that for preparing the compound (A-1a) from the compound (M-2), said method being described in the Process 1.

Process 17

A compound represented by formula (A-22) (hereinafter, referred to as "Compound (A-22)") can be prepared according to the below-mentioned scheme.

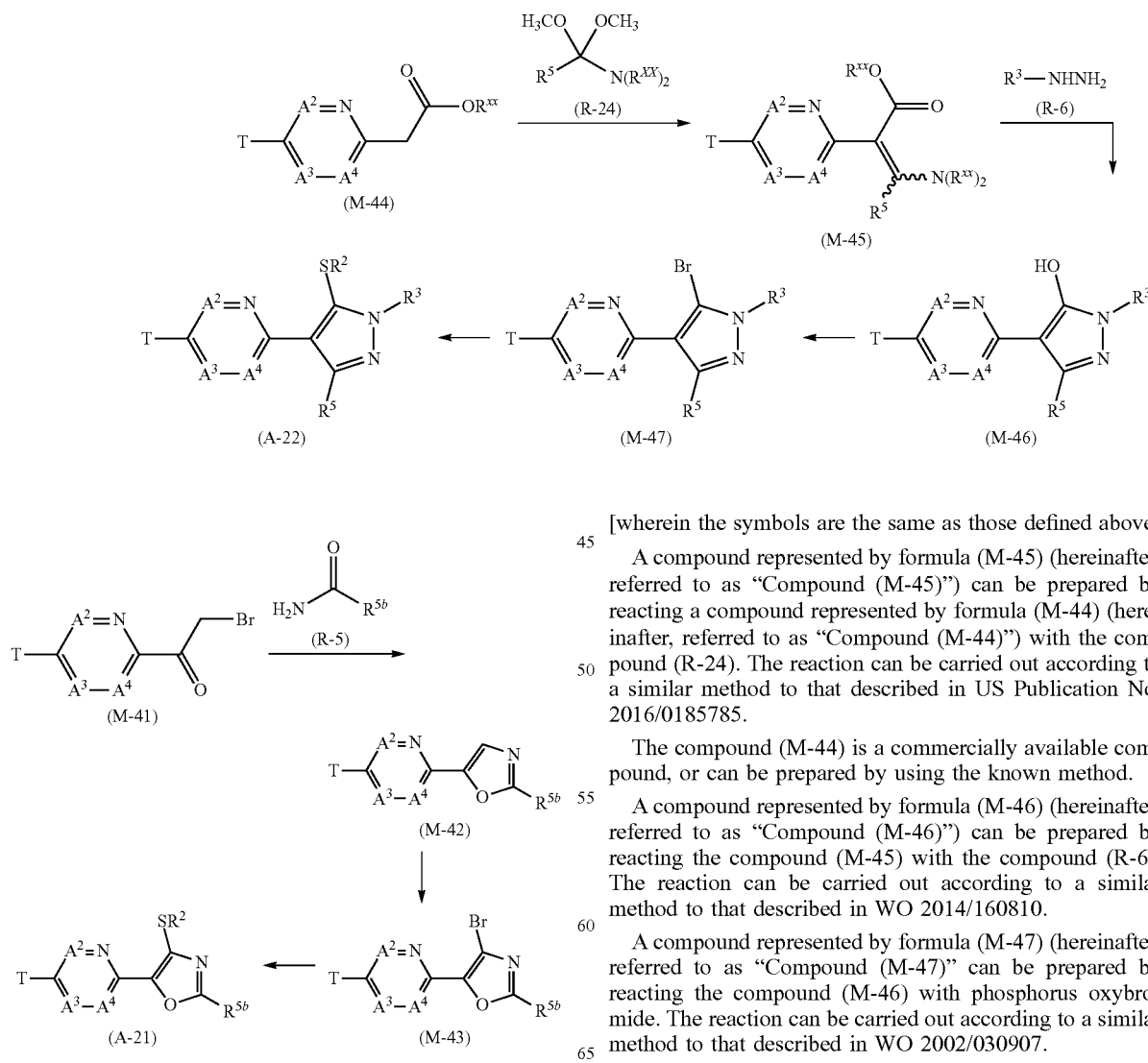

[wherein the symbols are the same as those defined above]

A compound represented by formula (M-45) (hereinafter, referred to as "Compound (M-45)") can be prepared by reacting a compound represented by formula (M-44) (hereinafter, referred to as "Compound (M-44)") with the compound (R-24). The reaction can be carried out according to a similar method to that described in US Publication No. 2016/0185785.

The compound (M-44) is a commercially available compound, or can be prepared by using the known method.

A compound represented by formula (M-46) (hereinafter, referred to as "Compound (M-46)") can be prepared by reacting the compound (M-45) with the compound (R-6). The reaction can be carried out according to a similar method to that described in WO 2014/160810.

A compound represented by formula (M-47) (hereinafter, referred to as "Compound (M-47)" can be prepared by reacting the compound (M-46) with phosphorus oxybromide. The reaction can be carried out according to a similar method to that described in WO 2002/030907.

A compound (A-22) can be prepared by using the compound (M-47) in place of the compound (M-5) according to

[wherein the symbols are the same as those defined above.]

a similar method to that for preparing the compound (A-3a) from the compound (M-5), said method being described in the Process 3.

Process 18

A compound represented by formula (A-23) (hereinafter, referred to as "Compound (A-23)") can be prepared according to the below-mentioned scheme.

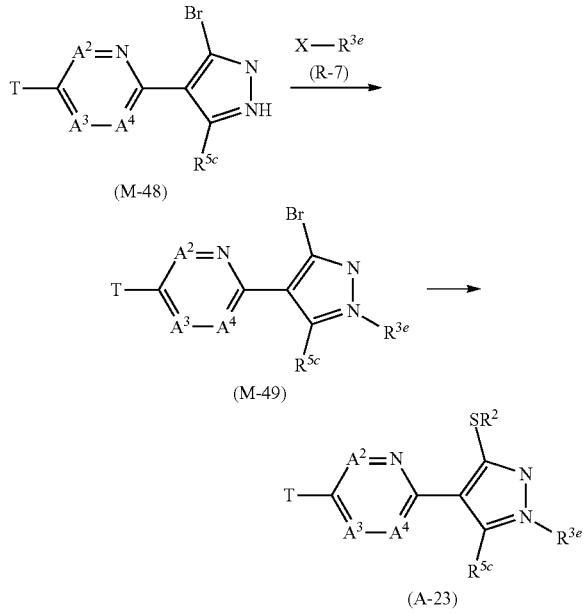

(M-48)

(M-49)

(A-23)

[wherein the symbols are the same as those defined above]

A compound represented by formula (M-49) (hereinafter, referred to as "Compound (M-49)") can be prepared by using a compound represented by formula (M-48) (hereinafter, referred to as "Compound (M-48)") in place of the Compound (A-19) according to a similar method to that for preparing the compound (A-20) from the compound (A-19), said method being described in the Process 14.

The compound (A-23) can be prepared by using the compound (M-49) in place of the compound (M-3) according to a similar method to that for preparing the compound (A-2a) from the compound (M-3), said method being described in the Process 2.

Process 19

A compound represented by formula (A-24) (hereinafter, referred to as "Compound (A-24)") can be prepared according to the below-mentioned scheme.

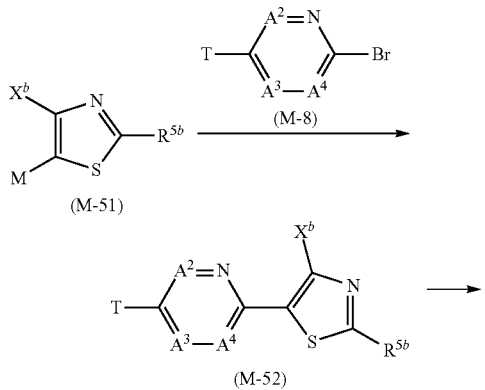

(M-51)

(M-8)

(M-52)

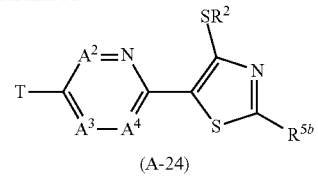

(A-24)

[wherein M represents a C1-C3 alkoxyboranyl group, a 4,4,5,5-tetramethyl-1,3,2-dioxabororan-2-yl group, a tributylsutannyl group, ZnCl, MgCl, or MgBr, and the other symbols are the same as those defined above.]

A compound represented by formula (M-52) (hereinafter, referred to "Compound (M-52)") can be prepared by reacting the Compound (M-5) with the compound (M-8) in the presence of a catalyst.

The reaction can be usually carried out is a solvent. Examples of the solvents to be used in the reaction include ethers, aromatic hydrocarbons, aprotic polar solvents, water, and mixed solvents of two or more of these solvents.

Examples of the catalyst to be used in the reaction include palladium catalysts (such as tetrakis(triphenylphosphine) palladium (0), 1,1'-bis(diphenylphosphino)ferrocene palladium (II) dichloride, tris(dibenzylideneacetone) dipalladium (0), and palladium (II) acetate); nickel catalysts (such as bis(cyclooctadiene) nickel (0) and nickel(II) chloride); and copper catalysts (such as copper (I) iodide and copper (I) chloride).

A ligand, a base, and/or an alkali metal halide may be used in the reaction as needed.

Examples of the ligand include triphenylphosphine, Xantphos, 2,2'-bis(diphenylphosphino)-1,1'-binaphthyl, 1,1'-bis (diphenylphosphino)ferrocene, 2-dicyclohexylphosphino-2', 4',6'-triisopropylbiphenyl, 2-dicyclohexylphosphino-2',6'-dimethoxybiphenlnyl, 1,2-bis (diphenylphosphino)ethane, 2,2'-bipyridine, 2-aminoethanol, 8-hydroxyqunoline, and 1,10-phenanthroline. When a ligand is used in the reaction, the ligand is used within a range of 0.01 to 1 molar ratio(s) as opposed to 1 mole of the compound (M-51).

Examples of the base include alkali metal hydrides, alkali metal carbonates, and organic bases. When the base is used in the reaction, the base is usually used within a range of 0.1 to 4 molar ratios as opposed to 1 mole of the compound (M-51).

Examples of the alkali metal halides include potassium fluoride, sodium fluoride, lithium chloride, and sodium chloride. When the alkali metal halide is used in the reaction, the alkali metal halide is usually used within a range of 0.1 to 5 molar ratios as opposed to 1 mole of the compound (M-51).

In the reaction, the compound (M-8) is usually used within a range of 1 to 10 molar ratio(s), and the catalyst is usually used within a range of 0.01 to 0.5 molar ratios as opposed to 1 mole of the compound (M-51).

The reaction temperature in the reaction is usually within a range of −20 to 200° C. The reaction period in the reaction is usually within a range of 0.1 to 24 hours.

When the reaction is completed, water is added to reaction mixtures, and the reaction mixtures are extracted with organic solvent(s), and the organic layers are worked up (for example, drying and concentration) to obtain the compound (M-52).

The compound (A-24) can be prepared by reacting the compound (M-52) in place of the compound (M-2) according to a similar method to that for preparing the compound (A-1a) from the Compound (M-2), said method being described in the Process 1.

Process 20

A compound represented by formula (A-25) (hereinafter, referred to as "Compound (A-25)") can be prepared according to the below-mentioned scheme.

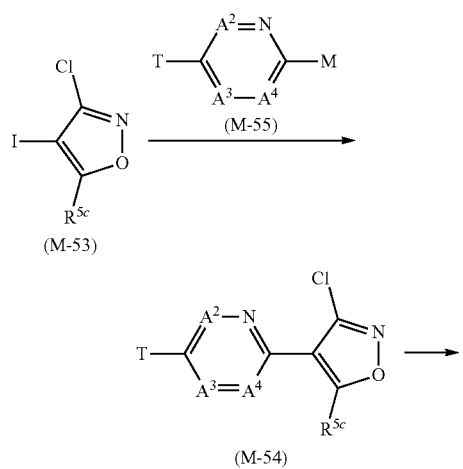

[wherein the symbols are the same as those defined above]

A compound represented by formula (M-54) (hereinafter, referred to as "Compound (M-54)") can be prepared by reacting a compound represented by formula (M-53) (hereinafter, referred to as "Compound (M-53)") with a compound represented by formula (M-55) (hereinafter, referred to as "Compound (M-55)") in the presence of a catalyst. The reaction can be carried out by using the compound (M-53) in place of the compound (M-51) and the compound (M-55) in place of the compound (M-8) according to a similar method to that for preparing the compound (M-52) from the compound (M-51).

The compound (M-53) is a commercially available compound, or can be prepared according to the method described in or Journal of Organic Chemistry, (2015), 80 (4), 2413.

The compound (M-55) is a commercially available compound, or can be prepared according to a similar method to those described in Angewandte Chemie, International Edition, 2018, 57 (4), 1108, European Journal of Inorganic Chemistry, 2017, (34), 4020, WO 2017/17902, or Chemical Science, 2017, 8 (11), 7492.

The compound (A-25) can be prepared by using the compound (M-54) in place of the compound (M-3) according to a similar method to that for preparing the compound (A-2a) from the Compound (M-3), said method being described in the Process 2.

Process 21

A compound represented by formula (A-26) (hereinafter, referred to as "Compound (A-26)") can be prepared according to the below-mentioned scheme.

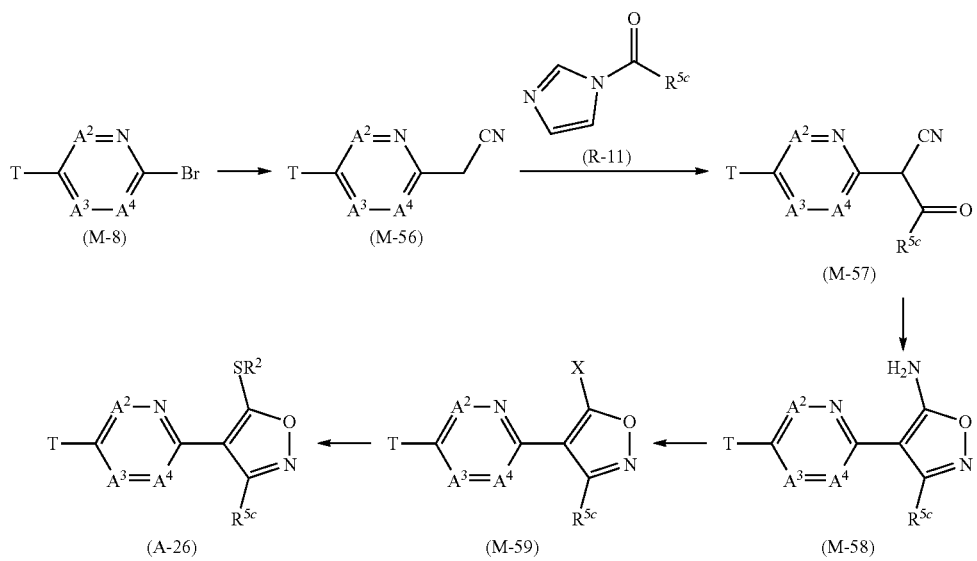

[wherein the symbols are the same as those defined above.]

A compound represented by formula (M-56) (hereinafter, referred to as "Compound (M-56)") can be prepared by reacting the compound (M-8) with acetonitrile in the presence of a base. The reaction can be carried out according to a similar method to that described in Synlett, 2000, (10), 1488.

A compound represented by formula (M-57) (hereinafter, referred to as "Compound (M-57)") can be prepared by reacting the compound (M-56) with a compound presented by formula (R11) (hereinafter, referred to as "Compound (R11)") in the presence of a base. The reaction can be carried -continued

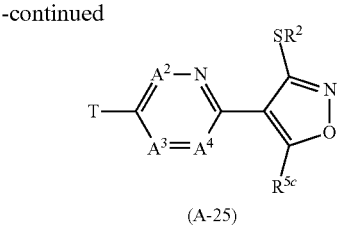

[wherein the symbols are the same as those defined above]

out according to a similar method to that described in Journal of the American Chemical Society (2011), 133, (37), 14785.

The compound (R11) is a commercially available compound, or can be prepared by using the known method.

A compound represented by formula (M-58) (hereinafter, referred to as "Compound (M-58)") can be prepared by reacting the Compound (M-57) with hydroxylamine in the presence of a base. The reaction can be carried out according to a similar method to that described in Bioorganic & Medicinal Chemistry (2017), 25, (6), 1914.

A compound represented by formula (M-59) (hereinafter, referred to as "Compound (M-59)") can be prepared by reacting the compound (M-58), tetrabutylammonium nitrite and trimethylsilyl chloride. The reaction can be carried out according to a similar method to that described in WO 2008/017361.

The compound (A-26) can be prepared by using the compound (M-59) in place of the compound (M-5) according to a similar method to that for preparing the compound (A-3a) from the compound (A-5), said method being described in the Process 3.

Process 22

A compound represented by formula (A-27) (hereinafter, referred to as "Compound (A-27)") can be prepared according the below-mentioned scheme.

A compound represented by formula (M-61) (hereinafter, referred to as "Compound (M-61)") can be prepared by reacting the compound (M-60) with butyl lithium. The reaction can be carried out according to the method described in Journal of Organic Chemistry, 1990, 55(2), 695.

A compound represented by formula (M-62) (hereinafter, referred to as "Compound (M-62)") can be prepared by reacting the compound (M-61) with a compound represented by formula (R-12) (hereinafter, referred to as "Compound (R-12)") in the presence of a butyl lithium, followed by reacting with a compound represented by formula (R13) (hereinafter, referred to as "Compound (R13)"). The reaction can be carried out according to a similar method to that described in Tetrahedron Letters, 2004, 45, (30), 5881.

The compound (R-12) and the compound (R-13) are commercially available compounds, or can be prepared by using a known method.

The compound (A-27) can be prepared by reacting the compound (M-62) with a catalyst (such as copper bromide). The reaction can be carried out according to a similar method to that described in Russian Journal of Organic Chemistry, 2010, 46, (7), 1038.

Process 23

A compound represented by formula (A-28) (hereinafter, referred to as "Compound (A-28)") can be prepared according to the below-mentioned scheme.

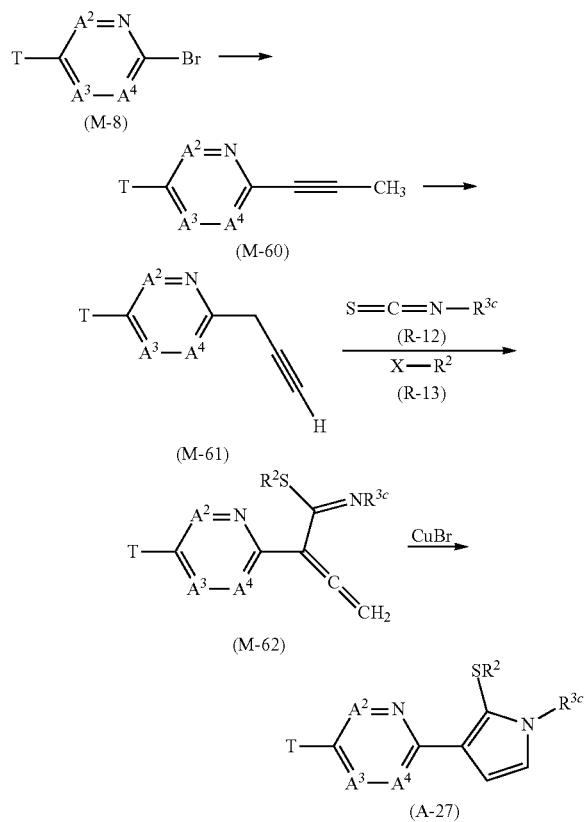

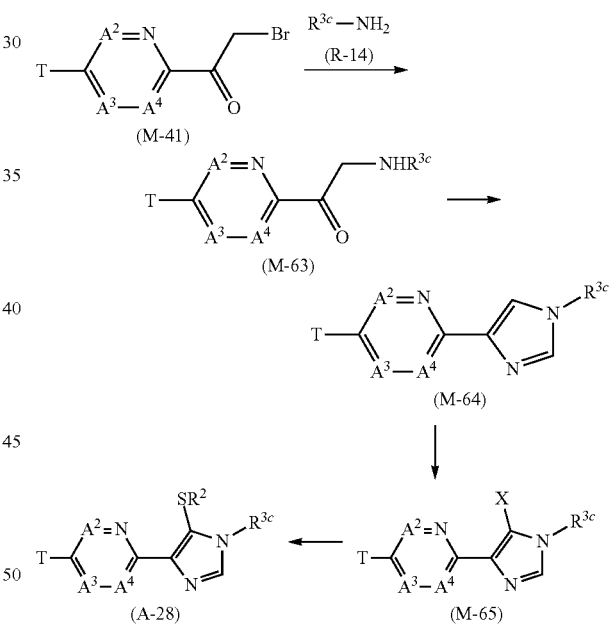

[wherein the symbols are the same as those defined above]

A compound represented by formula (M-60) (hereinafter, referred to as "Compound (M-60)") can be prepared by reacting the compound (M-8) with propyne in the presence of a catalyst. The reaction can be carried out according to a similar method to that described in Journal of Medicinal Chemistry, 2014, 57 (17), 7412.

[wherein the symbols are the same as those defined above]

A compound represented by formula (A-63) (hereinafter, referred to as "Compound (A-63)") can be prepared by reacting the compound (M-41) with a compound represented by formula (R14) (hereinafter, referred to as "Compound (R14)"). The reaction can be carried out according to a similar method to that described in WO 2009/152025.

The compound (R14) is a commercially available compound, or can be prepared by using a known method.

A compound represented by formula (M-64) (hereinafter, referred to as "Compound (M-64)") can be prepared by reacting the compound (M-63) with formamide in the presence of a base. The reaction can be carried out according to a similar method to that described in WO 2009/152025.

A compound represented by formula (M-65) (hereinafter, referred to as "Compound (M-65)" can be prepared by reacting the compound (M-64) with N-chlorosuccinimide, N-bromosuccinimide or N-iodosuccinimide. The reaction can be carried out according to a similar method to that described in ACS Medicinal Chemistry Letters, 2013, 4 (6), 509.

The compound (A-28) can be prepared by using the compound (M-65) in place of the compound (M-5) according to a similar method to that for preparing the compound (A-3a) from the compound (M-5), said method being described in the Process 3.

Hereinafter, a process for preparing a production intermediate compound is described.

Reference Process 1

The compound (M-4) can be prepared by reacting the compound (M-16) with a brominating agent.

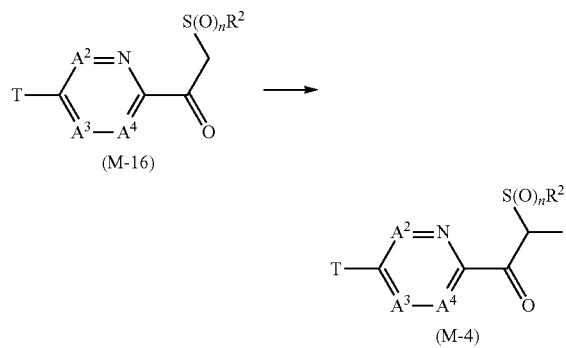

[wherein the symbols are the same as those defined above]

The reaction can be conducted according to a similar method to that described in WO 2013/191113.

Reference Process 2

The compound (M-14) and the compound (M-41) can be prepared according to the below-mentioned scheme.

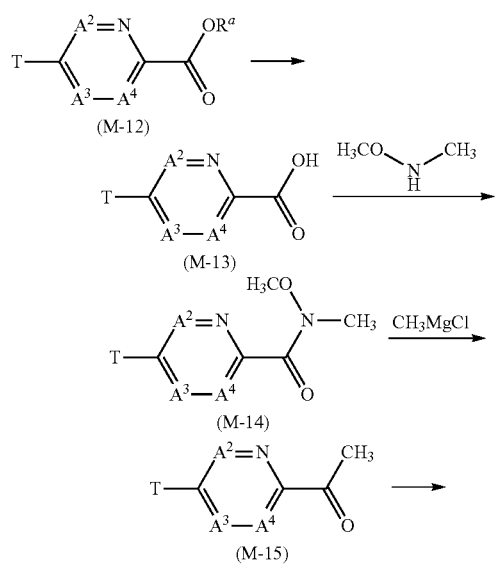

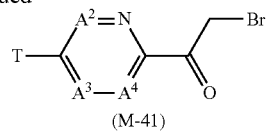

[wherein Ra represents a methyl group or an ethyl group, and the other symbols are the same as defied above]

The compound (M-14) can be prepared by hydrolyzing a compound represented by formula (M-12) (hereinafter, referred to as "Compound (M-12)"), followed by reacting with N,O-dimethyl hydroxyl amine. These reactions can be conducted according to a similar method to that described in Journal of Medicinal Chemistry, 56, 3980 (2013).

A compound represented by formula (M-15) (hereinafter, referred to as "Compound (M-15)") can be prepared by reacting the compound represented by formula (M-14) with methyl magnesium chloride. The reaction can be carried out according to a similar method to that described in WO 2008/116665.

The compound (M-41) can be prepared by reacting the compound (M-15) with a brominating agent. The reaction can be prepared according to a similar method to that described in WO 2013/191113.

Reference Process 3

A compound represented by formula (M-12a) (hereinafter, referred to as "Compound (M-12a)") can be prepared by reacting a compound represented by formula (M-18a) (hereinafter, referred to as "Compound (M-12a)") with a compound represented by formula (R15) (hereinafter, referred to as "Compound (R15)" in the presence of a base.

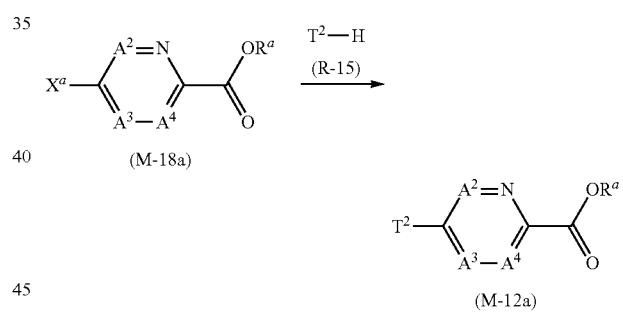

[wherein $X^a$ represents a fluorine atom or a chlorine atom, $T^2$ represents $OR^1$, $NR^1R^{29}$, a group represented by formula T-5, a group represented by formula T-6, a group represented by formula T-7 or a group represented by formula T-8, and the other symbols are the same as those defined above]

The reaction is usually carried out in a solvent. Examples of the solvents to be used in the reaction include ethers, aromatic hydrocarbons, nitriles, aprotic polar solvents, and mixed solvents of two or more of these solvents.

Examples of the base to be used in the reaction include alkali metal carbonates, and alkali metal hydrides.

In the reaction, the compound (R15) is usually used within a range of 1 to 2 molar ratio(s), and the base is usually used within a range of 1 to 10 molar ratio(s), as opposed to 1 mole of the compound (M-18a).

The reaction temperature in the reaction is usually within a range of −20 to 150° C. The reaction period in the reaction is usually within a range of 0.5 to 24 hours.

When the reaction is completed, water is added to the reaction mixtures, and the reaction mixtures are extracted with an organic solvent, and the organic layers are worked up (for example, drying and concentration) to obtain the compound (M-12a).

The compound (R15) and the compound (M-18a) are commercially available compounds, or can be prepared by using a known method.

Reference Process 4

A compound represented by formula (M-12b) can be prepared by reacting a compound represented by formula (M-18b) (hereinafter, referred to as "Compound (M-18b)") with a compound represented by formula (R16) (hereinafter, referred to as "Compound (R16)").

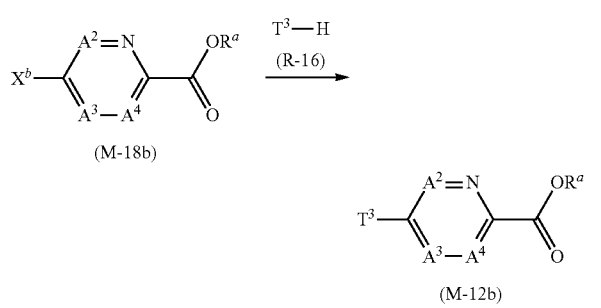

(M-18b)

(M-12b)

[wherein $T^3$ represents a group represented by the above-mentioned formula T-1, a group represented by the above-mentioned formula T-2, a group represented by the above-mentioned formula T-3, a group represented by the above-mentioned formula T-4, a group represented by the above-mentioned formula T-9, a group represented by the above-mentioned formula T-10, a group represented by the above-mentioned formula T-11 or a group represented by the above-mentioned formula T-12, and the other symbols are the same as those defined above]

The reaction can be conducted according to a similar method to that for preparing the compound (M-52) from the compound (M-51), said method being described in the Process 19.

The compound (R16) and the compound (M-18b) are commercially available compounds, or can be prepared by using a known method.

Reference Process 5

The compound represented by formula (M-12c) can be prepared by reacting a compound represented by formula (M-18c) (hereinafter, referred to as "Compound (M-18c)") with a compound represented by formula ($R^{17}$) (hereinafter, referred to as "Compound ($R^{17}$)").

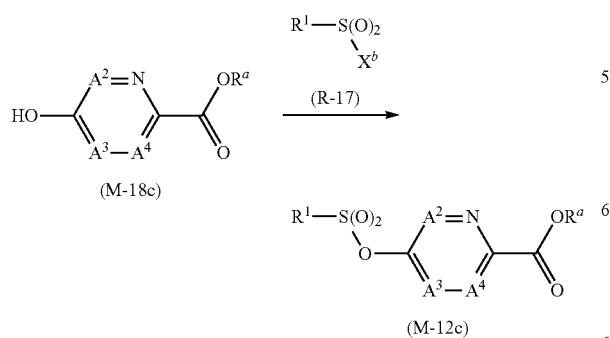

(M-18c)

(M-12c)

[wherein the symbols are the same as those defined above]

The reaction can be conducted according to a similar method to that described in WO 2016/121969.

The compound (R17) and the compound (M-18c) are commercially available compounds, or can be prepared according to known method.

Reference Process 6

A compound represented by formula (M-12d) (hereinafter, referred to as "Compound (M-12d)") can be prepared by reacting the compound (M-18b) with a compound represented by formula (R18) (hereinafter, referred to as "Compound (R18)") in the presence of a copper.

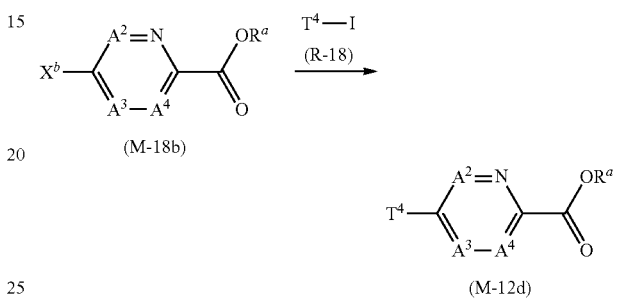

(M-18b)

(M-12d)

[wherein $T^4$ represents a C1-C10 chain hydrocarbon group which have one or more halogen atoms, a (C1-C5 alkoxy) C2-C5 alkyl group which have one or more halogen atoms, a (C1-C5 alkylsulfanyl)C2-C5 alkyl group which have one or more halogen atoms, a (C1-C5 alkylsulfinyl group)C2-C5 alkyl group which have one or more halogen atoms, a (C1-C5 alkylsulfonyl group)C2-C5 alkyl group which have one or more halogen atoms, a (C3-C7 cycloalkyl)C1-C3 alkyl group which may optionally have one or more substituents selected from Group G, or a C3-C7 cycloalkyl group which may optionally have one or more substituents selected from Group G, and the other symbols are the same as those defined above]

The reaction is usually carried out in a solvent. Examples of the solvents to be used in the reaction include aromatic hydrocarbons, aprotic polar solvents, and mixed solvents of two or more of these solvents.

In the reaction, the compound (R18) is usually used within a range of 1 to 18 molar ratio(s), and the copper is usually used within a range of 1 to 10 molar ratio(s), as opposed to 1 mole of the compound (M-18b).

The reaction temperature in the reaction is usually within a range of 40 to 200° C. The reaction period in the reaction is usually within a range of 0.1 to 24 hours.

When the reaction is completed, water is added to the reaction mixture, and the reaction mixture is extracted with an organic solvent, and the organic layer is worked up (for example, drying and concentration) to obtain the compound (M-12d).

The compound (R18) is a commercially available compound, or can be prepared by using a known method.

Reference Process 7

A compound represented by formula (M-12e) (hereinafter, referred to as "Compound (M-12e)") can be prepared by reacting a compound represented by formula (M-18d) (hereinafter, referred to as "Compound (M-18d)") with a compound represented by formula (R19) (hereinafter, referred to as "Compound (R19)")

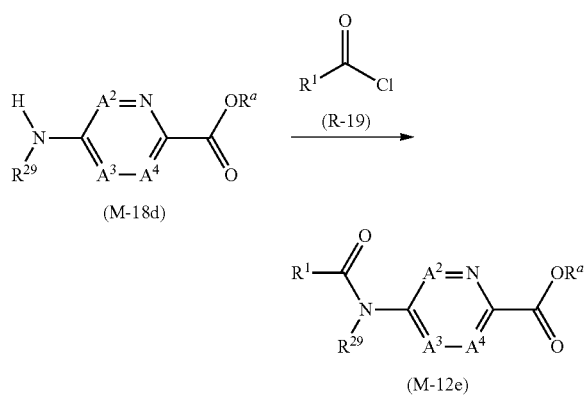

(M-18d)

(M-12e)

[wherein the symbols are the same as those defined above]

The reaction is usually carried out in a solvent. Examples of the solvent to be used in the reaction include ethers, halogenated hydrocarbons, aromatic hydrocarbons, aprotic polar solvents, and mixed solvents of two or more of these solvents.

A base may be used in the reaction as needed, and examples of the base include organic bases. When the base is used in the reaction, the base is used within a range of 0.1 to 10 molar ratios(s) as opposed to 1 mole of the compound (M-18d).

In the reaction, the compound (R19) is usually carried out within a range of 1 to 10 molar ratio(s), as opposed to 1 mole of the compound (M-18d).

The reaction temperature in the reaction is usually within a range of −20 to 120° C. The reaction period in the reaction include 0.1 to 24 hours.

When the reaction is completed, water is added to the reaction mixture, and the reaction mixture is extracted with an organic solvent, and the organic layer is worked up (for example, drying and concentration) to obtain the compound (M-12e).

The compound (M-18d) and the compound (R19) are commercially available compounds, or can be prepared by using a known method.

Reference Process 8

A compound represented by formula (M-12f) (hereinafter referred to as "Compound (M-12f)") can be prepared by the compound (M-18b) with a compound represented by formula (R-20) (hereinafter, referred to as "Compound (R-20)") in the presence of a base.

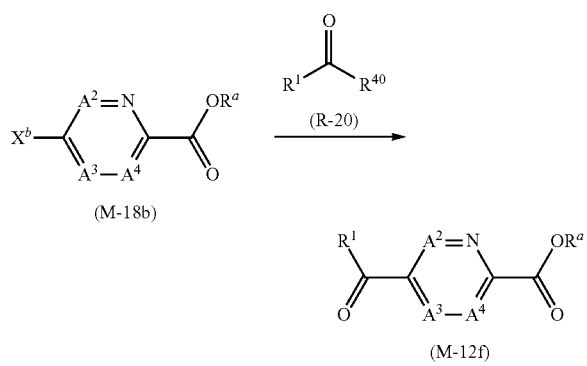

(M-18b)

(M-12f)

[wherein $R^{40}$ represents an ethoxy group, an ethoxy group, a phenoxy group, $N(CH_3)OCH_3$, and the other symbols are the same as those defined above]

The reaction is usually carried out in a solvent. Examples of the solvents to be used in the reaction include ethers, and aromatic hydrocarbons.

Examples of the bases to be used in the reaction include butyl lithium, lithium diisopropylamide, lithium tetramethylpiperidide, lithium bis(trimethylsilyl)amide and the others.

In the reaction, the compound (R-20) is usually used within a range of 1 to 10 molar ratio(s), and the base is usually used within a range of 1.0 to 2.0 molar ratio(s), as opposed to 1 mole of the compound (M-18b).

The reaction temperature in the reaction is usually within a range of −100 to 60° C. The reaction period in the reaction include 0.1 to 24 hours.

When the reaction is completed, water is added to the reaction mixture, and the reaction mixture is extracted with an organic solvent, and the organic layer is worked up (for example, drying and concentration) to obtain the compound (M-12f).

The compound (R-20) is a commercially available compound, or can be prepared by using a known method.

Reference Process 9

A compound represented by formula (M-12g) (hereinafter, referred to as "Compound (M-12g)") can be prepared by reacting a compound represented by formula (M-18e) (hereinafter, referred to as "Compound (M-18e)") with a compound represented by formula (R21) (hereinafter, referred to as "Compound (R21)") in the presence of a condensing agent.

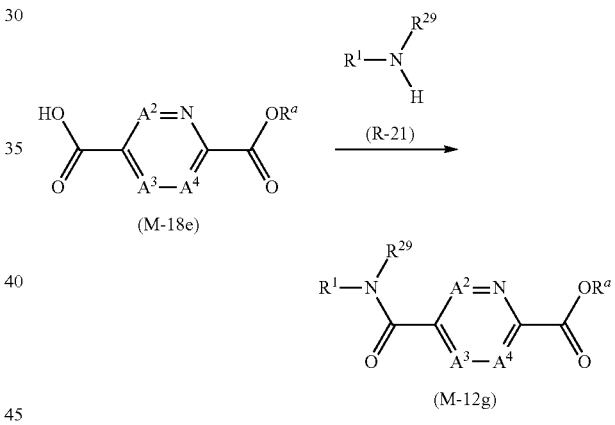

(M-18e)

(M-12g)

[wherein the symbols are the same as those defined above]

The reaction is usually carried out is a solvent. Examples of the solvents to be used in the reaction include ethers, aliphatic halogenated hydrocarbons, aromatic hydrocarbons, aprotic polar solvents, and mixed solvents of two or more of these solvents.

Examples of the condensing agents to be used in the reaction include 1-ethyl-3-(3-dimethylaminopropyl) carbodiimide hydrochloride salt.

A base may be used in the reaction as needed. Examples of the base include organic bases. When the base is used in the reaction, the base is usually used within a range of 0.1 to 10 molar ratios as opposed to 1 mole of the compound (M-18e).

In the reaction, the compound (R21) is usually used within a range of 1 to 10 molar ratio(s), and the condensing agent is usually used within a range of 1 to 5 molar ratio(s), as opposed to 1 mole of the compound (M-18e).

The reaction temperature in the reaction is usually within a range of −20 to 120° C. The reaction period in the reaction include 0.1 to 24 hours.

When the reaction is completed, water is added to the reaction mixture, and the reaction mixture is extracted with an organic solvent, and the organic layer is worked up (for example, drying and concentration) to obtain the compound (M-12g).

The compound (R-21) and the compound (M-18e) are commercially available compounds, or can be prepared by using a known method.

Reference Process 10

A compound represented by formula (M-12h) (hereinafter, referred to as "Compound (M-12h)") can be prepared by reacting a compound represented by formula (M-18f) (hereinafter, referred to as "Compound (M-18f)") with a compound represented by formula (R-22) (hereinafter, referred to as "Compound (R22)").

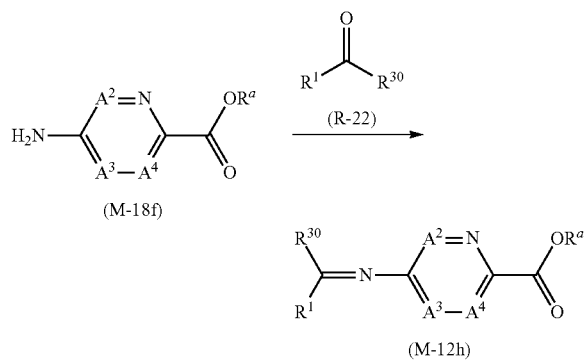

[wherein the symbols are the same as those defined above]

The reaction is usually carried out in a solvent. Examples of the solvents to be used in the reaction include ethers, aliphatic halogenated hydrocarbons, aromatic hydrocarbons, aprotic polar solvents, and mixed solvents of two or more of these solvents.

An acid may be used in the reaction as needed, and examples of the acid include p-toluenesulfonic acid, and camphor sulfonic acid, and the others. When the acid is used in the reaction, the acid is usually used within a range of 0.1 to 10 molar ratios, as opposed to 1 mole of the compound (M-18f).

In the reaction, the compound (R22) is usually used within a range of 1 to 10 molar ratio(s), as opposed to 1 mole of the compound (M-18f).

The reaction temperature in the reaction is usually within a range of −20 to 180° C. The reaction period in the reaction is usually within a range of 0.1 to 24 hours.

When the reaction is completed, water is added to the reaction mixture, and the reaction mixture is extracted with an organic solvent, and the organic layer is worked up (for example, drying and concentration) to obtain the compound (M-12h).

The compound (R22) and the compound (M-18f) are commercially available compounds, or can be prepared by using a known method.

Reference Process 11

A compound represented by formula (M-12i) (hereinafter, referred to as "Compound (M-12i)") can be prepared by reacting a compound represented by formula (M-18g) (hereinafter, referred to as "Compound (M-18g)") with a compound represented by formula (R23) (hereinafter, referred to as "Compound (R23)") in the presence of a base.

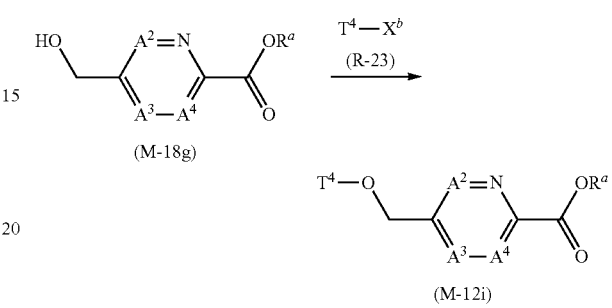

[wherein the symbols are the same as those defined above]

The reaction is usually carried out in a solvent. Examples of the solvents to be used in the reaction include ethers, aromatic hydrocarbons, aprotic polar solvents, and mixed solvents of two or more of these solvents.

Examples of the base to be used in the reaction include organic bases, alkali metal hydrides, and alkali metal carbonates.

In the reaction, the compound (R23) is usually used within a range of 1 to 10 molar ratio(s), and the base is usually used within a range of 0.1 to 5 molar ratios, as opposed to 1 mole of the compound (M-18g).

The reaction temperature in the reaction is usually within a range of −20 to 120° C. The reaction period in the reaction is usually within a range of 0.1 to 24 hours.

When the reaction is completed, water is added to the reaction mixture, and the reaction mixture is extracted with an organic solvent, and the organic layer is worked up (for example, drying and concentration) to obtain the compound (M-12i).

The compound (R23) and the compound (M-18g) are commercially available compounds, or can be prepared by using a known method.

Reference Process 12

A compound represented by formula (M-12j) (hereinafter, referred to as "Compound (M-12j)"), a compound represented by formula (M-12j-1) (hereinafter, referred to as "Compound (M-12j-1)"), and a compound represented by formula (M-12j-2) (hereinafter, referred to as "Compound (M-12j-2)") can be prepared according to the below-mentioned scheme.

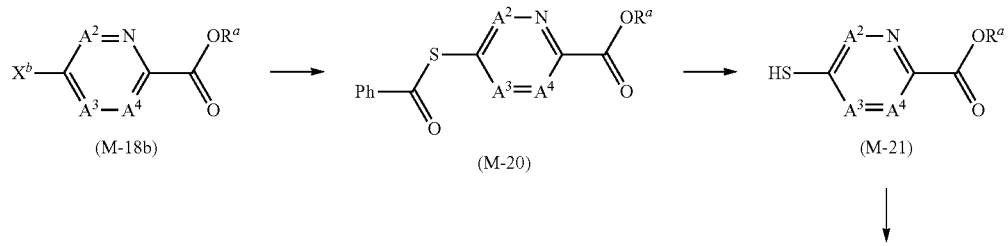

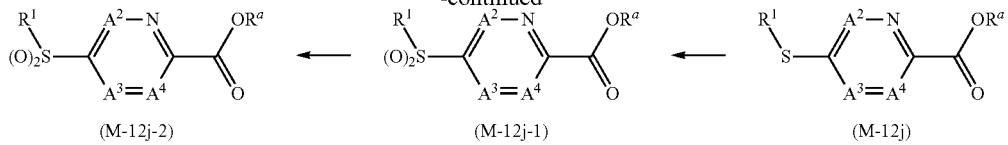

(M-12j-2)  (M-12j-1)  (M-12j)

[wherein the symbols are the same as those defined above]

A compound represented by formula (M-20) (hereinafter, referred to as "Compound (M-20)") can be prepared by reacting the compound (M-18b) with thiobenzoic acid in the presence of a copper catalyst and a base.

The reaction is usually carried out in a solvent. Examples of the solvent to be used in the reaction include ethers, aromatic hydrocarbons, aprotic polar solvents, water and mixed solvents of two or more of these solvents.

Examples of the copper catalysts to be used in the reaction include copper chloride, copper bromide, and copper iodide.

Examples of the bases to be used in the reaction include alkali metal hydrides, alkali metal carbonates, and organic bases.

A ligand may be used in the reaction as needed. Examples of the ligand include 2,2'-bipyridine, 2-aminoethanol, 8-hydroxyqunoline, and 1,10-phenanthroline and the others.

When a ligand is used in the reaction, the ligand is used within a range of 0.01 to 1 molar ratio(s) as opposed to 1 mole of the compound (M-18b).

In the reaction, thiobenzoic acid is usually used within a range of 1 to 10 molar ratio(s), the copper catalyst is usually used within a range of 0.01 to 0.5 molar ratios, and the base is usually used within a range of 0.1 to 5 molar ratios, as opposed to 1 mole of the compound (M-18b).

The reaction temperature in the reaction is usually within a range of −20 to 120° C. The reaction period in the reaction is usually within a range of 0.1 to 24 hours.

When the reaction is completed, water is added to the reaction mixture, and the reaction mixture is extracted with an organic solvent, and the organic layer is worked up (for example, drying and concentration) to obtain the compound (M-20).

A compound represented by formula (M-21) (hereinafter, referred to as "Compound (M-21)") can be prepared by hydrolyzing the compound (M-20). The reaction can be carried out according to a similar method to those described in WO 2011/068171, or Journal of Organic Chemistry, 1978, 43 (6), 1190-1192.

The compound (M-12j) can be prepared by using the compound (M-21) in place of the compound (M-18g) according to the method described in the Reference Process 11.

The compound (M-12-1) can be prepared by using the compound (M-12j) in place of the compound (A-1a) according to a similar method to that for preparing the compound (A-1b) from the compound (A-1a), said method being described in the Process 1.

The compound (M-12j-2) can be prepared by using the compound (M-12j-1) in place of the compound (A-1b) according to a similar method to that for preparing the compound (A-1c) from the compound (A-1b), said method being described in the Process 1.

Reference Process 13

A compound represented by formula (M-8a) (hereinafter, referred to as "Compound (M-8a)") can be prepared by reacting a compound represented by formula (M-19a) (hereinafter, referred to as "Compound (M-19a)") with the compound (R15).

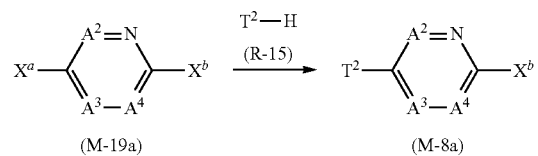

(M-19a)  (M-8a)

[wherein the symbols are the same as those defined above]

The reaction can be carried out according to the Reference Process 3.

The compound (M-19a) is a commercially available compound, or can be prepared by using a known method.

Reference Process 14

A compound represented by formula (M-8b) can be prepared by reacting a compound represented by formula (M-19b) (hereinafter, referred to as "Compound (M-19b)") with the compound (R16).

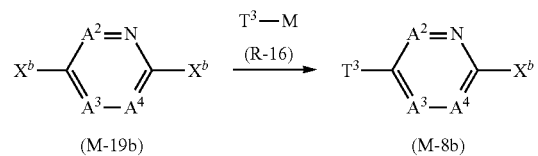

(M-19b)  (M-8b)

[wherein the symbols are the same as those defined above]

The reaction can be carried out according to the Reference Process 4.

The compound (M-19b) is a commercially available compound, or prepared by using a known method.

Reference Process 15

A compound represented by formula (M-8c) (hereinafter, referred to as "Compound (M-8c)") can be prepared by reacting a compound represented by formula (M-19c) (hereinafter, referred to as "Compound (M-19c)") with the compound (R17).

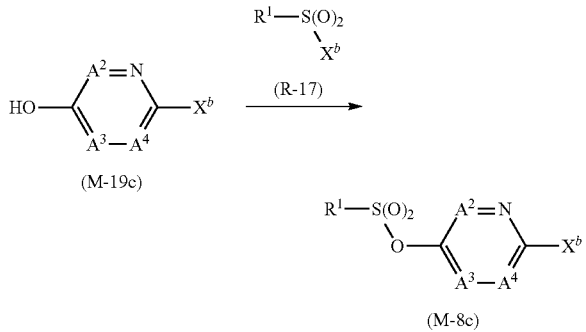

(M-19c)

(M-8c)

[wherein the symbols are the same as those defined above]

The reaction can be carried out according to the Reference Process 5.

The compound (M-19c) is a commercially available compound, or can be prepared by using a known method.

Reference Process 16

A compound represented by formula (M-8d) (hereinafter, referred to as "Compound (M-8d)") can be prepared by reacting the compound (M-19b) with the compound (R18).

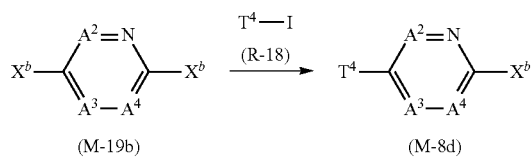

[wherein the symbols are the same as those defined above]

The reaction can be carried out according to the Reference Process 6.

Reference Process 17

A compound represented by formula (M-8e) (hereinafter, referred to as "Compound (M-8e)") can be prepared by reacting a compound represented by formula (M-19d) (hereinafter, referred to as "Compound (M-19d)") with the compound (R19).

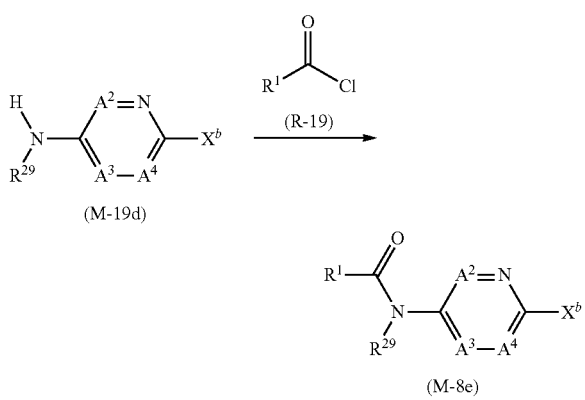

[wherein the symbols are the same as those defined above]

The reaction can be carried out according to the Reference Process 7.

The compound (M-19d) is a commercially available compound, or can be prepared by using a known method.

Reference Process 18

A compound represented by formula (M-8f) (hereinafter, referred to as "Compound (M-8f)") can be prepared by reacting the compound (M-19b) with the compound (R-20).

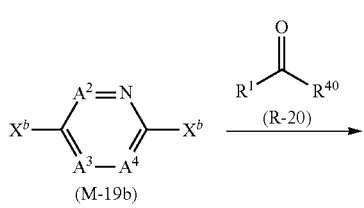

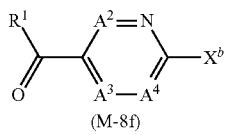

[wherein the symbols are the same as those defined above]

The reaction can be carried out according to the Reference Process 8.

Reference Process 19

A compound represented by formula (M-8g) (hereinafter, referred to as "Compound (M-8g)") can be prepared by reacting a compound represented by formula (M-19e) (hereinafter, referred to as "Compound (M-19e)") with the compound (R21).

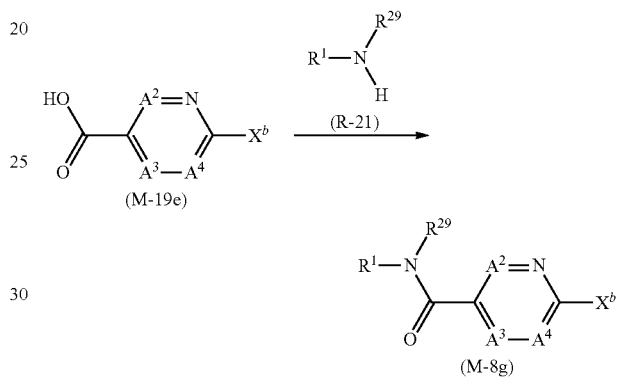

[wherein the symbols are the same as those defined above]

The reaction can be carried out according to the Reference Process 9.

The compound (M-19e) is a commercially available compound, or can be prepared by using a known method.

Reference Process 20

A compound represented by formula (M-8h) (hereinafter, referred to as "Compound (M-8h)") can be prepared by reacting a compound represented by formula (M-19f) (hereinafter, referred to as "Compound (M-19f)") with the compound (R22).

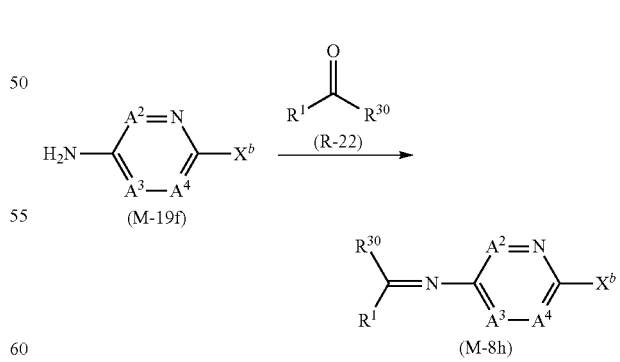

[wherein the symbols are the same as those defined above]

The reaction can be carried out according to the Reference Process 10.

The compound (M-19f) is a commercially available compound, or can be prepared by using a known method.

Reference Process 21

A compound represented by formula (M-8i) (hereinafter, referred to as "Compound (M-8i)") can be prepared by reacting a compound represented by formula (M-19g) (hereinafter, referred to as "Compound (M-19g)") with the compound (R23).

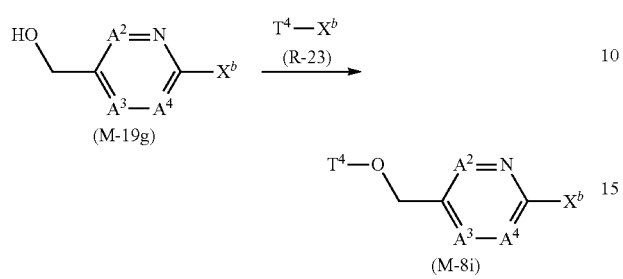

[wherein the symbols are the same as those defined above]

The reaction can be carried out according to the Reference process 11.

The compound (M-19g) is a commercially available compound, or can be prepared by a known method.

Reference Process 22

A compound represented by formula (M-8j) (hereinafter, referred to as "Compound (M-8j)"), a compound represented by formula (M-8j-1) (hereinafter, referred to as "Compound (M-8j-1)"), and a compound represented by formula (M-8j-2) (hereinafter, referred to as "Compound (M-8j-2)") can be prepared according to the below-mentioned scheme.

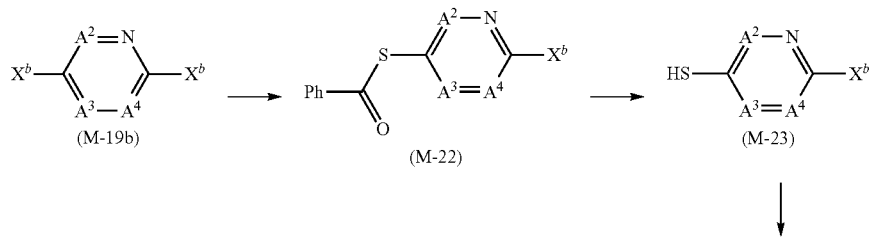

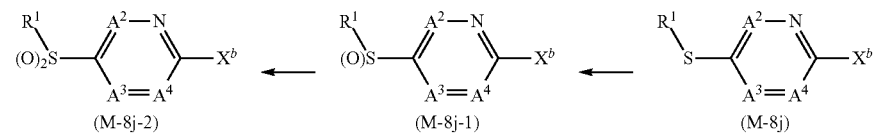

[wherein the symbols are the same as those defined above]

These reactions can be carried out according to the Reference Process 12.

Reference Process 23

The compound (M-2) can be prepared by reacting the compound (M-8) with a compound represented by formula (M-66) (hereinafter, referred to as "Compound (M-66)") in the presence of a catalyst.

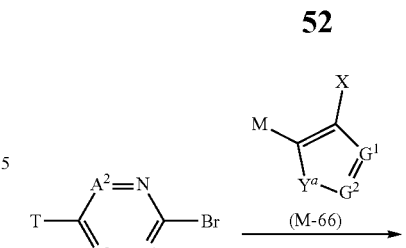

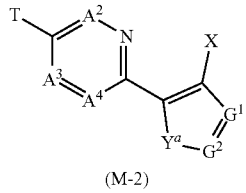

[wherein the symbols are the same as those defined above]

The reaction can be carried out by using the compound (M-66) in place of the compound (M-51) according to a similar method to that for preparing the compound (M-52) from the compound (M-51), said method being described in the Process 19.

The compound (M-66) is a commercially available compound, or can be prepared according to a similar method to that described in WO 2016/168914.

Reference Process 24

The compound (M-3) can be prepared by reacting the compound (M-8) with a compound represented by formula (M-67) (hereinafter, referred to as "Compound (M-67)") in the presence of a catalyst.

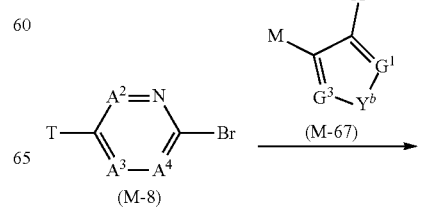

-continued

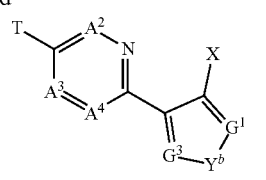

(M-3)

[wherein the symbols are the same as those defined above]

The reaction can be carried out by using the compound (M-67) in place of the compound (M-51) according to a similar method to that for preparing the compound (M-52) from the compound (M-51), said method being described in the Process 19.

The compound (M-67) is a commercially available compound, or can be prepared according to a similar method to that described in WO 2013/052394.

Reference Process 25

The compound (M-5) can be prepared by reacting the compound (M-8) with a compound represented by formula (M-68) (hereinafter, referred to as "Compound (M-68)") in the presence of a catalyst.

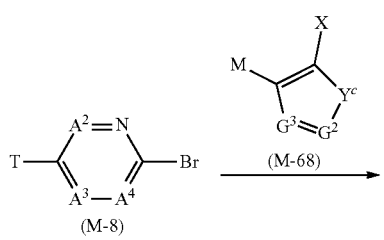

(M-8)    (M-68)

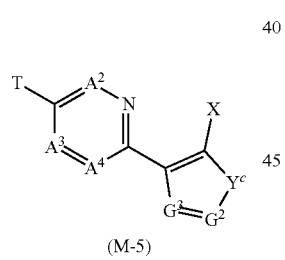

(M-5)

[wherein the symbols are the same as those defined above]

The reaction can be carried out by using the compound (M-68) in place of the compound (M-51) according to a similar method to that for preparing the compound (M-52) from the compound (M-51), said method being described in the Process 19.

The compound (M-68) is a commercially available compound, or can be prepared according to a similar method to that described in Chemistry–A European Journal, 2015, 21 (25), 9236.

Reference Process 26

The compound (M-2) can be prepared by reacting the compound (M-55) with a compound represented by formula (M-69) (hereinafter, referred to as "Compound (M-69)") in the presence of a catalyst.

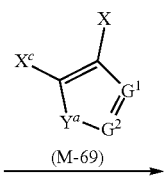

(M-55)    (M-69)

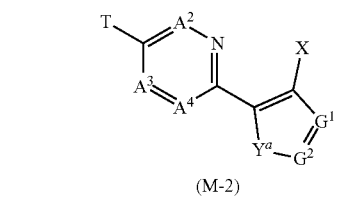

(M-2)

[wherein $X^c$ represents a bromine atom or an iodine atom, and the other symbols are the same as those defined above]

The reaction can be carried out by using the compound (M-55) in place of the compound (M-51) and using the compound (M-69) in place of the compound (M-8) according to a similar method to that for preparing the compound (M-52) from the compound (M-51), said method being described in the Process 19.

The compound (M-69) is a commercially available compound, or can be prepared by using a known method.

Reference Process 27

The compound (M-3) can be prepared by reacting the compound (M-55) with a compound represented by formula (M-70) (hereinafter, referred to as "Compound (M-70)") in the presence of a catalyst.

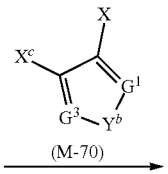

(M-55)    (M-70)

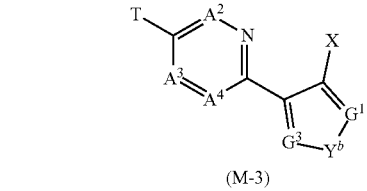

(M-3)

[wherein the symbols are the same as those defined above]

The reaction can be carried out by using the compound (M-55) in place of the compound (M-51) and using the compound (M-70) in place of the compound (M-8) according to a similar method to that for preparing the compound (M-52) from the compound (M-51), said method being described in the Process 19.

The compound (M-70) is a commercially available compound, or can be prepared according to a similar method to those described in Journal of Medicinal Chemistry, 2015, 58 (17), 6766, WO 2009/123695, Journal of Organic Chemistry, 1981, 46 (11), 2221, JP 2011-098956 A, Synlett, 2010, (19), 2875, Journal of Organic Chemistry, 2015, 80 (4), 2413.

Reference Process 28

The compound (M-5) can be prepared by reacting the compound (M-55) with a compound represented by formula (M-71) (hereinafter, referred to as "Compound (M-71)") in the presence of a catalyst.

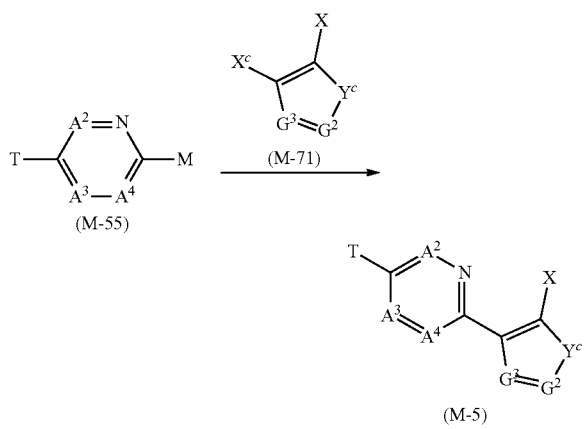

[wherein the symbols are the same as those defined above]

The reaction can be carried out by using the compound (M-55) in place of the compound (M-51) and using the compound (M-71) in place of the compound (M-8) according to a similar method to that for preparing the compound (M-52) from the compound (M-51), said method being described in the Process 19.

The compound (M-71) is a commercially available compound, or can be prepared according to a similar method to those described in Angewandte Chemie, International Edition, 2018, 57 (4), 1039, European Journal of Inorganic Chemistry, 2017, (33), 3878, WO 2017/100819, WO 2017/087837, Journal of Agricultural and Food Chemistry, 2017, 65 (26), 5397, WO 2017/027312, or Journal of Organic Chemistry, 82 (11), 2017, 5947 and so on.

Reference Process 29

A compound represented by formula (M-51Z) (hereinafter, referred to as "Compound (M-51Z)") can be prepared by reacting the compound (M-50) with a compound represented by formula (R9) (hereinafter, referred to as "Compound (R9)") in the presence of a base.

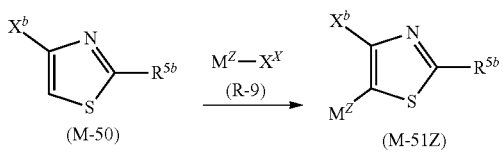

[wherein $M^Z$ represents a tributylstannyl group, ZnCl, MgCl, or MgBr, $X^X$ represents a halogen atom, and the other symbols are the same as those defined above]

The reaction is usually carried out in a solvent. Examples of the solvents to be used in the reaction include ethers, aromatic hydrocarbons, and mixed solvents of two or more of these solvents.

Examples of the base to be used in the reaction include lithium diisopropylamide, lithium bis(triethylsilyl)amide, and potassium bis(trimethylsilyl)amide.

Examples of the compound (R9) include zinc chloride, magnesium bromide, tributyl stannyl chloride.

In the reaction, the compound (R9) is usually used within a range of 1 to 2 molar ratio(s), and the base is usually used within a range of 1 to 2 molar ratio(s), as opposed to 1 mole of the compound (M-50).

The reaction temperature in the reaction is usually within a range of −100 to 0° C. The reaction period in the reaction is usually within a range of 0.1 to 24 hours.

When the reaction is completed, water is added to reaction mixtures, and the reaction mixtures are extracted with organic solvent(s), and the organic layers re worked up (for example, drying and concentration) to obtain the compound (M-51Z). After the completion of the reaction, a mixture containing the compound (M-51A) may be used as itself to a next reaction.

The compound (R9) is a commercially available compound, or can be prepared by using a known method.

The compound (M-50) is a commercially available compound, or can be prepared by using a known method.

Reference Process 30

A compound represented by formula (M-51B) (hereinafter, referred to as "Compound (M-51B)") can be prepared by reacting the compound (M-50) with a compound represented by formula (R10) (hereinafter, referred to as "Compound (R10)") in the presence of a base.

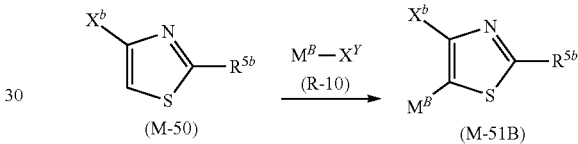

[wherein $M^B$ represents a diC1-C3 alkoxyboranil group, or a 4,4,5,5-tetramethyl-1,3,2-dioxaborolan-2-yl group, and XY represents a C1-C3 alkoxy group, and the other symbols are the same as those defined above]

The reaction can be carried out by using the compound (R10) in place of the compound (R9) according to the Reference process 29.

The compound (R10) is a commercially available compound, or can be prepared by using a known method.

The present compound can be mixed or combined with one or more ingredients selected from the group consisting of the following Group (a), Group (b), Group (c), Group (d), Group (e), Group (f), Group (g), and Group (h) (hereinafter, referred to as "present ingredient").

The mixing or combining represents that the present compound and the present ingredient are used concurrently, separately, or at an interval.

When the present compound and the present ingredient are concurrently used, the present compound and the present ingredient may be incorporated as a separate formulation or one formulation.

One aspect of the present invention relates to a composition comprising one or more ingredients selected from the group consisting of the Group (a) and the Group (b), and the present compound (hereinafter, referred to as "Composition A").

The Group (a) represents insecticidal ingredients, miticidal ingredients and nematicidal ingredients that are a group consisting of acetylcholinesterase inhibitors (for example, carbamate insecticides and organophosphate insecticides), GABA-gated chloride ion channel antagonists (for example, phenylpyrazole insecticides), sodium channel modulators (for example, pyrethroid insecticides), nicotinic acetylcholine receptor antagonist modulators (for example, neonicotinoid insecticides), nicotinic acetylcholine receptor allosteric modulators, glutamate-gated chloride ion channel allosteric modulators (for example, macrolide insecticides), juvenile hormone mimics, multisite inhibitors, chordotonal organ TRPV channel modulators, mites growth regulators, mitochondrial ATP synthase inhibitors, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, Inhibitors of mitochondrial electron transport chain complex I, II, III, and IV, voltage-dependent sodium channel blockers, Inhibitors of acetyl CoA carboxylase, ryanodine receptor modulators (for example, diamide insecticides), chordotonal organ modulators, each active ingredient of microbial fungicides, and other insecticidal ingredients, miticidal ingredients and nematicidal ingredients. These agents are described in the classification based on the IRAC mode of action.

The Group (b) represents fungicidal ingredients that are a group consisting of nucleic acid synthesis inhibitors (for example, phenylamide fungicides and acylamino acid fungicides), cytostatic and cytoskeletal inhibitors (for example, MBC fungicides), respiration inhibitors (for example, QoI fungicides and QiI fungicides), amino-acid synthesis and protein synthesis inhibitors (for example, anilinopyridine fungicides), signal-transduction inhibitors, lipid synthesis and membrane synthesis inhibitors, sterol biosynthesis inhibitors (for example, DMI fungicides such as triazoles), cell wall synthesis inhibitors, melanin synthesis inhibitors, plant defense inducer, multisite fungicides, microbial fungicides, and other fungicidal ingredients. These agents are described in the classification based on the FRAC mode of action.

The Group (c) represents a group of plant growth modulating ingredients including mycorrhizal fungus and rhizobia.

The Group (d) represents a group of phytotoxicity mitigation ingredients.

The Group (e) represents a group of synergists.

The Group (f) represents a group of repellent ingredients consisting of bird repellent ingredients, insect repellent ingredients, and animal repellent ingredients.

The Group (g) represents a group of molluscicide ingredients.

The Group (h) represents a group of insect pheromones.

Examples of combinations of the present ingredient and the present compound are recited as follows. For example, the "alanycarb+SX" indicates a combination of alanycarb and SX.

The abbreviation "SX" means to any one of the present compounds selected from the compound classes SX1 to SX960 described in Examples. Further, any of the present ingredients as described below are a known ingredient, and can be obtained as a commercially available drug or prepared according to a known method. When the present ingredient represents a microorganism, the present ingredient can be obtained from a microorganism depositary authority. The number in parentheses represents CAS RN (registered trademark).

A combination of the present ingredient in the above-mentioned Group (a) and the present compound:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, *Celastrus angulatus* (bark of *Celastrus angulatus*)+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, dried leaves of Dryopteris filix-mas+SX, emamectin-benzoate+SX, empenthrin+SX, endosulfan+SX, EPN (O-ethyl O-(4-nitrophenyl)phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+

SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, selamnectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides* (Brand name: Terpenoid blend QRD 460)+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietane-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus BV-0001+SX, *Anticarsia gemmatalis* mNPV+SX, *Autographa californica* mNPV+SX, *Cydia pomonella* GV V15+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* I-1582+SX, *Bacillus megaterium*+SX, *Bacillus* sp.AQ175+SX, *Bacillus* sp.AQ177+SX, *Bacillus* sp.AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. *aizawai* ABTS-1857+SX, *Bacillus thuringiensis* subsp. *aizawai* AM65-52+SX, *Bacillus thuringiensis* subsp. *aizawai* GC-91+SX, *Bacillus thuringiensis* subsp. *aizawai* Serotype H-7+SX, *Bacillus thuringiensis* subsp. *kurstaki* ABTS351+SX, *Bacillus thuringiensis* subsp. *kurstaki* BMP123+SX, *Bacillus thuringiensis* subsp. *kurstaki* EG234+SX, *Bacillus thuringiensis* subsp. *kurstaki* EG7841+SX, *Bacillus thuringiensis* subsp. *kurstaki* EVB113-19+SX, *Bacillus thuringiensis* subsp. *kurstaki* F810+SX, *Bacillus thuringiensis* subsp. *kurstaki* HD-1+SX, *Bacillus thuringiensis* subsp. *kurstaki* PB54+SX, *Bacillus thuringiensis* subsp. *kurstaki* SA-11+SX, *Bacillus thuringiensis* subsp. *kurstaki* SA-12+SX, *Bacillus thuringiensis* subsp. *tenebriosis* NB176+SX, *Bacillus thuringiensis* subsp. *thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *japonensis buibui*+SX, *Bacillus thuringiensis* var. *san diego* M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*)+SX, *Hirsutella rhossiliensis*+SX, *Hirsutella thompsonii*+SX, *Lagenidium giganteum*+SX, *Lecanicillium lecanii* KV01+SX, *Lecanicillium lecanii* conidia of strain DAOM198499+SX, *Lecanicillium lecanii* conidia of strain DAOM216596+SX, *Metarhizium anisopliae* F52+SX, *Metarhizium anisopliae* var. *acridum*+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* NCIM1312+SX, lenoremycin+SX, concanamycin A+SX, acetoprole)+SX, lotilaner+SX, sarolaner+SX, isocycloseram+SX, *Metarhizium anisopliae* var. *anisopliae* BIPESCO 5/F52+SX, *Lecanicillium muscarium* Ve6+SX, N-ethyl-5-methyl-1-(3-methylbutan-2-yl)-N-(pyridazin-4-yl)-1H-pyrazole-4-carboxamide (1403615-77-9)+SX, and imidaclothiz+SX.

A combination of the present ingredient in the above-mentioned Group (b) and the present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, *Quillaja* extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, 3-(difluorodifluoromethyl)-N-methoxy-1-methyl-N-[(1R)-1-methyl-2-(2,4,6-trichlorophenyl)ethyl)pyrazole-4-carboxamide (1639015-48-7)+SX, 3-(difluorodifluoromethyl)-N-methoxy-1-methyl-N-((1S)-1-methyl-2-(2,4,6-trichlorophenyl)ethyl] pyrazole-4-carboxamide (1639015-49-8)+SX, 3-(difluorodifluoromethyl)-1-methyl-N-(1,1,3-trimethylindan-4-yl)pyrazole-4-carboxamide (141573-94-6)+SX, 3-(difluorodifluoromethyl)-N-[(3R)-7-fluoro-1,1,3-trimethylindan-4-yl]-1-methylpyrazole-4-carboxamide (1513466-73-3)+SX, N'-[4-({3-[(4-chlorophenyl)methyl]-1,2,4-thiadiazol-5-yl}oxy)-2,5-dimethylphenyl]-N-ethyl-N-methylmethaneimidamide (1202781-91-6)+SX, 2-{3-[2-(1-{[3,5-bis(difluorodifluoromethyl)-1H-pyrazol-1-yl] acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo4-fluorophenyl)-N-(2-chloro-6-fluorophenyl)-1,3-dimethyl-1H-pyrazole-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridine-2-amine (1446247-98-8)+SX, α-[3-(4-chloro-2-fluorophenyl)-5-(2,4-difluorophenyl)-4-isoxazolyl]-3-pyridinemethanol (1229605-96-2)+SX, (αS)-[3-(4-chloro-2-fluorophenyl)-5-(2,4-difluorophenyl)-4-isoxazolyl]-3-pyridinemethanol (1229606-46-5)+SX, (αR)-[3-(4-chloro-2-fluorophenyl)-5-(2,4-difluorophenyl)-4-isoxazolyl]-3-pyridinemethanol (1229606-02-3)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-({[2R,3S)-3-(2-chlorophenyl)-2-(2,4-difluorophenyl) oxiran-2-yl]methyl}-2,4-dihydro-3H-1,2,4-triazole-3-thione (1638897-70-7)+SX, 2-{[2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+

SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanato (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanate (1638897-84-3)+SX, 1-([(2R,3R)-3-(2-chlorophenyl)-2-(2,4-difluorophenyl)oxiran-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5R)-5-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, methyl=3-[(4-chlorophenyl)methyl]-2-hydroxy-1-methyl-2-(1H-1,2,4-triazol-1-ylmethyl)cyclopentanecarboxylate (1791398-02-1)+SX, methyl=(1R,2S,3S)-3-[(4-chlorophenyl)methyl]-2-hydroxy-1-methyl-2-(1H-1,2,4-triazol-1-ylmethyl)cyclopentanecarboxylate (2080743-90-2)+SX, methyl=(1S,2R,3R)-3-[(4-chlorophenyl)methyl]-2-hydroxy-1-methyl-2-(1H-1,2,4-triazol-1-ylmethyl)cyclopentanecarboxylate (2080743-91-3)+SX, methyl=(1R,2R,3R)-3-[(4-chlorophenyl)methyl]-2-hydroxy-1-methyl-2-(1H-1,2,4-triazol-1-ylmethyl)cyclopentanecarboxylate (2080743-92-4)+SX, methyl=(1S,2S,3S)-3-[(4-chlorophenyl)methyl]-2-hydroxy-1-methyl-2-(1H-1,2,4-triazol-1-ylmethyl)cyclopentanecarboxylate (2080743-93-5)+SX, methyl=(1R,2R,3S)-3-[(4-chlorophenyl)methyl]-2-hydroxy-1-methyl-2-(1H-1,2,4-triazol-1-ylmethyl)cyclopentanecarboxylate (2080743-94-6)+SX, methyl=(1S,2S,3R)-3-[(4-chlorophenyl)methyl]-2-hydroxy-1-methyl-2-(1H-1,2,4-triazol-1-ylmethyl)cyclopentanecarboxylate (2080743-95-7)+SX, methyl=(1R,2S,3R)-3-[(4-chlorophenyl)methyl]-2-hydroxy-1-methyl-2-(1H-1,2,4-triazol-1-ylmethyl)cyclopentanecarboxylate (2081061-22-3)+SX, methyl=(1S,2R,3S)-3-[(4-chlorophenyl)methyl]-2-hydroxy-1-methyl-2-(1H-1,2,4-triazol-1-ylmethyl)cyclopentanecarboxylate (2081061-23-4)+SX, 2-chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1801930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4)+SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1)+SX, (1S,2S,5R)-2-chloromethyl-5-(4-fluorobenzyl)-2-methyl-1-(1H-1,2,4-triazol-1-ylmethyl)cyclopentanol (1638898-16-4)+SX, (1R,2S,5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy)phenyl]-1-(1,2,4-triazol-1-yl)pent-3-in-2-ol (1801919-59-4)+SX, (R)-2-[4-(4-chlorophenoxy)-2-(trifluoromethyl)phenyl]-1-(1,2,4-triazol-1-yl)propan-2-ol (1616236-94-2)+SX, (R)-1-[4-(4-chlorophenoxy)-2-(trifluoromethyl)phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butan-2-ol (1801919-61-8)+SX, 3-[5-(4-chlorophenyl)-2,3-dimethyl-1,2-oxazolin-3-yl]pyridine (847749-37-5)+SX, *Agrobacterium radiobactor* K1026+SX, *Agrobacterium radiobactor* K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SB3086)+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX, *Bacillus subtilis* FZB24+SX, *Bacillus subtilis* GB03+SX, *Bacillus subtilis* HA10404+SX, *Bacillus subtilis* IAB/BS03+SX, *Bacillus subtilis* MBI600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* 0+SX, *Candida saitoana*+SX, *Chaetomium cupreum*+SX, *Clonostachys rosea*+SX, *Coniothyrium minitans* CGMCC8325+SX, *Coniothyrium minitans* CON/M/91-8+SX, *Cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, *Pseudozyma flocculosa* PF-A22UL+SX, *Pseudomonas rhodesiae* HAI-0804+SX, *Pythium* oligand Rum DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* V117b+SX, *Trichoderma asperellum* ICC012+SX, *Trichoderma asperellum* SKT-1+SX,

*Trichoderma asperellum* T34+SX, *Trichoderma atroviride* CNCM 1-1237+SX, *Trichoderma atroviride* LC52+SX, *Trichoderma atroviride* SC1+SX, *Trichoderma atroviride* SKT-1+SX, *Trichoderma gamsii* ICC080+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum* kd+SX, *Trichoderma harzianum* MOl+SX, *Trichoderma harzianum* SF+SX, *Trichoderma harzianum* T22+SX, *Trichoderma harzianum* T39+SX, *Trichoderma harzianum* TEM908+SX, *Trichoderma harzianum* TH35+SX, *Trichoderma polysporum* IMI206039+SX, *Trichoderma stromaticum*+SX, *Trichoderma virens* G-41+SX, *Trichoderma virens* GL-21+SX, *Trichoderma viride*)+SX, *Variovorax paradoxus* CGF4526+SX, Harpin protein+SX, *Trichoderma harzianum* ITEM908+SX, *Trichoderma harzianum* T78+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Bacillus amyloliquefaciens* subsp. *plantarum* D747+SX, *Pythium oligandrum* M1+SX, *Trichoderma asperellum* T25+SX, richoderma *asperellum* TV1+SX, *Trichoderma atroviride* IMI 206040+SX, *Trichoderma atroviride* T11+SX, *Bacillus amyloliquefaciens* (Aveo (trademark) EZ Nematicide)+SX.

A combination of the present ingredient in the above-mentioned Group (c) and the present compound:

1-methylcyclopropene+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butylate+SX, methyl 5-(trifluoromethyl)benzo[b]thiophene-2-carboxylate+SX, 3-[(6-chloro-4-phenylquinazolin-2-yl)amino]-1-propanol+SX, formononetin+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium tropici*+SX, *Sinorhizobium fredii*+SX, *Sinorhizobium meliloti*+SX, lipochitooligosaccharide SP104+SX, Zucchini Yellow Mosaik Virus weak strain+SX.

A combination of the present ingredient in the above-mentioned Group (d) and the present compound:

allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dichloroacetyl)-1-oxa-4-azaspiro[4.5]decane)+SX, CL-304415 (4-carboxy-3,4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, TI-35 (1-(dichloroacetyl)azepane)+SX.

A combination of the present ingredient in the above-mentioned Group (e) and the present compound:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)SX, TPP (triphenyl phosphate)+SX.

A combination of the present ingredient in the above-mentioned Group (f) and the present compound:

anthraquinone+SX, chloralose+SX, acrep+SX, butopyronoxyl+SX, camphor+SX, d-camphor+SX, carboxide+SX, dibutyl phthalate+SX, deet+SX, dimethyl carbate+SX, dimethyl phthalate+SX, dibutyl succinate+SX, dibutyl adipate+SX, ethohexadiol+SX, hexamide+SX, icaridin+SX, methoquin-butyl+SX, methylneodecanamide+SX, 2-(octylthio)

ethanol+SX, butoxypolypropylene glycol+SX, oxamate+SX, quwenzhi+SX, quyingding+SX, zengxiaon+SX, rebemide+SX, copper naphthenate+SX, zinc naphthenate+SX.

A combination of the present ingredient in the above-mentioned Group (g) and the present compound:

bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, trifenmorph+SX.

A combination of the present ingredient in the above-mentioned Group (h) and the present compound:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2,4-dimethyl-5-ethyl-6,8-dioxabicyclo(3,2,1)octane+SX, (−)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyl eugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, (S)-verbenone+SX.

Examples of a ratio of the present compound to the present ingredient include, but are not particularly limited to 1000:1 to 1:1000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, and 1:50 in the weight ratio (the present compound X: the present ingredient).

The present compound has control effect on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), *Tagosodes orizicolus*, and the like;

from the family Cicadellidae, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and the like;

from the family Cercopidae, *Mahanarva posticata, Mahanarva fimbriolata*, and the like;

from the family Aphididae, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and the like;

from the family Phylloxeridae, grapevine *Phylloxera* (*Daktulosphaira vitifoliae*), Pecan *Phylloxera* (*Phylloxera devastatrix*), Pecan leaf *Phylloxera* (*Phylloxera notabilis*), Southern pecan leaf *Phylloxera* (*Phylloxera russellae*), and the like;

from the family Adelgidae, hemlock woolly aphid (*Adelges tsugae*), *Adelges piceae, Aphrastasia pectinatae*, and the like;

from the family Pentatomidae, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax, Dichelops melacanthus*, and the like;

from the family Cydnidae, Burrower brown bug (*Scaptocoris castanea*);

from the family Alydidae, for example, bean bug (*Riptortus pedestris*), corbett rice bug (*Leptocorisa chinensis*), rice bug (*Leptocorisa acuta*), and the like;

from the family Coreidae, *Cletus punctiger*, Australian leaf-footed bug (*Leptoglossus australis*), and the like;

from the family Lygaeidae, oriental chinch bug (*Caverelius saccharivorus*), seed bug (*Togo hemipterus*), chinch bug (*Blissus leucopterus*), and the like;

from the family Miridae, rice leaf bug (*Trigonotylus caelestialium*), sorghum plant bug (*Stenotus rubrovittatus*), wheat leaf bug (*Stenodema calcarata*), American tarnished plant bug (*Lygus lineolaris*), and the like;

from the family Aleyrodidae, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), *Pealius euryae*, and the like;

from the family Diaspididae, *Abgrallaspis cyanophylli*, red scale (*Aonidiella aurantii*), San Jose scale (*Diaspidiotus perniciosus*), white peach scale (*Pseudaulacaspis pentagona*), arrowhead scale (*Unaspis yanonensis*), citrus snow scale (*Unaspis citri*), and the like;

from the family Coccidae, pink wax scale (*Ceroplastes rubens*);

from the family Margarodidae, fluted scale (*Icerya purchasi*) seychelles fluted scale (*Icerya seychellarum*), and the like;

from the family Pseudococcidae, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), tuttle mealybug (*Brevennia rehi*), and the like;

from the family Psyllidae, citrus *psylla* (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), Pear *psylla* (*Cacopsylla pyricola*), and the like;

from the family Tingidae, sycamore lace bug (*Corythucha ciliata*), aster tingid (*Corythucha marmorata*), Japanese pear lace bug (*Stephanitis nashi*), azalea lace bug (*Stephanitis pyrioides*), and the like;

from the family Cimicidae, common bed bug (*Cimex lectularius*), tropical bed bug (*Cimex lectularius*), and the like;

from the family Cicadidae, Giant Cicada (*Quesada gigas*), and the like;

from the family Reduviidae, *Triatoma infestans, Rhodonius prolixus*, and the like, *Triatoma* spp.

Lepidoptera:

from the family Crambidae, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), Sugarcane borer (*Diatraea saccharalis*), and the like;

from the family Pyralidae, lesser cornstalk borer (*Elasmopalpus lignosellus*), mealworm moth (*Plodia interpunctella*), persimmon bark borer (*Euzophera batangensis*), fig moth (*Cadra cautella*), and the like;

from the family Noctuidae, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), Velvetbean caterpillar (*Anticarsia gemmatalis*), Cotton leafworm (*Alabama argillacea*), Hop vine borer (*Hydraecia immanis*), and the like;

from the family Pieridae, common cabbage worm (*Pieris rapae*), and the like;

from the family Tortricidae, oriental fruit moth (*Grapholita molesta*), *Grapholita dimorpha*, soybean moth (*Leguminivora glycinivorella*), *Matsumuraeses azukivora*, summer fruit *tortrix* (*Adoxophyes orana fasciata*), smaller tea *tortrix* (*Adoxophyes honmai*), Japanese tea *tortrix* (*Homona magnanima*), apple *tortrix* (*Archips fuscocupreanus*), codling moth (*Cydia pomonella*), sugarcane shoot borer (*Tetramoera schistaceana*), Bean Shoot Borer (*Epinotia aporema*), Citrus fruit borer (*Ecdytolopha aurantiana*), and the like;

from the family Gracillariidae, tea leaf roller (*Caloptilia theivora*), Asiatic apple leaf miner (*Phyllonorycter ringoniella*), and the like;

from the family Carposinidae, peach fruit moth (*Carposina sasakii*), and the like;

from the family Lyonetiidae, Coffee Leaf miner (*Leucoptera coffeella*), peach leaf miner (*Lyonetia clerkella*), *Lyonetia prunifoliella*, and the like;

from the family Lymantriidae, *Lymantria* spp. (such as gypsy moth (*Lymantria dispar*)), *Euproctis* spp. (such as tea lymantriid (*Euproctis pseudoconspersa*)), and the like;

from the family Plutellidae, diamondback moth (*Plutella xylostella*), and the like;

from the family Gelechiidae, peach worm (*Anarsia lineatella*), sweetpotato leaf folder (*Helcystogramma triannulella*), pink bollworm (*Pectinophora gossypiella*), potato moth (*Phthorimaea operculella*), *Tuta absoluta*, and the like;

from the family Arctiidae, American white moth (*Hyphantria cunea*), and the like;

from the family Castniidae, Giant Sugarcane borer (*Telchin licus*), and the like;

from the family Cossidae, *Cossus insularis*, and the like;

from the family Geometridae, *Ascotis selenaria*, and the like;

from the family Limacodidae, blue-striped nettle grub (*Parasa lepida*), and the like;

from the family Stathmopodidae, persimmon fruit moth (*Stathmopoda masinissa*), and the like;

from the family Sphingidae, tobacco hornworm (*Acherontia lachesis*), and the like;

from the family Sesiidae, *Nokona feralis*, cherry borer (*Synanthedon hector*), *Synanthedon tenuis*, and the like:

from the family Hesperiidae, rice skipper (*Parnara guttata*), and the like;

from the family Tineidae, casemaking clothes moth (*Tinea translucens*), common clothes moth (*Tineola bisselliella*), and the like.

Thysanoptera:

from the family Thripidae, western flower *Thrips* (*Frankliniella occidentalis*), oriental *Thrips* (*Thrips palmi*), yellow tea *Thrips* (*Scirtothrips dorsalis*), onion *Thrips* (*Thrips tabaci*), eastern flower *Thrips* (*Frankliniella intonsa*), rice *Thrips* (*Stenchaetothrips biformis*), *Echinothrips americanus*, and the like;

from the family Phlaeothripidae, aculeated rice *Thrips* (*Haplothrips aculeatus*), and the like.

Diptera:

from the family Anthomyiidae, seedcorn maggot (*Delia platura*), onion maggot (*Delia antiqua*), beet leaf miner (*Pegomya cunicularia*), and the like;

from the family Ulidiidae, sugarbeet root maggot (*Tetanops myopaeformis*), and the like;

from the family Agromyzidae, rice leaf miner (*Agromyza oryzae*), tomato leaf miner (*Liriomyza sativae*), chrysanthemum leaf miner (*Liriomyza trifolii*), pea leafminer (*Chromatomyia horticola*), and the like;

from the family Chloropidae, rice stem maggot (*Chlorops oryzae*), and the like;

from the family Tephritidae, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), Japanese cherry fruit fly (*Rhacochlaena japonica*), and the like;

from the family Ephydridae, smaller rice leaf miner (*Hydrellia griseola*), whorl maggot (*Hydrellia philippina*), paddy stem maggot (*Hydrellia sasakii*), and the like;

from the family Drosophilidae, cherry *Drosophila* (*Drosophila suzukii*), and the like;

from the family Phoridae, *Megaselia spiracularis*, and the like;

from the family Psychodidae, *Clogmia albipunctata*, and the like;

from the family Sciaridae, *Bradysia difformis*, and the like;

from the family Cecidomyiidae, hessian fly (*Mayetiola destructor*), paddy gall fly (*Orseolia oryzae*), and the like;

from the family Diopsidae, *Diopsis macrophthalma*, and the like;

from the family Tipulidae, rice crane fly (*Tipula aino*), Common cranefly (*Tipula oleracea*), European cranefly (*Tipula paludosa*), and the like;

from the family Culicidae, southern house mosquito (*Culex pipiens pallens*), *Culex tritaeniorhynchus*, *Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae*, *Anopheles stephensi*, *Anopheles coluzzii*, *Anopheles albimanus*, *Anopheles sundaicus*, *Anopheles arabiensis*, *Anopheles funestus*, *Anopheles darlingi*, *Anopheles farauti*, *Anopheles minimus*, and the like;

from the family Simulidae, *Prosimulium yezoensis*, *Simulium ornatum*, and the like;

from the family Tabanidae, *Tabanus trigonus*, and the like;

from the family Muscidae, house fly (*Musca domestica*), false stable fly (*Muscina stabulans*), biting house fly (*Stomoxys calcitrans*), buffalo fly (*Haematobia irritans*), and the like;

from the family Calliphoridae;

from the family Sarcophagidae;

from the family Chironomidae, *Chironomus plumosus, Chironomus yoshimatsui, Glyptotendipes tokunagai*, and the like;

from the family Eannidae.

Coleoptera:

from the family Chrysomelidae, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape Colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, tobacco flea beetle (*Epitrix hirtipennis*), and the like;

from the family Carabidae, Seedcorn beetle (*Stenolophus lecontei*), Slender seedcorn beetle (*Clivina impressifrons*), and the like;

from the family Scarabaeidae, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*), and the like;

from the family Curculionidae, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize weevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineatocollis*, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), cotton root borer (*Eutinobothrus brasiliensis*), and the like;

from the family Tenebrionidae, red meal beetle (*Tribolium castaneum*), mason beetle (*Tribolium confusum*), lesser mealworm (*Alphitobius diaperinus*), and the like;

from the family Coccinellidae, twenty-eight-spotted ladybird (*Epilachna vigintioctopunctata*), and the like;

from the family Bostrychidae, common powder-post beetle (*Lyctus brunneus*), lesser grain borer (*Rhizopertha dominica*), and the like;

from the family Ptinidae;

from the family Cerambycidae, citrus long-horned beetle (*Anoplophora malasiaca*), *Migdolus fryanus*, and the like;

from the family Elateridae, *Melanotus okinawensis*, barley wireworm (*Agriotes fuscicollis*), *Melanotus legatus*, *Anchastus* spp., *Conoderus* spp., *Ctenicera* spp., *Limonius* spp., *Aeolus* spp., and the like;

from the family Staphylinidae, *Paederus fuscipes*, and the like;

from the family Dermestidae, varied carpet beetle (*Anthrenus verbasci*), hide beetle (*Dermestes maculates*), khapra beetle (*Trogoderma granarium*), and the like;

from the family Anobidae, tobacco beetle (*Lasioderma serricorne*) and biscuit beetle (*Stegobium paniceum*), and the like;

from the family Laemophloeidae, flat grain beetle (*Cryptolestes ferrugineus*), and the like;

from the family Silvanidae, saw-toothed grain beetle (*Oryzaephilus surinamensis*), and the like.

Orthoptera:

from the family Acrididae, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*) Japanese grasshopper (*Oxya yezoensis*), rice grasshopper (*Oxya japonica*), Bombay locust (*Patanga succincta*), and the like;

from the family Gryllotalpidae, oriental mole cricket (*Gryllotalpa orientalis*), and the like;

from the family Gryllidae, house cricket (*Acheta domestica*), emma field cricket (*Teleogryllus emma*), and the like;

from the family Tettigoniidae, for example, Mormon cricket (*Anabrus simplex*), and the like.

Hymenoptera:

from the family Tenthredinidae, beet sawfly (*Athalia rosae*), nippon cabbage sawfly (*Athalia japonica*), and the like;

from the family Formicidae, *Solenopsis* spp. (such as red imported fire ant (*Solenopsis invicta*), tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica fusca japonica*, *Pristomyrmex punctutus*, *Pheidole noda*, big-headed ant (*Pheidole megacephala*), *Camponotus* spp. (such as *Camponotus japonicus*, *Camponotus obscuripes*), *Pogonomyrmex* spp. (such as western harvester ant (*Pogonomyrmex occidentalis*)), *Wasmania* spp. (such as *Wasmania auropunctata*), long-legged ant (*Anoplolepis gracilipes*), and the like;

from the family Vespidae, Asian giant hornet (*Vespa mandarinia japonica*), *Vespa simillima*, *Vespa analis* Fabriciusi, Asian hornet (*Vespa velutina*), *Polistes jokahamae*, and the like;

from the family Siricidae, pine wood wasp (*Urocerus gigas*), and the like;

from the family Bethylidae.

Blattodea:

from the family Blattellidae, German cockroach (*Blattella germanica*), and the like;

from the family Blattidae, smoky-brown cockroach (*Periplaneta fuliginosa*), American cockroach (*Periplaneta americana*), brown cockroach (*Periplaneta brunnea*), black cockroach (*Blatta orientalis*), and the like;

from the family Termitidae, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, *Cornitermes cumulans*, and the like.

Siphonaptera:

*Pulex* spp. (such as human flea (*Pulex irritans*)), *Ctenocephalides* spp. (such as cat flea (*Ctenocephalides felis*), dog flea (*Ctenocephalides canis*)), *Xenopsylla* spp. (such as oriental rat flea (*Xenopsylla cheopis*)), *Tunga* spp. (such as chigoe flea (*Tunga penetrans*)), *Echidnophaga* spp. (such as chicken flea (*Echidnophaga gallinacea*)), *Nosopsyllus* spp. (such as European rat flea (*Nosopsyllus fasciatus*)).

Psocodae:

*Pediculus* spp. (such as head louse (*Pediculus humanus capitis*)); *Phtirus* spp. (such as crab louse (*Pthirus pubis*)); *Haematopinus* spp. (such as short-nosed cattle louse (*Haematopinus eurysternus*), pig louse (*Haematopinus suis*)); *Damalinia* spp. (such as *Dalmalinia ovis*, *Damalinia bovis*); *Linognathus* spp. (such as blue cattle louse (*Linognathus vituli*), sheep face louse (*Linognathus ovillus*)); *Solenopotes* spp. (such as capillate louse (*Solenopotes capillatus*)); *Menopon* spp. (such as common chicken louse (*Menopon gallinae*)); *Trimenopon* spp.; *Trinoton* spp.; *Trichodectes* spp. (such as dog biting louse (*Trichodectes canis*)); *Felicola* spp. (such as cat louse (*Felicola subrostratus*)); *Bovicola* spp. (such as cattle biting louse (*Bovicola bovis*)); *Menacanthus* spp. (such as chicken body louse (*Menacanthus stramineus*)); *Werneckiella* spp.; *Lepikentron* spp.;

from the family Liposcelididae, book louse (*Liposcelis subfuscas*), *Liposcelis bostrychophilus*, *Liposcelis simulans*, *Liposcelis divinatorius*, *Liposcelis entomophila*, and the like.

Thysanura:

from the family Lepismatidae, oriental silverfish (*Ctenolepisma villosa*), moth fish (*Lepisma saccharina*), and the like.

Acari:

from the family Tetranychidae, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), *Oligonychus* spp., and the like;

from the family Eriophyidae, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, *Shevtchenkella* sp., and the like;

from the family Tarsonemidae, broad mite (*Polyphagotarsonemus latus*), and the like;

from the family Tenuipalpidae, *Brevipalpus phoenicis*, and the like;

from the family Tuckerellidae;

from the family Ixodidae, for example, *Haemaphysalis* spp. (such as *Haemaphysalis longicornis, Haemaphysalis flava, Haemaphysalis campanulata*), *Dermacentor* spp. (such as American dog tick (*Dermacentor variabilis*), *Dermacentor taiwanicus*, Rocky Mountain wood tick (*Dermacentor andersoni*)), *Ixodes* spp. (such as *Ixodes ovatus, Ixodes persulcatus*, black-legged tick (*Ixodes scapularis*), *Ixodes pacificus, Ixodes holocyclus*), *Amblyomma* spp. (such as lone star tick (*Amblyomma americanum*), gulf coast tick (*Amblyomma maculatum*)), *Boophilus* spp. (such as *Rhipicephalus* (*Boophilus*) *microplus, Boophilus annulatus*), and *Rhipicephalus* spp. (such as brown dog tick (*Rhipicephalus sanguineus*), *Rhipicephalus appendiculatus*);

from the family Acaridae, cereal mite (*Tyrophagus putrescentiae*), grassland mite (*Tyrophagus similis*), and the like;

from the family Pyroglyphidae, American house dust mite (*Dermatophagoides farinae*), European house dust mite (*Dermatophagoides pteronyssinus*), and the like;

from the family Cheyletidae, *Cheyletus eruditus, Cheyletus malaccensis, Chelacaropsis moorei, Cheyletiella yasguri*, and the like;

*Argas* spp. (such as fowl tick (*Argas persicus*)), *Ornithodorus* spp. (such as *Ornithodorus hermsi, Ornithodorus turicata*), *Psoroptes* spp. (such as sheep scab mite (*Psoroptes ovis*), horse psoroptic mange mite (*Psoroptes equi*)), *Knemidocoptes* spp. (such as *Knemidocoptes mutans*), *Notoedres* spp. (such as *Notoedres cati, Notoedres muris*), *Sarcoptes* spp. (such as itch mite (*Sarcoptes scabiei*)), *Otodectes* spp. (such as ear mange mite (*Otodectes cynotis*)), *Listrophorus* spp. (such as *Listrophorus gibbus*), *Chorioptes* spp., *Hypodectes* spp., *Pterolichus* spp., *Cytodites* spp., *Laminosioptes* spp., *Dermanyssus* spp. (such as bird mite (*Dermanyssus gallinae*)), *Ornithonyssus* spp. (such as feather mite (*Ornithonyssus sylviarum*), tropical rat mite (*Ornithonyssus bacoti*)), *Varroa* spp. (such as *Varroa jacobsoni*), *Cheyletiella* spp. (such as *Cheyletiella yasguri, Cheyletiella blakei*), *Ornithocheyletia* spp., *Demodex* spp. (such as dog follicle mite (*Demodex canis*), cat follicle mite (*Demodex cati*)), *Myobia* spp., *Psorergates* spp., *Trombicula* spp. (such as *Trombicula akamushi, Trombicula pallida, Trombicula scutellaris*).

Araneae:

from the family Eutichuridae, *Cheiracanthium japonicum*, and the like;

from the family Theridiidae, red-back spider (*Latrodectus hasseltii*), and the like.

Polydesmida:

from the family Paradoxosomatidae, flat-backed millipede (*Oxidus gracilis*), *Nedyopus tambanus*, and the like;

Isopoda:

from the family Armadillidiidae, common pill bug (*Armadillidium vulgare*), and the like;

Chilopoda:

from the family Scutigeridae, *Thereuonema hilgendorfi*, and the like;

from the family Scolopendridae, giant tropical centipede (*Scolopendra subspinipes*), and the like;

from the family Ethopolyidae, *Bothropolys rugosus*, and the like;

Gastropoda:

from the family Limacidae, tree slug (*Limax marginatus*), garden tawny slug (*Limax flavus*), and the like;

from the family Philomycidae, *Meghimatium bilineatum*, and the like;

from the family Ampullariidae, golden apple snail (*Pomacea canaliculata*), and the like;

from the family Lymnaeidae, *Austropeplea ollula*, and the like.

Nematoda:

from the family Aphelenchoididae, rice white-tip nematode (*Aphelenchoides besseyi*), and the like;

from the family Pratylenchidae, root lesion nematode (*Pratylenchus coffeae*), *Pratylenchus brachyurus*, California meadow nematode (*Pratylenchus neglectus*), *Radopholus similis*, and the like;

from the family Heteroderidae, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), white potato cyst nematode (*Globodera pallida*), and the like;

from the family Hoplolaimidae, *Rotylenchulus reniformis*, and the like;

from the family Anguinidae, strawberry bud nematode (*Nothotylenchus acris*), stem nematode (*Ditylenchus dipsaci*), and the like;

from the family Tylenchulidae, citrus nematode (*Tylenchulus semipenetrans*), and the like;

from the family Longidoridae, dagger nematode (*Xiphinema index*), and the like;

from the family Trichodoridae;

from the family Parasitaphelenchidae, pine wilt disease (*Bursaphelenchus xylophilus*), and the like.

Present compound may be also applied to harmful arthropods such as harmful insects and harmful mites, harmful mollusks, and harmful nematodes which have a reduced agent-sensitivity to or a developed agent-resistance to an insecticide or a miticide, a molluscicide or a nematicide.

Present compound may be also used to protect a plant from a plant disease caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, *Chrysanthemum* stem necrosis virus, *Impatiens* necrotic spot virus, Iris yellow spot virus, Lily mottle virus, Lilly symptomless virus, Tulip mosaic virus, and the others.

Examples of the insect-borne bacteria are recited as follows.

Candidatus Phytoplasma *oryzae*, Candidatus Phytoplasma asteris, Maize bushy stunt phytoplasma, Candidatus Liberbacter asiaticus, Candidatus Liberbacter africanus, Candidatus Liberbacter americanus.

The composition for controlling harmful arthropods of the present invention comprises the present compound or the composition A and an inert carrier. The composition for controlling harmful arthropods of the present invention is usually prepared by mixing the present compound or the composition A with an inert carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, and tablets and the others. Such formulations may be processed into mosquito repellent coils, electric mosquito repellent mats, liquid mosquito formulations, smoking agents, fumigants, sheet formulations, spot-on formulations or formulations for oral treatment. The composition for controlling harmful arthropods of the present invention comprises usually 0.01 to 95% by weight of the present compound or the composition A.

Examples of the solid carrier to be used in the formulation include fine powders or granules of clays (for example, kaolin clay, diatomaceous earth, bentonite, Fubasami clay, or acid white clay), dry silica, wet silica, hydrated silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl etheR14-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, N,N-dimethylformamide (hereinafter, referred to as "DMF") or N,N-dimethylacetamide); sulfoxides (for example, dimethyl sulfoxide); propylene carbonate; and vegetable oils (for example, soybean oil or cottonseed oil).

Examples of gaseous carrier include fluorocarbon, butane gas, LPG (liquefied petroleum gas), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of a base material of the resin formulation include polyvinyl chloride polymers, polyurethane, and the others, and a plasticizer such as phthalate esters (for example, dimethyl phthalate, and dioctyl phthalate), adipic acid esters and stearic acid may be added to the base material, if necessary. The resin formulation can be prepared by kneading the present compound in the base material with a conventional kneading machine, and then molding it by injection molding, extrusion molding, or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the present compound, or the composition A to a harmful arthropod directly and/or a habitat where the harmful arthropod lives (for example, plant bodies, soil, an interior of a house, and animal bodies). Further, the effective amount of the same can be applied to seeds. Examples of a method for controlling harmful arthropods of the present invention include foliar application, soil application, root application, shower application, smoking application, water-surface application, and seed application.

As used herein, examples of the plant include whole plant, stem and leaf, flower, ear, fruit, tree stem, branch, crown, seed, vegetative reproductive organ, and seedling.

The vegetative reproductive organ represents a part of plant such as root, stem and leaf, which has a growth capacity if the part is cut off from its plant and then placed in the soil. Examples of the vegetative reproductive organ include tuberous root, creeping root, bulb, corm or solid bulb, tuber, rhizome, stolon, rhizophore, cane cuttings, propagule, and vine cutting. The "stolon" is often referred to as "runner", and the "propagule" is often referred to as "brood bud", which is divided into broad bud and bulbil. The vine cutting represents a shoot (which is a generic name of leaf and stem) of sweet potato (*Ipomoea batatas*) and Japanese yam (*Dioscorea japonica*), etc. The bulb, corm or solid bulb, tuber, rhizome, cane cuttings, rhizophore, and tuberous root are also collectively referred to as "bulb". For example, when the cultivation of potato starts with planting tubers in the soil, the used tuber is generally referred to as "seed potato".

Examples of a method for controlling harmful arthropods by applying an effective amount of the present compound or the composition A to soils include a method of applying an effective amount of the present composition or the composition A to soils before planting plants or after planting plants, a method of applying an effective amount of the present composition or the composition A to a root part of a crop to be protected from damage such as ingestion by harmful arthropods, and a method of controlling harmful arthropods that ingest a plant by permeating and transferring an effective amount of the present composition or the composition A from a root into the interior of the plant body. More specifically, examples of the application method include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering with soils), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

When the composition for controlling harmful arthropod of the present invention is used for controlling pests in an agricultural field, an applied dose as an amount of the present compound is usually within a range from 1 to 10,000 g per 10,000 $m^2$. When the present composition is applied to seeds, an applied dose as an amount of the present compound is usually within a range from 0.001 to 100 g relative to 1 kg of the seeds. When the composition for controlling harmful arthropod of the present invention is formulated into the emulsifiable concentrate, the wettable powder, or the flowable formulation etc., the present composition is usually applied by diluting it with water in such a way that a concentration of the active ingredient of the present composition is usually within a range from 0.01 to 10,000 ppm. The granular formulation, or the powder formulation etc., is usually applied as itself.

These formulations and diluents of the formulations with water may be directly sprayed to a harmful arthropod or a plant such as a crop to be protected from the harmful arthropod, or applied to a soil in a cultivated area to control the pests that inhabits the soil.

Also, the resin formulation processed into a sheet shape or string shape may be wrapped around a crop, stretched near a crop, spread on a foot soil of a plant, or the like.

When the composition for controlling harmful arthropod of the present invention is used to control harmful arthropods that live inside a house, an applied dose as an amount of the present compound is usually within a range from 0.001 to 1,000 mg per 1 $m^2$ of an area to be treated, in the case of using it on a planar area. In the case of using it spatially, the applied dose as an amount of the present compound is usually within a range from 0.001 to 500 mg per 1 $m^3$ of the space to be treated. When the composition for controlling harmful arthropod of the present invention is formulated into emulsifiable concentrates, wettable powders, flowables or the others, the formulation is usually applied after diluting it with water in such a way that a concentration of the active ingredient is usually within a range from 0.1 to 10,000 ppm, and then sparging it. In the case of being formulated into oil solutions, aerosols, smoking agents, poison baits and the others, the formulation is used as itself.

When the composition for controlling harmful arthropod of the present invention is used for controlling external parasites of livestock such as cows, horses, pigs, sheep, goats and chickens, and small animals such as dogs, cats, rats and mice, the present composition can be applied to the animal by a known method in the veterinary field. Specifically, when systemic control is intended, the present composition is administered to the animal as a tablet, a mixture with feed or a suppository, or by injection (including intramuscular, subcutaneous, intravenous and intraperitoneal injections). On the other hand, when non-systemic control is intended, the present composition is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound is usually within a range from 0.1 to 1,000 mg per 1 kg of a body weight of the animal.

Also the present compound or the composition A can be used as an agent for controlling harmful arthropods in the agricultural land such as field, paddy, lawn and orchard. The present compound can control harmful arthropods in an agricultural land in which the below-mentioned plants are cultivated.

Crops:
   corn, rice, wheat, barley, rye, oat, sorghum, cotton, soybean, peanut, buckwheat, beet, rapeseed, sunflower, sugarcane, tobacco, and the others;
Vegetables:
   solanaceous vegetables (for example, eggplant, tomato, green pepper, hot pepper, and potato),
   cucurbitaceous vegetables (for example, cucumber, pumpkin, zucchini, water melon, and melon),
   cruciferous vegetables (for example, Japanese radish, white turnip, horseradish, kohlrabi, Chinese cabbage, cabbage, leaf mustard, broccoli, and cauliflower),
   asteraceous vegetables (for example, burdock, crown daisy, artichoke, and lettuce),
   liliaceous vegetables (for example, green onion, onion, garlic, and asparagus),
   ammiaceous vegetables (for example, carrot, parsley, celery, and parsnip),
   chenopodiaceous vegetables (for example, spinach and Swiss chard),
   lamiaceous vegetables (for example, *Perilla frutescens*, mint, and basil),
   strawberry, sweet potato, *Dioscorea japonica*, *Colocasia*, flowering plants, foliage plants, and the others;
Fruits:
   pomaceous fruits (for example, apple, pear, Japanese pear, Chinese quince, and quince),
   stone fleshy fruits (for example, peach, plum, nectarine, *Prunus mume*, cherry fruit, apricot, and prune),
   citrus fruits (for example, citrus unshiu, orange, lemon, lime, and grapefruit),
   nuts (for example, chestnut, walnuts, hazelnuts, almond, pistachio, cashew nuts, and macadamia nuts),
   berry fruits (for example, blueberry, cranberry, blackberry, and raspberry),
   grape, kaki persimmon, olive, Japanese plum, banana, coffee, date palm, coconuts,
   and the others;
Trees Other than Fruits
   tea, mulberry, flowering plants, roadside trees (for example, ash, birch, dogwood, *eucalyptus, Ginkgo biloba*, lilac, maple, *Quercus*, poplar, Judas tree, *Liquidambar formosana*, plane tree, *Zelkova*, Japanese arborvitae, fir wood, hemlock, juniper, *Pinus, Picea*, and *Taxus cuspidate*),
   The above plants also include a plant that can be generated by a natural crossbreeding, a plant that can be generated by mutations, an F1 hybrid plant, and a genetically modified crop. Examples of the genetically modified crop include a plant modified to have the resistance to HPPD (4-hydroxyphenylpyruvate dioxygenase) inhibitors such as isoxaflutole, ALS (acetolactate synthase) inhibitors such as imazethapyr and thifensulfuron-methyl, EPSP (5-enolpyruvoylshikimate-3-phosphate synthase) inhibitors, glutamine synthetase inhibitors, PPO (protoporphyrinogen oxidase) inhibitors, or herbicides such as bromoxynil and dicamba; a plant modified to synthesize a selective toxin known to be produced in *Bacillus* such as *Bacillus thuringiensis*; and a plant modified to have a specific insecticidal activity by synthesizing a gene fragment partially corresponding to an endogenous gene derived from a harmful insect to induce the gene silencing (RNAi; RNA interference) in the target harmful insect.
   The above-mentioned plants may be genetically modified crops.

EXAMPLES

Hereinafter, the present invention is explained in more detail by using the Preparation Example, the Reference Preparation Example, the Formulation Example, and the Test Example, however, the present invention should not be limited to these examples.

Preparation Example 1

A mixture of 2,4-dibromothiazole 15 g, 4-fluorophenyl boronic acid 9.5 g, palladium (II) acetate 690 mg, 4,5'-bis (diphenylphoshino)-9,9'-dimethyl xanthene 1.8 g, tripotassium phosphate 39 g, and THF 300 mL was stirred at 60° C. for 10 hours. Water was added to the resulting mixture, and the mixture was extracted with ethyl acetate. The resulting organic layer was dried over anhydrous sodium sulfate, and concentrated under reduced pressure. The resulting residue was subjected to silica gel column chromatography to obtain an intermediate compound 1 represented by the below-mentioned formula 12 g.

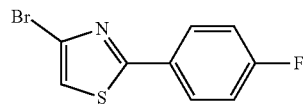

Intermediate compound 1: $^1$H-NMR (CDCl$_3$) δ: 7.95-7.91 (2H, m), 7.21 (1H, s), 7.16-7.11 (2H, m).

Preparation Example 2

To a mixture of diisopropyl amine 1.2 mL and THF 5 mL was added butyl lithium (1.6 M hexane solution) 5.7 mL at −50° C., and the mixture was stirred for 20 minutes. To the resulting mixture was added a mixture of the intermediate compound 1 1.5 g and THF 7 mL, and the mixture was stirred for 1 hour. To the resulting mixture was added zinc chloride (1.0 M diethyl ether solution) 15 mL. The resulting mixture was raised gradually from −50° C. to room temperature, and the mixture was stirred at room temperature for 2 hours. To the resulting mixture were added 2-bromo-5-(2, 2,3,3,3-pentafluoropropoxy)pyridine 0.59 g, which was prepared according to the method described in WO 2016/121969, tetrakis(triphenylphosphine)palladium (0) 340 mg, and THE 5 mL, and the mixture was stirred at 50° C. for 3 hours. To the resulting mixture was added 2N hydrochloric acid, and the mixture was extracted with ethyl acetate. The resulting organic layer was dried over anhydrous magnesium sulfate, and concentrated under reduced pressure. The resulting residue was subjected to silica gel column chromatography to obtain an intermediate compound 2 represented by the below-mentioned formula 920 mg.

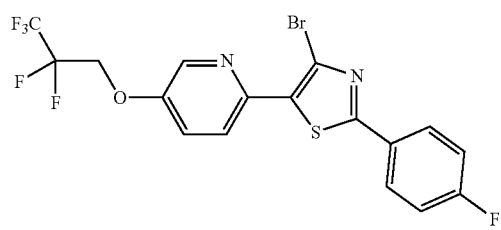 [SMILES: Fc1ccc(-c2nc(Br)c(-c3ccc(OCC(F)(F)C(F)(F)F)cn3)s2)cc1]

Intermediate compound 2: $^1$H-NMR (CDCl$_3$) δ: 8.39 (1H, d), 8.37 (1H, d), 7.97 (2H, dd), 7.38 (1H, dd), 7.15 (2H, t), 4.53 (2H, t).

Preparation Example 3

To a mixture of the intermediate compound 2 920 mg, sodium hydride (60%, oily) 76 mg, and DMF 5 mL was added ethanethiol 0.14 mL, and the mixture was stirred at room temperature for 8 hours. To the resulting mixture was added saturated aqueous sodium hydrocarbonate solution, and the mixture was extracted with ethyl acetate. The resulting organic layer was dried over anhydrous sodium sulfate and concentrated under reduced pressure. The resulting residue was subjected to a silica gel column chromatography to obtain the present compound 1 represented by the below-mentioned formula 270 mg.

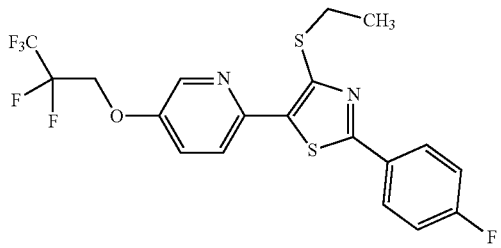 [SMILES: CCSc1nc(-c2ccc(F)cc2)sc1-c1ccc(OCC(F)(F)C(F)(F)F)cn1]

Present compound 1: $^1$H-NMR (CDCl$_3$) δ: 8.38-8.36 (2H, m), 8.00-7.93 (2H, m), 7.38-7.33 (1H, m), 7.17-7.12 (2H, m), 4.53 (2H, t), 3.02 (2H, q), 1.37 (3H, t).

Preparation Example 4

To a mixture of the present compound 1 270 mg, and ethyl acetate 5 mL was added m-chloroperbenzoic acid (74%) 320 mg under ice-cooling, and the mixture was raised to room temperature, and thereafter, the mixture was stirred for 4 hours. To the resulting mixture were added saturated aqueous sodium thiosulfate solution and saturated aqueous sodium hydrogen carbonate solution, and the mixture was extracted with ethyl acetate. The resulting organic layer was dried over anhydrous sodium sulfate, and concentrated under reduced pressure. The resulting residue was subjected to a silica gel column chromatography to obtain the present compound 2 represented by the below-mentioned formula 150 mg.

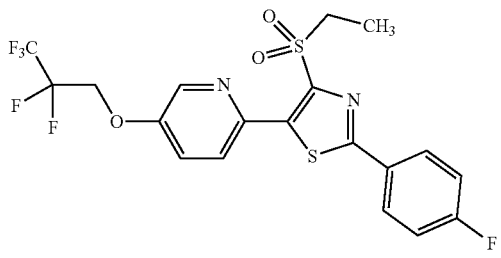 [SMILES: CCS(=O)(=O)c1nc(-c2ccc(F)cc2)sc1-c1ccc(OCC(F)(F)C(F)(F)F)cn1]

Present compound 2: $^1$H-NMR (CDCl$_3$) δ: 8.38 (1H, d), 8.26 (1H, d), 7.98-7.94 (2H, m), 7.35 (1H, dd), 7.20-7.14 (2H, m), 4.53 (2H, t), 3.62 (2H, q), 1.42 (3H, t).

Preparation Example 5

An intermediate compound 3 was obtained by using cyclopropyl boronic acid in place of 4-fluorophenyl boronic acid according to the method described in the Preparation Example 1.

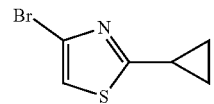

Intermediate compound 3: $^1$H-NMR (CDCl$_3$) δ: 6.96 (1H, s), 2.34-2.24 (1H, m), 1.18-1.07 (4H, m).

Preparation Example 6

An intermediate compound 4 was obtained by using the intermediate compound 3 in place of the intermediate compound 1 according to the method described in the Preparation Example 2.

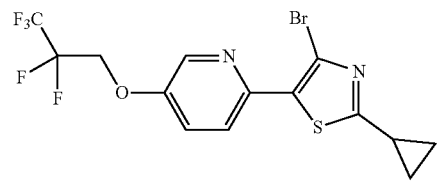 [SMILES: FC(F)(F)C(F)(F)COc1ccc(-c2sc(C3CC3)nc2Br)nc1]

Intermediate compound 4: $^1$H-NMR (CDCl$_3$) δ: 8.32 (1H, dd), 8.28 (1H, dd), 7.34 (1H, dd), 4.56-4.43 (2H, m), 2.34-2.26 (1H, m), 1.23-1.08 (4H, m).

Preparation Example 7

A mixture of the intermediate compound 705 mg, ethanethiol 190 μL, tris(benzylideneacetone)palladium (0) 300 mg, 4,5'-bis(diphenylphoshino)-9,9'-dimethylxanthene 380 mg, diisopropylethylamine 840 μL, and cyclopently methyl ether 5 mL was stirred at 100° C. for 8 hours. The resulting mixture was allowed to cool, and thereafter, thereto was added saturated aqueous sodium hydrogen carbonate solution, and the mixture was extracted with ethyl acetate. The resulting organic layer was dried over anhydrous sodium sulfate, and concentrated under reduced pressure. The resulting residue was subjected to a silica gel column chromatography to obtain the present compound 3 represented by the below-mentioned formula 490 mg.

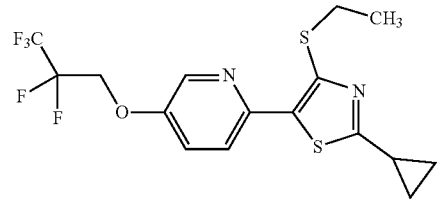 [SMILES: CCSc1nc(C2CC2)sc1-c1ccc(OCC(F)(F)C(F)(F)F)cn1]

Present compound 3: $^1$H-NMR (CDCl$_3$) δ: 8.31 (1H, d), 8.03 (1H, dd), 7.42-7.28 (1H, m), 4.53-4.45 (2H, m), 3.32-3.11 (2H, m), 2.40-2.24 (1H, m), 1.33 (3H, t), 1.18-1.09 (4H, m).

Preparation Example 8

The present compound 4 was obtained by using the present compound 3 in place of the present compound 1 according to the method described in the Preparation Example 4.

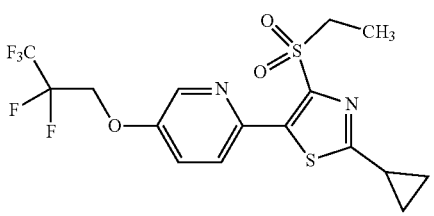 [SMILES: CCS(=O)(=O)c1nc(C2CC2)sc1-c1ccc(OCC(F)(F)C(F)(F)F)cn1]

Present compound 4: 1H-NMR (CDCl₃) δ: 8.33 (1H, dd), 8.12 (1H, dd), 7.31 (1H, dd), 4.50 (2H, d), 3.48 (2H, q), 2.36-2.28 (1H, m), 1.34 (3H, t), 1.25-1.18 (2H, m), 1.14-1.10 (2H, m).

Preparation Example 9

A mixture of ethyl chloro(hydroxyimimo) acetate 0.15 g, which was prepared according to the method described in WO 2012/117421, 2-ethanesulfonyl-1-[5-(2,2,3,3,3-pentafluoropropoxy)pyridin-2-yl]ethanone (hereinafter, referred to as "Intermediate compound 5"), which was prepared according to the method described in WO 2016/121969, 0.38 g, trimethylamine 0.22 g, and ethanol 3 mL was stirred at room temperature for 12 hours. To the resulting mixture was added water, and the mixture was extracted with ethyl acetate. The resulting organic layer was dried anhydrous sodium sulfate, and concentrated under reduced pressure. The resulting residue was subjected to a silica gel column chromatography to obtain the present compound 5 represented by the below-mentioned formula 100 mg.

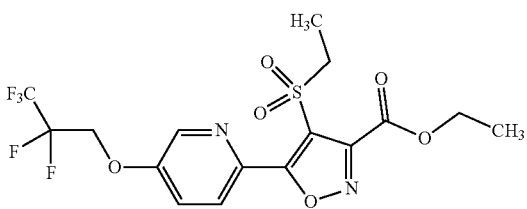 [SMILES: CCOC(=O)c1noc(-c2ccc(OCC(F)(F)C(F)(F)F)cn2)c1S(=O)(=O)CC]

Present compound 5: 1H-NMR (CDCl₃) δ: 8.54 (1H, d), 7.97 (1H, d), 7.42 (1H, dd), 4.57 (2H, t), 4.51 (2H, q), 3.77 (2H, q), 1.47-1.28 (6H, m).

Preparation Example 10

A mixture of the present compound 5 400 mg, 1N aqueous lithium hydroxide solution 1 mL, and THF 3 mL was stirred at room temperature for 5 hours. To the resulting mixture was added water 5 mL, and the mixture was extracted with MTBE. To the resulting aqueous layer was added 2N hydrochloric acid to adjust pH to 4, and the mixture was extracted with ethyl acetate. The resulting organic layer was dried over anhydrous sodium sulfate and concentrated under reduced pressure. The resulting residue was added to a mixture of triethylamine 222 mg, 1-ethyl-3-(3-dimethylaminopropyl)carbodiimide hydrochloride salt 0.38 g, and isobutyl amine 141 mg under ice-cooling. The resulting mixture was raised to room temperature, and stirred for 8 hours. To the resulting mixture was added water, and the mixture was extracted with ethyl acetate. The resulting organic layer was dried over anhydrous sodium sulfate, and concentrated under reduced pressure. The resulting residue was subjected to a silica gel column chromatography to obtain the present compound 6 represented by the below-mentioned formula 260 mg.

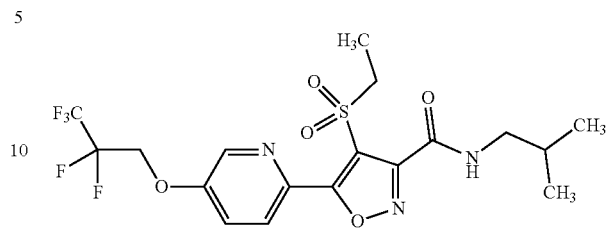

Present compound 6: 1H-NMR (CDCl₃) δ: 8.52 (1H, d), 7.90 (1H, d), 7.40 (1H, dd), 6.63 (1H, br s), 4.56 (2H, t), 3.80 (2H, q), 3.33 (2H, t), 1.98-1.91 (1H, m), 1.45 (3H, t), 1.01 (6H, d).

Preparation Example 11

The present compound 7 and the present compound 8 each represented by the below-mentioned formula were obtained according to the Preparation Example 9.

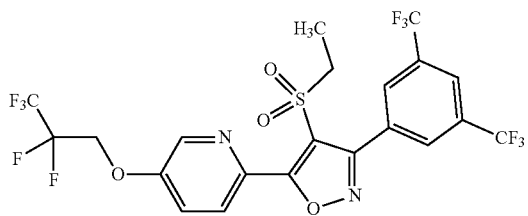 [SMILES: CCS(=O)(=O)c1c(-c2cc(C(F)(F)F)cc(C(F)(F)F)c2)noc1-c1ccc(OCC(F)(F)C(F)(F)F)cn1]

Present compound 7: 1H-NMR (CDCl₃) δ: 8.56 (1H, t), 8.13 (2H, s), 8.07-8.03 (2H, m), 7.47 (1H, dd), 4.60 (2H, t), 3.77 (2H, q), 1.37 (3H, t).

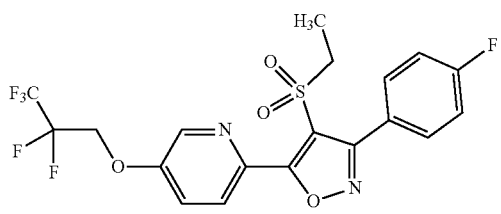 [SMILES: CCS(=O)(=O)c1c(-c2ccc(F)cc2)noc1-c1ccc(OCC(F)(F)C(F)(F)F)cn1]

Present compound 8: 1H-NMR (CDCl₃) δ: 8.54 (1H, dd), 7.99 (1H, dd), 7.72-7.66 (2H, m), 7.44 (1H, dd), 7.23-7.15 (2H, m), 4.58 (2H, t), 3.55 (2H, q), 1.29 (3H, t).

Preparation Example 12

To a mixture of the intermediate compound 5 1.7 g, and ally bromide 320 mg, and DMSO 10 mL was added potassium hydroxide 320 mg at room temperature under nitrogen atmosphere, and the mixture was stirred at 80° C. for 30 minutes. To the resulting mixture was added water at room temperature, and the mixture was extracted with ethyl acetate. The resulting organic layer was washed with saturated brine, dried over anhydrous magnesium sulfate, and concentrated under reduced pressure. To the resulting residue was added methanol 10 mL, and ozone was bubbled to the resulting mixture at room temperature for 10 minutes. To the resulting mixture was added dimethyl sulfide 530 μL at −78° C., and the mixture was stirred at room temperature for 1 day. The resulting mixture was concentrated under reduced pressure. The resulting residue was subjected to a silica gel column chromatography to obtain an intermediate compound 6 represented by the below-mentioned formula 1.2 g.

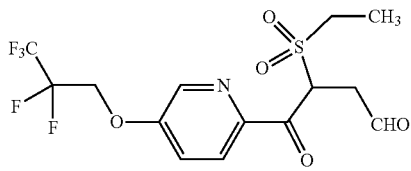 [SMILES: CCS(=O)(=O)C(CC=O)C(=O)c1ccc(OCC(F)(F)C(F)(F)F)cn1]

Intermediate compound 6: $^1$H-NMR (CDCl$_3$) δ: 9.77 (1H, s), 8.49 (1H, d), 8.18 (1H, d), 7.41 (1H, dd), 6.39 (1H, dd), 4.59 (2H, t), 3.62-3.53 (2H, m), 3.30-3.07 (2H, m), 1.40 (3H, t).

Preparation Example 13

To a mixture of the intermediate compound 6 250 mg and ethanol 2 mL was added ammonium acetate 53 mg at room temperature under nitrogen atmosphere, and the mixture was stirred at 80° C. for 1 hour. To the resulting mixture was added water at room temperature, and the mixture was extracted with ethyl acetate. The resulting organic layer was washed with saturated brine, and dried over anhydrous magnesium sulfate, and concentrated under reduced pressure. The resulting residue was subjected to a silica gel column chromatography to obtain the present compound 9 represented by the below-mentioned formula 31 mg.

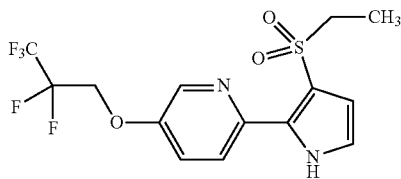 [SMILES: CCS(=O)(=O)c1cc[nH]c1-c1ccc(OCC(F)(F)C(F)(F)F)cn1]

Present compound 9: $^1$H-NMR (CDCl$_3$) δ: 10.13 (1H, s), 8.55 (1H, dd), 8.32 (1H, d), 7.32 (1H, dd), 6.90 (1H, t), 6.74 (1H, t), 4.51 (2H, t), 3.14 (2H, q), 1.26 (3H, t).

Preparation Example 14

To a mixture of the present compound 9 200 mg, methyl iodide 160 μL and DMF 2 mL was added sodium hydride (60%, oily) 23 mg at room temperature, and the mixture was stirred for 30 minutes. To the resulting mixture was added water, and the mixture was extracted with ethyl acetate. The resulting organic layer was washed with saturated brine, dried over anhydrous magnesium sulfate, and concentrated under reduced pressure. The resulting residue was subjected to a silica gel column chromatography to obtain the present compound 10 represented by the below-mentioned formula 120 mg.

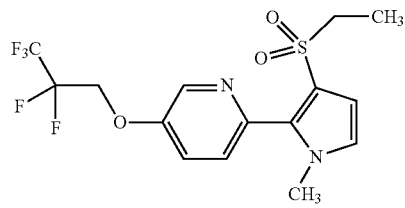 [SMILES: CCS(=O)(=O)c1ccn(C)c1-c1ccc(OCC(F)(F)C(F)(F)F)cn1]

Present compound 10: 1H-NMR (CDCl$_3$) δ: 8.44 (1H, dd), 7.74 (1H, dd), 7.35 (1H, dd), 6.73 (1H, d), 6.63 (1H, d), 4.53 (2H, t), 3.58 (3H, s), 2.92 (2H, q), 1.14 (3H, t).

Preparation Example 15

The present compound 11 was obtained by using isopropyl iodide in place of methyl iodide according to the Preparation Example 14.

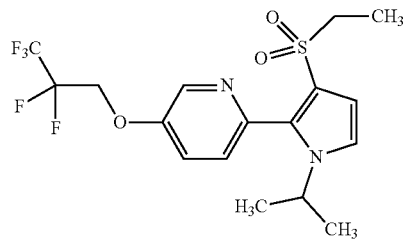 [SMILES: CCS(=O)(=O)c1ccn(C(C)C)c1-c1ccc(OCC(F)(F)C(F)(F)F)cn1]

Present compound 11: $^1$H-NMR (CDCl$_3$) δ: 8.44 (1H, dd), 7.67 (1H, dd), 7.35 (1H, dd), 6.88 (1H, d), 6.67 (1H, d), 4.53 (2H, t), 4.31-4.24 (1H, m), 2.91 (2H, q), 1.37 (6H, d), 1.15 (3H, t).

Preparation Example 16

To a mixture of the intermediate compound 6 240 mg and toluene 10 mL was added lowesson reagent 630 mg at room temperature, and the mixture was stirred at 80° C. for 1 hour. To the resulting mixture was added water at room temperature, and the mixture was extracted with ethyl acetate. The resulting organic layer was washed with saturated brine, dried over anhydrous magnesium sulfate, and concentrated under reduced pressure. The resulting residue was subjected to a silica gel column chromatography to obtain the present compound 12 represented by the below-mentioned formula 190 mg.

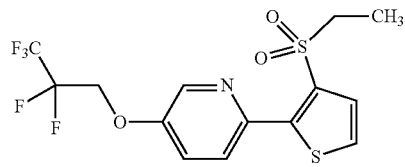 [SMILES: CCS(=O)(=O)c1ccsc1-c1ccc(OCC(F)(F)C(F)(F)F)cn1]

Present compound 12: $^1$H-NMR (CDCl$_3$) δ: 8.44 (1H, d), 7.94 (1H, d), 7.53 (1H, d), 7.42 (1H, d), 7.36 (1H, dd), 4.54 (2H, t), 3.34 (2H, q), 1.27 (3H, t).

Preparation Example 17

To a mixture of the intermediate compound 5 10 g and chloroform 40 mL were added N-chlorosuccinimide 4.1 g and p-toluenesulfonic acid 530 mg successively, and the mixture was stirred at 60° C. for 2 hours. The resulting mixture was allowed to cool to room temperature, and thereto was added aqueous sodium thiosulfate solution, and the mixture was extracted with ethyl acetate. The resulting organic layer was washed with saturated brine, dried over anhydrous magnesium sulfate, and concentrated under reduced pressure. The resulting reside was subjected to a silica gel column chromatography to obtain the intermediate compound 7 represented by the below-mentioned formula 2.1 g.

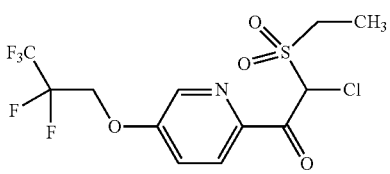

Intermediate compound 7: $^1$H-NMR (CDCl$_3$) δ: 8.46 (1H, d), 8.19 (1H, d), 7.41 (1H, dd), 4.59 (2H, t), 3.61-3.47 (1H, m), 3.43-3.28 (2H, m), 1.46 (3H, t).

Preparation Example 18

To a mixture of the intermediate compound 7 1.0 g and ethanol 40 mL were added thiourea 580 mg and pyridine 400 mg successively at room temperature, and the mixture was stirred under reflux for 2 hours. The resulting mixture was allowed to cool to room temperature, water was added thereto, and the mixture was extracted with ethyl acetate. The resulting organic layer was washed with saturated brine, and dried over anhydrous magnesium sulfate, and concentrated under reduced pressure. The resulting residue was subjected to a silica gel column chromatography to obtain the present compound 13 represented by the below-mentioned formula 200 mg.

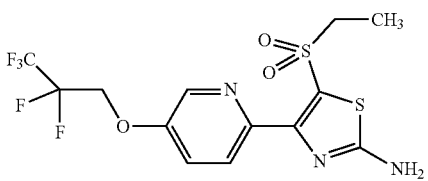 [SMILES: CCS(=O)(=O)c1sc(N)nc1-c1ccc(OCC(F)(F)C(F)(F)F)cn1]

Present compound 13: $^1$H-NMR (CDCl$_3$) δ: 8.40 (1H, dd), 7.93 (1H, dd), 7.32 (1H, dd), 5.40 (2H, s), 4.52 (2H, t), 3.87 (2H, q), 1.41 (3H, t).

Preparation Example 19

To a mixture of the intermediate compound 7 500 mg and ethanol 5 mL was added thiobenzamide 520 mg at room temperature, and the mixture was stirred at 100° C. for 30 minutes. The resulting mixture was allowed to cool to room temperature, and water was added thereto, and the mixture was extracted with ethyl acetate. The resulting organic layer was washed with saturated brine, dried over anhydrous magnesium sulfate, and concentrated under reduced pressure. The resulting residue was subjected to silica gel column chromatography to obtain the present compound 14 represented by the below-mentioned formula 74 mg.

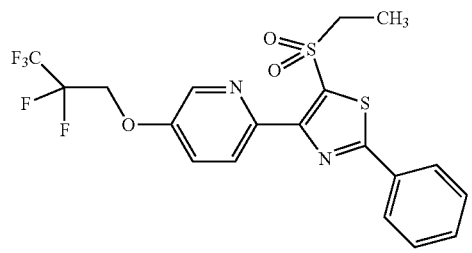 [SMILES: CCS(=O)(=O)c1sc(-c2ccccc2)nc1-c1ccc(OCC(F)(F)C(F)(F)F)cn1]

Present compound 14: $^1$H-NMR (CDCl$_3$) δ: 8.45 (1H, d), 8.23 (1H, d), 8.02 (2H, dd), 7.56-7.48 (3H, m), 7.40 (1H, dd), 4.56 (2H, t), 4.05 (2H, q), 1.46 (3H, t).

Preparation Example 20

To a mixture of the present compound 13 230 mg and DMF 2 mL was added t-butyl nitrite 80 µL at 60° C., and the mixture was stirred under reflux for 30 minutes. The resulting mixture was allowed to cool to room temperature, water was added thereto, and the mixture was extracted with ethyl acetate. The resulting organic layer was washed with saturated brine, dried over anhydrous magnesium sulfate, and concentrated under reduced pressure. The resulting residue was subjected to a silica gel column chromatography to obtain the present compound 15 represented by the below-mentioned formula 73 mg.

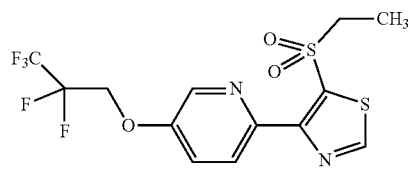 [SMILES: CCS(=O)(=O)c1scnc1-c1ccc(OCC(F)(F)C(F)(F)F)cn1]

Present compound 15: $^1$H-NMR (CDCl$_3$) δ: 8.99 (1H, s), 8.44 (1H, d), 8.14 (1H, d), 7.39 (1H, dd), 4.55 (2H, t), 4.04 (2H, q), 1.42 (3H, t).

Preparation Example 21

A mixture of the intermediate compound 5 30 g and N,N-dimethylformamide dimethyl acetal 120 mL was stirred at room temperature for 12 hours. The precipitated out-solids were filtered, and washed with MTBE. The resulting solids were dried under reduced pressure to obtain the intermediate compound 8 represented by the below-mentioned formula 24 g.

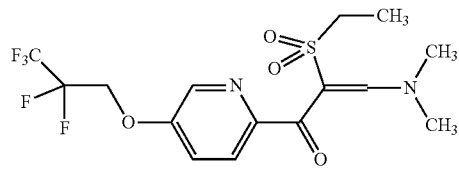 [SMILES: CCS(=O)(=O)C(=CN(C)C)C(=O)c1ccc(OCC(F)(F)C(F)(F)F)cn1]

Intermediate compound 8: $^1$H-NMR (CDCl$_3$) δ: 8.30 (1H, dd), 7.96 (1H, dd), 7.84 (1H, s), 7.34 (1H, dd), 4.52 (2H, t), 3.47 (2H, q), 3.26 (3H, s), 2.70 (3H, s), 1.33 (3H, t).

Preparation Example 22

To a mixture of the intermediate compound 8 0.5 mg, sodium hydrogen carbonate 0.2 g, and ethanol 3 mL was added 4-fluorophenyl hydrazine hydrochloride salt 0.3 mg, and the mixture was stirred under reflux for 5 hours. The resulting mixture was allowed to cool to room temperature, water was added thereto, and the mixture was extracted with MTBE. The resulting organic layer was dried over anhydrous sodium sulfate, and concentrated under reduced pressure. The resulting residue was subjected to a silica gel column chromatography to obtain the present compound 16 represented by the below-mentioned formula 0.53 g.

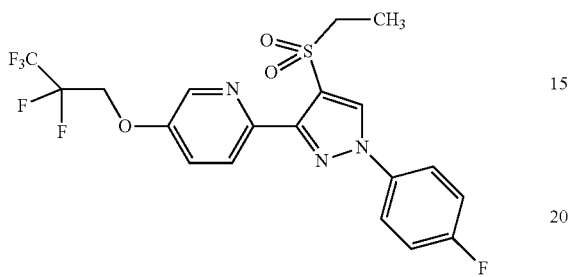

Present compound 16: $^1$H-NMR (CDCl$_3$) δ: 8.38 (1H, d), 8.13 (1H, d), 7.36-7.33 (1H, m), 7.25-7.22 (3H, m), 7.07-7.00 (2H, m), 4.49 (2H, t), 3.29 (2H, q), 1.31 (3H, t).

Next, examples of the present compounds which are prepared by either the Preparation Examples described in Examples or the Process described herein are shown below.

As used herein, "Me" represents a methyl group, "Et" represents an ethyl group, "Pr" represents a propyl group, "i-Pr" represents an isopropyl group, "c-Pr" represents a cyclopropyl group, "Ph" represents a phenyl group, "Py2" represents a 2-pyridyl group, "Py3" represents a 3-pyridyl group, "Py4" represents a 4-pyridyl group, and "Bn" represents a benzyl group. When c-Pr, Ph, Py2, Py3, and Py4 have a substituent, the substituent is written with its substituted position before the symbol. For example, "1-CN-c-Pr" represents a 1-cyanocyclopropyl group, "3,4-F$_2$-Ph" represents a 3,4-difluorophenyl group, "4-CF$_3$—Py2" represents a 4-(trifluoromethyl)-2-pyridyl group, and "5-OCH$_2$CF$_2$CF$_3$-Py2" represents a 5-(2,2,3,3,3-pentafluoropropoxy)-2-pyridyl group.

Here Q10 to Q28 represents the following groups respectively.

Q10

Q11

Q12

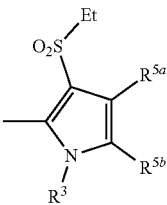

Q13

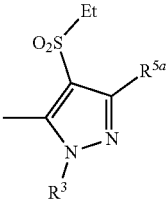

Q14

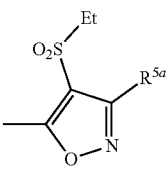

Q15

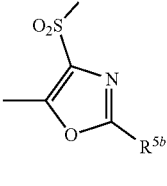

Q16

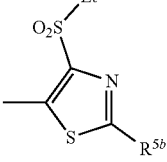

Q17

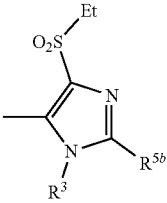

Q18

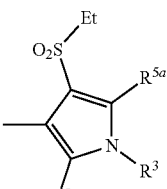

Q19

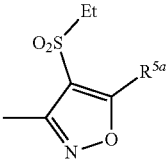

Q20 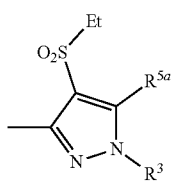

Q21 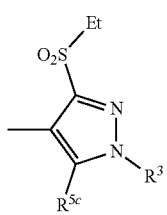

Q22 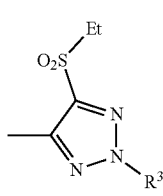

Q23 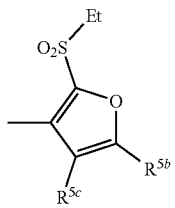

Q24 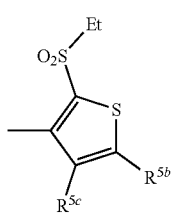

Q25 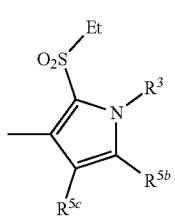

Q26 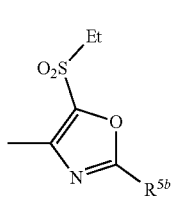

Q27 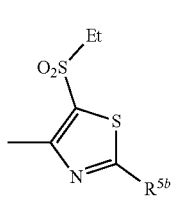

Q28 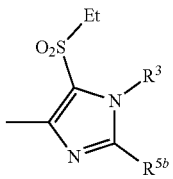

A present compound wherein $A^2$, $A^3$, and $A^4$ represent CH, Q represents a group represented by Q10, and $R^{5a}$ and $R^{5b}$ represent a hydrogen atom, and T represents any one substituent indicated in [Table 1A] to [Table 6A] (hereinafter, referred to as "Compound class SX1").

[Table 1]

| TABLE 1A |
|---|
| $CF_3$ |
| $CHF_2$ |
| $CH_2CF_3$ |
| $CF_2CF_3$ |
| $CH_2CF_2CF_3$ |
| $CF_2CF_2CF_3$ |
| $CF_2CF_2CF_2CF_3$ |
| $CF_2CF_2CF_2CF_2CF_3$ |
| $OCF_3$ |
| $OCHF_2$ |
| $OCH_2CF_3$ |
| $OCH_2CHF_2$ |
| $OCF_2CF_3$ |
| $OCH(CH_3)CF_3$ |
| $OCH_2CF_2CHF_2$ |
| $OCH_2CF_2CF_3$ |
| $OCF_2CF_2CF_3$ |
| $OCH_2CF_2CHFCF_3$ |
| $OCH_2CF_2CF_2CF_3$ |
| $OCF_2CF_2CF_2CF_3$ |
| $OCH_2CF_2CF_2CF_2CF_3$ |

| TABLE 2A |
|---|
| $SCF_3$ |
| $SCH_2CF_3$ |
| $SCF_2CF_3$ |
| $SCH_2CF_2CF_3$ |
| $SCF_2CF_2CF_3$ |
| $SCH_2CF_2CF_2CF_3$ |
| $SCF_2CF_2CF_2CF_3$ |
| $S(O)CF_3$ |
| $S(O)CH_2CF_3$ |
| $S(O)CF_2CF_3$ |
| $S(O)CH_2CF_2CF_3$ |
| $S(O)CF_2CF_2CF_3$ |
| $S(O)CH_2CF_2CF_2CF_3$ |
| $S(O)CF_2CF_2CF_2CF_3$ |
| $S(O)_2CF_3$ |
| $S(O)_2CH_2CF_3$ |
| $S(O)_2CF_2CF_3$ |
| $S(O)_2CH_2CF_2CF_3$ |
| $S(O)_2CF_2CF_2CF_3$ |
| $S(O)_2CH_2CF_2CF_2CF_3$ |
| $S(O)_2CF_2CF_2CF_2CF_3$ |

| TABLE 3A |
|---|
| $NHCH_2CF_3$ |
| $NHCH_2CF_2CF_3$ |
| $NHCH_2CF_2CF_2CF_3$ |
| $NMeCH_2CF_3$ |
| $NMeCH_2CF_2CF_3$ |
| $NMeCH_2CF_2CF_2CF_3$ |
| $NEtCH_2CF_3$ |

TABLE 3A-continued

NEtCH$_2$CF$_2$CF$_3$
NEtCH$_2$CF$_2$CF$_2$CF$_3$
OS(O)$_2$CF$_3$
OS(O)$_2$CF$_2$CF$_3$
OS(O)$_2$CF$_2$CF$_2$CF$_3$
CH$_2$OCF$_3$
CH$_2$OCH$_2$CF$_3$
CH$_2$OCF$_2$CF$_3$
C(O)CF$_3$
C(O)CF$_2$CF$_3$
C(O)CF$_2$CF$_2$CF$_3$
C(O)NMeCH$_2$CF$_3$
NMeC(O)CF$_3$
N=CEtCH$_2$CF$_3$

TABLE 4A

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph

TABLE 5A

4-CF$_3$—Py2
5-CF$_3$—Py2
4-SCF$_3$—Py2
4-S(O)CF$_3$—Py2
4-S(O)$_2$CF$_3$—Py2
5-SCF$_3$—Py2
5-S(O)CF$_3$—Py2
5-S(O)$_2$CF$_3$—Py2
5-NMeCH$_2$CF$_3$—Py2

TABLE 6A

5-CF$_3$—Py3
6-CF$_3$—Py3
5-SCF$_3$—Py3
5-S(O)CF$_3$—Py3
5-S(O)$_2$CF$_3$—Py3
6-SCF$_3$—Py3
6-S(O)CF$_3$—Py3
6-S(O)$_2$CF$_3$—Py3
6-NMeCH$_2$CF$_3$—Py3

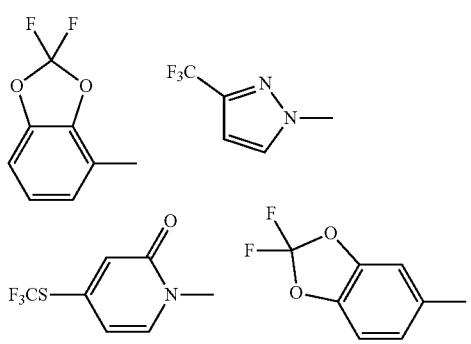

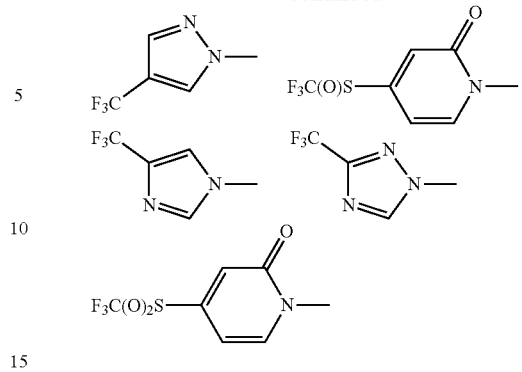

A present compound wherein A$^2$, A$^3$, and A$^4$ represent CH, Q represents a group represented by Q10, and R$^{5a}$ represents a hydrogen atom, R$^{5b}$ represents a cyclopropyl group, and T represents any one substituent indicated in [Table 1A] to [Table 6A] (hereinafter, referred to as "Compound class SX2").

A present compound wherein A$^2$, A$^3$, and A$^4$ represent CH, Q represents a group represented by Q10, and R$^{5a}$ represents a hydrogen atom, R$^{5b}$ represents a 4-fluorophenyl group, and T represents any one substituent indicated in [Table 1A] to [Table 6A] (hereinafter, referred to as "Compound class SX3").

A present compound wherein A$^2$ represents a nitrogen atom, A$^3$ and A$^4$ represent CH, Q represents a group represented by Q10, and R$^{5a}$ and R$^{5b}$ represent a hydrogen atom, and T represents any one substituent indicated in [Table 1A] to [Table 6A] (hereinafter, referred to as "Compound class SX4").

A present compound wherein A$^2$ represents a nitrogen atom, A$^3$ and A$^4$ represent CH, Q represents a group represented by Q10, and R$^{5a}$ represents a hydrogen atom, R$^{5b}$ represents a cyclopropyl group, and T represents any one substituent indicated in [Table 1A] to [Table 6A] (hereinafter, referred to as "Compound class SX5").

A present compound wherein A$^2$ represents a nitrogen atom, A$^3$ and A$^4$ represent CH, Q represents a group represented by Q10, and R$^{5a}$ represents a hydrogen atom, R$^{5b}$ represents a 4-fluorophenyl group, and T represents any one substituent indicated in [Table 1A] to [Table 6A] (hereinafter, referred to as "Compound class SX6").

A present compound wherein A$^3$ represents a nitrogen atom, A$^2$ and A$^4$ represent CH, Q represents a group represented by Q10, and R$^{5a}$ and R$^{5b}$ represent a hydrogen atom, and T represents any one substituent indicated in [Table 1A] to [Table 6A] (hereinafter, referred to as "Compound class SX7").

A present compound wherein A$^3$ represents a nitrogen atom, A$^2$ and A$^4$ represent CH, Q represents a group represented by Q10, and R$^{5a}$ represents a hydrogen atom, R$^{5b}$ represents a cyclopropyl group, and T represents any one substituent indicated in [Table 1A] to [Table 6A] (hereinafter, referred to as "Compound class SX8").

A present compound wherein A$^3$ represents a nitrogen atom, A$^2$ and A$^4$ represent CH, Q represents a group represented by Q10, and R$^{5a}$ represents a hydrogen atom, R$^{5b}$ represents a 4-fluorophenyl group, and T represents any one substituent indicated in [Table 1A] to [Table 6A] (hereinafter, referred to as "Compound class SX9").

A present compound wherein A$^4$ represents a nitrogen atom, A$^2$ and A$^3$ represent CH, Q represents a group represented by Q10, and R$^{5a}$ and R$^{5b}$ represent a hydrogen atom, and T represents any one substituent indicated in [Table 1A] to [Table 6A] (hereinafter, referred to as "Compound class SX10").

A present compound wherein $A^4$ represents a nitrogen atom, $A^2$ and $A^3$ represent CH, Q represents a group represented by Q10, and $R^{5a}$ represents a hydrogen atom, $R^{5b}$ represents a cyclopropyl group, and T represents any one substituent indicated in [Table 1A] to [Table 6A] (hereinafter, referred to as "Compound class SX9").

A present compound wherein $A^4$ represents a nitrogen atom, $A^2$ and $A^3$ represent CH, Q represents a group represented by Q10, and $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX12").

A present compound wherein $A^2$, $A^3$ and $A^4$ represent CH, Q represents a group represented by Q11, and $R^{5a}$ and $R^{5b}$ represent a hydrogen atom, and T represents any one substituent indicated in [Table 1A] to [Table 6A] (hereinafter, referred to as "Compound class SX13").

A present compound wherein $A^2$, $A^3$ and $A^4$ represent CH, Q represents a group represented by Q11, $R^{5a}$ represents a hydrogen atom, $R^{5b}$ represents a cyclopropyl group, and T represents any one substituent indicated in [Table 1A] to [Table 6A] (hereinafter, referred to as "Compound class SX14").

A present compound wherein $A^2$, $A^3$ and $A^4$ represent CH, Q represents a group represented by Q11, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX15").

A present compound wherein $A^2$ represents a nitrogen atom, $A^3$ and $A^4$ represent CH, Q represents a group represented by Q11, $R^{5a}$ and $R^{5b}$ represent a hydrogen atom, and T represents any one substituent indicated in [Table 1A] to [Table 6A] (hereinafter, referred to as "Compound class SX16").

A present compound wherein $A^2$ represents a nitrogen represented by Q11, $R^{5a}$ represents a hydrogen atom, $R^{5b}$ represents a cyclopropyl group, and T represents any one substituent indicated in [Table 1A] to [Table 6A] (hereinafter, referred to as "Compound class SX17").

A present compound wherein $A^2$ represents a nitrogen atom, $A^3$ and $A^4$ represent CH, Q represents a group represented by Q11, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX18").

A present compound wherein $A^3$ represents a nitrogen atom, $A^2$ and $A^3$ represent CH, Q represents a group represented by Q11, $R^{5a}$ and $R^{5b}$ represent a hydrogen atom, and T represents any one substituent indicated in [Table 1A] to [Table 6A] (hereinafter, referred to as "Compound class SX19").

A present compound wherein $A^3$ represents a nitrogen atom, $A^2$ and $A^4$ represent CH, Q represents a group represented by Q11, $R^{5a}$ represents a hydrogen atom, $R^{5b}$ represents a cyclopropyl group, and T represents any one substituent indicated in [Table 1A] to [Table 6A] (hereinafter, referred to as "Compound class SX20").

A present compound wherein $A^3$ represents a nitrogen atom, $A^2$ and $A^4$ represent CH, Q represents a group represented by Q11, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX21").

A present compound wherein $A^4$ represents a nitrogen atom, $A^2$ and $A^4$ represent CH, Q represents a group represented by Q11, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX21").

A present compound wherein $A^4$ represents a nitrogen atom, $A^2$ and $A^3$ represent CH, Q represents a group represented by Q11, $R^{5a}$ and $R^{5b}$ represent a hydrogen atom, and T represents any one substituent indicated in [Table 1A] to [Table 6A] (hereinafter, referred to as "Compound class SX22").

A present compound wherein $A^4$ represents a nitrogen atom, $A^2$ and $A^3$ represent CH, Q represents a group represented by Q11, $R^{5a}$ represents a hydrogen atom, $R^{5b}$ represents a cyclopropyl group, and T represents any one substituent indicated in [Table 1A] to [Table 6A] (hereinafter, referred to as "Compound class SX23").

A present compound wherein $A^4$ represents a nitrogen atom, $A^2$ and $A^3$ represent CH, Q represents a group represented by Q11, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX24").

A present compound wherein $A^2$, $A^3$ and $A^4$ represent CH, Q represents a group represented by Q12, $R^3$, $R^{5a}$ and $R^{5b}$ represent a hydrogen atom, and T represents any one substituent indicated in [Table 1A] to [Table 6A] (hereinafter, referred to as "Compound class SX25").

A present compound wherein $A^2$, $A^3$ and $A^4$ represent CH, Q represents a group represented by Q12, $R^3$ and $R^{5a}$ represent a hydrogen atom, and $R^{5b}$ represents a cyclopropyl group, and T represents any one substituent indicated in [Table 1A] to [Table 6A] (hereinafter, referred to as "Compound class SX26").

A present compound wherein $A^2$, $A^3$ and $A^4$ represent CH, Q represents a group represented by Q12, $R^3$ and $R^{5a}$ represent a hydrogen atom, and $R^{5b}$ represents a 4-fluorophenyl group, and T represents any one substituent indicated in [Table 1A] to [Table 6A] (hereinafter, referred to as "Compound class SX27").

A present compound wherein $A^2$ represents a nitrogen atom, $A^3$ and $A^4$ represent CH, Q represents a group represented by Q12, $R^3$, $R^{5a}$ and $R^{5b}$ represent a hydrogen atom and T represents any one substituent indicated in [Table 1A] to [Table 6A] (hereinafter, referred to as "Compound class SX28").

A present compound wherein $A^2$ represents a nitrogen atom, $A^3$ and $A^4$ represent CH, Q represents a group represented by Q12, $R^3$ and $R^{5a}$ represent a hydrogen atom, $R^{5b}$ represents a cyclopropyl group, and T represents any one substituent indicated in [Table 1A] to [Table 6A] (hereinafter, referred to as "Compound class SX29").

A present compound wherein $A^2$ represents a nitrogen atom, $A^3$ and $A^4$ represent CH, Q represents a group represented by Q12, $R^3$ and $R^{5a}$ represent a hydrogen atom, $R^{5b}$ represents a 4-fluorophenyl group, and T represents any one substituent indicated in [Table 1A] to [Table 6A] (hereinafter, referred to as "Compound class SX30").

A present compound wherein $A^3$ represents a nitrogen atom, $A^2$ and $A^4$ represent CH, Q represents a group represented by Q12, $R^3$, $R^{5a}$ and $R^{5b}$ represent a hydrogen atom, and T represents any one substituent indicated in [Table 1A] to [Table 6A] (hereinafter, referred to as "Compound class SX31").

A present compound wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents a cyclopropyl group, and T represents any one substituent indicated in [Table 1A] to [Table 6A] (hereinafter, referred to as "Compound class SX32").

A present compound wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents a 4-fluorophenyl group, and T represents any one substituent indicated in [Table 1A] to [Table 6A] (hereinafter, referred to as "Compound class SX33").

A present compound wherein $A^4$ represents a nitrogen atom, $A^2$ and $A^3$ represent CH, Q represents a group represented by Q12, $R^3$, $R^{5a}$ and $R^{5b}$ represent a hydrogen atom, and T represents any one substituent indicated in [Table 1A] to [Table 6A] (hereinafter, referred to as "Compound class SX34").

A present compound wherein $A^4$ represents a nitrogen atom, $A^2$ and $A^3$ represent CH, Q represents a group represented by Q12, $R^3$ and $R^{5a}$ represent a hydrogen atom, and $R^{5b}$ represent a cyclopropyl group, and T represents any one substituent indicated in [Table 1A] to [Table 6A] (hereinafter, referred to as "Compound class SX35").

A present compound wherein $A^4$ represents a nitrogen atom, $A^2$ and $A^3$ represent CH, Q represents a group represented by Q12, $R^3$ and $R^{5a}$ represent a hydrogen atom, and $R^{5b}$ represent a 4-fluorophenyl group, and T represents any one substituent indicated in [Table 1A] to [Table 6A] (hereinafter, referred to as "Compound class SX36").

A present compound wherein $A^2$, $A^3$ and $A^4$ represent CH, Q represents a group represented by Q12, $R^3$ represents a methyl group, $R^{5a}$ and $R^{5b}$ represent a hydrogen atom, and T represents any one substituent indicated in [Table 1A] to [Table 6A] (hereinafter, referred to as "Compound class SX37").

A present compound wherein $A^2$, $A^3$ and $A^4$ represent CH, Q represents a group represented by Q12, $R^3$ represents a methyl group, $R^{5a}$ represents a hydrogen atom, $R^{5b}$ represents a cyclopropyl group, and T represents any one substituent indicated in [Table 1A] to [Table 6A] (hereinafter, referred to as "Compound class SX38").

A present compound wherein $A^2$, $A^3$ and $A^4$ represent CH, Q represents a group represented by Q12, $R^3$ represents a methyl group, $R^{51}$ represents a hydrogen atom, $R^{5b}$ represents a 4-fluorophenyl group, and T represents any one substituent indicated in [Table 1A] to [Table 6A] (hereinafter, referred to as "Compound class SX39").

A present compound wherein $A^2$ represents a nitrogen atom, $A^3$ and $A^4$ represent CH, Q represents a group represented by Q12, $R^3$ represents a methyl group, $R^{5a}$ and $R^{5b}$ represent a hydrogen atom, and T represents any one substituent indicated in [Table 1A] to [Table 6A] (hereinafter, referred to as "Compound class SX40").

A present compound wherein $A^2$ represents a nitrogen represented by Q12, $R^3$ represents a methyl group, $R^{5a}$ represents a hydrogen atom, $R^{5b}$ represents a cyclopropyl group, and T represents any one substituent indicated in [Table 1A] to [Table 6A] (hereinafter, referred to as "Compound class SX41").

A present compound wherein $A^2$ represents a nitrogen atom, $A^3$ and $A^4$ represent CH, Q represents a group represented by Q12, $R^3$ represents a methyl group, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX42").

A present compound wherein $A^3$ represents a nitrogen atom, $A^2$ and $A^4$ represent CH, Q represents a group represented by Q12, $R^3$ represents a methyl group, $R^{5a}$ and $R^{5b}$ represents a hydrogen atom, and T represents any one substituent indicated in [Table 1A] to [Table 6A] (hereinafter, referred to as "Compound class SX43").

A present compound wherein $A^3$ represents a nitrogen atom, $A^2$ and $A^4$ represent CH, Q represents a group represented by Q12, $R^3$ represents a methyl group, $R^{5a}$ represents a hydrogen atom, $R^{5b}$ represents a cyclopropyl group, and T represents any one substituent indicated in [Table 1A] to [Table 6A] (hereinafter, referred to as "Compound class SX44").

A present compound wherein $A^3$ represents a nitrogen atom, $A^2$ and $A^4$ represent CH, Q represents a group represented by Q12, $R^3$ represents a methyl group, $R^{5a}$ represents a hydrogen atom, $R^{5b}$ represents a 4-fluorophenyl group, and T represents any one substituent indicated in [Table 1A] to [Table 6A] (hereinafter, referred to as "Compound class SX45").

A present compound wherein $A^3$ represents a nitrogen atom, $A^2$ and $A^4$ represent CH, Q represents a group represented by Q12, $R^3$ represents a methyl group, $R^{5a}$ and $R^{5b}$ represent a hydrogen atom, and T represents any one substituent indicated in [Table 1A] to [Table 6A] (hereinafter, referred to as "Compound class SX46").

A present compound wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents a cyclopropyl group, and T represents any one substituent indicated in [Table 1A] to [Table 6A] (hereinafter, referred to as "Compound class SX47").

A present compound wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents a 4-fluorophenyl group, and T represents any one substituent indicated in [Table 1A] to [Table 6A] (hereinafter, referred to as "Compound class SX48").

A present compound wherein $A^2$, $A^3$ and $A^4$ represent CH, Q represents a group represented by Q13, $R^3$ and $R^{5a}$ represents a hydrogen atom, and T represents any one substituent indicated in [Table 1A] to [Table 6A] (hereinafter, referred to as "Compound class SX49").

A present compound wherein $A^2$ represents a nitrogen atom, $A^3$ and $A^4$ represent CH, Q represents a group represented by Q13, $R^3$ and $R^{5a}$ represents a hydrogen atom, and T represents any one substituent indicated in [Table 1A] to [Table 6A] (hereinafter, referred to as "Compound class SX50").

A present compound wherein $A^3$ represents a nitrogen atom, $A^2$ and $A^4$ represent CH, Q represents a group represented by Q13, $R^3$ and $R^{5a}$ represents a hydrogen atom, and T represents any one substituent indicated in [Table 1A] to [Table 6A] (hereinafter, referred to as "Compound class SX51").

A present compound wherein $A^4$ represents a nitrogen atom, $A^2$ and $A^3$ represent CH, Q represents a group represented by Q13, $R^3$ and $R^{5a}$ represents a hydrogen atom, and T represents any one substituent indicated in [Table 1A] to [Table 6A] (hereinafter, referred to as "Compound class SX52").

A present compound wherein $A^2$, $A^3$ and $A^4$ represent CH, Q represents a group represented by Q13, $R^3$ represents a methyl group, $R^{5a}$ represents a hydrogen atom, and T represents any one substituent indicated in [Table 1A] to [Table 6A] (hereinafter, referred to as "Compound class SX53").

A present compound wherein $A^2$ represents a nitrogen atom, $A^3$ and $A^4$ represent CH, Q represents a group represented by Q13, $R^3$ represents a methyl group, $R^{5a}$ represents a hydrogen atom, and T represents any one substituent indicated in [Table 1A] to [Table 6A] (hereinafter, referred to as "Compound class SX54").

A present compound wherein $A^3$ represents a nitrogen atom, $A^2$ and $A^4$ represent CH, Q represents a group represented by Q13, $R^3$ represents a methyl group, $R^{5a}$ represents a hydrogen atom, and T represents any one substituent indicated in [Table 1A] to [Table 6A] (hereinafter, referred to as "Compound class SX55").

A present compound wherein $A^4$ represents a nitrogen atom, $A^2$ and $A^4$ represent CH, Q represents a group represented by Q13, $R^3$ represents a methyl group, $R^{5a}$ represents a hydrogen atom, and T represents any one substituent indicated in [Table 1A] to [Table 6A] (hereinafter, referred to as "Compound class SX56").

A present compound wherein $A^2$, $A^3$, and $A^4$ represent CH, Q represents a group represented by Q14, $R^{5a}$ represents a hydrogen atom, and T represents any one substituent indicated in [Table 1A] to [Table 6A] (hereinafter, referred to as "Compound class SX57").

A present compound wherein $A^2$ represents a nitrogen atom, $A^3$ and $A^4$ represent CH, Q represents a group represented by Q14, $R^{5a}$ represents a hydrogen atom, and T represents any one substituent indicated in [Table 1A] to [Table 6A] (hereinafter, referred to as "Compound class SX58").

A present compound wherein $A^3$ represents a nitrogen atom, $A^2$ and $A^4$ represent CH, Q represents a group represented by Q14, $R^{5a}$ represents a hydrogen atom, and T represents any one substituent indicated in [Table 1A] to [Table 6A] (hereinafter, referred to as "Compound class SX59").

A present compound wherein $A^4$ represents a nitrogen atom, $A^2$ and $A^3$ represent CH, Q represents a group represented by Q14, $R^{5a}$ represents a hydrogen atom, and T represents any one substituent indicated in [Table 1A] to [Table 6A] (hereinafter, referred to as "Compound class SX60").

A present compound wherein $A^2$, $A^3$ and $A^4$ represent CH, Q represents a group represented by Q15, $R^{5b}$ represents a hydrogen atom, and T represents any one substituent indicated in [Table 1A] to [Table 6A] (hereinafter, referred to as "Compound class SX61").

A present compound wherein $A^2$, $A^3$ and $A^4$ represent CH, Q represents a group represented by Q15, $R^{5b}$ represents a cyclopropyl group, and T represents any one substituent indicated in [Table 1A] to [Table 6A] (hereinafter, referred to as "Compound class SX62").

A present compound wherein $A^2$, $A^3$ and $A^4$ represent CH, Q represents a group represented by Q15, $R^{5b}$ represents a 4-fluorophenyl group, and T represents any one substituent indicated in [Table 1A] to [Table 6A] (hereinafter, referred to as "Compound class SX63").

A present compound wherein $A^4$ represents a nitrogen atom, $A^3$ and $A^4$ represent CH, Q represents a group represented by Q15, $R^{5b}$ represents a hydrogen atom, and T represents any one substituent indicated in [Table 1A] to [Table 6A] (hereinafter, referred to as "Compound class SX64").

A present compound wherein $A^2$ represents a nitrogen atom, $A^3$ and $A^4$ represent CH, Q represents a group represented by Q15, $R^{5b}$ represents a cyclopropyl group, and T represents any one substituent indicated in [Table 1A] to [Table 6A] (hereinafter, referred to as "Compound class SX65").

A present compound wherein $A^2$ represents a nitrogen atom, $A^3$ and $A^4$ represent CH, Q represents a group represented by Q15, $R^{5b}$ represents a 4-fluorophenyl group, and T represents any one substituent indicated in [Table 1A] to [Table 6A] (hereinafter, referred to as "Compound class SX66").

A present compound wherein $A^3$ represents a nitrogen atom, $A^2$ and $A^4$ represent CH, Q represents a group represented by Q15, $R^{5b}$ represents a hydrogen atom, and T represents any one substituent indicated in [Table 1A] to [Table 6A] (hereinafter, referred to as "Compound class SX67").

A present compound wherein $A^3$ represents a nitrogen atom, $A^2$ and $A^4$ represent CH, Q represents a group represented by Q15, $R^{5b}$ represents a cyclopropyl group, and T represents any one substituent indicated in [Table 1A] to [Table 6A] (hereinafter, referred to as "Compound class SX68").

A present compound wherein $A^3$ represents a nitrogen atom, $A^2$ and $A^4$ represent CH, Q represents a group represented by Q15, $R^{5b}$ represents a 4-fluorophenyl group, and T represents any one substituent indicated in [Table 1A] to [Table 6A] (hereinafter, referred to as "Compound class SX69").

A present compound wherein $A^4$ represents a nitrogen atom, $A^2$ and $A^3$ represent CH, Q represents a group represented by Q15, $R^{5b}$ represents a hydrogen atom, and T represents any one substituent indicated in [Table 1A] to [Table 6A] (hereinafter, referred to as "Compound class SX70").

A present compound wherein $A^4$ represents a nitrogen atom, $A^2$ and $A^3$ represent CH, Q represents a group represented by Q15, $R^{5b}$ represents a cyclopropyl group, and T represents any one substituent indicated in [Table 1A] to [Table 6A] (hereinafter, referred to as "Compound class SX71").

A present compound wherein $A^4$ represents a nitrogen atom, $A^2$ and $A^3$ represent CH, Q represents a group represented by Q15, $R^{5b}$ represents a fluorophenyl group, and T represents any one substituent indicated in [Table 1A] to [Table 6A] (hereinafter, referred to as "Compound class SX72").

A present compound wherein $A^2$, $A^3$, and $A^4$ represent CH, Q represents a group represented by Q16, $R^{5b}$ represents a hydrogen atom, and T represents any one substituent indicated in [Table 1A] to [Table 6A] (hereinafter, referred to as "Compound class SX73").

A present compound wherein $A^2$, $A^3$, and $A^4$ represent CH, Q represents a group represented by Q16, $R^{5b}$ represents a cyclopropyl group, and T represents any one substituent indicated in [Table 1A] to [Table 6A] (hereinafter, referred to as "Compound class SX74").

A present compound wherein $A^2$, $A^3$, and $A^4$ represent CH, Q represents a group represented by Q16, $R^{5b}$ represents a 4-fluorophenyl group, and T represents any one substituent indicated in [Table 1A] to [Table 6A] (hereinafter, referred to as "Compound class SX75").

A present compound wherein $A^2$ represents a nitrogen atom, $A^3$ and $A^4$ represent CH, Q represents a group represented by Q16, $R^{5b}$ represents a hydrogen atom, and T represents any one substituent indicated in [Table 1A] to [Table 6A] (hereinafter, referred to as "Compound class SX76").

A present compound wherein $A^2$ represents a nitrogen atom, $A^3$ and $A^4$ represent CH, Q represents a group represented by Q16, $R^{5b}$ represents a cyclopropyl group, and T represents any one substituent indicated in [Table 1A] to [Table 6A] (hereinafter, referred to as "Compound class SX77").

A present compound wherein $A^2$ represents a nitrogen atom, $A^3$ and $A^4$ represent CH, Q represents a group represented by Q16, $R^{5b}$ represents a 4-fluorophenyl group, and T represents any one substituent indicated in [Table 1A] to [Table 6A] (hereinafter, referred to as "Compound class SX78").

A present compound wherein $A^3$ represents a nitrogen atom, $A^2$ and $A^4$ represent CH, Q represents a group represented by Q16, $R^{5b}$ represents a hydrogen atom, and T represents any one substituent indicated in [Table 1A] to [Table 6A] (hereinafter, referred to as "Compound class SX79").

A present compound wherein $A^3$ represents a nitrogen atom, $A^2$ and $A^4$ represent CH, Q represents a group represented by Q16, $R^{5b}$ represents a cyclopropyl group, and T represents any one substituent indicated in [Table 1A] to [Table 6A] (hereinafter, referred to as "Compound class SX80").

A present compound wherein $A^3$ represents a nitrogen atom, $A^2$ and $A^4$ represent CH, Q represents a group represented by Q16, $R^{5b}$ represents a 4-fluorophenyl group, and T represents any one substituent indicated in [Table 1A] to [Table 6A] (hereinafter, referred to as "Compound class SX81").

A present compound wherein $A^4$ represents a nitrogen atom, $A^2$ and $A^3$ represent CH, Q represents a group represented by Q16, $R^{5b}$ represents a hydrogen atom, and T represents any one substituent indicated in [Table 1A] to [Table 6A] (hereinafter, referred to as "Compound class SX82").

A present compound wherein $A^4$ represents a nitrogen atom, $A^2$ and $A^3$ represent CH, Q represents a group represented by Q16, $R^{5b}$ represents a cyclopropyl group, and T represents any one substituent indicated in [Table 1A] to [Table 6A] (hereinafter, referred to as "Compound class SX83").

A present compound wherein $A^4$ represents a nitrogen atom, $A^2$ and $A^3$ represent CH, Q represents a group represented by Q16, $R^{5b}$ represents a 4-fluorophenyl group, and T represents any one substituent indicated in [Table 1A] to [Table 6A] (hereinafter, referred to as "Compound class SX84").

A present compound wherein $A^2$, $A^3$ and $A^4$ represent CH, Q represents a group represented by Q17, $R^3$ and $R^{5b}$ represent a hydrogen atom, and T represents any one substituent indicated in [Table 1A] to [Table 6A] (hereinafter, referred to as "Compound class SX85").

A present compound wherein $A^2$, $A^3$ and $A^4$ represent CH, Q represents a group represented by Q17, $R^3$ represents a hydrogen atom, $R^{5b}$ represents a cyclopropyl group, and T represents any one substituent indicated in [Table 1A] to [Table 6A] (hereinafter, referred to as "Compound class SX86").

A present compound wherein $A^2$, $A^3$ and $A^4$ represent CH, Q represents a group represented by Q17, $R^3$ represents a hydrogen atom, $R^{5b}$ represents a 4-fluorophenyl group, and T represents any one substituent indicated in [Table 1A] to [Table 6A] (hereinafter, referred to as "Compound class SX87").

A present compound wherein $A^2$ represents a nitrogen atom, $A^3$ and $A^4$ represent CH, Q represents a group represented by Q17, $R^3$ and $R^{5b}$ represent a hydrogen atom, and T represents any one substituent indicated in [Table 1A] to [Table 6A] (hereinafter, referred to as "Compound class SX88").

A present compound wherein $A^2$ represents a nitrogen atom, $A^3$ and $A^4$ represent CH, Q represents a group represented by Q17, $R^3$ represents a hydrogen atom, $R^{5b}$ represents a cyclopropyl group, and T represents any one substituent indicated in [Table 1A] to [Table 6A] (hereinafter, referred to as "Compound class SX89").

A present compound wherein $A^2$ represents a nitrogen atom, $A^3$ and $A^4$ represent CH, Q represents a group represented by Q17, $R^3$ represents a hydrogen atom, $R^{5b}$ represents a 4-fluorophenyl group, and T represents any one substituent indicated in [Table 1A] to [Table 6A] (hereinafter, referred to as "Compound class SX90)).

A present compound wherein $A^3$ represents a nitrogen atom, $A^2$ and $A^4$ represent CH, Q represents a group represented by Q17, $R^3$ and $R^{5b}$ represent a hydrogen atom, and T represents any one substituent indicated in [Table 1A] to [Table 6A] (hereinafter, referred to as "Compound class SX91").

A present compound wherein $A^3$ represents a nitrogen atom, $A^2$ and $A^4$ represent CH, Q represents a group represented by Q17, $R^3$ represents a hydrogen atom, $R^{5b}$ represents a cyclopropyl group, and T represents any one substituent indicated in [Table 1A] to [Table 6A] (hereinafter, referred to as "Compound class SX92").

A present compound wherein $A^3$ represents a nitrogen atom, $A^2$ and $A^4$ represent CH, Q represents a group represented by Q17, $R^3$ represents a hydrogen atom, $R^{5b}$ represents a 4-fluorophenyl group, and T represents any one substituent indicated in [Table 1A] to [Table 6A] (hereinafter, referred to as "Compound class SX93").

A present compound wherein $A^4$ represents a nitrogen atom, $A^2$ and $A^3$ represent CH, Q represents a group represented by Q17, $R^3$ and $R^{5b}$ represent a hydrogen atom, and T represents any one substituent indicated in [Table 1A] to [Table 6A] (hereinafter, referred to as "Compound class SX94").

A present compound wherein $A^4$ represents a nitrogen atom, $A^2$ and $A^3$ represent CH, Q represents a group represented by Q17, $R^3$ represents a hydrogen atom, and $R^{5b}$ represent a cyclopropyl group, and T represents any one substituent indicated in [Table 1A] to [Table 6A] (hereinafter, referred to as "Compound class SX95").

A present compound wherein $A^4$ represents a nitrogen atom, $A^2$ and $A^3$ represent CH, Q represents a group represented by Q17, $R^3$ represents a hydrogen atom, and $R^{5b}$ represent a 4-fluorophenyl group, and T represents any one substituent indicated in [Table 1A] to [Table 6A] (hereinafter, referred to as "Compound class SX96").

A present compound wherein $A^2$, $A^3$ and $A^4$ represent CH, Q represents a group represented by Q17, $R^3$ represents a methyl group, and $R^{5b}$ represents a hydrogen atom, and T represents any one substituent indicated in [Table 1A] to [Table 6A] (hereinafter, referred to as "Compound class SX97").

A present compound wherein $A^2$, $A^3$ and $A^4$ represent CH, Q represents a group represented by Q17, $R^3$ represents a methyl group, and $R^{5b}$ represents a cyclopropyl group, and T represents any one substituent indicated in [Table 1A] to [Table 6A] (hereinafter, referred to as "Compound class SX98").

A present compound wherein $A^2$, $A^3$ and $A^4$ represent CH, Q represents a group represented by Q17, $R^3$ represents a methyl group, and $R^{5b}$ represents a 4-fluorophenyl group, and T represents any one substituent indicated in [Table 1A] to [Table 6A] (hereinafter, referred to as "Compound class SX99").

A present compound wherein $A^2$ represents a nitrogen atom, $A^3$ and $A^4$ represent CH, Q represents a group represented by Q17, $R^3$ represents a methyl group, and $R^{5b}$ represents a hydrogen atom, and T represents any one substituent indicated in [Table 1A] to [Table 6A] (hereinafter, referred to as "Compound class SX100").

A present compound wherein $A^2$ represents a nitrogen atom, $A^3$ and $A^4$ represent CH, Q represents a group represented by Q17, $R^3$ represents a methyl group, and $R^{5b}$ represents a cyclopropyl group, and T represents any one substituent indicated in [Table 1A] to [Table 6A] (hereinafter, referred to as "Compound class SX101").

A present compound wherein $A^2$ represents a nitrogen atom, $A^3$ and $A^4$ represent CH, Q represents a group represented by Q17, $R^3$ represents a methyl group, and $R^{5b}$ represents a 4-fluorophenyl group, and T represents any one substituent indicated in [Table 1A] to [Table 6A] (hereinafter, referred to as "Compound class SX102").

A present compound wherein $A^3$ represents a nitrogen atom, $A^2$ and $A^4$ represent CH, Q represents a group represented by 17, $R^3$ represents a methyl group, and $R^{5b}$ represents a hydrogen atom, and T represents any one substituent indicated in [Table 1A] to [Table 6A] (hereinafter, referred to as "Compound class SX103").

A present compound wherein $A^3$ represents a nitrogen atom, $A^2$ and $A^4$ represent CH, Q represents a group represented by Q17, $R^3$ represents a methyl group, and $R^{5b}$ represents a cyclopropyl group, and T represents any one substituent indicated in [Table 1A] to [Table 6A] (hereinafter, referred to as "Compound class SX104").

A present compound wherein $A^3$ represents a nitrogen atom, $A^2$ and $A^4$ represent CH, Q represents a group represented by Q17, $R^3$ represents a methyl group, and $R^{5b}$ represents a 4-fluorophenyl group, and T represents any one substituent indicated in [Table 1A] to [Table 6A] (hereinafter, referred to as "Compound class SX105").

A present compound wherein $A^4$ represents a nitrogen atom, $A^2$ and $A^3$ represent CH, Q represents a group represented by Q17, $R^3$ represents a methyl group, and $R^{5b}$ represents a hydrogen atom, and T represents any one substituent indicated in [Table 1A] to [Table 6A] (hereinafter, referred to as "Compound class SX106").

A present compound wherein $A^4$ represents a nitrogen atom, $A^2$ and $A^3$ represent CH, Q represents a group represented by Q17, $R^3$ represents a methyl group, and $R^{5b}$ represents a cyclopropyl group, and T represents any one substituent indicated in [Table 1A] to [Table 6A] (hereinafter, referred to as "Compound class SX107").

A present compound wherein $A^4$ represents a nitrogen atom, $A^2$ and $A^3$ represent CH, Q represents a group represented by Q17, $R^3$ represents a methyl group, and $R^{5b}$ represents a 4-fluorophenyl group, and T represents any one substituent indicated in [Table 1A] to [Table 6A] (hereinafter, referred to as "Compound class SX108").

A present compound wherein $A^2$, $A^3$ and $A^4$ represent CH, Q represents a group represented by Q18, $R^3$, $R^{5b}$ and $R^{5c}$ represent a hydrogen atom, and T represents any one substituent indicated in [Table 1A] to [Table 6A] (hereinafter, referred to as "Compound class SX109").

A present compound wherein $A^2$, $A^3$ and $A^4$ represent CH, Q represents a group represented by Q18, $R^3$ represents a cyclopropyl group, $R^{5b}$ and $R^{5c}$ represent a hydrogen atom, and T represents any one substituent indicated in [Table 1A] to [Table 6A] (hereinafter, referred to as "Compound class SX110").

A present compound wherein $A^2$, $A^3$ and $A^4$ represent CH, Q represents a group represented by Q18, $R^3$ represents a 4-fluorophenyl group, $R^{5b}$ and $R^{5c}$ represent a hydrogen atom, and T represents any one substituent indicated in [Table 1A] to [Table 6A] (hereinafter, referred to as "Compound class SX111").

A present compound wherein $A^2$ represents a nitrogen atom, $A^3$ and $A^4$ represent CH, Q represents a group represented by Q18, $R^3$ represents a hydrogen atom, $R^{5b}$ and $R^{5c}$ represent a hydrogen atom, and T represents any one substituent indicated in [Table 1A] to [Table 6A] (hereinafter, referred to as "Compound class SX112").

A present compound wherein $A^2$ represents a nitrogen atom, $A^3$ and $A^4$ represent CH, Q represents a group represented by Q18, $R^3$ represents a hydrogen atom, $R^{5b}$ and $R^{5c}$ represent a hydrogen atom, and T represents any one substituent indicated in [Table 1A] to [Table 6A] (hereinafter, referred to as "Compound class SX112").

A present compound wherein $A^2$ represents a nitrogen atom, $A^3$ and $A^4$ represent CH, Q represents a group represented by Q18, $R^3$ represents a cyclopropyl group, $R^{5b}$ and $R^{5c}$ represent a hydrogen atom, and T represents any one substituent indicated in [Table 1A] to [Table 6A] (hereinafter, referred to as "Compound class SX113").

A present compound wherein $A^2$ represents a nitrogen atom, $A^3$ and $A^4$ represent CH, Q represents a group represented by Q18, $R^3$ represents a 4-fluorophenyl group, $R^{5b}$ and $R^{5c}$ represent a hydrogen atom, and T represents any one substituent indicated in [Table 1A] to [Table 6A] (hereinafter, referred to as "Compound class SX114").

A present compound wherein $A^3$ represents a nitrogen atom, $A^2$ and A4 represent CH, Q represents a group represented by Q18, $R^3$ represents a hydrogen atom, $R^{5b}$ and $R^{5c}$ represent a hydrogen atom, and T represents any one substituent indicated in [Table 1A] to [Table 6A] (hereinafter, referred to as "Compound class SX115").

A present compound wherein $A^3$ represents a nitrogen atom, $A^2$ and A4 represent CH, Q represents a group represented by Q18, $R^3$ represents a cyclopropyl group, $R^{5b}$ and $R^{5c}$ represent a hydrogen atom, and T represents any one substituent indicated in [Table 1A] to [Table 6A] (hereinafter, referred to as "Compound class SX116").

A present compound wherein $A^3$ represents a nitrogen atom, $A^2$ and A4 represent CH, Q represents a group represented by Q18, $R^3$ represents a 4-fluorophenyl group, $R^{5b}$ and $R^{5c}$ represent a hydrogen atom, and T represents any one substituent indicated in [Table 1A] to [Table 6A] (hereinafter, referred to as "Compound class SX117").

A present compound wherein A4 represents a nitrogen atom, $A^2$ and $A^3$ represent CH, Q represents a group represented by Q18, $R^3$ represents a hydrogen atom, $R^{5b}$ and $R^{5c}$ represent a hydrogen atom, and T represents any one substituent indicated in [Table 1A] to [Table 6A] (hereinafter, referred to as "Compound class SX118").

A present compound wherein A4 represents a nitrogen atom, $A^2$ and $A^3$ represent CH, Q represents a group represented by Q18, $R^3$ represents a cyclopropyl group, $R^{5b}$ and $R^{5c}$ represent a hydrogen atom, and T represents any one substituent indicated in [Table 1A] to [Table 6A] (hereinafter, referred to as "Compound class SX119").

A present compound wherein $A^4$ represents a nitrogen atom, $A^2$ and $A^3$ represent CH, Q represents a group represented by Q18, $R^3$ represents a 4-fluorophenyl group, $R^{5b}$ and $R^{5c}$ represent a hydrogen atom, and T represents any one substituent indicated in [Table 1A] to [Table 6A] (hereinafter, referred to as "Compound class SX120").

A present compound wherein $A^2$, $A^3$ and $A^4$ represent CH, Q represents a group represented by Q19, $R^{5a}$ represents a hydrogen atom, and T represents any one substituent indicated in [Table 1A] to [Table 6A] (hereinafter, referred to as "Compound class SX121").

A present compound wherein $A^2$ represents a nitrogen atom, $A^3$ and $A^4$ represent CH, Q represents a group represented by Q19, $R^{5a}$ represents a hydrogen atom, and T represents any one substituent indicated in [Table 1A] to [Table 6A] (hereinafter, referred to as "Compound class SX122").

A present compound wherein $A^3$ represents a nitrogen atom, $A^2$ and $A^4$ represent CH, Q represents a group represented by Q19, $R^{5a}$ represents a hydrogen atom, and T represents any one substituent indicated in [Table 1A] to [Table 6A] (hereinafter, referred to as "Compound class SX123").

A present compound wherein $A^3$ represents a nitrogen atom, $A^2$ and $A^3$ represent CH, Q represents a group represented by Q19, $R^{5a}$ represents a hydrogen atom, and T represents any one substituent indicated in [Table 1A] to [Table 6A] (hereinafter, referred to as "Compound class SX124").

A present compound wherein $A^2$, $A^3$ and $A^4$ represent CH, Q represents a group represented by Q20, $R^3$ and $R^{5a}$ represent a hydrogen atom, and T represents any one substituent indicated in [Table 1A] to [Table 6A] (hereinafter, referred to as "Compound class SX125").

A present compound wherein $A^2$, $A^3$ and $A^4$ represent CH, Q represents a group represented by Q20, $R^3$ represents a cyclopropyl group, $R^{5a}$ represent a hydrogen atom, and T represents any one substituent indicated in [Table 1A] to [Table 6A] (hereinafter, referred to as "Compound class SX126").

A present compound wherein $A^2$, $A^3$ and $A^4$ represent CH, Q represents a group represented by Q20, $R^3$ represents a cyclopropyl group, $R^{5a}$ represent a hydrogen atom, and T represents any one substituent indicated in [Table 1A] to [Table 6A] (hereinafter, referred to as "Compound class SX127").

A present compound wherein $A^2$ represents a nitrogen atom, $A^3$ and $A^4$ represent CH, Q represents a group represented by Q20, $R^3$ and $R^{5a}$ represent a hydrogen atom, and T represents any one substituent indicated in [Table 1A] to [Table 6A] (hereinafter, referred to as "Compound class SX128").

A present compound wherein $A^2$ represents a nitrogen atom, $A^3$ and $A^4$ represent CH, Q represents a group represented by Q20, $R^3$ represents a cyclopropyl group, $R^{5a}$ represents a hydrogen atom, and T represents any one substituent indicated in [Table 1A] to [Table 6A] (hereinafter, referred to as "Compound class SX129").

A present compound wherein $A^2$ represents a nitrogen atom, $A^3$ and $A^4$ represent CH, Q represents a group represented by Q20, $R^3$ represents a 4-fluorophenyl group, $R^{5a}$ represents a hydrogen atom, and T represents any one substituent indicated in [Table 1A] to [Table 6A] (hereinafter, referred to as "Compound class SX130").

A present compound wherein $A^3$ represents a nitrogen atom, $A^2$ and $A^4$ represent CH, Q represents a group represented by Q20, $R^3$ and $R^{5a}$ represents a hydrogen atom, and T represents any one substituent indicated in [Table 1A] to [Table 6A] (hereinafter, referred to as "Compound class SX131").

A present compound wherein $A^3$ represents a nitrogen atom, $A^2$ and $A^4$ represent CH, Q represents a group represented by Q20, $R^3$ represents a cyclopropyl group, $R^{5a}$ represents a hydrogen atom, and T represents any one substituent indicated in [Table 1A] to [Table 6A] (hereinafter, referred to as "Compound class SX132").

A present compound wherein $A^3$ represents a nitrogen atom, $A^2$ and $A^4$ represent CH, Q represents a group represented by Q20, $R^3$ represents a 4-fluorophenyl group, $R^{5a}$ represents a hydrogen atom, and T represents any one substituent indicated in [Table 1A] to [Table 6A] (hereinafter, referred to as "Compound class SX133").

A present compound wherein $A^4$ represents a nitrogen atom, $A^2$ and $A^3$ represent CH, Q represents a group represented by Q20, $R^3$ and $R^{5a}$ represent a hydrogen atom, and T represents any one substituent indicated in [Table 1A] to [Table 6A] (hereinafter, referred to as "Compound class SX134").

A present compound wherein $A^4$ represents a nitrogen atom, $A^2$ and $A^3$ represent CH, Q represents a group represented by Q20, $R^3$ represents a cyclopropyl group, $R^{5a}$ represents a hydrogen atom, and T represents any one substituent indicated in [Table 1A] to [Table 6A] (hereinafter, referred to as "Compound class SX135").

A present compound wherein $A^4$ represents a nitrogen atom, $A^2$ and $A^3$ represent CH, Q represents a group represented by Q20, $R^3$ represents a 4-fluorophenyl group, $R^{5a}$ represents a hydrogen atom, and T represents any one substituent indicated in [Table 1A] to [Table 6A] (hereinafter, referred to as "Compound class SX136").

A present compound wherein $A^2$, $A^3$ and $A^4$ represent CH, Q represents a group represented by Q21, $R^3$ and $R^{5c}$ represent a hydrogen atom, and T represents any one substituent indicated in [Table 1A] to [Table 6A] (hereinafter, referred to as "Compound class SX137").

A present compound wherein $A^2$, $A^3$ and $A^4$ represent CH, Q represents a group represented by Q21, $R^3$ represents a cyclopropyl group, and $R^{5c}$ represent a hydrogen atom, and T represents any one substituent indicated in [Table 1A] to [Table 6A] (hereinafter, referred to as "Compound class SX138").

A present compound wherein $A^2$, $A^3$ and $A^4$ represent CH, Q represents a group represented by Q21, $R^3$ represents a 4-fluorophenyl group, and $R^{5c}$ represent a hydrogen atom, and T represents any one substituent indicated in [Table 1A] to [Table 6A] (hereinafter, referred to as "Compound class SX139").

A present compound wherein $A^2$ represents a nitrogen atom, $A^3$ and $A^4$ represent CH, Q represents a group represented by Q21, $R^3$ and $R^{5c}$ represent a hydrogen atom, and T represents any one substituent indicated in [Table 1A] to [Table 6A] (hereinafter, referred to as "Compound class SX140").

A present compound wherein $A^2$ represents a nitrogen atom, $A^3$ and $A^4$ represent CH, Q represents a group represented by Q21, $R^3$ represents a cyclopropyl group, $R^{5c}$ represents a hydrogen atom, and T represents any one substituent indicated in [Table 1A] to [Table 6A] (hereinafter, referred to as "Compound class SX141").

A present compound wherein $A^2$ represents a nitrogen atom, $A^3$ and $A^4$ represent CH, Q represents a group represented by Q21, $R^3$ represents a 4-fluorophenyl group, $R^{5c}$ represents a hydrogen atom, and T represents any one substituent indicated in [Table 1A] to [Table 6A] (hereinafter, referred to as "Compound class SX142").

A present compound wherein $A^3$ represents a nitrogen atom, $A^2$ and $A^4$ represent CH, Q represents a group represented by Q21, $R^3$ and $R^{5c}$ represents a hydrogen atom, and T represents any one substituent indicated in [Table 1A] to [Table 6A] (hereinafter, referred to as "Compound class SX143").

A present compound wherein $A^3$ represents a nitrogen atom, $A^2$ and $A^4$ represent CH, Q represents a group represented by Q21, $R^3$ represents a cyclopropyl group, $R^{5c}$ represents a hydrogen atom, and T represents any one substituent indicated in [Table 1A] to [Table 6A] (hereinafter, referred to as "Compound class SX144").

A present compound wherein $A^3$ represents a nitrogen atom, $A^2$ and $A^4$ represent CH, Q represents a group represented by Q21, $R^3$ represents a 4-fluorophenyl group, $R^{5c}$ represents a hydrogen atom, and T represents any one substituent indicated in [Table 1A] to [Table 6A] (hereinafter, referred to as "Compound class SX145").

A present compound wherein $A^4$ represents a nitrogen atom, $A^2$ and $A^3$ represent CH, Q represents a group represented by Q21, $R^3$ and $R^{5c}$ represent a hydrogen atom, and T represents any one substituent indicated in [Table 1A] to [Table 6A] (hereinafter, referred to as "Compound class SX146").

A present compound wherein $A^4$ represents a nitrogen atom, $A^2$ and $A^3$ represent CH, Q represents a group represented by Q21, $R^3$ represents a cyclopropyl group, $R^{5c}$ represents a hydrogen atom, and T represents any one substituent indicated in [Table 1A] to [Table 6A] (hereinafter, referred to as "Compound class SX147").

A present compound wherein $A^4$ represents a nitrogen atom, $A^2$ and $A^3$ represent CH, Q represents a group represented by Q21, $R^3$ represents a 4-fluorophenyl group, $R^{5c}$ represents a hydrogen atom, and T represents any one substituent indicated in [Table 1A] to [Table 6A] (hereinafter, referred to as "Compound class SX148").

A present compound wherein $A^2$, $A^3$, and $A^4$ represent CH, Q represents a group represented by Q22, $R^3$ represents a hydrogen atom, and T represents any one substituent indicated in [Table 1A] to [Table 6A] (hereinafter, referred to as "Compound class SX149").

A present compound wherein $A^2$, $A^3$, and $A^4$ represent CH, Q represents a group represented by Q22, $R^3$ represents a cyclopropyl group, and T represents any one substituent indicated in [Table 1A] to [Table 6A] (hereinafter, referred to as "Compound class SX150").

A present compound wherein $A^2$, $A^3$, and $A^4$ represent CH, Q represents a group represented by Q22, $R^3$ represents a 4-fluorophenyl group, and T represents any one substituent indicated in [Table 1A] to [Table 6A] (hereinafter, referred to as "Compound class SX151").

A present compound wherein $A^2$ represents a nitrogen atom, $A^3$ and $A^4$ represent CH, Q represents a group represented by Q22, $R^3$ represents a hydrogen atom, and T represents any one substituent indicated in [Table 1A] to [Table 6A] (hereinafter, referred to as "Compound class SX152").

A present compound wherein $A^2$ represents a nitrogen atom, $A^3$ and A4 represent CH, Q represents a group represented by Q22, $R^3$ represents a cyclopropyl group, and T represents any one substituent indicated in [Table 1A] to [Table 6A] (hereinafter, referred to as "Compound class SX153").

A present compound wherein $A^2$ represents a nitrogen atom, $A^3$ and A4 represent CH, Q represents a group represented by Q22, $R^3$ represents a 4-fluorophenyl group, and T represents any one substituent indicated in [Table 1A] to [Table 6A] (hereinafter, referred to as "Compound class SX154").

A present compound wherein $A^3$ represents a nitrogen atom, $A^2$ and A4 represent CH, Q represents a group represented by Q22, $R^3$ represents a hydrogen atom, and T represents any one substituent indicated in [Table 1A] to [Table 6A] (hereinafter, referred to as "Compound class SX155").

A present compound wherein $A^3$ represents a nitrogen atom, $A^2$ and A4 represent CH, Q represents a group represented by Q22, $R^3$ represents a cyclopropyl group, and T represents any one substituent indicated in [Table 1A] to [Table 6A] (hereinafter, referred to as "Compound class SX156").

A present compound wherein $A^3$ represents a nitrogen atom, $A^2$ and $A^4$ represent CH, Q represents a group represented by Q22, $R^3$ represents a 4-fluorophenyl group, and T represents any one substituent indicated in [Table 1A] to [Table 6A] (hereinafter, referred to as "Compound class SX157").

A present compound wherein $A^4$ represents a nitrogen atom, $A^2$ and $A^3$ represent CH, Q represents a group represented by Q22, $R^3$ represents a hydrogen atom, and T represents any one substituent indicated in [Table 1A] to [Table 6A] (hereinafter, referred to as "Compound class SX158").

A present compound wherein $A^4$ represents a nitrogen atom, $A^2$ and $A^3$ represent CH, Q represents a group represented by Q22, $R^3$ represents a cyclopropyl group, and T represents any one substituent indicated in [Table 1A] to [Table 6A] (hereinafter, referred to as "Compound class SX159").

A present compound wherein $A^4$ represents a nitrogen atom, $A^2$ and $A^3$ represent CH, Q represents a group represented by Q22, $R^3$ represents a 4-fluorophenyl group, and T represents any one substituent indicated in [Table 1A] to [Table 6A] (hereinafter, referred to as "Compound class SX160").

A present compound wherein $A^2$, $A^3$ and $A^4$ represent CH, Q represents a group represented by Q23, $R^{5a}$ and $R^{5c}$ represent a hydrogen atom, and T represents any one substituent indicated in [Table 1A] to [Table 6A] (hereinafter, referred to as "Compound class SX161").

A present compound wherein $A^2$, $A^3$ and $A^4$ represent CH, Q represents a group represented by Q23, $R^{5c}$ represents a hydrogen atom, $R^{5b}$ represents a cyclopropyl group, and T represents any one substituent indicated in [Table 1A] to [Table 6A] (hereinafter, referred to as "Compound class SX162").

A present compound wherein $A^2$, $A^3$ and $A^4$ represent CH, Q represents a group represented by Q23, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX163").

A present compound wherein $A^2$ represents a nitrogen atom, $A^3$ and $A^4$ represent CH, Q represents a group represented by Q23, $R^{5b}$ and $R^{5c}$ represent a hydrogen atom, and T represents any one substituent indicated in [Table 1A] to [Table 6A] (hereinafter, referred to as "Compound class SX164").

A present compound wherein $A^2$ represents a nitrogen represented by Q23, $R^{5c}$ represents a hydrogen atom, $R^{5b}$ represents a cyclopropyl group, and T represents any one substituent indicated in [Table 1A] to [Table 6A] (hereinafter, referred to as "Compound class SX165").

A present compound wherein $A^2$ represents a nitrogen atom, $A^3$ and $A^4$ represent CH, Q represents a group represented by Q23, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX166").

A present compound wherein $A^2$ represents a nitrogen atom, $A^3$ and $A^4$ represent CH, Q represents a group represented by Q23, $R^{5b}$ and $R^{5c}$ represent a hydrogen atom, and T represents any one substituent indicated in [Table 1A] to [Table 6A] (hereinafter, referred to as "Compound class SX167").

A present compound wherein $A^3$ represents a nitrogen atom, $A^2$ and $A^4$ represent CH, Q represents a group represented by Q23, $R^{5c}$ represent a hydrogen atom, $R^{5b}$ represents a cyclopropyl group, and T represents any one substituent indicated in [Table 1A] to [Table 6A] (hereinafter, referred to as "Compound class SX168").

A present compound wherein $A^3$ represents a nitrogen atom, $A^2$ and $A^4$ represent CH, Q represents a group represented by Q23, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX169").

A present compound wherein $A^4$ represents a nitrogen atom, $A^2$ and $A^3$ represents CH, Q represents a group represented by Q23, $R^{5b}$ and $R^{5c}$ represent a hydrogen atom, and T represents any one substituent indicated in [Table 1A] to [Table 6A] (hereinafter, referred to as "Compound class SX170").

A present compound wherein $A^4$ represents a nitrogen atom, $A^2$ and $A^3$ represent CH, Q represents a group represented by Q23, $R^{5c}$ represents a hydrogen atom, $R^{5b}$ represents a cyclopropyl group, and T represents any one substituent indicated in [Table 1A] to [Table 6A] (hereinafter, referred to as "Compound class SX171").

A present compound wherein $A^4$ represents a nitrogen atom, $A^2$ and $A^3$ represent CH, Q represents a group represented by Q23, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX172").

A present compound wherein $A^2$, $A^3$ and $A^4$ represent CH, Q represents a group represented by Q24, $R^{5b}$ and $R^{5c}$ represent a hydrogen atom, and T represents any one substituent indicated in [Table 1A] to [Table 6A] (hereinafter, referred to as "Compound class SX173").

A present compound wherein $A^2$, $A^3$ and $A^4$ represent CH, Q represents a group represented by Q24, $R^{5c}$ represents a hydrogen atom, $R^{5b}$ represents a cyclopropyl group, and T represents any one substituent indicated in [Table 1A] to [Table 6A] (hereinafter, referred to as "Compound class SX174").

A present compound wherein $A^2$, $A^3$ and $A^4$ represent CH, Q represents a group represented by Q24, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX175").

A present compound wherein $A^2$ represents a nitrogen atom, $A^3$ and $A^4$ represent CH, Q represents a group represented by Q24, $R^{5b}$ and $R^{5c}$ represent a hydrogen atom, and T represents any one substituent indicated in [Table 1A] to [Table 6A] (hereinafter, referred to as "Compound class SX176").

A present compound wherein $A^2$ represents a nitrogen atom, $A^3$ and $A^4$ represent CH, Q represents a group represented by Q24, $R^{5c}$ represents a hydrogen atom, $R^{5b}$ represents a cyclopropyl group, and T represents any one substituent indicated in [Table 1A] to [Table 6A] (hereinafter, referred to as "Compound class SX177").

A present compound wherein $A^2$ represents a nitrogen atom, $A^3$ and $A^4$ represent CH, Q represents a group represented by Q24, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX178").

A present compound wherein $A^3$ represents a nitrogen atom, $A^2$ and $A^4$ represent CH, Q represents a group represented by Q24, $R^{5b}$ and $R^{5c}$ represent a hydrogen atom, and T represents any one substituent indicated in [Table 1A] to [Table 6A] (hereinafter, referred to as "Compound class SX179").

A present compound wherein $A^3$ represents a nitrogen atom, $A^2$ and $A^4$ represent CH, Q represents a group represented by Q24, $R^{5c}$ represents a hydrogen atom, $R^{5b}$ represents a cyclopropyl group, and T represents any one substituent indicated in [Table 1A] to [Table 6A] (hereinafter, referred to as "Compound class SX180").

A present compound wherein $A^3$ represents a nitrogen atom, $A^2$ and $A^4$ represent CH, Q represents a group represented by Q24, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX181").

A present compound wherein $A^3$ represents a nitrogen atom, $A^2$ and $A^4$ represent CH, Q represents a group represented by Q24, $R^{5b}$ and $R^{5c}$ represent a hydrogen atom, and T represents any one substituent indicated in [Table 1A] to [Table 6A] (hereinafter, referred to as "Compound class SX182").

A present compound wherein $A^4$ represents a nitrogen atom, $A^2$ and $A^3$ represent CH, Q represents a group represented by Q24, $R^{5c}$ represents a hydrogen atom, $R^{5b}$ represents a cyclopropyl group, and T represents any one substituent indicated in [Table 1A] to [Table 6A] (hereinafter, referred to as "Compound class SX183").

A present compound wherein $A^4$ represents a nitrogen atom, $A^2$ and $A^3$ represent CH, Q represents a group represented by Q24, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX184").

A present compound wherein $A^2$, $A^3$ and $A^4$ represent CH, Q represents a group represented by Q25, $R^{5c}$ represents a hydrogen atom, $R^3$, $R^{5b}$ and $R^{5c}$ represents a hydrogen atom, and T represents any one substituent indicated in [Table 1A] to [Table 6A] (hereinafter, referred to as "Compound class SX185").

A present compound wherein $A^2$, $A^3$ and $A^4$ represent CH, Q represents a group represented by Q25, $R^3$ and $R^{5c}$ represent a hydrogen atom, $R^{5b}$ represents a cyclopropyl group, and T represents any one substituent indicated in [Table 1A] to [Table 6A] (hereinafter, referred to as "Compound class SX186").

A present compound wherein $A^2$, $A^3$ and $A^4$ represent CH, Q represents a group represented by Q25, $R^3$ and $R^{5c}$ represent a hydrogen atom, $R^{5b}$ represents a 4-fluorophenyl group, and T represents any one substituent indicated in [Table 1A] to [Table 6A] (hereinafter, referred to as "Compound class SX187").

A present compound wherein $A^2$ represents a nitrogen atom, $A^3$ and $A^4$ represent CH, Q represents a group represented by Q25, $R^3$, $R^{5b}$ and $R^{5c}$ represent a hydrogen atom, and T represents any one substituent indicated in [Table 1A] to [Table 6A] (hereinafter, referred to as "Compound class SX188").

A present compound wherein $A^2$ represents a nitrogen atom, $A^3$ and $A^4$ represent CH, Q represents a group represented by Q25, $R^3$ and $R^{5c}$ represent a hydrogen atom, $R^{5b}$ represents a cyclopropyl group, and T represents any one substituent indicated in [Table 1A] to [Table 6A] (hereinafter, referred to as "Compound class SX189").

A present compound wherein $A^2$ represents a nitrogen represented by Q25, $R^3$ and $R^{5c}$ represent a hydrogen atom, $R^{5b}$ represents a 4-fluorophenyl group, and T represents any one substituent indicated in [Table 1A] to [Table 6A] (hereinafter, referred to as "Compound class SX190").

A present compound wherein $A^3$ represents a nitrogen atom, $A^2$ and $A^4$ represent CH, Q represents a group represented by Q25, $R^3$, $R^{5b}$ and $R^{5c}$ represent a hydrogen atom, and T represents any one substituent indicated in [Table 1A] to [Table 6A] (hereinafter, referred to as "Compound class SX191").

A present compound wherein $A^3$ represents a nitrogen atom, $A^2$ and $A^4$ represent CH, Q represents a group represented by Q25, $R^3$ and $R^{5c}$ represent a hydrogen atom, $R^{5b}$ represents a cyclopropyl group, and T represents any one substituent indicated in [Table 1A] to [Table 6A] (hereinafter, referred to as "Compound class SX192").

A present compound wherein $A^3$ represents a nitrogen atom, $A^2$ and $A^4$ represent CH, Q represents a group represented by Q25, $R^3$ and $R^{5c}$ represent a hydrogen atom, $R^{5b}$ represents a 4-fluorophenyl group, and T represents any one substituent indicated in [Table 1A] to [Table 6A] (hereinafter, referred to as "Compound class SX193").

A present compound wherein A4 represents a nitrogen atom, $A^2$ and $A^3$ represent CH, Q represents a group represented by Q25, $R^3$, $R^{5b}$ and $R^{5c}$ represent a hydrogen atom, and T represents any one substituent indicated in [Table 1A] to [Table 6A] (hereinafter, referred to as "Compound class SX194").

A present compound wherein $A^4$ represents a nitrogen atom, $A^2$ and $A^3$ represent CH, Q represents a group represented by Q25, $R^3$ and $R^{5c}$ represent a hydrogen atom, $R^{5b}$ represents a cyclopropyl group, and T represents any one substituent indicated in [Table 1A] to [Table 6A] (hereinafter, referred to as "Compound class SX195").

A present compound wherein $A^4$ represents a nitrogen atom, $A^2$ and $A^3$ represent CH, Q represents a group represented by Q25, $R^3$ and $R^{5c}$ represent a hydrogen atom, $R^{5b}$ represents a 4-fluorophenyl group, and T represents any one substituent indicated in [Table 1A] to [Table 6A] (hereinafter, referred to as "Compound class SX196").

A present compound wherein $A^2$, $A^3$ and $A^4$ represent CH, Q represents a group represented by Q25, $R^3$ represents a methyl group, $R^{5b}$ and $R^{5c}$ represent a hydrogen atom, and T represents any one substituent indicated in [Table 1A] to [Table 6A] (hereinafter, referred to as "Compound class SX197").

A present compound wherein $A^2$, $A^3$ and $A^4$ represent CH, Q represents a group represented by Q25, $R^3$ represents a methyl group, $R^{5c}$ represents a hydrogen atom, $R^{5b}$ represents a cyclopropyl group, and T represents any one substituent indicated in [Table 1A] to [Table 6A] (hereinafter, referred to as "Compound class SX198").

A present compound wherein $A^2$, $A^3$ and $A^4$ represent CH, Q represents a group represented by Q25, $R^3$ represents a methyl group, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX199").

A present compound wherein $A^2$ represents a nitrogen atom, $A^3$ and $A^4$ represent CH, Q represents a group represented by Q25, $R^3$ represents a methyl group, $R^{5b}$ and $R^{5c}$ represent a hydrogen atom, and T represents any one substituent indicated in [Table 1A] to [Table 6A] (hereinafter, referred to as "Compound class SX200").

A present compound wherein $A^2$ represents a nitrogen atom, $A^3$ and $A^4$ represent CH, Q represents a group represented by Q25, $R^3$ represents a methyl group, $R^{5c}$ represents a hydrogen atom, $R^{5b}$ represents a cyclopropyl group, and T represents any one substituent indicated in [Table 1A] to [Table 6A] (hereinafter, referred to as "Compound class SX201").

A present compound wherein $A^2$ represents a nitrogen atom, $A^3$ and $A^4$ represent CH, Q represents a group represented by Q25, $R^3$ represents a methyl group, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX202").

A present compound wherein $A^2$ represents a nitrogen atom, $A^3$ and $A^4$ represent CH, Q represents a group represented by Q25, $R^3$ represents a methyl group, $R^{5b}$ and $R^{5c}$ represent a hydrogen atom, and T represents any one substituent indicated in [Table 1A] to [Table 6A] (hereinafter, referred to as "Compound class SX203").

A present compound wherein $A^3$ represents a nitrogen atom, $A^2$ and $A^4$ represent CH, Q represents a group represented by Q25, $R^3$ represents a methyl group, $R^{5c}$ represents a hydrogen atom, $R^{5b}$ represents a cyclopropyl group, and T represents any one substituent indicated in [Table 1A] to [Table 6A] (hereinafter, referred to as "Compound class SX204").

A present compound wherein $A^3$ represents a nitrogen atom, $A^2$ and $A^4$ represent CH, Q represents a group represented by Q25, $R^3$ represents a methyl group, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX205").

A present compound wherein $A^3$ represents a nitrogen atom, $A^2$ and $A^3$ represent CH, Q represents a group represented by Q25, $R^3$ represents a methyl group, $R^{5b}$ and $R^{5c}$ represent a hydrogen atom, and T represents any one substituent indicated in [Table 1A] to [Table 6A] (hereinafter, referred to as "Compound class SX206").

A present compound wherein $A^4$ represents a nitrogen atom, $A^2$ and $A^3$ represent CH, Q represents a group represented by Q25, $R^3$ represents a methyl group, $R^{5c}$ represents a hydrogen atom, $R^{5b}$ represents a cyclopropyl group, and T represents any one substituent indicated in [Table 1A] to [Table 6A] (hereinafter, referred to as "Compound class SX207").

A present compound wherein $A^4$ represents a nitrogen atom, $A^2$ and $A^3$ represent CH, Q represents a group represented by Q25, $R^3$ represents a methyl group, $R^{5c}$ represents a hydrogen atom, $R^{5b}$ represents a 4-fluorophenyl group, and T represents any one substituent indicated in [Table 1A] to [Table 6A] (hereinafter, referred to as "Compound class SX208").

A present compound wherein $A^2$, $A^3$ and $A^4$ represent CH, Q represents a group represented by Q26, $R^{5b}$ represents a hydrogen atom, and T represents any one substituent indicated in [Table 1A] to [Table 6A] (hereinafter, referred to as "Compound class SX209").

A present compound wherein $A^2$, $A^3$ and $A^4$ represent CH, Q represents a group represented by Q26, $R^{5b}$ represents a cyclopropyl group, and T represents any one substituent indicated in [Table 1A] to [Table 6A] (hereinafter, referred to as "Compound class SX210").

A present compound wherein $A^2$, $A^3$ and $A^4$ represent CH, Q represents a group represented by Q26, $R^{5b}$ represents a 4-fluorophenyl group, and T represents any one substituent indicated in [Table 1A] to [Table 6A] (hereinafter, referred to as "Compound class SX211").

A present compound wherein $A^2$ represents a nitrogen atom, $A^3$ and $A^4$ represent CH, Q represents a group represented by Q26, $R^{5b}$ represents a hydrogen atom, and T represents any one substituent indicated in [Table 1A] to [Table 6A] (hereinafter, referred to as "Compound class SX212").

A present compound wherein $A^2$ represents a nitrogen atom, $A^3$ and $A^4$ represent CH, Q represents a group represented by Q26, $R^{5b}$ represents a cyclopropyl group, and T represents any one substituent indicated in [Table 1A] to [Table 6A] (hereinafter, referred to as "Compound class SX213").

A present compound wherein $A^2$ represents a nitrogen atom, $A^3$ and $A^4$ represent CH, Q represents a group represented by Q26, $R^{5b}$ represents a 4-fluorophenyl group, and T represents any one substituent indicated in [Table 1A] to [Table 6A] (hereinafter, referred to as "Compound class SX214").

A present compound wherein $A^3$ represents a nitrogen atom, $A^2$ and $A^4$ represent CH, Q represents a group represented by Q26, $R^{5b}$ represents a hydrogen atom, and T represents any one substituent indicated in [Table 1A] to [Table 6A] (hereinafter, referred to as "Compound class SX215").

A present compound wherein $A^3$ represents a nitrogen atom, $A^2$ and $A^4$ represent CH, Q represents a group represented by Q26, $R^{5b}$ represents a cyclopropyl group, and T represents any one substituent indicated in [Table 1A] to [Table 6A] (hereinafter, referred to as "Compound class SX216").

A present compound wherein $A^3$ represents a nitrogen atom, $A^2$ and $A^4$ represent CH, Q represents a group represented by Q26, $R^{5b}$ represents a 4-fluorophenyl group, and T represents any one substituent indicated in [Table 1A] to [Table 6A] (hereinafter, referred to as "Compound class SX217").

A present compound wherein $A^4$ represents a nitrogen atom, $A^2$ and $A^3$ represent CH, Q represents a group represented by Q26, $R^{5b}$ represents a hydrogen atom, and T represents any one substituent indicated in [Table 1A] to [Table 6A] (hereinafter, referred to as "Compound class SX218").

A present compound wherein $A^4$ represents a nitrogen atom, $A^2$ and $A^3$ represent CH, Q represents a group represented by Q26, $R^{5b}$ represents a cyclopropyl group, and T represents any one substituent indicated in [Table 1A] to [Table 6A] (hereinafter, referred to as "Compound class SX219").

A present compound wherein $A^4$ represents a nitrogen atom, $A^2$ and $A^3$ represent CH, Q represents a group represented by Q26, $R^{5b}$ represents a 4-fluorophenyl group, and T represents any one substituent indicated in [Table 1A] to [Table 6A] (hereinafter, referred to as "Compound class SX220").

A present compound wherein $A^2$, $A^3$ and $A^4$ represent CH, Q represents a group represented by Q27, $R^{5b}$ represents a hydrogen atom, and T represents any one substituent indicated in [Table 1A] to [Table 6A] (hereinafter, referred to as "Compound class SX221").

A present compound wherein $A^2$, $A^3$ and $A^4$ represent CH, Q represents a group represented by Q27, $R^{5b}$ represents a cyclopropyl group, and T represents any one substituent indicated in [Table 1A] to [Table 6A] (hereinafter, referred to as "Compound class SX222").

A present compound wherein $A^2$, $A^3$ and $A^4$ represent CH, Q represents a group represented by Q27, $R^{5b}$ represents a 4-fluorophenyl group, and T represents any one substituent indicated in [Table 1A] to [Table 6A] (hereinafter, referred to as "Compound class SX223").

A present compound wherein $A^2$ represents a nitrogen atom, $A^3$ and $A^4$ represent CH, Q represents a group represented by Q27, $R^{5b}$ represents a hydrogen atom, and T represents any one substituent indicated in [Table 1A] to [Table 6A] (hereinafter, referred to as "Compound class SX224").

A present compound wherein $A^2$ represents a nitrogen atom, $A^3$ and $A^4$ represent CH, Q represents a group represented by Q27, $R^{5b}$ represents a cyclopropyl group, and T represents any one substituent indicated in [Table 1A] to [Table 6A] (hereinafter, referred to as "Compound class SX225").

A present compound wherein $A^2$ represents a nitrogen atom, $A^3$ and $A^4$ represent CH, Q represents a group represented by Q27, $R^{5b}$ represents a 4-fluorophenyl group, and T represents any one substituent indicated in [Table 1A] to [Table 6A] (hereinafter, referred to as "Compound class SX226").

A present compound wherein $A^3$ represents a nitrogen atom, $A^2$ and $A^4$ represent CH, Q represents a group represented by Q27, $R^{5b}$ represents a hydrogen atom, and T represents any one substituent indicated in [Table 1A] to [Table 6A] (hereinafter, referred to as "Compound class SX227").

A present compound wherein $A^3$ represents a nitrogen atom, $A^2$ and $A^4$ represent CH, Q represents a group represented by Q27, $R^{5b}$ represents a cyclopropyl group, and T represents any one substituent indicated in [Table 1A] to [Table 6A] (hereinafter, referred to as "Compound class SX228").

A present compound wherein $A^3$ represents a nitrogen atom, $A^2$ and $A^4$ represent CH, Q represents a group represented by Q27, $R^{5b}$ represents a 4-fluorophenyl group, and T represents any one substituent indicated in [Table 1A] to [Table 6A] (hereinafter, referred to as "Compound class SX229").

A present compound wherein $A^4$ represents a nitrogen atom, $A^2$ and $A^3$ represent CH, Q represents a group represented by Q27, $R^{5b}$ represents a hydrogen atom, and T represents any one substituent indicated in [Table 1A] to [Table 6A] (hereinafter, referred to as "Compound class SX230").

A present compound wherein $A^4$ represents a nitrogen atom, $A^2$ and $A^3$ represent CH, Q represents a group represented by Q27, $R^{5b}$ represents a cyclopropyl group, and T represents any one substituent indicated in [Table 1A] to [Table 6A] (hereinafter, referred to as "Compound class SX231").

A present compound wherein $A^4$ represents a nitrogen atom, $A^2$ and $A^3$ represent CH, Q represents a group represented by Q27, $R^{5b}$ represents a 4-fluorophenyl group, and T represents any one substituent indicated in [Table 1A] to [Table 6A] (hereinafter, referred to as "Compound class SX232").

A present compound wherein $A^2$, $A^3$ and $A^4$ represent CH, Q represents a group represented by Q28, $R^3$ and $R^{5b}$ represent a hydrogen atom, and T represents any one substituent indicated in [Table 1A] to [Table 6A] (hereinafter, referred to as "Compound class SX233").

A present compound wherein $A^2$, $A^3$ and $A^4$ represent CH, Q represents a group represented by Q28, $R^3$ represents a hydrogen atom, $R^{5b}$ represents a cyclopropyl group, and T represents any one substituent indicated in [Table 1A] to [Table 6A] (hereinafter, referred to as "Compound class SX234").

A present compound wherein $A^2$, $A^3$ and $A^4$ represent CH, Q represents a group represented by Q28, $R^3$ represents a hydrogen atom, $R^{5b}$ represents a 4-fluorophenyl group, and T represents any one substituent indicated in [Table 1A] to [Table 6A] (hereinafter, referred to as "Compound class SX235").

A present compound wherein $A^2$ represents a nitrogen atom, $A^3$ and $A^4$ represent CH, Q represents a group represented by Q28, $R^3$ and $R^{5b}$ represents a hydrogen atom, and T represents any one substituent indicated in [Table 1A] to [Table 6A] (hereinafter, referred to as "Compound class SX236").

A present compound wherein $A^2$ represents a nitrogen atom, $A^3$ and $A^4$ represent CH, Q represents a group represented by Q28, $R^3$ represents a hydrogen atom, $R^{5b}$ represents a cyclopropyl group, and T represents any one substituent indicated in [Table 1A] to [Table 6A] (hereinafter, referred to as "Compound class SX237").

A present compound wherein $A^2$ represents a nitrogen atom, $A^3$ and $A^4$ represent CH, Q represents a group represented by Q28, $R^3$ represents a hydrogen atom, $R^{5b}$ represents a 4-fluorophenyl group, and T represents any one substituent indicated in [Table 1A] to [Table 6A] (hereinafter, referred to as "Compound class SX238").

A present compound wherein $A^3$ represents a nitrogen atom, $A^2$ and $A^4$ represent CH, Q represents a group represented by Q28, $R^3$ and $R^{5b}$ represent a hydrogen atom, and T represents any one substituent indicated in [Table 1A] to [Table 6A] (hereinafter, referred to as "Compound class SX239").

A present compound wherein $A^3$ represents a nitrogen atom, $A^2$ and $A^4$ represent CH, Q represents a group represented by Q28, $R^3$ represents a hydrogen atom, and $R^{5b}$ represents a cyclopropyl group, and T represents any one substituent indicated in [Table 1A] to [Table 6A] (hereinafter, referred to as "Compound class SX240").

A present compound wherein $A^3$ represents a nitrogen atom, $A^2$ and $A^4$ represent CH, Q represents a group represented by Q28, $R^3$ represents a hydrogen atom, and $R^{5b}$ represents a 4-fluorophenyl group, and T represents any one substituent indicated in [Table 1A] to [Table 6A] (hereinafter, referred to as "Compound class SX241").

A present compound wherein $A^4$ represents a nitrogen atom, $A^2$ and $A^3$ represent CH, Q represents a group represented by Q28, $R^3$ and $R^{5b}$ represents a hydrogen atom, and T represents any one substituent indicated in [Table 1A] to [Table 6A] (hereinafter, referred to as "Compound class SX242").

A present compound wherein $A^4$ represents a nitrogen atom, $A^2$ and $A^3$ represent CH, Q represents a group represented by Q28, $R^3$ represents a hydrogen atom, $R^{5b}$ represents a cyclopropyl group, and T represents any one substituent indicated in [Table 1A] to [Table 6A] (hereinafter, referred to as "Compound class SX243").

A present compound wherein $A^4$ represents a nitrogen atom, $A^2$ and $A^3$ represent CH, Q represents a group represented by Q28, $R^3$ represents a hydrogen atom, $R^{5b}$ represents a 4-fluorophenyl group, and T represents any one substituent indicated in [Table 1A] to [Table 6A] (hereinafter, referred to as "Compound class SX244").

A present compound wherein $A^2$, $A^3$ and $A^4$ represent CH, Q represents a group represented by Q28, $R^3$ represents a methyl group, $R^{5b}$ represents a hydrogen atom, and T represents any one substituent indicated in [Table 1A] to [Table 6A] (hereinafter, referred to as "Compound class SX245").

A present compound wherein $A^2$, $A^3$ and $A^4$ represent CH, Q represents a group represented by Q28, $R^3$ represents a methyl group, $R^{5b}$ represents a cyclopropyl group, and T represents any one substituent indicated in [Table 1A] to [Table 6A] (hereinafter, referred to as "Compound class SX246").

A present compound wherein $A^2$, $A^3$ and $A^4$ represent CH, Q represents a group represented by Q28, $R^3$ represents a methyl group, $R^{5b}$ represents a 4-fluorophenyl group, and T represents any one substituent indicated in [Table 1A] to [Table 6A] (hereinafter, referred to as "Compound class SX247").

A present compound wherein $A^2$ represents a nitrogen represented by Q28, $R^3$ represents a methyl group, $R^{5b}$ represents a hydrogen atom, and T represents any one substituent indicated in [Table 1A] to [Table 6A] (hereinafter, referred to as "Compound class SX248").

A present compound wherein $A^2$ represents a nitrogen atom, $A^3$ and $A^4$ represent CH, Q represents a group represented by Q28, $R^3$ represents a methyl group, $R^{5b}$ represents a cyclopropyl group, and T represents any one substituent indicated in [Table 1A] to [Table 6A] (hereinafter, referred to as "Compound class SX249").

A present compound wherein $A^2$ represents a nitrogen atom, $A^3$ and $A^4$ represent CH, Q represents a group represented by Q28, $R^3$ represents a methyl group, $R^{5b}$ represents a 4-fluorophenyl group, and T represents any one substituent indicated in [Table 1A] to [Table 6A] (hereinafter, referred to as "Compound class SX250").

A present compound wherein $A^3$ represents a nitrogen atom, $A^2$ and $A^4$ represent CH, Q represents a group represented by Q28, $R^3$ represents a methyl group, $R^{5b}$ represents a hydrogen atom, and T represents any one substituent indicated in [Table 1A] to [Table 6A] (hereinafter, referred to as "Compound class SX251").

A present compound wherein $A^3$ represents a nitrogen atom, $A^2$ and $A^4$ represent CH, Q represents a group represented by Q28, $R^3$ represents a methyl group, $R^{5b}$ represents a cyclopropyl group, and T represents any one substituent indicated in [Table 1A] to [Table 6A] (hereinafter, referred to as "Compound class SX252").

A present compound wherein $A^3$ represents a nitrogen atom, $A^2$ and $A^4$ represent CH, Q represents a group represented by Q28, $R^3$ represents a methyl group, $R^{5b}$ represents a 4-fluorophenyl group, and T represents any one substituent indicated in [Table 1A] to [Table 6A] (hereinafter, referred to as "Compound class SX253").

A present compound wherein $A^4$ represents a nitrogen atom, $A^2$ and $A^3$ represent CH, Q represents a group represented by Q28, $R^3$ represents a methyl group, $R^{5b}$ represents a hydrogen atom, and T represents any one substituent indicated in [Table 1A] to [Table 6A] (hereinafter, referred to as "Compound class SX254").

A present compound wherein $A^4$ represents a nitrogen atom, $A^2$ and $A^3$ represent CH, Q represents a group represented by Q28, $R^3$ represents a methyl group, $R^{5b}$ represents a cyclopropyl group, and T represents any one substituent indicated in [Table 1A] to [Table 6A] (hereinafter, referred to as "Compound class SX255").

A present compound wherein $A^4$ represents a nitrogen atom, $A^2$ and $A^3$ represent CH, Q represents a group represented by Q28, $R^3$ represents a methyl group, $R^{5b}$ represents a 4-fluorophenyl group, and T represents any one substituent indicated in [Table 1A] to [Table 6A] (hereinafter, referred to as "Compound class SX256").

A compound represented by formula (L-1):

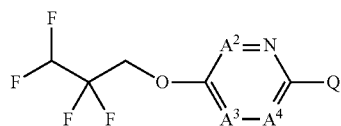

(L-1)

(hereinafter, referred to as "Compound (L-1)") wherein $A^2$, $A^3$ and $A^4$ represent CH, Q represents a group represented by Q10, $R^{5a}$ represents a hydrogen atom, $R^{5b}$ represents any one substituent indicated in [Table 7A] to [Table 14A] (hereinafter, referred to as "Compound class SX257").

[Table 3]

TABLE 7A

Et
Pr
i-Pr
1-CN-c-Pr
C(O)Me
C(O)OEt
C(O)NHEt
C(O)NHCH$_2$CHMe$_2$
C(O)NMe$_2$
Ph
3-F—Ph
3-Cl—Ph
4-Cl—Ph
3-CF$_3$—Ph
4-CF$_3$—Ph
3-NMe$_2$—Ph
4-NMe$_2$—Ph
3-CN—Ph
4-CN—Ph
4-C(O)NMe$_2$—Ph
4-NHC(O)Me—Ph
3,4-F$_2$—Ph
3,5-F$_2$—Ph
2,4-F$_2$—Ph
3,4,5-F$_3$—Ph

TABLE 8A 3,4-Cl$_2$—Ph
3,5-Cl$_2$—Ph
3,5-Cl$_2$-4-F—Ph
3,5-(CF$_3$)$_2$—Ph
Py2
4-F—Py2
5-F—Py2
4-Cl—Py2
5-Cl—Py2
4-CF$_3$—Py2
5-CF$_3$—Py2
3-Me—Py2
4-Me—Py2
5-Me—Py2
6-Me—Py2
5-CN—Py2
5-OCH$_2$CF$_2$CF$_3$—Py2
3,5-F$_2$—Py2
Py3

TABLE 8A-continued

6-CF$_3$—Py3
5-CF$_3$—Py3
6-F—Py3
6-Cl—Py3
Py4

[Table 4]

TABLE 9A

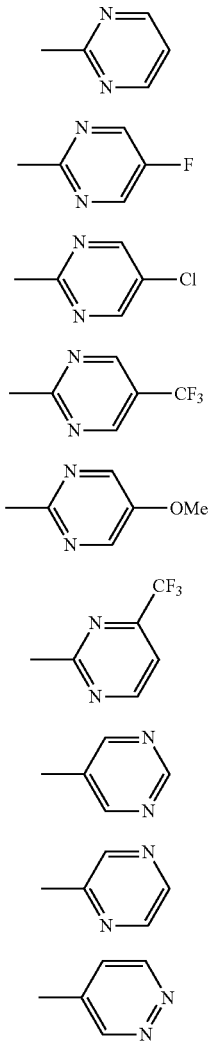

[Table 5]

TABLE 10

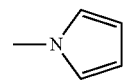

TABLE 10-continued

TABLE 11A-continued

[Table 5]

TABLE 11A

TABLE 12A

TABLE 12A-continued

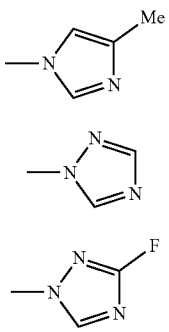

TABLE 13A

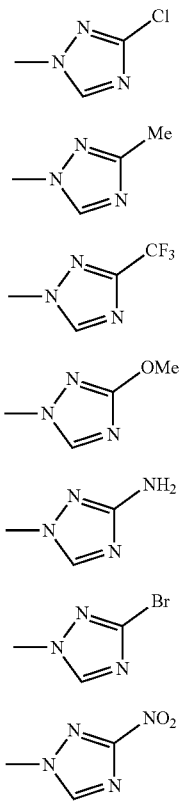

[Table 6]

TABLE 14A

F
Cl
Br
Me
CF$_3$
OMe
Et
OPr
Oi—Pr
NH$_2$
NHCH$_2$CF$_3$
CN
NHC(O)c-Pr
NMeC(O)c-Pr
CH=N—OH

TABLE 14A-continued

CH=N—OMe
OPh
O-2-F—Ph
OPy2
OPy3

The compound (L-1) wherein $A^2$ represents a nitrogen atom, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX258").

The compound (L-1) wherein $A^3$ represents a nitrogen atom, $A^2$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX259").

The compound (L-1) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX260").

The compound (L-1) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX261").

The compound (L-1) wherein $A^2$ represents a nitrogen atom, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX262").

The compound (L-1) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX263").

The compound (L-1) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX264").

The compound (L-1) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX265").

The compound (L-1) wherein $A^2$ represents a nitrogen atom, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX266").

The compound (L-1) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX267").

The compound (L-1) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX268").

The compound (L-1) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX269").

The compound (L-1) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX270").

The compound (L-1) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX271").

The compound (L-1) wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX272").

The compound (L-1) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX273").

The compound (L-1) wherein $A^2$ represents a nitrogen represented by Q15, and $R^{5b}$ represents any one substituent indicated in [Table 7A] to [Table 14A] (hereinafter, referred to as "Compound class SX274").

The compound (L-1) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX275").

The compound (L-1) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX276").

The compound (L-1) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX277").

The compound (L-1) wherein $A^2$ represents a nitrogen atom, $A^3$ and $A^4$ represent CH, Q represents a group represented by Q16, and $R^{5b}$ represents any one substituent indicated in [Table 7A] to [Table 14A] (hereinafter, referred to as "Compound class SX278").

The compound (L-1) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX279").

The compound (L-1) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX280").

The compound (L-1) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX281").

The compound (L-1) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX282").

The compound (L-1) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX283").

The compound (L-1) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX284").

The compound (L-1) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX285").

The compound (L-1) wherein $A^2$ represents a nitrogen atom, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX286").

The compound (L-1) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX287").

The compound (L-1) wherein A4 represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX288").

The compound (L-1) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX289").

The compound (L-1) wherein $A^2$ represents a nitrogen atom, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX290").

The compound (L-1) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX291").

The compound (L-1) wherein $A^4$ represents a nitrogen atom, $A^2$ and $A^3$ represent CH, 0 represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX292").

The compound (L-1) wherein $A^2$, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX293").

The compound (L-1) wherein $A^2$ represents a nitrogen atom, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX294").

The compound (L-1) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX295").

The compound (L-1) wherein A4 represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX296").

The compound (L-1) wherein $A^2$, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX297").

The compound (L-1) wherein $A^2$ represents a nitrogen atom, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX298").

The compound (L-1) wherein $A^3$ represents a nitrogen atom, $A^2$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX299").

The compound (L-1) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX300").

The compound (L-1) wherein $A^2$, A3 and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX301").

The compound (L-1) wherein $A^2$ represents a nitrogen atom, A3 and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX302").

The compound (L-1) wherein $A^3$ represents a nitrogen atom, $A^2$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX303").

The compound (L-1) wherein $A^4$ represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX304").

The compound (L-1) wherein $A^2$, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX305").

The compound (L-1) wherein $A^2$ represents a nitrogen atom, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX306").

The compound (L-1) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX307").

The compound (L-1) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX308").

The compound (L-1) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX309").

The compound (L-1) wherein $A^2$ represents a nitrogen atom, $A^3$ and $A^4$ represent CH, Q represents a group represented by Q22, and $R^3$ represents any one substituent indicated in [Table 7A] to [Table 9A] (hereinafter, referred to as "Compound class SX310").

The compound (L-1) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX311").

The compound (L-1) wherein $A^4$ represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX312").

The compound (L-1) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX313").

The compound (L-1) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX314").

The compound (L-1) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX315").

The compound (L-1) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX316").

The compound (L-1) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX317").

The compound (L-1) wherein $A^2$ represents a nitrogen represented by Q24, $R^{5c}$ represents a hydrogen atom, and $R^{5b}$ represents any one substituent indicated in [Table 7A] to [Table 14A] (hereinafter, referred to as "Compound class SX318").

The compound (L-1) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX319").

The compound (L-1) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX320").

The compound (L-1) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX321").

The compound (L-1) wherein $A^2$ represents a nitrogen represented by Q25, $R^3$ and $R^{5c}$ represent a hydrogen atom, and $R^{5b}$ represents any one substituent indicated in [Table 7A] to [Table 14A] (hereinafter, referred to as "Compound class SX322").

The compound (L-1) wherein $A^3$ represents a nitrogen atom, $A^2$ and A4 represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX323").

The compound (L-1) wherein $A^3$ represents a nitrogen atom, $A^2$ and A4 represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX324").

The compound (L-1) wherein $A^2$, $A^3$ and A4 represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX325").

The compound (L-1) wherein $A^2$ represents a nitrogen atom, $A^3$ and A4 represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX326").

The compound (L-1) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX327").

The compound (L-1) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX328").

The compound (L-1) wherein $A^2$, $A^3$ and $A^4$ represent CH, Q represents a group represented by Q26, and $R^{5b}$ represents any one substituent indicated in [Table 7A] to [Table 14A] (hereinafter, referred to as "Compound class SX329").

The compound (L-1) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX330").

The compound (L-1) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX331").

The compound (L-1) wherein $A^4$ represents a nitrogen atom, $A^2$ and $A^3$ represent CH, Q represents a group represented by Q26, and $R^{5b}$ represents any one substituent indicated in [Table 7A] to [Table 14A] (hereinafter, referred to as "Compound class SX332").

The compound (L-1) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX333").

The compound (L-1) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX334").

The compound (L-1) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX335").

The compound (L-1) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX336").

The compound (L-1) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX337").

The compound (L-1) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX338").

The compound (L-1) wherein $A^3$ represents a nitrogen atom, $A^2$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX339").

The compound (L-1) wherein $A^2$ represents a nitrogen represented by Q28, $R^3$ represents a hydrogen atom, and $R^{5b}$ represents any one substituent indicated in [Table 7A] to [Table 14A] (hereinafter, referred to as "Compound class SX340").

The compound (L-1) wherein $A^2$, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX341").

The compound (L-1) wherein $A^2$ represents a nitrogen atom, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX342").

The compound (L-1) wherein $A^3$ represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX343").

The compound (L-1) wherein $A^4$ represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX344").

A compound represented by formula (L-2):

(L-2)

(hereinafter, referred to as "Compound (L-2)") wherein $A^2$, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX345").

The compound (L-2) wherein $A^2$ represents a nitrogen atom, A3 and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX346").

The compound (L-2) wherein $A^3$ represents a nitrogen atom, $A^2$ and $A^4$ represent CH, Q represents a group represented by Q10, $R^{5'}$ represents a hydrogen atom, and $R^{5b}$ represents any one substituent indicated in [Table 7A] to [Table 14A] (hereinafter, referred to as "Compound class SX347").

The compound (L-2) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX348").

The compound (L-2) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX349").

The compound (L-1) wherein $A^2$ represents a nitrogen atom, $A^3$ and $A^4$ represent CH, Q represents a group represented by Q11, $R^5$ represents a hydrogen atom, and $R^{5b}$ represents any one substituent indicated in [Table 7A] to [Table 14A] (hereinafter, referred to as "Compound class SX350").

The compound (L-1) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX351").

The compound (L-2) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX352").

The compound (L-2) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX353").

The compound (L-2) wherein $A^2$ represents a nitrogen atom, $A^3$ and $A^4$ represent CH, Q represents a group represented by Q12, $R^3$ and $R^{51}$ represent a hydrogen atom, and $R^{5b}$ represents any one substituent indicated in [Table 7A] to [Table 14A] (hereinafter, referred to as "Compound class SX354").

The compound (L-2) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX355").

The compound (L-2) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX356").

The compound (L-2) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX357").

The compound (L-2) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX358").

The compound (L-2) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX359").

The compound (L-2) wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX360").

The compound (L-2) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX361").

The compound (L-2) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX362").

The compound (L-2) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX363").

The compound (L-2) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX364").

The compound (L-2) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX365").

The compound (L-2) wherein $A^2$ represents a nitrogen atom, $A^3$ and A4 represent CH, Q represents a group represented by Q16, and $R^{5b}$ represents any one substituent indicated in [Table 7A] to [Table 14A] (hereinafter, referred to as "Compound class SX366").

The compound (L-2) wherein $A^3$ represents a nitrogen atom, $A^2$ and A4 represent CH, Q represents a group represented by Q16, and $R^{5b}$ represents any one substituent indicated in [Table 7A] to [Table 14A] (hereinafter, referred to as "Compound class SX367").

The compound (L-2) wherein A4 represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX368").

The compound (L-2) wherein $A^2$, $A^3$ and A4 represent CH, Q represents a group represented by Q17, $R^3$ represents a hydrogen atom, and $R^{5b}$ represents any one substituent indicated in [Table 7A] to [Table 14A] (hereinafter, referred to as "Compound class SX369").

The compound (L-2) wherein $A^2$ represents a nitrogen atom, $A^3$ and $A^4$ represent CH, 0 represents a group represented by Q17, $R^3$ represents a hydrogen atom, and $R^{5b}$ represents any one substituent indicated in [Table 7A] to [Table 14A] (hereinafter, referred to as "Compound class SX370").

The compound (L-2) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX371").

The compound (L-2) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX372").

The compound (L-2) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX373").

The compound (L-2) wherein $A^2$ represents a nitrogen atom, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX374").

The compound (L-2) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX375").

The compound (L-2) wherein $A^4$ represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX376").

The compound (L-2) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX377").

The compound (L-2) wherein $A^2$ represents a nitrogen atom, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX378").

The compound (L-2) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX379).

The compound (L-2) wherein $A^4$ represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX380").

The compound (L-2) wherein $A^2$, A3 and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX381").

The compound (L-2) wherein $A^2$ represents a nitrogen atom, A3 and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX382").

The compound (L-2) wherein $A^3$ represents a nitrogen atom, $A^2$ and A4 represent CH, Q represents a group represented by Q20, $R^3$ represents a hydrogen atom, and $R^{5a}$ represents any one substituent indicated in [Table 7A] to [Table 14A] (hereinafter, referred to as "Compound class SX383").

The compound (L-2) wherein A4 represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX384").

The compound (L-2) wherein $A^2$, $A^3$ and A4 represent CH, Q represents a group represented by Q20, $R^3$ represents a methyl group, and $R^{5a}$ represents any one substituent indicated in [Table 7A] to [Table 14A] (hereinafter, referred to as "Compound class SX385").

The compound (L-2) wherein $A^2$ represents a nitrogen atom, $A^3$ and A4 represent CH, Q represents a group represented by Q20, $R^3$ represents a methyl group, and $R^{5a}$ represents any one substituent indicated in [Table 7A] to [Table 14A] (hereinafter, referred to as "Compound class SX386").

The compound (L-2) wherein $A^3$ represents a nitrogen atom, $A^2$ and A4 represent CH, Q represents a group represented by Q20, $R^3$ represents a methyl group, and $R^{5a}$ represents any one substituent indicated in [Table 7A] to [Table 14A] (hereinafter, referred to as "Compound class SX387").

The compound (L-2) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX388").

The compound (L-2) wherein $A^2$, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX389").

The compound (L-2) wherein $A^2$ represents a nitrogen atom, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX390").

The compound (L-2) wherein $A^3$ represents a nitrogen atom, $A^2$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX391").

The compound (L-2) wherein $A^4$ represents a nitrogen atom, $A^2$ and $A^3$ represent CH, Q represents a group represented by Q20, $R^{5A}$ represents a hydrogen atom, and $R^3$ represents any one substituent indicated in [Table 7A] to [Table 9A] (hereinafter, referred to as "Compound class SX392").

The compound (L-2) wherein $A^2$, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX393").

The compound (L-2) wherein $A^2$ represents a nitrogen atom, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX394").

The compound (L-2) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX395").

The compound (L-2) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX396").

The compound (L-2) wherein $A^2$, $A^3$ and A4 represent CH, Q represents a group represented by Q22, and $R^3$ represents any one substituent indicated in [Table 7A] to [Table 9A] (hereinafter, referred to as "Compound class SX397").

The compound (L-2) wherein $A^2$ represents a nitrogen atom, $A^3$ and A4 represent CH, Q represents a group represented by Q22, and $R^3$ represents any one substituent indicated in [Table 7A] to [Table 9A] (hereinafter, referred to as "Compound class SX398").

The compound (L-2) wherein $A^3$ represents a nitrogen atom, $A^2$ and A4 represent CH, Q represents a group represented by Q22, and $R^3$ represents any one substituent indicated in [Table 7A] to [Table 9A] (hereinafter, referred to as "Compound class SX399").

The compound (L-2) wherein A4 represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX400").

The compound (L-2) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX401").

The compound (L-2) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX402").

The compound (L-2) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX403").

The compound (L-2) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX404").

The compound (L-2) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX405").

The compound (L-2) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX406").

The compound (L-2) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX407").

The compound (L-2) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX408").

The compound (L-2) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX409").

The compound (L-2) wherein $A^2$ represents a nitrogen atom, $A^3$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX410").

The compound (L-2) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX411").

The compound (L-2) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX412").

The compound (L-2) wherein $A^2$, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX413").

The compound (L-2) wherein $A^2$ represents a nitrogen atom, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX414").

The compound (L-2) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX415").

The compound (L-2) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX416").

The compound (L-2) wherein $A^2$, $A^3$ and $A^4$ represent CH, Q represents a group represented by Q26, and $R^{5b}$ represents any one substituent indicated in [Table 7A] to [Table 14A] (hereinafter, referred to as "Compound class SX417").

The compound (L-2) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX418").

The compound (L-2) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX419").

The compound (L-2) wherein $A^4$ represents a nitrogen atom, $A^2$ and $A^3$ represent CH, Q represents a group represented by Q26, and $R^{5b}$ represents any one substituent indicated in [Table 7A] to [Table 14A] (hereinafter, referred to as "Compound class SX420").

The compound (L-2) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX421").

The compound (L-2) wherein $A^2$ represents a nitrogen represented by Q27, and $R^{5b}$ represents any one substituent indicated in [Table 7A] to [Table 14A] (hereinafter, referred to as "Compound class SX422").

The compound (L-2) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX423").

The compound (L-2) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX424").

The compound (L-2) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX425").

The compound (L-2) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX426").

The compound (L-2) wherein A3 represents a nitrogen atom, $A^2$ and A4 represent CH, Q represents a group represented by Q28, $R^3$ represents a hydrogen atom, and $R^{5b}$ represents any one substituent indicated in [Table 7A] to [Table 14A] (hereinafter, referred to as "Compound class SX427").

The compound (L-2) wherein $A^2$ represents a nitrogen atom, A3 and A4 represent CH, Q represents a group represented by Q28, $R^3$ represents a hydrogen atom, and $R^{5b}$ represents any one substituent indicated in [Table 7A] to [Table 14A] (hereinafter, referred to as "Compound class SX428").

The compound (L-2) wherein $A^2$, $A^3$ and A4 represent CH, Q represents a group represented by Q28, $R^3$ represents a methyl group, and $R^{5b}$ represents any one substituent indicated in [Table 7A] to [Table 14A] (hereinafter, referred to as "Compound class SX429").

The compound (L-2) wherein $A^2$ represents a nitrogen atom, $A^3$ and A4 represent CH, Q represents a group represented by Q28, $R^3$ represents a methyl group, and $R^{5b}$ represents any one substituent indicated in [Table 7A] to [Table 14A] (hereinafter, referred to as "Compound class SX430").

The compound (L-2) wherein $A^3$ represents a nitrogen atom, $A^2$ and A4 represent CH, Q represents a group represented by Q28, $R^3$ represents a methyl group, and $R^{5b}$ represents any one substituent indicated in [Table 7A] to [Table 14A] (hereinafter, referred to as "Compound class SX431").

The compound (L-2) wherein A4 represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX432").

A compound represented by formula (L-3):

(L-3)

$$F_3C-\underset{F\ F}{\overset{F}{C}}-CH_2-O-\underset{A^3-A^4}{\overset{A^2=N}{\bigcirc}}-Q$$

(hereinafter, referred to as "Compound (L-3)") wherein $A^2$, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX433").

The compound (L-3) wherein $A^2$ represents a nitrogen atom, $A^3$ and A4 represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX434").

The compound (L-3) wherein $A^3$ represents a nitrogen atom, $A^2$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX435").

The compound (L-3) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX436").

The compound (L-3) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX437").

The compound (L-3) wherein $A^2$ represents a nitrogen atom, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX438").

The compound (L-3) wherein $A^3$ represents a nitrogen atom, $A^2$ and $A^4$ represent CH, Q represents a group represented by Q11, $R^5$ represents a hydrogen atom, and $R^{5b}$ represents any one substituent indicated in [Table 7A] to [Table 14A] (hereinafter, referred to as "Compound class SX439").

The compound (L-3) wherein $A^4$ represents a nitrogen atom, $A^2$ and $A^3$ represent CH, Q represents a group represented by Q11, $R^5$ represents a hydrogen atom, and $R^{5b}$ represents any one substituent indicated in [Table 7A] to [Table 14A] (hereinafter, referred to as "Compound class SX440").

The compound (L-3) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX441").

The compound (L-3) wherein $A^2$ represents a nitrogen atom, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX442").

The compound (L-3) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX443").

The compound (L-2) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX444").

The compound (L-3) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX445").

The compound (L-3) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX446").

The compound (L-3) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX447").

The compound (L-3) wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX448").

The compound (L-3) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX449").

The compound (L-3) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX450").

The compound (L-3) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX451").

The compound (L-3) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX452").

The compound (L-3) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX453").

The compound (L-3) wherein $A^2$ represents a nitrogen atom, $A^3$ and $A^4$ represent CH, Q represents a group represented by Q16, and $R^{5b}$ represents any one substituent indicated in [Table 7A] to [Table 14A] (hereinafter, referred to as "Compound class SX454").

The compound (L-3) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX455").

The compound (L-3) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX456").

The compound (L-3) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX457").

The compound (L-3) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX458").

The compound (L-3) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX459").

The compound (L-3) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX460").

The compound (L-3) wherein $A^2$, A3 and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX461").

The compound (L-3) wherein $A^2$ represents a nitrogen atom, A3 and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX462").

The compound (L-3) wherein A3 represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX463").

The compound (L-3) wherein $A^4$ represents a nitrogen atom, $A^2$ and A3 represent CH, Q represents a group represented by Q17, $R^3$ represents a methyl group, and $R^{5b}$ represents any one substituent indicated in [Table 7A] to [Table 14A] (hereinafter, referred to as "Compound class SX464").

The compound (L-3) wherein $A^2$, A3 and A4 represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX465").

The compound (L-3) wherein $A^2$ represents a nitrogen atom, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX466").

The compound (L-3) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX467).

The compound (L-3) wherein $A^4$ represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX468").

The compound (L-3) wherein $A^2$, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX469").

The compound (L-3) wherein $A^2$ represents a nitrogen atom, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX470").

The compound (L-3) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX471").

The compound (L-3) wherein $A^4$ represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX472").

The compound (L-3) wherein $A^2$, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX473").

The compound (L-3) wherein $A^2$ represents a nitrogen atom, $A^3$ and $A^4$ represent CH, Q represents a group represented by Q20, $R^3$ represents a methyl group, and $R^5$ represents any one substituent indicated in [Table 7A] to [Table 14A] (hereinafter, referred to as "Compound class SX474").

The compound (L-3) wherein $A^3$ represents a nitrogen atom, $A^2$ and $A^4$ represent CH, Q represents a group represented by Q20, $R^3$ represents a methyl group, and $R^5$ represents any one substituent indicated in [Table 7A] to [Table 14A] (hereinafter, referred to as "Compound class SX475").

The compound (L-3) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX476").

The compound (L-3) wherein $A^2$, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX477").

The compound (L-3) wherein $A^2$ represented by Q20, $R^{5a}$ represents a hydrogen atom, and $R^3$ represents any one substituent indicated in [Table 7A] to [Table 9A] (hereinafter, referred to as "Compound class SX478").

The compound (L-3) wherein $A^3$ represents a nitrogen atom, $A^2$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX479").

The compound (L-3) wherein $A^4$ represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX480").

The compound (L-3) wherein $A^2$, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX481").

The compound (L-3) wherein $A^2$ represents a nitrogen atom, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX482").

The compound (L-3) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX483").

The compound (L-3) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX484").

The compound (L-3) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX485").

The compound (L-3) wherein $A^2$ represents a nitrogen atom, $A^3$ and $A^4$ represent CH, Q represents a group represented by Q22, and $R^3$ represents any one substituent indicated in [Table 7A] to [Table 9A] (hereinafter, referred to as "Compound class SX486").

The compound (L-3) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX487").

The compound (L-3) wherein $A^4$ represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX488").

The compound (L-3) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX489").

The compound (L-3) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX490").

The compound (L-3) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX491").

The compound (L-3) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX492").

The compound (L-3) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX493").

The compound (L-3) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX494").

The compound (L-3) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX495").

The compound (L-3) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX496").

The compound (L-3) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX497").

The compound (L-3) wherein $A^2$ represents a nitrogen atom, $A^3$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX498").

The compound (L-3) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX499").

The compound (L-3) wherein $A^3$ represents a nitrogen atom, $A^2$ and A4 represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX500").

The compound (L-3) wherein $A^2$, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX501").

The compound (L-3) wherein $A^2$ represents a nitrogen atom, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX502").

The compound (L-3) wherein $A^3$ represents a nitrogen atom, $A^2$ and A4 represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX503").

The compound (L-3) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX504").

The compound (L-3) wherein $A^2$, $A^3$ and $A^4$ represent CH, Q represents a group represented by Q26, and $R^{5b}$ represents any one substituent indicated in [Table 7A] to [Table 14A] (hereinafter, referred to as "Compound class SX505").

The compound (L-3) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX506").

The compound (L-3) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX507").

The compound (L-3) wherein $A^4$ represents a nitrogen atom, $A^2$ and $A^3$ represent CH, 0 represents a group represented by Q26, and $R^{5b}$ represents any one substituent indicated in [Table 7A] to [Table 14A] (hereinafter, referred to as "Compound class SX508").

The compound (L-3) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX509").

The compound (L-3) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX510").

The compound (L-3) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX511").

The compound (L-3) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX512").

The compound (L-3) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX513").

The compound (L-3) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX514").

The compound (L-3) wherein $A^3$ represents a nitrogen atom, $A^2$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX515").

The compound (L-3) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX516").

The compound (L-3) wherein $A^2$, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX517").

The compound (L-3) wherein $A^2$ represents a nitrogen atom, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX518").

The compound (L-3) wherein $A^3$ represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX519").

The compound (L-3) wherein $A^4$ represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX520").

A compound represented by formula (L-4):

(hereinafter, referred to as "Compound (L-4)") wherein $A^2$, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX521").

The compound (L-4) wherein $A^2$ represents a nitrogen atom, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX522").

The compound (L-4) wherein $A^3$ represents a nitrogen atom, $A^2$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX523").

The compound (L-4) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX524").

The compound (L-4) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX525").

The compound (L-4) wherein $A^2$ represents a nitrogen atom, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX526").

The compound (L-4) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX527").

The compound (L-4) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX528").

The compound (L-4) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX529").

The compound (L-4) wherein $A^2$ represents a nitrogen atom, A3 and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX530").

The compound (L-4) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX531").

The compound (L-4) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX532").

The compound (L-4) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX533").

The compound (L-4) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX534").

The compound (L-4) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX535").

The compound (L-4) wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX536").

The compound (L-4) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX537").

The compound (L-4) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX538").

The compound (L-4) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX539").

The compound (L-4) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX540").

The compound (L-4) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX541").

The compound (L-4) wherein $A^2$ represents a nitrogen atom, $A^3$ and $A^4$ represent CH, Q represents a group represented by Q16, and $R^{5b}$ represents any one substituent indicated in [Table 7A] to [Table 14A] (hereinafter, referred to as "Compound class SX542").

The compound (L-4) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX543").

The compound (L-4) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX544").

The compound (L-4) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX545").

The compound (L-4) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX546").

The compound (L-4) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX547").

The compound (L-4) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX548").

The compound (L-4) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX549").

The compound (L-4) wherein $A^2$ represents a nitrogen atom, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX550").

The compound (L-4) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX551").

The compound (L-4) wherein $A^4$ represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX552").

The compound (L-4) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX553").

The compound (L-4) wherein $A^2$ represents a nitrogen atom, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX554").

The compound (L-4) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX555").

The compound (L-4) wherein $A^4$ represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX556").

The compound (L-4) wherein $A^2$, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX557").

The compound (L-4) wherein $A^2$ represents a nitrogen atom, A3 and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX558").

The compound (L-4) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX559").

The compound (L-4) wherein $A^4$ represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX560").

The compound (L-4) wherein $A^2$, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX561").

The compound (L-4) wherein $A^2$ represents a nitrogen atom, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX562").

The compound (L-4) wherein $A^3$ represents a nitrogen atom, $A^2$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX563").

The compound (L-4) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX564").

The compound (L-4) wherein $A^2$, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX565").

The compound (L-4) wherein $A^2$ represents a nitrogen atom, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX566").

The compound (L-4) wherein $A^3$ represents a nitrogen atom, $A^2$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX567").

The compound (L-4) wherein $A^4$ represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX568").

The compound (L-4) wherein $A^2$, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX569").

The compound (L-4) wherein $A^2$ represents a nitrogen atom, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX570").

The compound (L-4) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX571").

The compound (L-4) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX572").

The compound (L-4) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX573").

The compound (L-4) wherein $A^2$ represents a nitrogen atom, $A^3$ and $A^4$ represent CH, Q represents a group represented by Q22, and $R^3$ represents any one substituent indicated in [Table 7A] to [Table 9A] (hereinafter, referred to as "Compound class SX574").

The compound (L-4) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX575").

The compound (L-4) wherein $A^4$ represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX576").

The compound (L-4) wherein $A^2$, $A^3$ and A4 represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX577").

The compound (L-4) wherein $A^2$ represents a nitrogen atom, $A^3$ and A4 represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX578").

The compound (L-4) wherein $A^3$ represents a nitrogen atom, A2 and A4 represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX579").

The compound (L-4) wherein A4 represents a nitrogen atom, A2 and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX580").

The compound (L-4) wherein $A^2$, $A^3$ and A4 represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX581").

The compound (L-4) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX582").

The compound (L-4) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX583").

The compound (L-4) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX584").

The compound (L-4) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX585").

The compound (L-4) wherein $A^2$ represents a nitrogen atom, $A^3$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX586").

The compound (L-4) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX587").

The compound (L-4) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX588").

The compound (L-4) wherein $A^2$, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX589").

The compound (L-4) wherein $A^2$ represents a nitrogen represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX590").

The compound (L-4) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX591").

The compound (L-4) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX592").

The compound (L-4) wherein $A^2$, $A^3$ and $A^4$ represent CH, Q represents a group represented by Q26, and $R^{5b}$ represents any one substituent indicated in [Table 7A] to [Table 14A] (hereinafter, referred to as "Compound class SX593").

The compound (L-4) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX594").

The compound (L-4) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX595").

The compound (L-4) wherein $A^4$ represents a nitrogen atom, $A^2$ and $A^3$ represent CH, Q represents a group represented by Q26, and $R^{5b}$ represents any one substituent indicated in [Table 7A] to [Table 14A] (hereinafter, referred to as "Compound class SX596").

The compound (L-4) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX597").

The compound (L-4) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX598").

The compound (L-4) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX599").

The compound (L-4) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX600").

The compound (L-4) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX601").

The compound (L-4) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX602").

The compound (L-4) wherein $A^3$ represents a nitrogen atom, $A^2$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX603").

The compound (L-4) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX604").

The compound (L-4) wherein $A^2$, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX605").

The compound (L-4) wherein $A^2$ represents a nitrogen atom, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX606").

The compound (L-4) wherein $A^3$ represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX607").

The compound (L-4) wherein $A^4$ represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX608").

A compound represented by formula (L-5):

(L-5)

(hereinafter, referred to as "Compound (L-5)") wherein $A^2$, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX609").

The compound (L-5) wherein $A^2$ represents a nitrogen atom, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX610").

The compound (L-5) wherein $A^3$ represents a nitrogen atom, $A^2$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX611").

The compound (L-5) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX612").

The compound (L-5) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX613").

The compound (L-5) wherein $A^2$ represents a nitrogen atom, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX614").

The compound (L-5) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX615").

The compound (L-5) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX616").

The compound (L-5) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX617").

The compound (L-5) wherein $A^2$ represents a nitrogen atom, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX618").

The compound (L-5) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX619").

The compound (L-5) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX620").

The compound (L-5) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX621").

The compound (L-5) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX622").

The compound (L-5) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX623").

The compound (L-5) wherein A4 represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX624").

The compound (L-5) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX625").

The compound (L-5) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX626").

The compound (L-5) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX627").

The compound (L-5) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX628").

The compound (L-5) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX629").

The compound (L-5) wherein $A^2$ represents a nitrogen atom, $A^3$ and $A^4$ represent CH, Q represents a group represented by Q16, and $R^{5b}$ represents any one substituent indicated in [Table 7A] to [Table 14A] (hereinafter, referred to as "Compound class SX630").

The compound (L-5) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX631").

The compound (L-4) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX632").

The compound (L-5) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX633").

The compound (L-5) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX634").

The compound (L-5) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX635").

The compound (L-5) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX636").

The compound (L-5) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX637").

The compound (L-5) wherein $A^2$ represents a nitrogen represented by Q17, $R^3$ represents a methyl group, and $R^{5b}$ represents any one substituent indicated in [Table 7A] to [Table 14A] (hereinafter, referred to as "Compound class SX638").

The compound (L-5) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX639").

The compound (L-5) wherein $A^4$ represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX640").

The compound (L-5) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX641").

The compound (L-5) wherein $A^2$ represents a nitrogen represented by Q18, and $R^{5a}$ and $R^{5c}$ represent a hydrogen atom, and $R^3$ represents any one substituent indicated in [Table 7A] to [Table 9A] (hereinafter, referred to as "Compound class SX642").

The compound (L-5) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX643).

The compound (L-5) wherein $A^4$ represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX644").

The compound (L-5) wherein $A^2$, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX645").

The compound (L-5) wherein $A^2$ represents a nitrogen atom, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX646").

The compound (L-5) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX647").

The compound (L-5) wherein $A^4$ represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX648").

The compound (L-5) wherein $A^2$, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX649").

The compound (L-5) wherein $A^2$ represents a nitrogen atom, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX650").

The compound (L-5) wherein $A^3$ represents a nitrogen atom, $A^2$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX651").

The compound (L-5) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX652").

The compound (L-5) wherein $A^2$, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX653").

The compound (L-5) wherein $A^2$ represents a nitrogen atom, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX654").

The compound (L-5) wherein $A^3$ represents a nitrogen atom, $A^2$ and A4 represent CH, Q represents a group represented by Q20, $R^{5a}$ represents a hydrogen atom, and $R^3$ represents any one substituent indicated in [Table 7A] to [Table 9A] (hereinafter, referred to as "Compound class SX655").

The compound (L-5) wherein A4 represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX656").

The compound (L-5) wherein $A^2$, $A^3$ and A4 represent CH, Q represents a group represented by Q21, $R^{5c}$ represents a hydrogen atom, and $R^3$ represents any one substituent indicated in [Table 7A] to [Table 9A] (hereinafter, referred to as "Compound class SX657").

The compound (L-5) wherein $A^2$ represents a nitrogen atom, $A^3$ and A4 represent CH, Q represents a group represented by Q21, $R^{5c}$ represents a hydrogen atom, and $R^3$ represents any one substituent indicated in [Table 7A] to [Table 9A] (hereinafter, referred to as "Compound class SX658").

The compound (L-5) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX659").

The compound (L-5) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX660").

The compound (L-5) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX661").

The compound (L-5) wherein $A^2$ represents a nitrogen atom, $A^3$ and $A^4$ represent CH, Q represents a group represented by Q22, and $R^3$ represents any one substituent indicated in [Table 7A] to [Table 9A] (hereinafter, referred to as "Compound class SX662").

The compound (L-5) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX663").

The compound (L-5) wherein $A^4$ represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX664").

The compound (L-5) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX665").

The compound (L-5) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX666").

The compound (L-5) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX667").

The compound (L-5) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX668").

The compound (L-5) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX669").

The compound (L-5) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX670").

The compound (L-5) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX671").

The compound (L-5) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX672").

The compound (L-5) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX673").

The compound (L-5) wherein $A^2$ represents a nitrogen atom, $A^3$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX674").

The compound (L-5) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX675").

The compound (L-5) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX676").

The compound (L-5) wherein $A^2$, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX677").

The compound (L-5) wherein $A^2$ represents a nitrogen atom, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX678").

The compound (L-5) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX679").

The compound (L-5) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX680").

The compound (L-5) wherein $A^2$, $A^3$ and A4 represent CH, Q represents a group represented by Q26, and $R^{5b}$ represents any one substituent indicated in [Table 7A] to [Table 14A] (hereinafter, referred to as "Compound class SX681").

The compound (L-5) wherein $A^2$ represents a nitrogen atom, $A^3$ and A4 represent CH, Q represents a group represented by Q26, and $R^{5b}$ represents any one substituent indicated in [Table 7A] to [Table 14A] (hereinafter, referred to as "Compound class SX682").

The compound (L-5) wherein $A^3$ represents a nitrogen atom, $A^2$ and A4 represent CH, Q represents a group represented by Q26, and $R^{5b}$ represents any one substituent indicated in [Table 7A] to [Table 14A] (hereinafter, referred to as "Compound class SX683").

The compound (L-5) wherein A4 represents a nitrogen atom, $A^2$ and $A^3$ represent CH, Q represents a group represented by Q26, and $R^{5b}$ represents any one substituent indicated in [Table 7A] to [Table-14A] (hereinafter, referred to as "Compound class SX684").

The compound (L-5) wherein $A^2$, $A^3$ and A4 represent CH, Q represents a group represented by Q27, and $R^{5b}$ represents any one substituent indicated in [Table 7A] to [Table 14A] (hereinafter, referred to as "Compound class SX685").

The compound (L-5) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX686").

The compound (L-5) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX687").

The compound (L-5) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX688").

The compound (L-5) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX689").

The compound (L-5) wherein $A^2$ represents a nitrogen represented by Q28, $R^3$ represents a hydrogen atom, and $R^{5b}$ represents any one substituent indicated in [Table 7A] to [Table 14A] (hereinafter, referred to as "Compound class SX690").

The compound (L-5) wherein $A^3$ represents a nitrogen atom, $A^2$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX691").

The compound (L-5) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX692").

The compound (L-5) wherein $A^2$, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX693").

The compound (L-5) wherein $A^2$ represents a nitrogen atom, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX694").

The compound (L-5) wherein A3 represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX695").

The compound (L-5) wherein $A^4$ represents a nitrogen atom, $A^2$ and A3 represent CH, Q represents a group represented by Q28, $R^3$ represents a methyl group, and $R^{5b}$ represents any one substituent indicated in [Table 7A] to [Table 14A] (hereinafter, referred to as "Compound class SX696").

A compound represented by formula (L-6):

(L-6)

(hereinafter, referred to as "Compound (L-6)") wherein $A^2$, A3 and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX697").

The compound (L-6) wherein $A^2$ represents a nitrogen represented by Q10, $R^{5a}$ represents a hydrogen atom, and $R^{5b}$ represents any one substituent indicated in [Table 7A] to [Table 14A] (hereinafter, referred to as "Compound class SX698").

The compound (L-6) wherein $A^3$ represents a nitrogen atom, $A^2$ and A4 represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX699").

The compound (L-6) wherein A4 represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX700").

The compound (L-6) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX701").

The compound (L-6) wherein $A^2$ represents a nitrogen represented by Q11, $R^{5a}$ represents a hydrogen atom, and $R^{5b}$ represents any one substituent indicated in [Table 7A] to [Table 14A] (hereinafter, referred to as "Compound class SX702").

The compound (L-6) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX703").

The compound (L-6) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX704").

The compound (L-6) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX705").

The compound (L-6) wherein $A^2$ represents a nitrogen atom, $A^3$ and A4 represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX706").

The compound (L-6) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX707").

The compound (L-6) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX708").

The compound (L-6) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX709").

The compound (L-6) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX710").

The compound (L-6) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX711").

The compound (L-6) wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX712").

The compound (L-6) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX713").

The compound (L-6) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX714").

The compound (L-6) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX715").

The compound (L-6) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX716").

The compound (L-6) wherein $A^2$, $A^3$ and A4 represent CH, Q represents a group represented by Q16, and $R^{5b}$ represents any one substituent indicated in [Table 7A] to [Table 14A] (hereinafter, referred to as "Compound class SX717").

The compound (L-6) wherein $A^2$ represents a nitrogen atom, $A^3$ and $A^4$ represent CH, Q represents a group represented by Q16, and $R^{5b}$ represents any one substituent indicated in [Table 7A] to [Table 14A] (hereinafter, referred to as "Compound class SX718").

The compound (L-6) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX719").

The compound (L-6) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX720").

The compound (L-6) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX721").

The compound (L-6) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX722").

The compound (L-6) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX723").

The compound (L-6) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX724").

The compound (L-6) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX725").

The compound (L-6) wherein $A^2$ represents a nitrogen atom, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX726").

The compound (L-6) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX727").

The compound (L-6) wherein $A^4$ represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX728").

The compound (L-6) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX729").

The compound (L-6) wherein $A^2$ represents a nitrogen atom, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX730").

The compound (L-6) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX731).

The compound (L-6) wherein $A^4$ represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX732").

The compound (L-6) wherein $A^2$, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX733").

The compound (L-6) wherein $A^2$ represents a nitrogen atom, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX734").

The compound (L-6) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX735").

The compound (L-6) wherein $A^4$ represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX736").

The compound (L-6) wherein $A^2$, $A^3$ and $A^4$ represent CH, Q represents a group represented by Q20, $R^3$ represents a methyl group, and $R^5$ represents any one substituent indicated in [Table 7A] to [Table 14A] (hereinafter, referred to as "Compound class SX737").

The compound (L-6) wherein $A^2$ represents a nitrogen atom, $A^3$ and A4 represent CH, Q represents a group represented by Q20, $R^3$ represents a methyl group, and $R^{5a}$ represents any one substituent indicated in [Table 7A] to [Table 14A] (hereinafter, referred to as "Compound class SX738").

The compound (L-6) wherein $A^3$ represents a nitrogen atom, $A^2$ and A4 represent CH, Q represents a group represented by Q20, $R^3$ represents a methyl group, and $R^{5a}$ represents any one substituent indicated in [Table 7A] to [Table 14A] (hereinafter, referred to as "Compound class SX739").

The compound (L-6) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX740").

The compound (L-6) wherein $A^2$, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX741").

The compound (L-6) wherein $A^2$ represents a nitrogen atom, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX742").

The compound (L-6) wherein $A^3$ represents a nitrogen atom, $A^2$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX743").

The compound (L-6) wherein $A^4$ represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX744").

The compound (L-6) wherein $A^2$, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX745").

The compound (L-6) wherein $A^2$ represents a nitrogen atom, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX746").

The compound (L-6) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX747").

The compound (L-6) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX748").

The compound (L-6) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX749").

The compound (L-6) wherein $A^2$ represents a nitrogen represented by Q22, and $R^3$ represents any one substituent indicated in [Table 7A] to [Table 9A] (hereinafter, referred to as "Compound class SX750").

The compound (L-6) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX751").

The compound (L-6) wherein $A^4$ represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX752").

The compound (L-6) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX753").

The compound (L-6) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX754").

The compound (L-6) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX755").

The compound (L-6) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX756").

The compound (L-6) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX757").

The compound (L-6) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX758").

The compound (L-6) wherein $A^3$ represents a nitrogen atom, $A^2$ and A4 represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX759").

The compound (L-6) wherein A4 represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX760").

The compound (L-6) wherein $A^2$, $A^3$ and A4 represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX761").

The compound (L-6) wherein $A^2$ represents a nitrogen atom, $A^3$ and A4 represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX762").

The compound (L-6) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX763").

The compound (L-6) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX764").

The compound (L-6) wherein $A^2$, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX765").

The compound (L-6) wherein $A^2$ represents a nitrogen atom, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX766").

The compound (L-6) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX767").

The compound (L-6) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX768").

The compound (L-6) wherein $A^2$, $A^3$ and $A^4$ represent CH, Q represents a group represented by Q26, and $R^{5b}$ represents any one substituent indicated in [Table 7A] to [Table 14A] (hereinafter, referred to as "Compound class SX769").

The compound (L-6) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX770").

The compound (L-6) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX771").

The compound (L-6) wherein $A^4$ represents a nitrogen atom, $A^2$ and $A^3$ represent CH, Q represents a group represented by Q26, and $R^{5b}$ represents any one substituent indicated in [Table 7A] to [Table 14A] (hereinafter, referred to as "Compound class SX772").

The compound (L-6) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX773").

The compound (L-6) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX774").

The compound (L-6) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX775").

The compound (L-6) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX776").

The compound (L-6) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX777").

The compound (L-6) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX778").

The compound (L-6) wherein $A^3$ represents a nitrogen atom, $A^2$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX779").

The compound (L-6) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX780").

The compound (L-6) wherein $A^2$, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX781").

The compound (L-6) wherein $A^2$ represents a nitrogen atom, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX782").

The compound (L-6) wherein $A^3$ represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX783").

The compound (L-6) wherein $A^4$ represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX784").

A compound represented by formula (L-7):

(L-7)

(hereinafter, referred to as "Compound (L-7)") wherein $A^2$, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX785").

The compound (L-7) wherein $A^2$ represents a nitrogen atom, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX786").

The compound (L-7) wherein $A^3$ represents a nitrogen atom, $A^2$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX787").

The compound (L-7) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX788").

The compound (L-7) wherein $A^2$, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX789").

The compound (L-7) wherein $A^2$ represents a nitrogen atom, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX790").

The compound (L-7) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX791").

The compound (L-7) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX792").

The compound (L-7) wherein $A^2$, $A^3$ and A4 represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX793").

The compound (L-7) wherein $A^2$ represents a nitrogen atom, $A^3$ and A4 represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX794").

The compound (L-7) wherein $A^3$ represents a nitrogen atom, $A^2$ and A4 represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX795").

The compound (L-7) wherein A4 represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX796").

The compound (L-7) wherein $A^2$, $A^3$ and A4 represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX797").

The compound (L-7) wherein $A^2$ represents a nitrogen atom, $A^3$ and A4 represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX798").

The compound (L-7) wherein $A^3$ represents a nitrogen atom, $A^2$ and A4 represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX799").

The compound (L-7) wherein A4 represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX800").

The compound (L-7) wherein $A^2$, $A^3$ and A4 represent CH, Q represents a group represented by Q15, and $R^{5b}$ represents any one substituent indicated in [Table 7A] to [Table 14A] (hereinafter, referred to as "Compound class SX801").

The compound (L-7) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX802").

The compound (L-7) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX803").

The compound (L-7) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX804").

The compound (L-7) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX805").

The compound (L-7) wherein $A^2$ represents a nitrogen represented by Q16, and $R^{5b}$ represents any one substituent indicated in [Table 7A] to [Table 14A] (hereinafter, referred to as "Compound class SX806").

The compound (L-7) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX807").

The compound (L-7) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX808").

The compound (L-7) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX809").

The compound (L-7) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX810").

The compound (L-7) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX811").

The compound (L-7) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX812").

The compound (L-7) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX813").

The compound (L-7) wherein $A^2$ represents a nitrogen atom, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX813").

The compound (L-7) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX815").

The compound (L-7) wherein $A^4$ represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX816").

The compound (L-7) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX817").

The compound (L-7) wherein $A^2$ represents a nitrogen atom, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX818").

The compound (L-7) wherein $A^3$ represents a nitrogen atom, $A^2$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX819).

The compound (L-7) wherein $A^4$ represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX820").

The compound (L-7) wherein $A^2$, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX821").

The compound (L-7) wherein $A^2$ represents a nitrogen atom, $A^3$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX822").

The compound (L-7) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX823").

The compound (L-7) wherein $A^4$ represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX824").

The compound (L-7) wherein $A^2$, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX825").

The compound (L-7) wherein $A^2$ represents a nitrogen atom, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX826").

The compound (L-7) wherein $A^3$ represents a nitrogen atom, $A^2$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX827").

The compound (L-7) wherein A4 represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX828").

The compound (L-7) wherein $A^2$, $A^3$ and A4 represent CH, Q represents a group represented by Q20, $R^{5a}$ represents a hydrogen atom, and $R^3$ represents any one substituent indicated in [Table 7A] to [Table 9A] (hereinafter, referred to as "Compound class SX829").

The compound (L-7) wherein $A^2$ represents a nitrogen atom, $A^3$ and A4 represent CH, Q represents a group represented by Q20, $R^{5a}$ represents a hydrogen atom, and $R^3$ represents any one substituent indicated in [Table 7A] to [Table 9A] (hereinafter, referred to as "Compound class SX830").

The compound (L-7) wherein $A^3$ represents a nitrogen atom, $A^2$ and A4 represent CH, Q represents a group represented by Q20, $R^{5a}$ represents a hydrogen atom, and $R^3$ represents any one substituent indicated in [Table 7A] to [Table 9A] (hereinafter, referred to as "Compound class SX831").

The compound (L-7) wherein A4 represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX832").

The compound (L-7) wherein $A^2$, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX833").

The compound (L-7) wherein $A^2$ represents a nitrogen atom, $A^3$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX834").

The compound (L-7) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX835").

The compound (L-7) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX836").

The compound (L-7) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX837").

The compound (L-7) wherein $A^2$ represents a nitrogen atom, $A^3$ and $A^4$ represent CH, Q represents a group represented by Q22, and $R^3$ represents any one substituent indicated in [Table 7A] to [Table 9A] (hereinafter, referred to as "Compound class SX838").

The compound (L-7) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX839").

The compound (L-7) wherein A4 represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX840").

The compound (L-7) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX841").

The compound (L-7) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX842").

The compound (L-7) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX843").

The compound (L-7) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX844").

The compound (L-7) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX845").

The compound (L-7) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX846").

The compound (L-7) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX847").

The compound (L-7) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX848").

The compound (L-7) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX849").

The compound (L-7) wherein $A^2$ represents a nitrogen atom, $A^3$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX850").

The compound (L-7) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX851").

The compound (L-7) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX852").

The compound (L-7) wherein $A^2$, A3 and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX853").

The compound (L-7) wherein $A^2$ represents a nitrogen atom, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX854").

The compound (L-7) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX855").

The compound (L-7) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX856").

The compound (L-7) wherein $A^2$, A3 and $A^4$ represent CH, Q represents a group represented by Q26, and $R^{5b}$ represents any one substituent indicated in [Table 7A] to [Table 14A] (hereinafter, referred to as "Compound class SX857").

The compound (L-7) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX858").

The compound (L-7) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX859").

The compound (L-7) wherein $A^4$ represents a nitrogen atom, $A^2$ and $A^3$ represent CH, Q represents a group represented by Q26, and $R^{5b}$ represents any one substituent indicated in [Table 7A] to [Table 14A] (hereinafter, referred to as "Compound class SX860").

The compound (L-7) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX861").

The compound (L-7) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX862").

The compound (L-7) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX863").

The compound (L-7) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX864").

The compound (L-7) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX865").

The compound (L-7) wherein $A^2$ represents a nitrogen atom, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX866").

The compound (L-7) wherein $A^3$ represents a nitrogen atom, $A^2$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX867").

The compound (L-7) wherein $A^4$ represents a nitrogen atom, $A^2$ and $A^3$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX868").

The compound (L-7) wherein $A^2$, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX869").

The compound (L-7) wherein $A^2$ represents a nitrogen atom, $A^3$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX870").

The compound (L-7) wherein $A^3$ represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX871").

The compound (L-7) wherein $A^4$ represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX872").

A compound represented by formula (L-8):

(hereinafter, referred to as "Compound (L-8)") wherein $A^2$, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX873").

The compound (L-8) wherein $A^2$ represents a nitrogen atom, $A^3$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX874").

The compound (L-8) wherein $A^3$ represents a nitrogen atom, $A^2$ and $A^4$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX875").

The compound (L-8) wherein $A^4$ represents a nitrogen atom, $A^2$ and $A^3$ represent CH, Q represents a group represented by Q10, $R^{5a}$ represents a hydrogen atom, and $R^{5b}$ represents any one substituent indicated in [Table 7A] to [Table 14A] (hereinafter, referred to as "Compound class SX876").

The compound (L-8) wherein $A^2$, $A^3$ and $A^4$ represent CH, Q represents a group represented by Q11, $R^{54}$ represents a hydrogen atom, and $R^{5b}$ represents any one substituent indicated in [Table 7A] to [Table 14A] (hereinafter, referred to as "Compound class SX877").

The compound (L-8) wherein $A^2$ represents a nitrogen atom, $A^3$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX878").

The compound (L-8) wherein $A^3$ represents a nitrogen atom, $A^2$ and $A^4$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX879").

The compound (L-8) wherein $A^4$ represents a nitrogen atom, $A^2$ and $A^3$ represent CH, Q represents a group represented by Q11, $R^{5a}$ represents a hydrogen atom, and $R^{5b}$ represents any one substituent indicated in [Table 7A] to [Table 14A] (hereinafter, referred to as "Compound class SX880").

The compound (L-8) wherein $A^2$, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX881").

The compound (L-8) wherein $A^2$ represents a nitrogen atom, $A^3$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX882").

The compound (L-8) wherein $A^3$ represents a nitrogen atom, $A^2$ and $A^4$ represent CH, Q represents a group represented by Q12, $R^3$ and $R^{5a}$ represent a hydrogen atom, and $R^{5b}$ represents any one substituent indicated in [Table 7A] to [Table 14A] (hereinafter, referred to as "Compound class SX883").

The compound (L-8) wherein $A^4$ represents a nitrogen atom, $A^2$ and $A^3$ represent CH, Q represents a group represented by Q12, $R^3$ and $R^{5a}$ represent a hydrogen atom, $R^{5b}$ represents any one substituent indicated in [Table 7A] to [Table 14A] (hereinafter, referred to as "Compound class SX884").

The compound (L-8) wherein $A^2$, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX885").

The compound (L-8) wherein $A^2$ represents a nitrogen atom, $A^3$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX886").

The compound (L-8) wherein $A^3$ represents a nitrogen atom, $A^2$ and $A^4$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX887").

The compound (L-8) wherein $A^4$ represents a nitrogen atom, $A^2$ and $A^3$ represent CH, Q represents a group represented by Q12, $R^3$ represents a methyl group, $R^{5a}$ represents a hydrogen atom, and $R^{5b}$ represents any one substituent indicated in [Table 7A] to [Table 14A] (hereinafter, referred to as "Compound class SX888").

The compound (L-8) wherein $A^2$, $A^3$ and $A^4$ represent CH, Q represents a group represented by Q15, and $R^{5b}$ represents any one substituent indicated in [Table 7A] to [Table 14A] (hereinafter, referred to as "Compound class SX889").

The compound (L-8) wherein $A^2$ represents a nitrogen atom, $A^3$ and $A^4$ represent CH, Q represents a group represented by Q15, and $R^{5b}$ represents any one substituent indicated in [Table 7A] to [Table 14A] (hereinafter, referred to as "Compound class SX890").

The compound (L-8) wherein $A^3$ represents a nitrogen atom, $A^2$ and $A^4$ represent CH, Q represents a group represented by Q15, and $R^{5b}$ represents any one substituent indicated in [Table 7A] to [Table 14A] (hereinafter, referred to as "Compound class SX891").

The compound (L-8) wherein $A^4$ represents a nitrogen atom, $A^2$ and $A^3$ represent CH, Q represents a group represented by Q15, and $R^{5b}$ represents any one substituent indicated in [Table 7A] to [Table 14A] (hereinafter, referred to as "Compound class SX892").

The compound (L-8) wherein $A^2$, $A^3$ and $A^4$ represent CH, Q represents a group represented by Q16, and $R^{5b}$ represents any one substituent indicated in [Table 7A] to [Table 14A] (hereinafter, referred to as "Compound class SX893").

The compound (L-8) wherein $A^2$ represents a nitrogen atom, $A^3$ and $A^4$ represent CH, Q represents a group represented by Q16, and $R^{5b}$ represents any one substituent indicated in [Table 7A] to [Table 14A] (hereinafter, referred to as "Compound class SX894").

The compound (L-8) wherein $A^3$ represents a nitrogen atom, $A^2$ and $A^4$ represent CH, Q represents a group represented by Q16, and $R^{5b}$ represents any one substituent indicated in [Table 7A] to [Table 14A] (hereinafter, referred to as "Compound class SX895").

The compound (L-8) wherein $A^4$ represents a nitrogen atom, $A^2$ and $A^3$ represent CH, Q represents a group represented by Q16, and $R^{5b}$ represents any one substituent indicated in [Table 7A] to [Table 14A] (hereinafter, referred to as "Compound class SX896").

The compound (L-8) wherein $A^2$, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX897").

The compound (L-8) wherein $A^2$ represents a nitrogen atom, $A^3$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX898").

The compound (L-8) wherein $A^3$ represents a nitrogen atom, $A^2$ and $A^4$ represent CH, Q represents a group represented by Q17, $R^3$ represents a hydrogen atom, and $R^{5b}$ represents any one substituent indicated in [Table 7A] to [Table 14A] (hereinafter, referred to as "Compound class SX899").

The compound (L-8) wherein $A^4$ represents a nitrogen atom, $A^2$ and $A^3$ represent CH, Q represents a group represented by Q17, $R^3$ represents a hydrogen atom, $R^{5b}$ represents any one substituent indicated in [Table 7A] to [Table 14A] (hereinafter, referred to as "Compound class SX900").

The compound (L-8) wherein $A^2$, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX901").

The compound (L-8) wherein $A^2$ represents a nitrogen atom, $A^3$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX902").

The compound (L-8) wherein $A^3$ represents a nitrogen atom, $A^2$ and $A^4$ represent CH, Q represents a group represented by Q17, $R^3$ represents a methyl group, and $R^{5b}$ represents any one substituent indicated in [Table 7A] to [Table 14A] (hereinafter, referred to as "Compound class SX903").

The compound (L-8) wherein $A^4$ represents a nitrogen atom, $A^2$ and $A^3$ represent CH, Q represents a group represented by Q17, $R^3$ represents a methyl group, and $R^{5b}$ represents any one substituent indicated in [Table 7A] to [Table 14A] (hereinafter, referred to as "Compound class SX904").

The compound (L-8) wherein $A^2$, $A^3$ and $A^4$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX905").

The compound (L-8) wherein $A^2$ represents a nitrogen atom, $A^3$ and A4 represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX906").

The compound (L-8) wherein $A^3$ represents a nitrogen atom, $A^2$ and A4 represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX907).

The compound (L-8) wherein A4 represents a nitrogen atom, $A^2$ and $A^3$ represent CH, Q represents a group represented by Q18, and $R^{5a}$ and $R^{5c}$ represent a hydrogen atom, and $R^3$ represents any one substituent indicated in [Table 7A] to [Table 9A] (hereinafter, referred to as "Compound class SX908").

The compound (L-8) wherein $A^2$, $A^3$ and A4 represent CH, Q represents a group represented by Q20, $R^3$ represents a hydrogen atom, and $R^{5a}$ represents any one substituent indicated in [Table 7A] to [Table 14A] (hereinafter, referred to as "Compound class SX909").

The compound (L-8) wherein $A^2$ represents a nitrogen represented by Q20, $R^3$ represents a hydrogen atom, and $R^{5a}$ represents any one substituent indicated in [Table 7A] to [Table 14A] (hereinafter, referred to as "Compound class SX910").

The compound (L-8) wherein $A^3$ represents a nitrogen atom, $A^2$ and $A^4$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX911").

The compound (L-8) wherein $A^4$ represents a nitrogen atom, $A^2$ and $A^3$ represent CH, Q represents a group represented by Q20, $R^3$ represents a hydrogen atom, and $R^{5a}$ represents any one substituent indicated in [Table 7A] to [Table 14A] (hereinafter, referred to as "Compound class SX912").

The compound (L-8) wherein $A^2$, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX913").

The compound (L-8) wherein $A^2$ represents a nitrogen atom, $A^3$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX914").

The compound (L-8) wherein $A^3$ represents a nitrogen atom, $A^2$ and $A^4$ represent CH, Q represents a group represented by Q20, $R^3$ represents a methyl group, and $R^{5a}$ represents any one substituent indicated in [Table 7A] to [Table 14A] (hereinafter, referred to as "Compound class SX915").

The compound (L-8) wherein $A^4$ represents a nitrogen atom, $A^2$ and $A^3$ represent CH, Q represents a group represented by Q20, $R^3$ represents a methyl group, and $R^{5a}$ represents any one substituent indicated in [Table 7A] to [Table 14A] (hereinafter, referred to as "Compound class SX916").

The compound (L-8) wherein $A^2$, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX917").

The compound (L-8) wherein $A^2$ represents a nitrogen atom, $A^3$ and $A^4$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX918").

The compound (L-8) wherein $A^3$ represents a nitrogen atom, $A^2$ and A4 represent CH, Q represents a group represented by Q20, $R^{5a}$ represents a hydrogen atom, and $R^3$ represents any one substituent indicated in [Table 7A] to [Table 9A] (hereinafter, referred to as "Compound class SX919").

The compound (L-8) wherein A4 represents a nitrogen atom, $A^2$ and $A^3$ represent CH, Q represents a group represented by Q20, $R^{5a}$ represents a hydrogen atom, and $R^3$ represents any one substituent indicated in [Table 7A] to [Table 9A] (hereinafter, referred to as "Compound class SX920").

The compound (L-8) wherein $A^2$, $A^3$ and A4 represent CH, Q represents a group represented by Q21, $R^{5c}$ represents a hydrogen atom, and $R^3$ represents any one substituent indicated in [Table 7A] to [Table 9A] (hereinafter, referred to as "Compound class SX921").

The compound (L-8) wherein $A^2$ represents a nitrogen atom, $A^3$ and A4 represent CH, Q represents a group represented by Q21, $R^{5c}$ represents a hydrogen atom, and $R^3$ represents any one substituent indicated in [Table 7A] to [Table 9A] (hereinafter, referred to as "Compound class SX922").

The compound (L-8) wherein $A^3$ represents a nitrogen atom, $A^2$ and $A^4$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX923").

The compound (L-8) wherein $A^4$ represents a nitrogen atom, $A^2$ and $A^3$ represent CH, Q represents a group represented by Q21, $R^{5c}$ represents a hydrogen atom, and $R^3$ represents any one substituent indicated in [Table 7A] to [Table 9A] (hereinafter, referred to as "Compound class SX924").

The compound (L-8) wherein $A^2$, $A^3$ and $A^4$ represent CH, Q represents a group represented by Q22, and $R^3$ represents any one substituent indicated in [Table 7A] to [Table 9A] (hereinafter, referred to as "Compound class SX925").

The compound (L-8) wherein $A^2$ represents a nitrogen atom, $A^3$ and $A^4$ represent CH, Q represents a group represented by Q22, and $R^3$ represents any one substituent indicated in [Table 7A] to [Table 9A] (hereinafter, referred to as "Compound class SX926").

The compound (L-8) wherein $A^3$ represents a nitrogen atom, $A^2$ and $A^4$ represent CH, Q represents a group represented by Q22, and $R^3$ represents any one substituent indicated in [Table 7A] to [Table 9A] (hereinafter, referred to as "Compound class SX927").

The compound (L-8) wherein $A^4$ represents a nitrogen atom, $A^2$ and $A^3$ represent CH, Q represents a group represented by Q22, $R^{5c}$ represents a hydrogen atom, and $R^3$ represents any one substituent indicated in [Table 7A] to [Table 9A] (hereinafter, referred to as "Compound class SX928").

The compound (L-8) wherein $A^2$, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX929").

The compound (L-8) wherein $A^2$ represents a nitrogen atom, $A^3$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX930").

The compound (L-8) wherein $A^3$ represents a nitrogen atom, $A^2$ and $A^4$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX931").

The compound (L-8) wherein $A^4$ represents a nitrogen atom, $A^2$ and $A^3$ represent CH, Q represents a group represented by Q23, $R^{5c}$ represents a hydrogen atom, and $R^{5b}$ represents any one substituent indicated in [Table 7A] to [Table 14A] (hereinafter, referred to as "Compound class SX932").

The compound (L-8) wherein $A^2$, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX933").

The compound (L-8) wherein $A^2$ represents a nitrogen atom, $A^3$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX934").

The compound (L-8) wherein $A^3$ represents a nitrogen atom, $A^2$ and $A^4$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX935").

The compound (L-8) wherein $A^4$ represents a nitrogen atom, $A^2$ and $A^3$ represent CH, Q represents a group represented by Q24, $R^{5c}$ represents a hydrogen atom, and $R^{5b}$ represents any one substituent indicated in [Table 7A] to [Table 14A] (hereinafter, referred to as "Compound class SX936").

The compound (L-8) wherein $A^2$, $A^3$ and $A^4$ represent CH, Q represents a group represented by Q25, $R^3$ and $R^{5c}$ represents a hydrogen atom, and $R^{5b}$ represents any one substituent indicated in [Table 7A] to [Table 9A] (hereinafter, referred to as "Compound class SX937").

The compound (L-8) wherein $A^2$ represents a nitrogen atom, $A^3$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX938").

The compound (L-8) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX939").

The compound (L-8) wherein $A^3$ represents a nitrogen atom, $A^2$ and $A^4$ represent CH, Q represents a group represented by Q25, $R^3$ and $R^{5c}$ represent a hydrogen atom, and $R^{5b}$ represents any one substituent indicated in [Table 7A] to [Table 14A] (hereinafter, referred to as "Compound class SX940").

The compound (L-8) wherein $A^2$, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX941").

The compound (L-8) wherein $A^2$ represents a nitrogen atom, $A^3$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX942").

The compound (L-8) wherein $A^3$ represents a nitrogen atom, $A^2$ and $A^4$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX943").

The compound (L-8) wherein $A^4$ represents a nitrogen atom, $A^2$ and $A^3$ represent CH, Q represents a group represented by Q25, $R^3$ represents a methyl group, $R^{5c}$ represents a hydrogen atom, and $R^{5b}$ represents any one substituent indicated in [Table 7A] to [Table 14A] (hereinafter, referred to as "Compound class SX944").

The compound (L-8) wherein $A^2$, $A^3$ and $A^4$ represent CH, Q represents a group represented by Q26, and $R^{5b}$ represents any one substituent indicated in [Table 7A] to [Table 14A] (hereinafter, referred to as "Compound class SX945").

The compound (L-8) wherein $A^2$ represents a nitrogen atom, $A^3$ and $A^4$ represent CH, Q represents a group represented by Q26, and $R^{5b}$ represents any one substituent indicated in [Table 7A] to [Table 14A] (hereinafter, referred to as "Compound class SX946").

The compound (L-8) wherein $A^3$ represents a nitrogen atom, $A^2$ and $A^4$ represent CH, Q represents a group represented by Q26, and $R^{5b}$ represents any one substituent indicated in [Table 7A] to [Table 14A] (hereinafter, referred to as "Compound class SX947").

The compound (L-8) wherein $A^4$ represents a nitrogen atom, $A^2$ and $A^3$ represent CH, Q represents a group represented by Q26, and $R^{5b}$ represents any one substituent indicated in [Table 7A] to [Table 14A] (hereinafter, referred to as "Compound class SX948").

The compound (L-8) wherein $A^2$, $A^3$ and $A^4$ represent CH, Q represents a group represented by Q27, and $R^{5b}$ represents any one substituent indicated in [Table 7A] to [Table 14A] (hereinafter, referred to as "Compound class SX949").

The compound (L-8) wherein $A^2$ represents a nitrogen atom, $A^3$ and $A^4$ represent CH, Q represents a group represented by Q27, and $R^{5b}$ represents any one substituent indicated in [Table 7A] to [Table 14A] (hereinafter, referred to as "Compound class SX950").

The compound (L-8) wherein $A^3$ represents a nitrogen atom, $A^2$ and $A^4$ represent CH, Q represents a group represented by Q27, and $R^{5b}$ represents any one substituent indicated in [Table 7A] to [Table 14A] (hereinafter, referred to as "Compound class SX951").

The compound (L-8) wherein $A^4$ represents a nitrogen atom, $A^2$ and $A^3$ represent CH, Q represents a group represented by Q27, and $R^{5b}$ represents any one substituent indicated in [Table 7A] to [Table 14A] (hereinafter, referred to as "Compound class SX952").

The compound (L-8) wherein $A^2$, $A^3$ and $A^4$ represent CH, Q represents a group represented by Q28, $R^3$ represents a hydrogen atom, and $R^{5b}$ represents any one substituent indicated in [Table 7A] to [Table 14A] (hereinafter, referred to as "Compound class SX953").

The compound (L-8) wherein $A^2$ represents a nitrogen atom, $A^3$ and A4 represent CH, Q represents a group represented by Q28, $R^3$ represents a hydrogen atom, and $R^{5b}$ represents any one substituent indicated in [Table 7A] to [Table 14A] (hereinafter, referred to as "Compound class SX954").

The compound (L-8) wherein $A^3$ represents a nitrogen atom, $A^2$ and A4 represent CH, Q represents a group represented by Q28, $R^3$ represents a hydrogen atom, and $R^{5b}$ represents any one substituent indicated in [Table 7A] to [Table 14A] (hereinafter, referred to as "Compound class SX955").

The compound (L-8) wherein $A^2$ represents a nitrogen atom, $A^3$ and A4 represent CH, Q represents a group represented by Q28, $R^3$ represents a hydrogen atom, and $R^{5b}$ represents any one substituent indicated in [Table 7A] to [Table 14A] (hereinafter, referred to as "Compound class SX956").

The compound (L-8) wherein $A^2$, $A^3$ and A4 represent CH, Q represents a group represented by Q28, $R^3$ represents a methyl group, and $R^{5b}$ represents any one substituent indicated in [Table 7A] to [Table 14A] (hereinafter, referred to as "Compound class SX957").

The compound (L-8) wherein $A^2$ represents a nitrogen atom, $A^3$ and A4 represent CH, Q represents a group represented by Q28, $R^3$ represents a methyl group, and $R^{5b}$ represents any one substituent indicated in [Table 7A] to [Table 14A] (hereinafter, referred to as "Compound class SX958").

The compound (L-8) wherein $A^3$ represents a nitrogen atom, $A^2$ and $A^4$ represent CH, Q represents a group represented by Q28, $R^3$ represents a methyl group, and $R^{5b}$ represents any one substituent indicated in [Table 7A] to [Table 14A] (hereinafter, referred to as "Compound class SX959").

The compound (L-8) wherein $A^4$ represents a nitrogen atom, $A^2$ and $A^3$ represent CH, Q represents a group represented by Q28, $R^3$ represents a methyl group, and $R^{5b}$ represents any one substituent indicated in [Table 7A] to [Table 14A] (hereinafter, referred to as "Compound class SX960").

Next, the Formulation examples of the present compound are shown below. The "parts" represents "part by weight". Further, the present compound S represents the compounds described as the compound groups SX1 to SX960.

Formulation Example 1

Into a mixture of 10 parts of any one of the present compounds S, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of wet process silica, and 54 parts of diatomaceous earth are mixed, and further 20 parts of any one of the present compounds S is added thereto, followed by mixing them to obtain each formulation.

Formulation Example 3

To 2 parts of any one of the present compounds S, 1 part of wet process silica, 2 parts of calcium lignin sulfonate, 30 parts of bentonite, and 65 parts of kaolin clay are added, followed by mixing them. To the mixtures is then added an appropriate amount of water, and the mixtures are further stirred, granulated with a granulator, and forced-air dried to obtain each formulation.

Formulation Example 4

Into an appropriate amount of acetone, 1 part of any one of the present compounds S is mixed, and then 5 parts of wet process silica, 0.3 parts of isopropyl acid phosphate, and 93.7 parts of kaolin clay are added, following by mixing them with stirring thoroughly and removal of acetone from the mixture by evaporation to obtain each formulation.

Formulation Example 5

A mixture of 35 parts of polyoxyethylene alkyl ether sulfate ammonium salt and wet process silica (weight ratio of 1:1), 20 parts of any one of the present compounds S, and 45 parts of water are enough mixed to obtain each formulation.

Formulation Example 6

Into a mixture of 5 parts of xylene and 5 parts of trichloroethane, 0.1 parts of any one of the present compounds S are mixed, and the resulting mixture is then mixed with 89.9 parts of kerosene to obtain each solution.

Formulation Example 7

Into 0.5 ml of acetone, 10 mg of any one of the present compounds S is mixed, and the solution is added dropwise to 5 g of a solid feed powder for an animal (solid feed powder for rearing and breeding CE-2, manufactured by CLEA Japan, Inc.), followed by mixing the resulting mixtures uniformly, and then by drying them by evaporation of acetone to obtain each poison bait.

Formulation Example 8

Into an aerosol can, 0.1 parts of any one of the present compounds S and 49.9 parts of Neothiozole (manufactured by Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 parts of any one of the present compounds S, 0.01 parts of 2,6-di-tert-butyl-4-methylphenol, 5 parts of xylene, 3.39 parts of kerosene, and 1 part of Rheodol (registered trademark) MO-60, and 50 parts of distilled water are filled into an aerosol container, and a valve part of the container is attached. Then, 40 parts of LPG is filled therein through the valve under pressure to obtain each aqueous aerosol.

Formulation Example 10

Zero point one (0.1) g of any one of the present compounds S is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 11

Five (5) parts of any one of the present compounds S, and 95 parts of ethylene-methyl methacrylate copolymer (the ratio of the methyl methacrylate in the copolymer: 10 weight %) are melted and kneaded, and the resulting kneaded product is extruded from an extrusion molding machine to obtain each rod-shaped molded product having a length of 15 cm and a diameter of 3 mm.

Formulation Example 12

Five (5) parts of any one of the present compounds S, and 95 parts of plasticized polyvinyl chloride resin are melted and kneaded, and the resulting kneaded product is extruded from an extrusion molding machine to obtain each rod-shaped molded product having a length of 15 cm and a diameter of 3 mm.

Formulation Example 13

One-hundred (100) mg of any one of the present compounds S, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 14

Twenty-five (25) mg of any one of the present compounds S, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 15

To 100 mg of any one of the present compounds S, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum (registered trademark) K (manufactured by Vanderbilt Co.), 35 mg of a perfume, and 500 mg of a coloring agent, distilled water is added so that a final volume is set to be 100 mL, followed by mixing the mixtures

Formulation Example 16

Into a mixture of 5 parts of an emulsifier, 3 parts of benzyl alcohol and 30 parts of propylene glycol, 5 parts of any one of the present compounds S is mixed, and phosphate buffer is added thereto so that a pH of the solution is set to be 6.0 to 6.5, and water is added as the rest parts to obtain each solution for oral administration.

Formulation Example 17

To a mixture of 57 parts of fractional distilled palm oil and 3 parts of polysorbate 85, 5 parts of aluminium distearate is added, and heated to disperse it. The resulting mixture is cooled to room temperature, and 25 parts of saccharin is dispersed in an oil vehicle. Ten (10) parts of any one of the present compounds S is divided thereto to obtain each paste for oral administration.

Formulation Example 18

Five (5) parts of any one of the present compounds S is mixed with 95 parts of limestone filler, followed by a wet-granulation of the resulting mixture to obtain each granule for oral administration.

Formulation Example 19

Into 80 parts of diethylene glycol monoethyl ether, 5 parts of any one of the present compounds S is mixed, and 15 parts of propylene carbonate is added thereto, and the resulting mixture is mixed to obtain each spot-on solution.

Formulation Example 20

Into 70 parts of diethylene glycol monoethyl ether, 10 parts of any one of the present compounds S is mixed, and 20 parts of 2-octyldodecanol is added thereto, and the resulting mixture is mixed to obtain each pour-on solution.

Formulation Example 21

To 0.1 parts of any one of the present compounds S, 40 parts of sodium polyoxyethylene lauryl ether sulfate (25% aqueous solution), 5 parts of lauramidopropyl betaine, 5 parts of coconut fatty acid monoethanolamide, 0.5 parts of carboxy vinyl polymer, and 49.4 parts of purified water are added, and the resulting mixture is enough mixed to obtain each shampoo formulation.

Formulation Example 22

Zero point fifteen (0.15) parts of any one of the present compounds S, 95 parts of animal feed, as well as 4.85 parts of a mixture of dibasic calcium phosphate, diatomaceous earth, Aerosil (registered trademark), and carbonate (or chalk) are enough mixed to obtain each premix for animal feed.

Formulation Example 23

Seven point two (7.2) g of any one of the present compounds S, and 92.8 g of Hosco (registered trademark) S-55 are mixed at 100° C., and the resulting mixture is poured into a suppository mold, followed by performing a cooling solidification to obtain each suppository.

Next, an efficacy of the present compound on controlling harmful arthropods is shown by Test examples. The following tests were conducted at 25° C.

Test Method 1

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cucumber (cucumber *sativus*) seedling (on the developmental stage of the second true leaf) is planted in a cup, and approximately 30 cotton aphids (*Aphis gossypii*) (all stages of life) are released onto the seedling. After one day, the diluted solutions are sprayed into the seedling at a ratio of 10 mL/seedling. After 5 days, the number of the surviving insects is examined and the controlling value is calculated by the following equation.

$$\text{Controlling value (\%)} = (1-(Cb \times Tai)/(Cai \times Tb)) \times 100$$

wherein the symbols in the equation represent the following descriptions.
Cb: Number of the test insects in untreated group;
Cai: Number of the surviving insects at the time of the examination in untreated group;
Tb: Number of the test insects in treated group;
Tai: Number of the surviving insects at the time of the examination in treated group;
Here the "untreated group" represents a group where a similar treatment procedure to that of treated group except not using the test compound is done.

Test Example 1

The test was conducted according to the Test method 1 by making the prescribed concentration 500 ppm and using the below-mentioned present compounds as a test compound, and, as the result of the test, the below-mentioned present compounds showed 90% or more as the controlling value.
Present compound Nos: 12 and 13
Test Method 2
Test compounds are made to a formulation according to a similar method to that described in the Formulation example 5, and thereto is added water to prepare a diluted solution containing a prescribed concentration of the test compound.
Cucumber (cucumber *sativus*) seedling (on the developmental stage of the second true leaf) is planted in a cup, and the diluted solutions are drenched to the foot of the seedling at a ratio of 5 mL/seedling. After 7 days, approximately 30 cotton aphids (*Aphis gossypii*) (all stages of life) are released onto the leaf of the seedling. After 6 days, the number of the surviving insects is examined and the controlling value is calculated by the following equation.

$$\text{Controlling value (\%)} = \{1-(Cb \times Tai)/(Cai \times Tb)\} \times 100$$

wherein the symbols in the equation represent the following descriptions.
Cb: Number of the test insects in untreated group;
Cai: Number of the surviving insects at the time of the examination in untreated group;
Tb: Number of the test insects in treated group;
Tai: Number of the surviving insects at the time of the examination in treated group;
Here the "untreated group" represents a group where a similar treatment procedure to that of treated group except not using the test compound is done.
Test Method 3
Test compounds are made to a formulation according to a similar method to that described in the Formulation example 5, and thereto is added water containing 0.03 v/v % of Shindain (registered trademark) to prepare a diluted solution containing a prescribed concentration of the test compound.
Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) tobacco cutworms (*Spodoptera litura*) at the second instar larval stage are released into the cup. After 5 days, the number of the surviving insects is counted, and the mortality of insects is calculated by the following equation.

$$\text{Mortality (\%)} = (1-\text{Number of surviving insects}/5) \times 100$$

Test Example 3-1

The test was conducted according to the Test method 3 by making the prescribed concentration 500 ppm and using the below-mentioned present compounds as a test compound, and, as the result of the test, the below-mentioned present compounds showed 80% or more as the mortality of insects.
Present compound Nos: 11 and 15

Test Example 3-2

The test was conducted according to the Test method 3 by making the prescribed concentration 200 ppm and using the below-mentioned present compounds as a test compound, and, as the result of the test, the below-mentioned present compounds showed 80% or more as the mortality of insects.
Present compound Nos: 2 and 11
Test Method 4
Test compounds are made to a formulation according to a similar method to that described in the Formulation example 5, and thereto is added water containing 0.03 v/v % of Shindain (registered trademark) to prepare a diluted solution containing a prescribed concentration of the test compound.
Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) diamondback moth (*Plutella xylostella*) at the second instar larval stage are released into the cup. After 5 days, the number of the surviving insects is counted, and the mortality of insects is calculated by the following equation.

$$\text{Mortality (\%)} = (1-\text{Number of surviving insects}/5) \times 100$$

Test Example 4-1

The test was conducted according to the Test method 4 by making the prescribed concentration 500 ppm and using the below-mentioned present compounds as a test compound, and, as the result of the test, the below-mentioned present compounds showed 80% or more as the mortality of insects.
Present compound Nos: 5, 15, and 16

Test Example 4-2

The test was conducted according to the Test method 4 by making the prescribed concentration 200 ppm and using the below-mentioned present compounds as a test compound, and, as the result of the test, the below-mentioned present compounds showed 80% or more as the mortality of insects.
Present compound Nos: 2, 5, and 16
Test Method 5
Each 1 mg of the test compounds is dissolved into 50 L of a mixed solution of polyoxyethylene sorbitan monococoate and acetone (polyoxyethylene sorbitan mono-co-coate:acetone=5:95 (v/v ratio)). Thereto is added water containing 0.03% by volume of Shindain (registered trademark) to prepare a diluted solution containing a prescribed concentration of the test compound.

A young entire seedling of Corns (*Zea mays*) is immersed into the diluted solution for 30 seconds. Thereafter, each two grains of the seedlings are installed in a plastic petri dish (90 mm radius), and 10 Western corn rootworms (*Diabrotica virgifera virgifera*) at the second instar larval stage are released into the dish. After 5 days, the number of the dead insects is counted, and the mortality of insects is calculated by the following equation.

Mortality (%)=(Number of dead insects/10)×100

Test Example 5

The test was conducted according to the Test method 5 by making the prescribed concentration 500 ppm and using the below-mentioned present compounds as a test compound, and, as the result of the test, the below-mentioned present compounds showed 80% or more as the mortality of insects.
Present compound Nos: 13 and 15

Test Method 6

Test compounds are made to a formulation according to a similar method to that described in the Formulation example 5, and thereto is added water to prepare a diluted solution containing a prescribed concentration of the test compound.

A filter paper having a diameter of 5.5 cm in diameter is spread on the bottom of the cup, and then 0.7 ml of the diluted solutions are added dropwise to the filter paper and 30 mg of sucrose is uniformly placed on the filter paper as a bait. Ten (10) housefly (*Musca domestica*) female adults are released into the cup, and the cup is then covered with the lid. After 24 hours, the number of the dead insects is counted, and the mortality of insects is calculated by the following equation.

Mortality (%)=(Number of dead insects/Number of tested insects)×100

Test Method 7

Test compounds are made to a formulation according to a similar method to that described in the Formulation example 5, and thereto is added water to prepare a diluted solution containing a prescribed concentration of the test compound.

A filter paper having a diameter of 5.5 cm is spread on the bottom of the cup, and then 0.7 ml of the diluted solutions are added dropwise to the filter paper and 30 mg of sucrose is uniformly placed on the filter paper as a bait. Two (2) German cockroach (*Blattella germanica*) male adults are released into the cup, and the cup is covered with the lid. After 6 days, the number of the dead insects is counted, and the mortality of insects is calculated by the following equation.

Mortality (%)=(Number of dead insects/Number of tested insects)×100

Test Method 8

Each 1 mg of the present compounds is dissolved into 10 µL of a mixed solution of xylene, DMF, and a surfactant (xylene:DMF:surfactant=4:4:1 (v/v ratio)). Thereto is added water containing 0.02% by volume of a spreader to prepare diluted solution A containing a prescribed concentration of the present compound.

Each 1 mg of the present ingredients is dissolved into 10 µL of a mixed solution of xylene, DMF, and a surfactant (xylene:DMF:surfactant=4:4:1 (v/v ratio)). Thereto is added water containing 0.02% by volume of a spreader to prepare diluted solution B containing a prescribed concentration of the present ingredient?

The diluted solution A is mixed with the diluted solution B to prepare diluted solution C.

Leaf discs of Cucumber (cucumber *sativus*) cotyledon (length 1.5 cm) are placed in each well of 24-well microplate. Two (2) apterous adults and 8 larvae of cotton aphids (*Aphis gossypii*) per one well are released and the diluted solution C is sprayed at 20 µL per one well. The group is defined as "treated group". A well that is sprayed with 20 µL of water containing 0.02% by volume of a spreader instead of the diluted solution C is defined as "untreated group".

After drying the diluted solution C, the upper microplate is covered with a film sheet. After 5 days, the number of the surviving insects in each well is examined.

The controlling value is calculated by the following equation.

Controlling value (%)={1−(*Tai*)/(*Cai*)}×100 wherein the symbols in the equation represent the following descriptions.
Cai: Number of the surviving insects at the time of the examination in untreated group;
Tai: Number of the surviving insects at the time of the examination in treated group.

Specific diluted solutions C, which can confirm their effect according to the Test method 8, are described in the following 1) to 5).

1) The diluted solution C comprises the combination recited in List A wherein a concentration of the present compound is 200 ppm and a concentration of the present ingredient is 2000 ppm. In List A, Comp X represents any compound selected from the present compounds 1 to 16.

List A:
Comp X+Clothianidin; Comp X+thiamethoxam; Comp X+imidacloprid; Comp X+thiacloprid; Comp x+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA-11; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the present compound is 200 ppm, and a concentration of the present ingredient is 200 ppm.
3) The diluted solution C comprises the combination recited in List A wherein a concentration of the present compound is 500 ppm, and a concentration of the present ingredient is 50 ppm.
4) The diluted solution C comprises the combination recited in List A wherein a concentration of the present compound is 500 ppm, and a concentration of the present ingredient is 5 ppm.
5) The diluted solution C comprises the combination recited in List A wherein a concentration of the present compound is 500 ppm, and a concentration of the present ingredient is 0.5 ppm.

INDUSTRIAL APPLICABILITY

The present compound shows an excellent control effect against a harmful arthropod.

The invention claimed is:
1. A compound represented by formula (I):

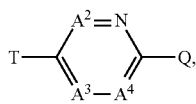

(I)

wherein
Q represents a group represented by formula Q1, a group represented by formula Q2, or a group represented by formula Q3,

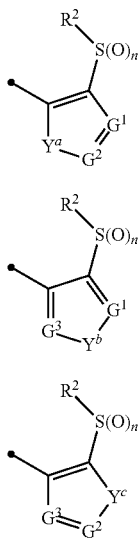

n is 0, 1 or 2,
$R^2$ represents a C2-C6 alkyl group which may optionally have one or more halogen atoms, a cyclopropyl group, or a cyclopropylmethyl group,
$Y^a$ represents an oxygen atom, a sulfur atom, or $NR^{3a}$,
$Y^b$ represents an oxygen atom, a sulfur atom, or $NR^{3b}$,
$Y^c$ represents an oxygen atom, a sulfur atom, or $NR^{3c}$,
$G^1$ represents a nitrogen atom, or $CR^{5a}$,
$G^2$ represents a nitrogen atom, or $CR^{5b}$,
$G^3$ represents a nitrogen atom, or $CR^{5c}$,
$R^{3a}$, $R^{3b}$, and $R^{3c}$ are identical to or different from each other, and each represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $C(O)R^{13}$, $C(O)OR^{17}$, $C(O)NR^{15a}R^{16a}$, $C(O)NR^{11}S(O)_2R^{23}$, or a hydrogen atom,
$R^{5a}$, $R^{5b}$ and $R^{5c}$ are identical to or different from each other, and each represents a C1-C6 chain hydrocarbon group which may optionally have one or more substituents selected from Group B, a C3-C7 cycloalkyl group which may optionally have one or more substituents selected from Group E, a phenyl group which may optionally have one or more substituents selected from Group H, a 5- or 6-membered aromatic heterocyclic group which may optionally have one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}R^{12}$, $NR^{24}OR^{14}$, $NR^{11}C(O)NR^{15a}R^{16a}$, $NR^{24}NR^{11}C(O)NR^{15a}R^{16a}$, $N=CHNR^{15a}R^{16a}$, $N=S(O)_xR^{15}R^{16}$, $C(O)R^{13}$, $C(O)OR^{17}$, $C(O)NR^{15a}R^{16a}$, $C(O)NR^{11}S(O)_2R^{23}$, $CR^{24}=NOR^{17}$, $NR^{11}CR^{24}=NOR^{17}$, a cyano group, a nitro group, a halogen atom, or a hydrogen atom,
x is 0 or 1,
$A^2$ represents $CR^{4a}$,
$A^3$ represents $CR^{4b}$,
$A^4$ represents $CR^{4c}$,
$R^{4a}$, $R^{4b}$, and $R^{4c}$ are identical to or different from each other, and each represents a C1-C6 chain hydrocarbon group which may optionally have one or more halogen atoms, a nitro group, $OR^{18}$, $NR^{18}R^{19}$, a cyan® group, a halogen atom, or a hydrogen atom,
$R^{18}$ represents a C1-C6 chain hydrocarbon group which may optionally have one or more halogen acorns,
$R^{19}$ represents a C1-C6 chain hydrocarbon group which optionally have one or more halogen atoms, or a hydrogen atom,
T represents a C1-C10 chain hydrocarbon group which has one or more halogen atoms, a (C1-C5 alkoxy)C2-C5 alkyl group which has one or more halogen atoms, a (C1-C5 alkylsulfanyl)C2-C5 alkyl group which has one or more halogen atoms, a (C1-C5 alkylsulfinyl)C2-C5 alkyl group which has one or more halogen atoms, a (C1-C5 alkysulfonyl group)C2-C5 alkyl group which has one or more halogen atoms, a (C3-C7 cycloalkyl)C1-C3 alkyl group which may optionally have one or more substituents selected from Group G, a C3-C7 cycloalkyl group which may optionally have one or more substituents selected from Group G, $OR^1$, $S(O)_mR^1$, $OS(O)_2R^1$, $NR^1R^{29}$, $C(O)R^1$, $C(O)NR^1R^{29}$, $CR^{29}C(O)R^1$, $N=CR^1R^{30}$,

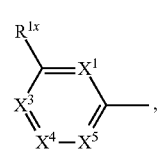

T-1

-continued

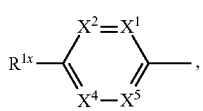

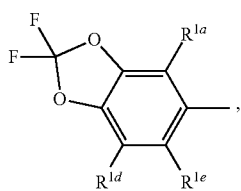

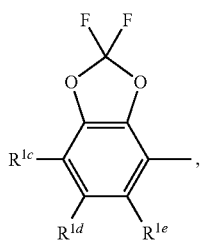

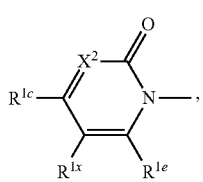

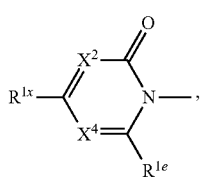

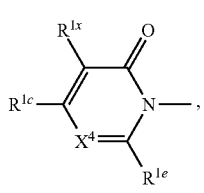

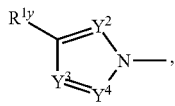

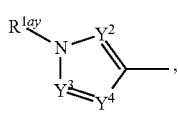

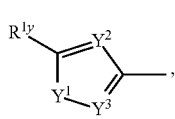

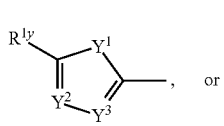, or

-continued

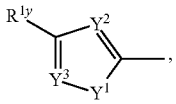

$X^1$ represents a nitrogen atom, or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{1e}$,
$R^{1a}$, $R^{1b}$, $R^{1c}$, $R^{1d}$, and $R^{1e}$ are identical to or different from each other, and each represents a C1-C6 chain hydrocarbon group which may optionally have one or more halogen atoms, a C3-C6 cycloalkyl group which may optionally have one or more halogen atoms, a halogen atom, or a hydrogen atom,
$Y^1$ represents $NR^{25}$, an oxygen atom, or a sulfur atom,
$Y^2$ represents a nitrogen atom, or $CR^{26}$,
$Y^3$ represents a nitrogen atom, or $CR^{27}$,
$Y^4$ represents a nitrogen atom, or $CR^{28}$,
$R^{25}$ represents a C1-C6 chain hydrocarbon group which may optionally have one or more halogen atoms, a C1-C6 alkoxy group which may optionally have one or more halogen atoms, a C3-C7 cycloalkyl group which may optionally have one or more halogen atoms, a (C3-C7 cycloalkyl) C1-C6 alkyl group which may optionally have one or more halogen atoms, or a hydrogen atom,
$R^{26}$, $R^{27}$, and $R^{28}$ are identical to or different from each other, and each represents a C1-C6 chain hydrocarbon group which may optionally have one or more halogen atoms, a C3-C6 cycloalkyl group which may optionally have one or more halogen atoms, a halogen atom, or a hydrogen atom,
$R^{1x}$ represents $OR^7$, $OS(O)_2R^7$, $S(O)_mR^7$, $NR^8S(O)_2R^7$, a C1-C5 chain hydrocarbon group which has one or more halogen atoms, a cyano group, or a halogen atom,
$R^{1y}$ represents $OR^7$, $OS(O)_2R^7$, $S(O)_mR^7$, $NR^8S(O)_2R^7$, a cyano group, a C1-C5 chain hydrocarbon group which has one or more halogen atoms, or a halogen atom,
$R^{1ay}$ and $R^7$ are identical to or different from each other, and each represents a C1-C6 chain hydrocarbon group which has one or more halogen atoms,
$R^8$ represents a C7-C6 chain hydrocarbon group which may optionally have one or more halogen atoms, or a hydrogen atom,
m is 0, 1, or 2,
$R^1$ represents a C1-C10 chain hydrocarbon group which has one or more halogen atoms, a (C1-C5 alkoxy)C2-C5 alkyl group which has one or more halogen atoms, a (C1-C5 alkylsulfanyl)C2-C5 alkyl group which has one or more halogen atoms, a (C1-C5 alkylsulfinyl group)C2-C5 alkyl group which has one or more halogen atoms, a (C1-C5 alkylsulfonyl)C2-C5 alkyl group which has one or more halogen atoms, a (C3-C7 cycloalkyl)C1-C3 alkyl group which has one or more substituents selected from Group G, or a C3-C7 cycloalkyl group which has one or more substituents selected from Group G,
$R^{11}$, $R^{17}$, $R^{24}$, and $R^{29}$ are identical to or different from each other, and each represents a C1-C6 chain hydrocarbon group which may optionally have one or more halogen atoms, or a hydrogen atom, $R^{30}$ represents a C1-C6 chain hydrocarbon group which may optionally have one or more halogen atoms, or a hydrogen atom, $R^{12}$ represents a C1-C6 chain hydrocarbon group which may optionally have one or more halogen atoms, a C1-C6 alkyl group having one substituent selected from Group F, a phenyl group which may optionally have one or more substituents selected from Group H, a 5- or 6-membered aromatic heterocyclic group which may optionally have one or more substituents selected from Group H, $S(O)_2R^{23}$, or a hydrogen atom, $R^{23}$ represents a C1-C6 chain hydrocarbon group which may optionally have one or more halogen atoms, or a phenyl group which may optionally have one or more substituents selected from Group D, $R^{11a}$ and $R^{12a}$ combined together with a nitrogen atom to which they are attached to form a 3 to 7 membered nonaromatic heterocyclic group which may optionally have one or more substituents selected from Group E, $R^{13}$ represents a C1-C6 chain hydrocarbon group which may optionally have one or more halogen atoms, a C3-C7 cycloalkyl group which may optionally have one or more halogen atoms, a (C3-C6 cycloalkyl)C1-C3 alkyl group which may optionally have one or more halogen atoms, a phenyl group which may optionally have one or more substituents selected from Group D, a 5- or 6-membered aromatic heterocyclic group which may optionally have one or more substituents selected from Group D, or a hydrogen atom, $R^{14}$ represents a C1-C6 chain hydrocarbon group which may optionally have one or more halogen atoms, a C3-C7 cycloalkyl group which may optionally have one or more halogen atoms, a (C3-C6 cycloalkyl)C1-C3 alkyl group which may optionally have one or more halogen atoms, or a phenyl C1-C3 alkyl group wherein the phenyl moiety in the phenyl C1-C3 alkyl group may have optionally one or more substituents selected from Group D, $R^{15}$ and $R^{16}$ are identical to or different from each other, and each represents a C1-C6 alkyl group which may optionally have one or more halogen atoms, $R^{15a}$ represents a C1-C6 alkyl group which may optionally have one or more halogen atoms, or a hydrogen atom, and $R^{16a}$ represents a C1-C6 chain hydrocarbon group which may optionally have one or more substituents selected from Group F, a C3-C7 cycloalkyl group which may optionally have one or more substituents selected from Group J, or a hydrogen atom, Group B: a group consisting of a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, a C1-C6 alkylsulfanyl group which may optionally have one or more halogen atoms, a C1-C6 alkylsulfinyl group which may optionally have one or more halogen atoms, a C1-C6 alkylsulfonyl group which may optionally have one or more halogen atoms, a C3-C6 cycloalkyl group which may optionally have one or more halogen atoms, a cyano group, a hydroxy group, and a halogen atom, Group C: a group consisting of a C1-C6 chain hydrocarbon group which may optionally have one or more halogen atoms, a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, and a halogen atom, Group D: a group consisting of a C1-C6 chain hydrocarbon group which may optionally have one or more halogen atoms, a hydroxy group, a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, a sulfanyl group, a C1-C6 alkylsulfanyl group which may optionally have one or more halogen atoms, a C1-C6 alkylsulfinyl group which may optionally have one or more halogen atoms, a C1-C6 alkylsulfonyl group which may optionally have one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, $R^{21}$ and $R^{22}$ are identical to or different from each other, and each represents a C1-C6 alkyl group which may optionally have one or more halogen atoms, Group E: a group consisting of a C1-C6 chain hydrocarbon group which may optionally have one or more halogen atoms, a C1-C6 alkoxy group which may optionally have one or more halogen atoms, a C3-C6 alkenyloxy group which may optionally have one or more halogen atoms, a C3-C6 alkynyloxy group which may optionally have one or more halogen atoms, a halogen atom, an oxo group, a hydroxy group, a cyano group, and a nitro group, Group F: a group consisting of a C1-C6 alkoxy group which may optionally have one or more halogen atoms, a phenyl group which may optionally have one or more substituents selected from Group D, a 5- or 6- membered aromatic heterocyclic group which may optionally have one or more substituents selected from Group D, a C3-C7 cycloalkyl group which may optionally have one or more halogen atoms, a 3 to 7 membered nonaromatic heterocyclic group which may optionally have one or more substituents selected from Group C, an amino group, $NHR^{21}$, $NR^{21}R^{22}$, and a cyano group, Group G: a group consisting of a C1-C6 alkyl group which has one or more halogen atoms, and a halogen atom, Group H: a group consisting of a C1-C6 alkyl group which may optionally have one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, an amino group, and a 5- or 6-membered aromatic heterocyclic group, $R^9$ represents a C1-C6 alkyl group which may optionally have one or more halogen atoms, or a C3-C6 cycloalkyl group which may optionally have one or more halogen atoms, $R^{10}$ represents a C1-C6 alkyl group which may optionally have one or more halogen atoms, a C3-C6 cycloalkyl group which may optionally have one or more halogen atoms, or a hydrogen atom, Group J: a group consisting of a C1-C6 alkyl group which may optionally have one or more halogen atoms, a halogen atom, and a cyano group.

2. The compound according to claim 1, wherein $R^2$ represents a C1-C6 alkyl group, $R^{3a}$, $R^{3b}$, and $R^{3c}$ are identical to or different from each other, and each represents a C1-C6 alkyl group which may optionally have one or more halogen atoms, a phenyl group, a pyridyl group, a pyrimidinyl group, a pyrazolyl group, a triazolyl group, wherein the phenyl group, the pyridyl group, the pyrimidinyl group, the pyrazolyl group, and the triazolyl group may optionally have one or more substituents selected from Group HUN, or a hydrogen atom, $R^{4a}$, $R^{4b}$, and $R^{4c}$ are identical to or different from each other, and each presents a hydrogen atom, or a halogen atom, T represents $OR^1$, and $R^1$ represents a C1-C5 chain hydrocarbon group which has one or more halogen atoms, Q represents a group represented by formula Q1, or a group represented by formula Q3, and $R^{5a}$, $R^{5b}$, and $R^{5c}$ are identical to or different from each other, and each represents a C1-C6 alkyl group which may optionally have one or more halogen atoms, a phenyl group, a pyridyl group, a pyrimidinyl group, a pyrazolyl group, a triazolyl group, wherein the phenyl group, the pyridyl group, the pyrimidinyl group, the pyrazolyl group, and the triazolyl group may optionally have one or more substituents selected from Group H, $OR^{12}$, $NR^{11}R^{12}NR^{11}C(O)OR^{14}$, a halogen atom, or a hydrogen atom.

3. The compound according to claim 1, wherein $R^1$ represents a C1-C5 alkyl group having three or more fluorine atoms, $R^{3a}$, $R^{3b}$, and $R^{3c}$ are identical to or different from each other, and each represent a C1-C6 alkyl group which may optionally have one or more halogen atoms, or a hydrogen atom, $R^{4a}$, $R^{4b}$, and $R^{4c}$ represent a hydrogen atom, and $R^{5a}$, $R^{5b}$, and $R^{5c}$ are identical to or different from each other, and each represents a C1-C6 alkyl group which may optionally have one or more halogen atoms, $OR^{12}$, a halogen atom, or a hydrogen atom.

4. The compound of claim 1, wherein $R^2$ represents an ethyl group.

5. The compound of claim 1, wherein Q represents a group represented by formula Q1.

6. The compound of claim 1, wherein Q represents a group represented by formula Q3.

7. A composition for controlling a harmful arthropod comprising the compound of claim 1 and an inert carrier.

8. A method for controlling a harmful arthropod, the method comprising:
    applying an effective amount of the compound of claim 1 to a harmful arthropod or a habitat where a harmful arthropod lives.

9. A composition comprising one or more ingredients selected from Group (a) and Group (b), and the compound of claim 1:
    Group (a): a group consisting of insecticidal ingredients, miticide ingredients, and nematicidal ingredients; and
    Group (b): fungicidal ingredient.

10. A method for controlling a, harmful arthropod, the method comprising:
    applying an effective amount of the composition of claim 9 to a harmful arthropod or a habitat where the harmful arthropod lives.

11. A seed or vegetative reproductive organ carrying an effective amount of the compound of claim 1.

* * * * *